US012454572B2

(12) United States Patent
Glimcher et al.

(10) Patent No.: US 12,454,572 B2

(45) Date of Patent: Oct. 28, 2025

(54) METHODS OF TREATING ANEMIA IN MYELODYSPLASTIC SYNDROMES

(71) Applicant: Dana-Farber Cancer Institute, Inc., Boston, MA (US)

(72) Inventors: Laurie H. Glimcher, Boston, MA (US); Mahesh Raundhal, Jamaica Plain, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 18/280,100

(22) PCT Filed: Mar. 2, 2022

(86) PCT No.: PCT/US2022/018538

§ 371 (c)(1),
(2) Date: Sep. 1, 2023

(87) PCT Pub. No.: WO2022/187374

PCT Pub. Date: Sep. 9, 2022

(65) Prior Publication Data

US 2024/0083995 A1 Mar. 14, 2024

Related U.S. Application Data

(60) Provisional application No. 63/155,430, filed on Mar. 2, 2021.

(51) Int. Cl.

| | |
|---|---|
| ***A61K 39/395*** | (2006.01) |
| ***A61K 45/06*** | (2006.01) |
| ***A61P 7/00*** | (2006.01) |
| ***C07K 16/24*** | (2006.01) |

(52) U.S. Cl.

CPC ............ *C07K 16/244* (2013.01); *A61K 45/06* (2013.01); *A61P 7/00* (2018.01)

(58) Field of Classification Search

CPC .............. C07K 16/244; C07K 2317/76; A61K 2039/505

See application file for complete search history.

(56) References Cited

U.S. PATENT DOCUMENTS

| | | | | |
|---|---|---|---|---|
| 2005/0054567 A1 | 3/2005 | Rowlinson | | |
| 2010/0210825 A1* | 8/2010 | Xu | A61P 17/06 | 530/387.3 |
| 2018/0147231 A1 | 5/2018 | McCuaig et al. | | |

FOREIGN PATENT DOCUMENTS

| | | | |
|---|---|---|---|
| CN | 110157733 A | 8/2019 | |
| EP | 1337636 A2 | 8/2003 | |
| WO | WO-2022/187374 A1 | 9/2022 | |

OTHER PUBLICATIONS

D'Silva et al., Immune Dysregulation in MDS: The Role of Cytokines and Immune Cells. Recent Developments in Myelodysplastic Syndromes (book); Jan. 28, 2019.*

Guttman-Yassky et al., Efficacy and safety of fezakinumab (an IL-22 monoclonal antibody) in adults with moderate-to-severe atopic dermatitis inadequately controlled by conventional treatments: A randomized,. J Am Acad Dermatol. May 2018;78(5):872-881.e6.*

Negrin et al., Maintenance Treatment of the Anemia of Myelodysplastic Syndromes With Recombinant Human Granulocyte Colony-Stimulating Factor and Erythropoietin: Evidence for In Vivo Synergy. Blood, 1996; 87(10): 4076-4081.*

Gelebart et al., "Interleukin 22 Signaling Promotes Cell Growth in Mantle Cell Lymphoma" Translational Oncology, 4(1): 9-19 (2011).

Gower et al., "There won'T be blood", Nature Immunology, 22(4): 396-397 (2021).

Hernandez et al., "A catch-22: Interleukin-22 and cancer" European Journal of Immunology, 48: 15-31 (2018).

International Search Report and Written Opinion for International Application No. PCT/US2022/018538 dated Jun. 1, 2022.

Ke Men et al., "Delivery of interleukin-22 binding protein (IL-22BP) gene by cationic micelle for colon cancer gene therapy" Royal Society of Chemistry, 8(30): 16537-16548 (2018).

Protopsaltis et al., "Interleukin-22 promotes tumor angiogenesis", Angiogenesis, 22(2): 311-328 (2018).

Raundhal et al., "Blockade of IL-22 signaling reverses erythroid dysfunction in stress-induced anemias", Nature Immunology, 22(4): 520-529 w/ Supplementary Information (2021).

Roessner et al., "EOMES and IL-10 regulate antitumor activity of T regulatory type 1 CD4+ T cells in chronic lymphocytic leukemia", Leukemia, 35(8): 2311-2324 (2021).

DeZern, "Nine years without a new FDA-approved therapy for MDS: how can we break through the impasse?" Hematology (2015): 308-316.

Fenaux et al., "Efficacy of azacitidine compared with that of conventional care regimens in the treatment of higher-risk myelodysplastic syndromes: a randomised, open-label, phase III study," Lancet Oncology 10.3 (2009): 223-232.

Greenberg et al., "International Scoring System for Evaluating Prognosis in Myelodysplastic Syndromes," Blood 89.6 (1997): 2079-2088.

Lewis et al., "Real-World Study of the Burden of Myelodysplastic Syndromes in Patients and Their Caregivers in Europe and the United States," Oncology and Therapy (2024): 22 pages.

Luzzatto, "Anemia," Comprehensive Pharmacology 4 (2022): 570-596.

Ma, "Epidemiology of Myelodysplastic Syndromes," American Journal of Medicine 125.7 (2012): S2-S5.

Mo et al., "Do anemia treatments improve quality of life and physical function in patients with myelodysplastic syndromes (MDS)? A systematic review," Blood Reviews 61 (2023): 101114 (16 pages).

Montalban-Bravo et al., "Myelodysplastic syndromes: 2018 update on diagnosis, risk-stratification and management," American Journal of Hematology 93 (2018): 129-147.

(Continued)

*Primary Examiner* — Dong Jiang

(74) *Attorney, Agent, or Firm* — Foley Hoag LLP; DeAnn F. Smith; Philip S. Choi

(57) ABSTRACT

The present invention relates, in part, to methods for treating red blood cell disorders, such as an MDS and/or an anemia, by down-regulating IL-22 signaling.

8 Claims, 53 Drawing Sheets

Specification includes a Sequence Listing.

(56) References Cited

OTHER PUBLICATIONS

Platzbecker et al., "Current challenges and unmet medical needs in myelodysplastic syndromes," Leukemia 35 (2021): 2182-2198.
Prebet et al., "Prolonged Administration of Azacitidine With or Without Entinostat for Myelodysplastic Syndrome and Acute Myeloid Leukemia With Myelodysplasia-Related Changes: Results of the US Leukemia Intergroup Trial E1905," Journal of Clinical Oncology 32.12 (2014): 1242-1249.
Sabat et al., "Therapeutic opportunities of the IL-22-IL-22R1 system." Nature reviews Drug discovery 13.1: 21-38 (2014).
Shao et al., "Th22 Cells as Well as Th17 Cells Expand Differentially in Patients with Early-Stage and Late-Stage Myelodysplastic Syndrome," PLoS ONE 7.12 (2012): e51339 (9 pages).

* cited by examiner

FIG. 4A
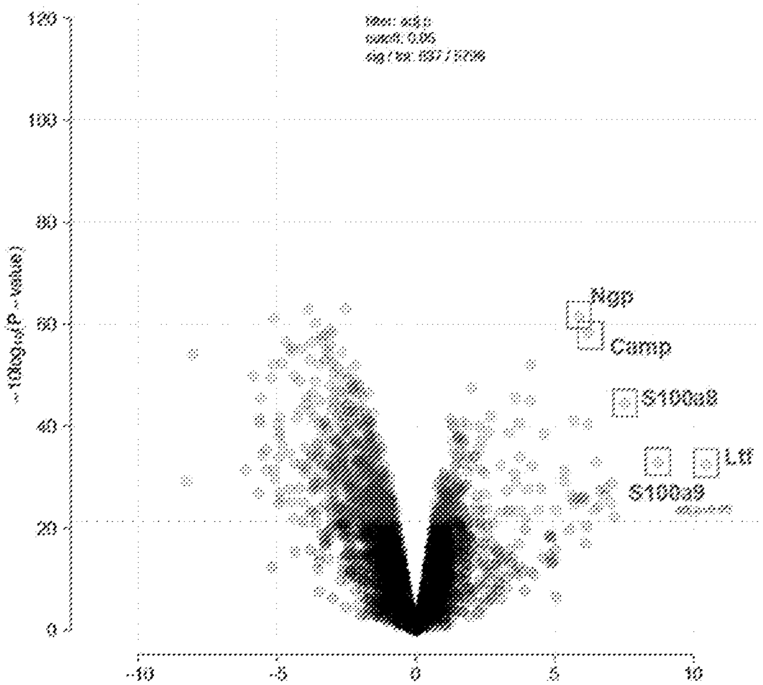
FIG. 4B
| | [illegible] | | [illegible] | |
|---|---|---|---|---|
| Proteins | Adj. p-val | Log Fold Change | Adj. p-val | Log Fold Change |
| Cathelicidin (Camp) | 0.002374 | 12.0330866 | 0.00365230 | 1.3705 |
| Ngp | 0.002690 | 8.73980983 | 0.00384830 | 1.3565 |
| S100A9 | 0.002965 | 8.57445432 | 0.00295955 | 1.4595 |
| Lactotransferrin (Ltf) | 0.001389 | 7.38835125 | 0.00558719 | 1.4575 |
| S100A8 | 0.003295 | 6.3910336 | 0.00197349 | 2.057 |
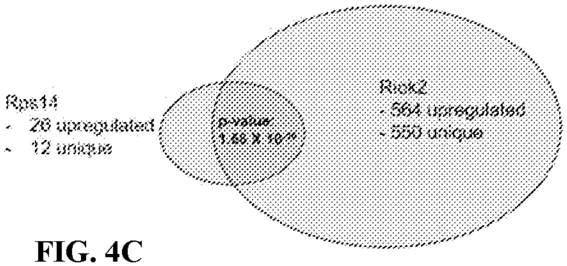
FIG. 4C
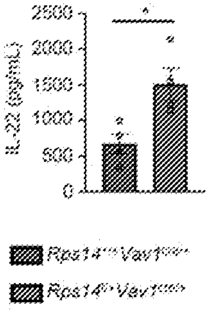
FIG. 4D Isotype
Stained
# cells
0.0299
23.1
RigG PE
IL-22RA1 PE RBCs (M/μL)
Hb (g/dL)
HCT (%)

RI
RII
RIII
RIV
whole BM (%)

Gated on viable erythroid precursors

Doublet exclusion
SSC-H
SSC-W
FSC-H
FSC-W
Live cell gate
# cells
DAPI
Lineage low gate
SSC-A
Lineage PerCP/Cy5.5
Erythroid progenitor gate
CD71 BV421
Ter119 BV605
Antibody
Isotype
IL-22RA1 PE
RIgG PE Modified light scatter gate
Ter119 BV605
FSC-A
IL-22RA1+ gate
Ery gate
CD71 PE-Cy7
RI
RII
RIII
RIV Erythroid progenitor gate Il22ra1 mRNA
Liver
T cells

SEQUENCE LISTING

```
<160> NUMBER OF SEQ ID NOS: 35

<210> SEQ ID NO 1
<211> LENGTH: 552
<212> TYPE: PRT
<213> ORGANISM: Homo sapiens

<400> SEQUENCE: 1

Met Gly Lys Val Asn Val Ala Lys Leu Arg Tyr Met Ser Arg Asp Asp
1               5                   10                  15

Phe Arg Val Leu Thr Ala Val Glu Met Gly Met Lys Asn His Glu Ile
            20                  25                  30

Val Pro Gly Ser Leu Ile Ala Ser Ile Ala Ser Leu Lys His Gly Gly
        35                  40                  45

Cys Asn Lys Val Leu Arg Glu Leu Val Lys His Lys Leu Ile Ala Trp
    50                  55                  60

Glu Arg Thr Lys Thr Val Gln Gly Tyr Arg Leu Thr Asn Ala Gly Tyr
65                  70                  75                  80

Asp Tyr Leu Ala Leu Lys Thr Leu Ser Ser Arg Gln Val Val Glu Ser
                85                  90                  95

Val Gly Asn Gln Met Gly Val Gly Lys Glu Ser Asp Ile Tyr Ile Val
            100                 105                 110

Ala Asn Glu Glu Gly Gln Gln Phe Ala Leu Lys Leu His Arg Leu Gly
        115                 120                 125

Arg Thr Ser Phe Arg Asn Leu Lys Asn Lys Arg Asp Tyr His Lys His
    130                 135                 140

Arg His Asn Val Ser Trp Leu Tyr Leu Ser Arg Leu Ser Ala Met Lys
```

```
145                 150                 155                 160

Glu Phe Ala Tyr Met Lys Ala Leu Tyr Glu Arg Lys Phe Pro Val Pro
                165                 170                 175

Lys Pro Ile Asp Tyr Asn Arg His Ala Val Val Met Glu Leu Ile Asn
            180                 185                 190

Gly Tyr Pro Leu Cys Gln Ile His His Val Glu Asp Pro Ala Ser Val
        195                 200                 205

Tyr Asp Glu Ala Met Glu Leu Ile Val Lys Leu Ala Asn His Gly Leu
    210                 215                 220

Ile His Gly Asp Phe Asn Glu Phe Asn Leu Ile Leu Asp Glu Ser Asp
225                 230                 235                 240

His Ile Thr Met Ile Asp Phe Pro Gln Met Val Ser Thr Ser His Pro
                245                 250                 255

Asn Ala Glu Trp Tyr Phe Asp Arg Asp Val Lys Cys Ile Lys Asp Phe
            260                 265                 270

Phe Met Lys Arg Phe Ser Tyr Glu Ser Glu Leu Phe Pro Thr Phe Lys
        275                 280                 285

Asp Ile Arg Arg Glu Asp Thr Leu Asp Val Glu Val Ser Ala Ser Gly
    290                 295                 300

Tyr Thr Lys Glu Met Gln Ala Asp Asp Glu Leu Leu His Pro Leu Gly
305                 310                 315                 320

Pro Asp Asp Lys Asn Ile Glu Thr Lys Glu Gly Ser Glu Phe Ser Phe
                325                 330                 335

Ser Asp Gly Glu Val Ala Glu Lys Ala Glu Val Tyr Gly Ser Glu Asn
            340                 345                 350

Glu Ser Glu Arg Asn Cys Leu Glu Glu Ser Glu Gly Cys Tyr Cys Arg
        355                 360                 365

Ser Ser Gly Asp Pro Glu Gln Ile Lys Glu Asp Ser Leu Ser Glu Glu
    370                 375                 380

Ser Ala Asp Ala Arg Ser Phe Glu Met Thr Glu Phe Asn Gln Ala Leu
385                 390                 395                 400

Glu Glu Ile Lys Gly Gln Val Val Glu Asn Asn Ser Val Thr Glu Phe
                405                 410                 415

Ser Glu Glu Lys Asn Arg Thr Glu Asn Tyr Asn Arg Gln Asp Gly Gln
            420                 425                 430

Arg Val Gln Gly Gly Val Pro Ala Gly Ser Asp Glu Tyr Glu Asp Glu
        435                 440                 445

Cys Pro His Leu Ile Ala Leu Ser Ser Leu Asn Arg Glu Phe Arg Pro
    450                 455                 460

Phe Arg Asp Glu Glu Asn Val Gly Ala Met Asn Gln Tyr Arg Thr Arg
465                 470                 475                 480

Thr Leu Ser Ile Thr Ser Ser Gly Ser Ala Val Ser Cys Ser Thr Ile
                485                 490                 495

Pro Pro Glu Leu Val Lys Gln Lys Val Lys Arg Gln Leu Thr Lys Gln
            500                 505                 510

Gln Lys Ser Ala Val Arg Arg Arg Leu Gln Lys Gly Glu Ala Asn Ile
        515                 520                 525

Phe Thr Lys Gln Arg Arg Glu Asn Met Gln Asn Ile Lys Ser Ser Leu
    530                 535                 540

Glu Ala Ala Ser Phe Trp Gly Glu
545                 550

<210> SEQ ID NO 2
```

<211> LENGTH: 28
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 2
gcatcagtga tttacagact aaaatgcc 28

<210> SEQ ID NO 3
<211> LENGTH: 26
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 3
gctcttaccc actgagtcat ctcacc 26

<210> SEQ ID NO 4
<211> LENGTH: 25
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 4
cccagactcc ttcttgaagt tctgc 25

<210> SEQ ID NO 5
<211> LENGTH: 22
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 5
ccaaacttaa cttgaccttg gc 22

<210> SEQ ID NO 6
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 6
ttcttcacag ctcccattgc 20

<210> SEQ ID NO 7
<211> LENGTH: 20
<212> TYPE: DNA
<213> ORGANISM: Artificial Sequence
<220> FEATURE:
<223> OTHER INFORMATION: /note="Description of Artificial Sequence: Synthetic primer"

<400> SEQUENCE: 7
agttaagttt ggaaatatcg 20

<210> SEQ ID NO 8
<211> LENGTH: 179

<212> TYPE: PRT
<213> ORGANISM: Homo sapiens

<400> SEQUENCE: 8

```
Met Ala Ala Leu Gln Lys Ser Val Ser Ser Phe Leu Met Gly Thr Leu
1               5                   10                  15

Ala Thr Ser Cys Leu Leu Leu Leu Ala Leu Leu Val Gln Gly Gly Ala
            20                  25                  30

Ala Ala Pro Ile Ser Ser His Cys Arg Leu Asp Lys Ser Asn Phe Gln
        35                  40                  45

Gln Pro Tyr Ile Thr Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

His Gly Val Ser Met Ser Glu Arg Cys Tyr Leu Met Lys Gln Val Leu
                85                  90                  95

Asn Phe Thr Leu Glu Glu Val Leu Phe Pro Gln Ser Asp Arg Phe Gln
            100                 105                 110

Pro Tyr Met Gln Glu Val Val Pro Phe Leu Ala Arg Leu Ser Asn Arg
        115                 120                 125

Leu Ser Thr Cys His Ile Glu Gly Asp Asp Leu His Ile Gln Arg Asn
    130                 135                 140

Val Gln Lys Leu Lys Asp Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Ile
```

<210> SEQ ID NO 9
<211> LENGTH: 1165
<212> TYPE: DNA
<213> ORGANISM: Homo sapiens

<400> SEQUENCE: 9

```
acaagcagaa tcttcagaac aggttctcct tccccagtca ccagttgctc gagttagaat     60

tgtctgcaat ggccgccctg cagaaatctg tgagctcttt ccttatgggg accctggcca    120

ccagctgcct ccttctcttg gccctcttgg tacagggagg agcagctgcg cccatcagct    180

cccactgcag gcttgacaag tccaacttcc agcagcccta tatcaccaac cgcaccttca    240

tgctggctaa ggaggctagc ttggctgata acaacacaga cgttcgtctc attggggaga    300

aactgttcca cggagtcagt atgagtgagc gctgctatct gatgaagcag gtgctgaact    360

tcacccttga agaagtgctg ttccctcaat ctgataggtt ccagccttat atgcaggagg    420

tggtgccctt cctggccagg ctcagcaaca ggctaagcac atgtcatatt gaaggtgatg    480

acctgcatat ccagaggaat gtgcaaaagc tgaaggacac agtgaaaaag cttggagaga    540

gtggagagat caaagcaatt ggagaactgg atttgctgtt tatgtctctg agaaatgcct    600

gcatttgacc agagcaaagc tgaaaaatga ataactaacc ccctttccct gctagaaata    660

acaattagat gccccaaagc gatttttttt aaccaaaagg aagatgggaa gccaaactcc    720

atcatgatgg gtggattcca aatgaacccc tgcgttagtt acaaaggaaa ccaatgccac    780

ttttgtttat aagaccagaa ggtagacttt ctaagcatag atatttattg ataacatttc    840

attgtaactg gtgttctata cacagaaaac aatttatttt ttaaataatt gtcttttttcc    900

ataaaaaaga ttactttcca ttcctttagg ggaaaaaacc cctaaatagc ttcatgtttc    960
```

```
cataatcagt actttatatt tataaatgta tttattatta ttataagact gcattttatt   1020

tatatcattt tattaatatg gatttattta tagaaacatc attcgatatt gctacttgag   1080

tgtaaggcta atattgatat ttatgacaat aattatagag ctataacatg tttatttgac   1140

ctcaataaac acttggatat cctaa                                         1165


<210> SEQ ID NO 10
<211> LENGTH: 574
<212> TYPE: PRT
<213> ORGANISM: Homo sapiens

<400> SEQUENCE: 10

Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240

Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335
```

```
Pro Ser Asn Val Pro Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
        355                 360                 365

Thr Pro Glu Ala Gln Phe Pro Phe Tyr Ala Pro Gln Ala Ile Ser Lys
    370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Gly Pro Cys Ser Pro Ser Asp Gln Gly Pro Ser
        515                 520                 525

Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570
```

<210> SEQ ID NO 11
<211> LENGTH: 2795
<212> TYPE: DNA
<213> ORGANISM: Homo sapiens

<400> SEQUENCE: 11

```
gggagggctc tgtgccagcc ccgatgagga cgctgctgac catcttgact gtgggatccc     60

tggctgctca cgcccctgag gacccctcgg atctgctcca gcacgtgaaa ttccagtcca    120

gcaactttga aaacatcctg acgtgggaca gcgggccaga gggcacccca gacacggtct    180

acagcatcga gtataagacg tacggagaga gggactgggt ggcaaagaag ggctgtcagc    240

ggatcacccg gaagtcctgc aacctgacgg tggagacggg caacctcacg gagctctact    300

atgccagggt caccgctgtc agtgcgggag gccggtcagc caccaagatg actgacaggt    360

tcagctctct gcagcacact accctcaagc cacctgatgt gacctgtatc tccaaagtga    420

gatcgattca gatgattgtt catcctaccc ccacgccaat ccgtgcaggc gatggccacc    480

ggctaaccct ggaagacatc ttccatgacc tgttctacca cttagagctc caggtcaacc    540

gcacctacca aatgcacctt ggagggaagc agagagaata tgagttcttc ggcctgaccc    600

ctgacacaga gttccttggc accatcatga tttgcgttcc cacctgggcc aaggagagtg    660

ccccctacat gtgccgagtg aagacactgc cagaccggac atggacctac tccttctccg    720

gagccttcct gttctccatg ggcttcctcg tcgcagtact ctgctacctg agctacagat    780
```

```
atgtcaccaa gccgcctgca cctcccaact ccctgaacgt ccagcgagtc ctgactttcc    840
agccgctgcg cttcatccag gagcacgtcc tgatccctgt ctttgacctc agcggcccca    900
gcagtctggc ccagcctgtc cagtactccc agatcagggt gtctggaccc agggagcccg    960
caggagctcc acagcggcat agcctgtccg agatcaccta cttagggcag ccagacatct   1020
ccatcctcca gccctccaac gtgccacctc cccagatcct ctccccactg tcctatgccc   1080
caaacgctgc ccctgaggtc gggcccccat cctatgcacc tcaggtgacc cccgaagctc   1140
aattcccatt ctacgcccca caggccatct ctaaggtcca gccttcctcc tatgcccctc   1200
aagccactcc ggacagctgg cctccctcct atggggtatg catggaaggt tctggcaaag   1260
actcccccac tgggacactt tctagtccta aacaccttag gcctaaaggt cagcttcaga   1320
aagagccacc agctggaagc tgcatgttag gtggcctttc tctgcaggag gtgacctcct   1380
tggctatgga ggaatcccaa gaagcaaaat cattgcacca gcccctgggg atttgcacag   1440
acagaacatc tgacccaaat gtgctacaca gtggggagga agggacacca cagtacctaa   1500
agggccagct cccccctcctc tcctcagtcc agatcgaggg ccaccccatg tccctccctt  1560
tgcaacctcc ttccggtcca tgttccccct cggaccaagg tccaagtccc tggggcctgc   1620
tggagtccct tgtgtgtccc aaggatgaag ccaagagccc agcccctgag acctcagacc   1680
tggagcagcc cacagaactg gattctcttt tcagaggcct ggccctgact gtgcagtggg   1740
agtcctgagg ggaatgggaa aggcttggtg cttcctccct gtccctaccc agtgtcacat   1800
ccttggctgt caatcccatg cctgcccatg ccacacactc tgcgatctgg cctcagacgg   1860
gtgcccttga gagaagcaga gggagtggca tgcagggccc ctgccatggg tgcgctcctc   1920
accggaacaa agcagcatga taaggactgc agcgggggag ctctggggag cagcttgtgt   1980
agacaagcgc gtgctcgctg agccctgcaa ggcagaaatg acagtgcaag gaggaaatgc   2040
agggaaactc ccgaggtcca gagccccacc tcctaacacc atggattcaa agtgctcagg   2100
gaatttgcct ctccttgccc cattcctggc cagtttcaca atctagctcg acagagcatg   2160
aggcccctgc ctcttctgtc attgttcaaa ggtgggaaga gagcctggaa aagaaccagg   2220
cctggaaaag aaccagaagg aggctgggca gaaccagaac aacctgcact tctgccaagg   2280
ccagggccag caggacggca ggactctagg gaggggtgtg gcctgcagct cattcccagc   2340
cagggcaact gcctgacgtt gcacgatttc agcttcattc ctctgataga acaaagcgaa   2400
atgcaggtcc accagggagg gagacacaca agccttttct gcaggcagga gtttcagacc   2460
ctatcctgag aatggggttt gaaaggaagg tgagggctgt ggcccctgga cgggtacaat   2520
aacacactgt actgatgtca caactttgca agctctgcct tgggttcagc ccatctgggc   2580
tcaaattcca gcctcaccac tcacaagctg tgtgacttca aacaaatgaa atcagtgccc   2640
agaacctcgg tttcctcatc tgtaatgtgg ggatcataac acctacctca tggagttgtg   2700
gtgaagatga aatgaagtca tgtctttaaa gtgcttaata gtgcctggta catgggcagt   2760
gcccaataaa cggtagctat ttaaaaaaaa aaaaa                              2795
```

<210> SEQ ID NO 12
<211> LENGTH: 325
<212> TYPE: PRT
<213> ORGANISM: Homo sapiens

<400> SEQUENCE: 12

```
Met Ala Trp Ser Leu Gly Ser Trp Leu Gly Gly Cys Leu Leu Val Ser
1               5                   10                  15
```

```
Ala Leu Gly Met Val Pro Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Asp Thr Ile
            100                 105                 110

Ile Gly Pro Pro Gly Met Gln Val Glu Val Leu Ala Asp Ser Leu His
        115                 120                 125

Met Arg Phe Leu Ala Pro Lys Ile Glu Asn Glu Tyr Glu Thr Trp Thr
    130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
                165                 170                 175

Val Leu Arg Asn Leu Glu Pro Trp Thr Thr Tyr Cys Val Gln Val Arg
            180                 185                 190

Gly Phe Leu Pro Asp Arg Asn Lys Ala Gly Glu Trp Ser Glu Pro Val
        195                 200                 205

Cys Glu Gln Thr Thr His Asp Glu Thr Val Pro Ser Trp Met Val Ala
    210                 215                 220

Val Ile Leu Met Ala Ser Val Phe Met Val Cys Leu Ala Leu Leu Gly
225                 230                 235                 240

Cys Phe Ala Leu Leu Trp Cys Val Tyr Lys Lys Thr Lys Tyr Ala Phe
                245                 250                 255

Ser Pro Arg Asn Ser Leu Pro Gln His Leu Lys Glu Phe Leu Gly His
            260                 265                 270

Pro His His Asn Thr Leu Leu Phe Phe Ser Phe Pro Leu Ser Asp Glu
        275                 280                 285

Asn Asp Val Phe Asp Lys Leu Ser Val Ile Ala Glu Asp Ser Glu Ser
    290                 295                 300

Gly Lys Gln Asn Pro Gly Asp Ser Cys Ser Leu Gly Thr Pro Pro Gly
305                 310                 315                 320

Gln Gly Pro Gln Ser
                325
```

<210> SEQ ID NO 13
<211> LENGTH: 1941
<212> TYPE: DNA
<213> ORGANISM: Homo sapiens

<400> SEQUENCE: 13

```
atctccgctg gttcccggaa gccgccgcgg acaagctctc ccgggcgcgg gcgggggtcg      60

tgtgcttgga ggaagccgcg gaacccccag cgtccgtcca tggcgtggag ccttgggagc     120

tggctgggtg gctgcctgct ggtgtcagca ttgggaatgg taccacctcc cgaaaatgtc     180

agaatgaatt ctgttaattt caagaacatt ctacagtggg agtcacctgc ttttgccaaa     240

gggaacctga ctttcacagc tcagtaccta agttatagga tattccaaga taaatgcatg     300
```

```
aatactacct tgacggaatg tgatttctca agtctttcca agtatggtga ccacaccttg    360

agagtcaggg ctgaatttgc agatgagcat tcagactggg taaacatcac cttctgtcct    420

gtggatgaca ccattattgg accccctgga atgcaagtag aagtacttgc tgattcttta    480

catatgcgtt tcttagcccc taaaattgag aatgaatacg aaacttggac tatgaagaat    540

gtgtataact catggactta taatgtgcaa tactggaaaa acggtactga tgaaaagttt    600

caaattactc cccagtatga ctttgaggtc ctcagaaacc tggagccatg gacaacttat    660

tgtgttcaag ttcgagggtt tcttcctgat cggaacaaag ctggggaatg gagtgagcct    720

gtctgtgagc aaacaaccca tgacgaaacg gtcccctcct ggatggtggc cgtcatcctc    780

atggcctcgg tcttcatggt ctgcctggca ctcctcggct gcttcgcctt gctgtggtgc    840

gtttacaaga agacaaagta cgccttctcc cctaggaatt ctcttccaca gcacctgaaa    900

gagtttttgg gccatcctca tcataacaca cttctgtttt tctcctttcc attgtcggat    960

gagaatgatg tttttgacaa gctaagtgtc attgcagaag actctgagag cggcaagcag   1020

aatcctggtg acagctgcag cctcgggacc ccgcctgggc aggggcccca aagctaggct   1080

ctgagaagga aacacactcg gctgggcaca gtgacgtact ccatctcaca tctgcctcag   1140

tgagggatca gggcagcaaa caagggccaa gaccatctga gccagcccca catctagaac   1200

tcccagaccc tggacttagc caccagagag ctacatttta aaggctgtct tggcaaaaat   1260

actccatttg ggaactcact gccttataaa ggctttcatg atgttttcag aagttggcca   1320

ctgagagtgt aattttcagc cttttatatc actaaaataa gatcatgttt taattgtgag   1380

aaacagggcc gagcacagtg gctcacgcct gtaataccag caccttagag gtcgaggcag   1440

gcggatcact tgaggtcagg agttcaagac cagcctggcc aatatggtga aacccagtct   1500

ctactaaaaa tacaaaaatt agctaggcat gatggcgcat gcctataatc ccagctactc   1560

gagtgcctga ggcaggagaa ttgcatgaac ccgggaggag gaggaggagg ttgcagtgag   1620

ccgagatagc ggcactgcac tccagcctgg gtgacaaagt gagactccat ctcaaaaaaa   1680

aaaaaaaaaa aaattgtgag aaacagaaat acttaaaatg aggaataaga atggagatgt   1740

tacatctggt agatgtaaca ttctaccaga ttatggatgg actgatctga aaatcgacct   1800

caactcaagg gtggtcagct caatgctaca cagagcacgg acttttggat tctttgcagt   1860

actttgaatt tatttttcta cctatatatg ttttatatgc tgctggtgct ccattaaagt   1920

tttactctgt gttgcactat a                                             1941


<210> SEQ ID NO 14
<211> LENGTH: 848
<212> TYPE: PRT
<213> ORGANISM: Homo sapiens

<400> SEQUENCE: 14

Met Asn Ser Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
            20                  25                  30

Ser Asn Pro Ser Lys Arg His Arg Asp Arg Leu Asn Thr Glu Leu Asp
        35                  40                  45

Arg Leu Ala Ser Leu Leu Pro Phe Pro Gln Asp Val Ile Asn Lys Leu
    50                  55                  60

Asp Lys Leu Ser Val Leu Arg Leu Ser Val Ser Tyr Leu Arg Ala Lys
65                  70                  75                  80
```

```
Ser Phe Phe Asp Val Ala Leu Lys Ser Ser Pro Thr Glu Arg Asn Gly
                85                  90                  95

Gly Gln Asp Asn Cys Arg Ala Ala Asn Phe Arg Glu Gly Leu Asn Leu
            100                 105                 110

Gln Glu Gly Glu Phe Leu Leu Gln Ala Leu Asn Gly Phe Val Leu Val
        115                 120                 125

Val Thr Thr Asp Ala Leu Val Phe Tyr Ala Ser Ser Thr Ile Gln Asp
    130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
            180                 185                 190

Ala Thr Gly Leu Pro Gln Thr Val Val Cys Tyr Asn Pro Asp Gln Ile
        195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Lys Gly Lys Asp Gly
                245                 250                 255

Ser Ile Leu Pro Pro Gln Leu Ala Leu Phe Ala Ile Ala Thr Pro Leu
            260                 265                 270

Gln Pro Pro Ser Ile Leu Glu Ile Arg Thr Lys Asn Phe Ile Phe Arg
        275                 280                 285

Thr Lys His Lys Leu Asp Phe Thr Pro Ile Gly Cys Asp Ala Lys Gly
    290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445

Asp Ser Leu Asn Pro Ser Ser Leu Leu Ala Ala Met Met Gln Gln Asp
    450                 455                 460

Glu Ser Ile Tyr Leu Tyr Pro Ala Ser Ser Thr Ser Ser Thr Ala Pro
465                 470                 475                 480

Phe Glu Asn Asn Phe Phe Asn Glu Ser Met Asn Glu Cys Arg Asn Trp
                485                 490                 495

Gln Asp Asn Thr Ala Pro Met Gly Asn Asp Thr Ile Leu Lys His Glu
```

```
            500                 505                 510

Gln Ile Asp Gln Pro Gln Asp Val Asn Ser Phe Ala Gly Gly His Pro
        515                 520                 525

Gly Leu Phe Gln Asp Ser Lys Asn Ser Asp Leu Tyr Ser Ile Met Lys
    530                 535                 540

Asn Leu Gly Ile Asp Phe Glu Asp Ile Arg His Met Gln Asn Glu Lys
545                 550                 555                 560

Phe Phe Arg Asn Asp Phe Ser Gly Glu Val Asp Phe Arg Asp Ile Asp
                565                 570                 575

Leu Thr Asp Glu Ile Leu Thr Tyr Val Gln Asp Ser Leu Ser Lys Ser
            580                 585                 590

Pro Phe Ile Pro Ser Asp Tyr Gln Gln Gln Gln Ser Leu Ala Leu Asn
        595                 600                 605

Ser Ser Cys Met Val Gln Glu His Leu His Leu Glu Gln Gln Gln Gln
    610                 615                 620

His His Gln Lys Gln Val Val Val Glu Pro Gln Gln Gln Leu Cys Gln
625                 630                 635                 640

Lys Met Lys His Met Gln Val Asn Gly Met Phe Glu Asn Trp Asn Ser
                645                 650                 655

Asn Gln Phe Val Pro Phe Asn Cys Pro Gln Gln Asp Pro Gln Gln Tyr
            660                 665                 670

Asn Val Phe Thr Asp Leu His Gly Ile Ser Gln Glu Phe Pro Tyr Lys
        675                 680                 685

Ser Glu Met Asp Ser Met Pro Tyr Thr Gln Asn Phe Ile Ser Cys Asn
    690                 695                 700

Gln Pro Val Leu Pro Gln His Ser Lys Cys Thr Glu Leu Asp Tyr Pro
705                 710                 715                 720

Met Gly Ser Phe Glu Pro Ser Pro Tyr Pro Thr Thr Ser Ser Leu Glu
                725                 730                 735

Asp Phe Val Thr Cys Leu Gln Leu Pro Glu Asn Gln Lys His Gly Leu
            740                 745                 750

Asn Pro Gln Ser Ala Ile Ile Thr Pro Gln Thr Cys Tyr Ala Gly Ala
        755                 760                 765

Val Ser Met Tyr Gln Cys Gln Pro Glu Pro Gln His Thr His Val Gly
    770                 775                 780

Gln Met Gln Tyr Asn Pro Val Leu Pro Gly Gln Gln Ala Phe Leu Asn
785                 790                 795                 800

Lys Phe Gln Asn Gly Val Leu Asn Glu Thr Tyr Pro Ala Glu Leu Asn
                805                 810                 815

Asn Ile Asn Asn Thr Gln Thr Thr Thr His Leu Gln Pro Leu His His
            820                 825                 830

Pro Ser Glu Ala Arg Pro Phe Pro Asp Leu Thr Ser Ser Gly Phe Leu
        835                 840                 845


<210> SEQ ID NO 15
<211> LENGTH: 6230
<212> TYPE: DNA
<213> ORGANISM: Homo sapiens

<400> SEQUENCE: 15

agtggctggg gagtcccgtc gacgctctgt tccgagagcg tgccccggac cgccagctca      60

gaacaggggc agccgtgtag ccgaacggaa gctgggagca gccgggactg gtggcccgcg     120

cccgagctcc gcaggcggga agcaccctgg atttaggaag tcccgggagc agcgcggcgg     180
```

-continued

```
cacctccctc acccaagggg ccgcggcgac ggtcacgggg cgcggcgcca ccgtgagcga    240
cccaggccag gattctaaat agacggccca ggctcctcct ccgcccgggc cgcctcacct    300
gcgggcattg ccgcgccgcc tccgccggtg tagacggcac ctgcgccgcc ttgctcgcgg    360
gtctccgccc ctcgcccacc ctcactgcgc caggcccagg cagctcacct gtactggcgc    420
gggctgcgga agcctgcgtg agccgaggcg ttgaggcgcg gcgcccacgc cactgtcccg    480
agaggacgca ggtggagcgg gcgcggcttc gcggaacccg gcgccggccg ccgcagtggt    540
cccagcctac accgggttcc ggggacccgg ccgccagtgc ccggggagta gccgccgccg    600
tcggctgggc accatgaaca gcagcagcgc caacatcacc tacgccagtc gcaagcggcg    660
gaagccggtg cagaaaacag taaagccaat cccagctgaa ggaatcaagt caaatccttc    720
caagcggcat agagaccgac ttaatacaga gttggaccgt ttggctagcc tgctgccttt    780
cccacaagat gttattaata agttggacaa actttcagtt cttaggctca gcgtcagtta    840
cctgagagcc aagagcttct ttgatgttgc attaaaatcc tcccctactg aaagaaacgg    900
aggccaggat aactgtagag cagcaaattt cagagaaggc ctgaacttac aagaaggaga    960
attcttatta caggctctga atggctttgt attagttgtc actacagatg ctttggtctt   1020
ttatgcttct tctactatac aagattatct agggtttcag cagtctgatg tcatacatca   1080
gagtgtatat gaacttatcc ataccgaaga ccgagctgaa tttcagcgtc agctacactg   1140
ggcattaaat ccttctcagt gtacagagtc tggacaagga attgaagaag ccactggtct   1200
cccccagaca gtagtctgtt ataacccaga ccagattcct ccagaaaact ctcctttaat   1260
ggagaggtgc ttcatatgtc gtctaaggtg tctgctggat aattcatctg gttttctggc   1320
aatgaatttc caagggaagt taaagtatct tcatggacag aaaaagaaag ggaaagatgg   1380
atcaatactt ccacctcagt tggctttgtt tgcgatagct actccacttc agccaccatc   1440
catacttgaa atccggacca aaaattttat ctttagaacc aaacacaaac tagacttcac   1500
acctattggt tgtgatgcca aaggaagaat tgttttagga tatactgaag cagagctgtg   1560
cacgagaggc tcaggttatc agtttattca tgcagctgat atgctttatt gtgccgagtc   1620
ccatatccga atgattaaga ctggagaaag tggcatgata gttttccggc ttcttacaaa   1680
aaacaaccga tggacttggg tccagtctaa tgcacgcctg ctttataaaa atggaagacc   1740
agattatatc attgtaactc agagaccact aacagatgag gaaggaacag agcatttacg   1800
aaaacgaaat acgaagttgc cttttatgtt taccactgga gaagctgtgt tgtatgaggc   1860
aaccaaccct tttcctgcca taatggatcc cttaccacta aggactaaaa atggcactag   1920
tggaaaagac tctgctacca catccactct aagcaaggac tctctcaatc ctagttccct   1980
cctggctgcc atgatgcaac aagatgagtc tatttatctc tatcctgctt caagtacttc   2040
aagtactgca ccttttgaaa acaacttttt caacgaatct atgaatgaat gcagaaattg   2100
gcaagataat actgcaccga tgggaaatga tactatcctg aaacatgagc aaattgacca   2160
gcctcaggat gtgaactcat ttgctggagg tcacccaggg ctctttcaag atagtaaaaa   2220
cagtgacttg tacagcataa tgaaaaacct aggcattgat tttgaagaca tcagacacat   2280
gcagaatgaa aaatttttca gaaatgattt ttctggtgag gttgacttca gagacattga   2340
cttaacggat gaaatcctga cgtatgtcca agattcttta agtaagtctc ccttcatacc   2400
ttcagattat caacagcaac agtccttggc tctgaactca agctgtatgg tacaggaaca   2460
cctacatcta gaacagcaac agcaacatca ccaaaagcaa gtagtagtgg agccacagca   2520
acagctgtgt cagaagatga agcacatgca agttaatggc atgtttgaaa attggaactc   2580
```

```
taaccaattc gtgcctttca attgtccaca gcaagaccca caacaatata atgtctttac   2640
agacttacat gggatcagtc aagagttccc ctacaaatct gaaatggatt ctatgcctta   2700
tacacagaac tttatttcct gtaatcagcc tgtattacca caacattcca aatgtacaga   2760
gctggactac cctatgggga gttttgaacc atccccatac cccactactt ctagtttaga   2820
agattttgtc acttgtttac aacttcctga aaaccaaaag catggattaa atccacagtc   2880
agccataata actcctcaga catgttatgc tggggccgtg tcgatgtatc agtgccagcc   2940
agaacctcag cacacccacg tgggtcagat gcagtacaat ccagtactgc caggccaaca   3000
ggcattttta aacaagtttc agaatggagt tttaaatgaa acatatccag ctgaattaaa   3060
taacataaat aacactcaga ctaccacaca tcttcagcca cttcatcatc cgtcagaagc   3120
cagacctttt cctgatttga catccagtgg attcctgtaa ttccaagccc aattttgacc   3180
ctggtttttg gattaaatta gtttgtgaag gattatggaa aaataaaact gtcactgttg   3240
gacgtcagca agttcacatg gaggcattga tgcatgctat tcacaattat tccaaaccaa   3300
attttaattt ttgcttttag aaaagggagt ttaaaaatgg tatcaaaatt acatatacta   3360
cagtcaagat agaaagggtg ctgccacgga gtggtgaggt accgtctaca tttcacatta   3420
ttctgggcac cacaaaatat acaaaacttt atcagggaaa ctaagattct tttaaattag   3480
aaaatattct ctatttgaat tatttctgtc acagtaaaaa taaaatactt tgagttttga   3540
gctactggat tcttattagt tccccaaata caaagttaga gaactaaact agtttttcct   3600
atcatgttaa cctctgcttt tatctcagat gttaaaataa atggtttggt gctttttata   3660
aaaagataat ctcagtgctt tcctccttca ctgtttcatc taagtgcctc acattttttt   3720
ctacctataa cactctagga tgtatatttt atataaagta ttcttttttct tttttaaatt   3780
aatatctttc tgcacacaaa tattatttgt gtttcctaaa tccaaccatt ttcattaatt   3840
caggcatatt ttaactccac tgcttaccta ctttcttcag gtaaagggca aataatgatc   3900
gaaaaaataa ttatttatta cataatttag ttgtttctag actataaatg ttgctatgtg   3960
ccttatgttg aaaaaattta aaagtaaaat gtctttccaa attatttctt aattattata   4020
aaaatattaa gacaatagca cttaaattcc tcaacagtgt tttcagaaga aataaatata   4080
ccactcttta cctttattga tatctccatg atgatagttg aatgttgcaa tgtgaaaaat   4140
ctgctgttaa ctgcaacctt gtttattaaa ttgcaagaag ctttatttct agctttttaa   4200
ttaagcaaag cacccatttc aatgtgtata aattgtcttt aaaaactgtt ttagacctat   4260
aatccttgat aatatattgt gttgacttta taaatttcgc ttcttagaac agtggaaact   4320
atgtgttttt ctcatatttg aggagtgtta agattgcaga tagcaaggtt tggtgcaaag   4380
tattgtaatg agtgaattga atggtgcatt gtatagatat aatgaacaaa attatttgta   4440
agatatttgc agtttttcat tttaaaaagt ccataccttta tatatgcact taatttgttg   4500
gggctttaca tactttatca atgtgtcttt ctaagaaatc aagtaatgaa tccaactgct   4560
taaagttggt attaataaaa agacaaccac atagttcgtt taccttcaaa ctttaggttt   4620
ttttaatgat atactgatct tcattaccaa taggcaaatt aatcacccta ccaactttac   4680
tgtcctaaca tggtttaaaa gaaaaaatga caccatcttt tattcttttt ttttttttt   4740
tttgagagag agtcttactc tgccgcccaa actggagtgc agtggcacaa tcttggctca   4800
ctgcaacctc tacctcctgg gttcaagtga ttctcttgcc tcagcctccc gagttgctgg   4860
gattacaggc atgtgccacc atgcccagct aatttttgta tttttagtag aaacgggttt   4920
```

```
caccatgttg gccagactgg tctcaaactc ctgacctcag gtgagcctcc caccttggcc   4980

tcccaaagtg ctgggattac aggcgtgagc cactgcattc agctcttctt ttctttagat   5040

atgagagctg aagagcttag acacattttg catgtattat ttgaaaatct gatggaatcc   5100

caaactgaga tgtattaaaa tacaattttt ggccgggtgc agtggctcac gcctgtaatc   5160

ccagcacttg gggagggcga ggagggtgga tcacgaggtc aagagatgga gaccatcctg   5220

accaacatgg tgaaaccctg tctctactaa aaatacagaa attagctggg catggtggcg   5280

tgagcctgta gtcctagcta ctcaggaggc tgaggcagga gaatagcctg aacctgggaa   5340

tcggaggttg cagagccaag atcgccccac tgcactccag cctggcaata gaccgagact   5400

ccgtctccaa aaaaaaaaaa aatacaattt ttatttcttt tacttttttt agtaagttaa   5460

tgtatataaa aatggcttcg gacaaaatat ctctgagttc tgtgtatttt cagtcaaaac   5520

tttaaacctg tagaatcaat ttaagtgttg gaaaaaattt gtctgaaaca tttcataatt   5580

tgtttccagc atgaggtatc taaggattta gaccagaggt ctagattaat actctatttt   5640

tacatttaaa ccttttatta taagtcttac ataaaccatt tttgttactc tcttccacat   5700

gttactggat aaattgttta gtggaaaata ggctttttaa tcatgaatat gatgacaatc   5760

agttatacag ttataaaatt aaaagtttga aaagcaatat tgtatatttt tatctatata   5820

aaataactaa aatgtatcta agaataataa aatcacgtta aaccaaatac acgtttgtct   5880

gtattgttaa gtgccaaaca aaggatactt agtgcactgc tacattgtgg gatttatttc   5940

tagatgatgt gcacatctaa ggatatggat gtgtctaatt tagtcttttc ctgtaccagg   6000

tttttcttac aatacctgaa gacttaccag tattctagtg tattatgaag ctttcaacat   6060

tactatgcac aaactagtgt ttttcgatgt tactaaattt taggtaaatg ctttcatggc   6120

tttttcttc aaaatgttac tgcttacata tatcatgcat agatttttgc ttaaagtatg   6180

atttataata tcctcattat caaagttgta tacaataata tataataaaa              6230
```

<210> SEQ ID NO 16
<211> LENGTH: 117
<212> TYPE: PRT
<213> ORGANISM: Homo sapiens

<400> SEQUENCE: 16

```
Met Ser Leu Val Ser Cys Leu Ser Glu Asp Leu Lys Val Leu Phe Phe
1               5                   10                  15

Arg Trp Gly Lys Ser Val Gly Ile Met Leu Thr Glu Leu Glu Lys Ala
            20                  25                  30

Leu Asn Ser Ile Ile Asp Val Tyr His Lys Tyr Ser Leu Ile Lys Gly
        35                  40                  45

Asn Phe His Ala Val Tyr Arg Asp Asp Leu Lys Lys Leu Leu Glu Thr
    50                  55                  60

Glu Cys Pro Gln Tyr Ile Arg Lys Lys Gly Ala Asp Val Trp Phe Lys
65                  70                  75                  80

Glu Leu Asp Ile Asn Thr Asp Gly Ala Val Asn Phe Gln Glu Phe Leu
                85                  90                  95

Ile Leu Val Ile Lys Met Gly Val Ala Ala His Lys Lys Ser His Glu
            100                 105                 110

Glu Ser His Lys Glu
        115
```

<210> SEQ ID NO 17
<211> LENGTH: 549

<212> TYPE: DNA
<213> ORGANISM: Homo sapiens

<400> SEQUENCE: 17
gagaaaccag agactgtagc aactctggca gggagaagct gtctctgatg gcctgaagct 60
gtgggcagct ggccaagcct aaccgctata aaaaggagct gcctctcagc cctgcatgtc 120
tcttgtcagc tgtctttcag aagacctgaa ggttctgttt ttcaggtggg gcaagtccgt 180
gggcatcatg ttgaccgagc tggagaaagc cttgaactct atcatcgacg tctaccacaa 240
gtactccctg ataaagggga atttccatgc cgtctacagg gatgacctga agaaattgct 300
agagaccgag tgtcctcagt atatcaggaa aaagggtgca gacgtctggt tcaaagagtt 360
ggatatcaac actgatggtg cagttaactt ccaggagttc ctcattctgg tgataaagat 420
gggcgtggca gcccacaaaa aaagccatga agaaagccac aaagagtagc tgagttactg 480
ggcccagagg ctgggcccct ggacatgtac ctgcagaata ataaagtcat caatacctca 540
aaaaaaaaa 549

<210> SEQ ID NO 18
<211> LENGTH: 114
<212> TYPE: PRT
<213> ORGANISM: Homo sapiens

<400> SEQUENCE: 18

Met Thr Cys Lys Met Ser Gln Leu Glu Arg Asn Ile Glu Thr Ile Ile
1 5 10 15

Asn Thr Phe His Gln Tyr Ser Val Lys Leu Gly His Pro Asp Thr Leu
20 25 30

Asn Gln Gly Glu Phe Lys Glu Leu Val Arg Lys Asp Leu Gln Asn Phe
35 40 45

Leu Lys Lys Glu Asn Lys Asn Glu Lys Val Ile Glu His Ile Met Glu
50 55 60

Asp Leu Asp Thr Asn Ala Asp Lys Gln Leu Ser Phe Glu Glu Phe Ile
65 70 75 80

Met Leu Met Ala Arg Leu Thr Trp Ala Ser His Glu Lys Met His Glu
85 90 95

Gly Asp Glu Gly Pro Gly His His His Lys Pro Gly Leu Gly Glu Gly
100 105 110

Thr Pro

<210> SEQ ID NO 19
<211> LENGTH: 573
<212> TYPE: DNA
<213> ORGANISM: Homo sapiens

<400> SEQUENCE: 19
aaacactctg tgtggctcct cggctttgac agagtgcaag acgatgactt gcaaaatgtc 60
gcagctggaa cgcaacatag agaccatcat caacaccttc caccaatact ctgtgaagct 120
ggggcaccca gacaccctga accaggggga attcaaagag ctggtgcgaa aagatctgca 180
aaattttctc aagaaggaga ataagaatga aaaggtcata gaacacatca tggaggacct 240
ggacacaaat gcagacaagc agctgagctt cgaggagttc atcatgctga tggcgaggct 300
aacctgggcc tcccacgaga agatgcacga gggtgacgag ggccctggcc accaccataa 360
gccaggcctc ggggagggca ccccctaaga ccacagtggc caagatcaca gtggccacgg 420
ccacggccac agtcatggtg gccacggcca cagccactaa tcaggaggcc aggccaccct 480
gcctctaccc aaccagggcc ccggggcctg ttatgtcaaa ctgtcttggc tgtggggcta 540
ggggctgggg ccaaataaag tctcttcctc caa 573

<210> SEQ ID NO 20
<211> LENGTH: 97
<212> TYPE: PRT
<213> ORGANISM: Homo sapiens

<400> SEQUENCE: 20

Met Pro Ser Gln Met Glu His Ala Met Glu Thr Met Met Phe Thr Phe
1 5 10 15

His Lys Phe Ala Gly Asp Lys Gly Tyr Leu Thr Lys Glu Asp Leu Arg
20 25 30

Val Leu Met Glu Lys Glu Phe Pro Gly Phe Leu Glu Asn Gln Lys Asp
35 40 45

Pro Leu Ala Val Asp Lys Ile Met Lys Asp Leu Asp Gln Cys Arg Asp
50 55 60

Gly Lys Val Gly Phe Gln Ser Phe Phe Ser Leu Ile Ala Gly Leu Thr
65 70 75 80

Ile Ala Cys Asn Asp Tyr Phe Val Val His Met Lys Gln Lys Gly Lys
85 90 95

Lys

<210> SEQ ID NO 21
<211> LENGTH: 671
<212> TYPE: DNA
<213> ORGANISM: Homo sapiens

<400> SEQUENCE: 21
acccacccgc cgcacgtact aaggaaggcg cacagcccgc cgcgctcgcc tctccgcccc 60
gcgtccagct cgcccagctc gcccagcgtc cgccgcgcct cggccaaggc ttcaacggac 120
cacaccaaaa tgccatctca aatggaacac gccatggaaa ccatgatgtt tacatttcac 180
aaattcgctg ggataaagg ctacttaaca aaggaggacc tgagagtact catggaaaag 240
gagttccctg gatttttgga aaatcaaaaa gaccctctgg ctgtggacaa aataatgaag 300
gacctggacc agtgtagaga tggcaaagtg ggcttccaga gcttcttttc cctaattgcg 360
ggcctcacca ttgcatgcaa tgactatttt gtagtacaca tgaagcagaa gggaaagaag 420
taggcagaaa tgagcagttc gctcctccct gataagagtt gtcccaaagg gtcgcttaag 480
gaatctgccc cacagcttcc cccatagaag gatttcatga gcagatcagg acacttagca 540
aatgtaaaaa taaaatctaa ctctcatttg acaagcagag aaagaaaagt taaataccag 600
ataagctttt gatttttgta ttgtttgcat ccccttgccc tcaataaata aagttctttt 660
ttagttccaa a 671

<210> SEQ ID NO 22
<211> LENGTH: 105
<212> TYPE: PRT
<213> ORGANISM: Homo sapiens

<400> SEQUENCE: 22

Met Ala Lys Ile Ser Ser Pro Thr Glu Thr Glu Arg Cys Ile Glu Ser
1 5 10 15

Leu Ile Ala Val Phe Gln Lys Tyr Ala Gly Lys Asp Gly Tyr Asn Tyr
20 25 30

Thr Leu Ser Lys Thr Glu Phe Leu Ser Phe Met Asn Thr Glu Leu Ala
35 40 45

Ala Phe Thr Lys Asn Gln Lys Asp Pro Gly Val Leu Asp Arg Met Met
50 55 60

Lys Lys Leu Asp Thr Asn Ser Asp Gly Gln Leu Asp Phe Ser Glu Phe
65 70 75 80

Leu Asn Leu Ile Gly Gly Leu Ala Met Ala Cys His Asp Ser Phe Leu
85 90 95

Lys Ala Val Pro Ser Gln Lys Arg Thr
100 105

<210> SEQ ID NO 23
<211> LENGTH: 563
<212> TYPE: DNA
<213> ORGANISM: Homo sapiens

<400> SEQUENCE: 23
gaggagaggc tccagacccg cacgccgcgc gcacagagct ctcagcgccg ctcccagcca 60
cagcctcccg cgcctcgctc agctccaaca tggcaaaaat ctccagccct acagagactg 120
agcggtgcat cgagtccctg attgctgtct tccagaagta tgctggaaag gatggttata 180
actacactct ctccaagaca gagttcctaa gcttcatgaa tacagaacta gctgccttca 240
caaagaacca gaaggaccct ggtgtccttg accgcatgat gaagaaactg gacaccaaca 300
gtgatggtca gctagatttc tcagaatttc ttaatctgat tggtggccta gctatggctt 360
gccatgactc cttcctcaag gctgtccctt cccagaagcg gacctgagga ccccttggcc 420
ctggccttca aacccacccc ctttccttcc agcctttctg tcatcatctc cacagcccac 480
ccatcccctg agcacactaa ccacctcatg caggccccac ctgccaatag taataaagca 540
atgtcacttt tttaaaacat gaa 563

<210> SEQ ID NO 24
<211> LENGTH: 770
<212> TYPE: PRT
<213> ORGANISM: Homo sapiens

<400> SEQUENCE: 24

Met Ala Gln Trp Asn Gln Leu Gln Gln Leu Asp Thr Arg Tyr Leu Glu
1 5 10 15

Gln Leu His Gln Leu Tyr Ser Asp Ser Phe Pro Met Glu Leu Arg Gln
20 25 30

Phe Leu Ala Pro Trp Ile Glu Ser Gln Asp Trp Ala Tyr Ala Ala Ser
35 40 45

Lys Glu Ser His Ala Thr Leu Val Phe His Asn Leu Leu Gly Glu Ile
50 55 60

Asp Gln Gln Tyr Ser Arg Phe Leu Gln Glu Ser Asn Val Leu Tyr Gln
65 70 75 80

His Asn Leu Arg Arg Ile Lys Gln Phe Leu Gln Ser Arg Tyr Leu Glu
85 90 95

Lys Pro Met Glu Ile Ala Arg Ile Val Ala Arg Cys Leu Trp Glu Glu
100 105 110

Ser Arg Leu Leu Gln Thr Ala Ala Thr Ala Ala Gln Gln Gly Gly Gln
115 120 125

Ala Asn His Pro Thr Ala Ala Val Val Thr Glu Lys Gln Gln Met Leu
130 135 140

Glu Gln His Leu Gln Asp Val Arg Lys Arg Val Gln Asp Leu Glu Gln

-continued

```
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
    210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
            260                 265                 270

Ser Gln Leu Gln Thr Arg Gln Gln Ile Lys Lys Leu Glu Glu Leu Gln
        275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
            340                 345                 350

Val Lys Phe Pro Glu Leu Asn Tyr Gln Leu Lys Ile Lys Val Cys Ile
        355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
            420                 425                 430

Thr Glu Glu Leu His Leu Ile Thr Phe Glu Thr Glu Val Tyr His Gln
        435                 440                 445

Gly Leu Lys Ile Asp Leu Glu Thr His Ser Leu Pro Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
        515                 520                 525

Ala Glu Lys Leu Leu Gly Pro Gly Val Asn Tyr Ser Gly Cys Gln Ile
    530                 535                 540

Thr Trp Ala Lys Phe Cys Lys Glu Asn Met Ala Gly Lys Gly Phe Ser
545                 550                 555                 560

Phe Trp Val Trp Leu Asp Asn Ile Ile Asp Leu Val Lys Lys Tyr Ile
                565                 570                 575
```

```
Leu Ala Leu Trp Asn Glu Gly Tyr Ile Met Gly Phe Ile Ser Lys Glu
            580                 585                 590

Arg Glu Arg Ala Ile Leu Ser Thr Lys Pro Pro Gly Thr Phe Leu Leu
        595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
            660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
    690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
            740                 745                 750

Glu Ser Leu Thr Phe Asp Met Glu Leu Thr Ser Glu Cys Ala Thr Ser
        755                 760                 765

Pro Met
    770
```

<210> SEQ ID NO 25
<211> LENGTH: 4921
<212> TYPE: DNA
<213> ORGANISM: Homo sapiens

<400> SEQUENCE: 25

```
gtcgcagccg agggaacaag ccccaaccgg atcctggaca ggcaccccgg cttggcgctg      60

tctctccccc tcggctcgga gaggcccttc ggcctgaggg agcctcgccg cccgtccccg     120

gcacacgcgc agccccggcc tctcggcctc tgccggagaa acagttggga cccctgattt     180

tagcaggatg gcccaatgga atcagctaca gcagcttgac acacggtacc tggagcagct     240

ccatcagctc tacagtgaca gcttcccaat ggagctgcgg cagtttctgg ccccttggat     300

tgagagtcaa gattgggcat atgcggccag caaagaatca catgccactt tggtgtttca     360

taatctcctg ggagagattg accagcagta tagccgcttc ctgcaagagt cgaatgttct     420

ctatcagcac aatctacgaa gaatcaagca gtttcttcag agcaggtatc ttgagaagcc     480

aatggagatt gcccggattg tggcccggtg cctgtgggaa gaatcacgcc ttctacagac     540

tgcagccact gcggcccagc aagggggcca ggccaaccac cccacagcag ccgtggtgac     600

ggagaagcag cagatgctgg agcagcacct tcaggatgtc cggaagagag tgcaggatct     660

agaacagaaa atgaaagtgg tagagaatct ccaggatgac tttgatttca actataaaac     720

cctcaagagt caaggagaca tgcaagatct gaatggaaac aaccagtcag tgaccaggca     780

gaagatgcag cagctggaac agatgctcac tgcgctggac cagatgcgga gaagcatcgt     840

gagtgagctg gcggggcttt tgtcagcgat ggagtacgtg cagaaaactc tcacggacga     900

ggagctggct gactggaaga ggcggcaaca gattgcctgc attggaggcc cgcccaacat     960
```

```
ctgcctagat cggctagaaa actggataac gtcattagca gaatctcaac ttcagacccg   1020
tcaacaaatt aagaaactgg aggagttgca gcaaaaagtt tcctacaaag gggaccccat   1080
tgtacagcac cggccgatgc tggaggagag aatcgtggag ctgtttagaa acttaatgaa   1140
aagtgccttt gtggtggagc ggcagccctg catgcccatg catcctgacc ggcccctcgt   1200
catcaagacc ggcgtccagt tcactactaa agtcaggttg ctggtcaaat tccctgagtt   1260
gaattatcag cttaaaatta aagtgtgcat tgacaaagac tctggggacg ttgcagctct   1320
cagaggatcc cggaaattta acattctggg cacaaacaca aaagtgatga acatggaaga   1380
atccaacaac ggcagcctct ctgcagaatt caaacacttg accctgaggg agcagagatg   1440
tgggaatggg ggccgagcca attgtgatgc ttccctgatt gtgactgagg agctgcacct   1500
gatcaccttt gagaccgagg tgtatcacca aggcctcaag attgacctag agacccactc   1560
cttgccagtt gtggtgatct ccaacatctg tcagatgcca aatgcctggg cgtccatcct   1620
gtggtacaac atgctgacca acaatcccaa gaatgtaaac tttttacca agcccccaat   1680
tggaacctgg gatcaagtgg ccgaggtcct gagctggcag ttctcctcca ccaccaagcg   1740
aggactgagc atcgagcagc tgactacact ggcagagaaa ctcttgggac ctggtgtgaa   1800
ttattcaggg tgtcagatca catgggctaa attttgcaaa gaaaacatgg ctggcaaggg   1860
cttctccttc tgggtctggc tggacaatat cattgacctt gtgaaaaagt acatcctggc   1920
cctttggaac gaagggtaca tcatgggctt tatcagtaag gagcgggagc gggccatctt   1980
gagcactaag cctccaggca ccttcctgct aagattcagt gaaagcagca aagaaggagg   2040
cgtcactttc acttgggtgg agaaggacat cagcggtaag acccagatcc agtccgtgga   2100
accatacaca aagcagcagc tgaacaacat gtcatttgct gaaatcatca tgggctataa   2160
gatcatggat gctaccaata tcctggtgtc tccactggtc tatctctatc ctgacattcc   2220
caaggaggag gcattcggaa agtattgtcg gccagagagc caggagcatc ctgaagctga   2280
cccaggtagc gctgccccat acctgaagac caagtttatc tgtgtgacac caacgacctg   2340
cagcaatacc attgacctgc cgatgtcccc ccgcacttta gattcattga tgcagtttgg   2400
aaataatggt gaaggtgctg aaccctcagc aggagggcag tttgagtccc tcacctttga   2460
catggagttg acctcggagt gcgctacctc ccccatgtga ggagctgaga acggaagctg   2520
cagaaagata cgactgaggc gcctacctgc attctgccac ccctcacaca gccaaacccc   2580
agatcatctg aaactactaa ctttgtggtt ccagattttt tttaatctcc tacttctgct   2640
atctttgagc aatctgggca cttttaaaaa tagagaaatg agtgaatgtg ggtgatctgc   2700
ttttatctaa atgcaaataa ggatgtgttc tctgagaccc atgatcaggg gatgtggcgg   2760
ggggtggcta gagggagaaa aaggaaatgt cttgtgttgt tttgttcccc tgccctcctt   2820
tctcagcagc tttttgttat tgttgttgtt gttcttagac aagtgcctcc tggtgcctgc   2880
ggcatccttc tgcctgtttc tgtaagcaaa tgccacaggc cacctatagc tacatactcc   2940
tggcattgca ctttttaacc ttgctgacat ccaaatagaa gataggacta tctaagccct   3000
aggtttcttt ttaaattaag aaataataac aattaaaggg caaaaaacac tgtatcagca   3060
tagcctttct gtatttaaga aacttaagca gccgggcatg gtggctcacg cctgtaatcc   3120
cagcactttg ggaggccgag gcggatcata aggtcaggag atcaagacca tcctggctaa   3180
cacggtgaaa ccccgtctct actaaaagta caaaaaatta gctgggtgtg gtggtgggcg   3240
cctgtagtcc cagctactcg ggaggctgag gcaggagaat cgcttgaacc tgagaggcgg   3300
```

```
aggttgcagt gagccaaaat tgcaccactg cacactgcac tccatcctgg gcgacagtct   3360

gagactctgt ctcaaaaaaa aaaaaaaaaa aaagaaactt cagttaacag cctccttggt   3420

gctttaagca ttcagcttcc ttcaggctgg taatttatat aatccctgaa acgggcttca   3480

ggtcaaaccc ttaagacatc tgaagctgca acctggcctt tggtgttgaa ataggaaggt   3540

ttaaggagaa tctaagcatt ttagactttt ttttataaat agacttattt tcctttgtaa   3600

tgtattggcc ttttagtgag taaggctggg cagagggtgc ttacaacctt gactcccttt   3660

ctccctggac ttgatctgct gtttcagagg ctaggttgtt tctgtgggtg ccttatcagg   3720

gctgggatac ttctgattct ggcttccttc ctgccccacc ctcccgaccc cagtccccct   3780

gatcctgcta gaggcatgtc tccttgcgtg tctaaaggtc cctcatcctg tttgttttag   3840

gaatcctggt ctcaggacct catggaagaa gagggggaga gagttacagg ttggacatga   3900

tgcacactat ggggccccag cgacgtgtct ggttgagctc agggaatatg gttcttagcc   3960

agtttcttgg tgatatccag tggcacttgt aatggcgtct tcattcagtt catgcagggc   4020

aaaggcttac tgataaactt gagtctgccc tcgtatgagg gtgtatacct ggcctccctc   4080

tgaggctggt gactcctccc tgctggggcc ccacaggtga ggcagaacag ctagagggcc   4140

tccccgcctg cccgccttgg ctggctagct cgcctctcct gtgcgtatgg gaacacctag   4200

cacgtgctgg atgggctgcc tctgactcag aggcatggcc ggatttggca actcaaaacc   4260

accttgcctc agctgatcag agtttctgtg gaattctgtt tgttaaatca aattagctgg   4320

tctctgaatt aagggggaga cgaccttctc taagatgaac agggttcgcc ccagtcctcc   4380

tgcctggaga cagttgatgt gtcatgcaga gctcttactt ctccagcaac actcttcagt   4440

acataataag cttaactgat aaacagaata tttagaaagg tgagacttgg gcttaccatt   4500

gggtttaaat catagggacc tagggcgagg gttcagggct tctctggagc agatattgtc   4560

aagttcatgg ccttaggtag catgtatctg gtcttaactc tgattgtagc aaaagttctg   4620

agaggagctg agccctgttg tggcccatta aagaacaggg tcctcaggcc ctgcccgctt   4680

cctgtccact gccccctccc catccccagc ccagccgagg gaatcccgtg ggttgcttac   4740

ctacctataa ggtggtttat aagctgctgt cctggccact gcattcaaat tccaatgtgt   4800

acttcatagt gtaaaaattt atattattgt gaggtttttt gtcttttttt tttttttttt   4860

tttttggtat attgctgtat ctactttaac ttccagaaat aaacgttata taggaaccgt   4920

c                                                                    4921
```

<210> SEQ ID NO 26
<211> LENGTH: 170
<212> TYPE: PRT
<213> ORGANISM: Homo sapiens

<400> SEQUENCE: 26

```
Met Lys Thr Gln Arg Asp Gly His Ser Leu Gly Arg Trp Ser Leu Val
1               5                   10                  15

Leu Leu Leu Leu Gly Leu Val Met Pro Leu Ala Ile Ile Ala Gln Val
            20                  25                  30

Leu Ser Tyr Lys Glu Ala Val Leu Arg Ala Ile Asp Gly Ile Asn Gln
        35                  40                  45

Arg Ser Ser Asp Ala Asn Leu Tyr Arg Leu Leu Asp Leu Asp Pro Arg
    50                  55                  60

Pro Thr Met Asp Gly Asp Pro Asp Thr Pro Lys Pro Val Ser Phe Thr
65                  70                  75                  80
```

```
Val Lys Glu Thr Val Cys Pro Arg Thr Thr Gln Gln Ser Pro Glu Asp
                85                  90                  95

Cys Asp Phe Lys Lys Asp Gly Leu Val Lys Arg Cys Met Gly Thr Val
            100                 105                 110

Thr Leu Asn Gln Ala Arg Gly Ser Phe Asp Ile Ser Cys Asp Lys Asp
        115                 120                 125

Asn Lys Arg Phe Ala Leu Leu Gly Asp Phe Phe Arg Lys Ser Lys Glu
    130                 135                 140

Lys Ile Gly Lys Glu Phe Lys Arg Ile Val Gln Arg Ile Lys Asp Phe
145                 150                 155                 160

Leu Arg Asn Leu Val Pro Arg Thr Glu Ser
                165                 170


<210> SEQ ID NO 27
<211> LENGTH: 591
<212> TYPE: DNA
<213> ORGANISM: Homo sapiens

<400> SEQUENCE: 27

aggcagacat ggggaccatg aagacccaaa gggatggcca ctccctgggg cggtggtcac      60

tggtgctcct gctgctgggc ctggtgatgc ctctggccat cattgcccag gtcctcagct     120

acaaggaagc tgtgcttcgt gctatagatg gcatcaacca gcggtcctcg gatgctaacc     180

tctaccgcct cctggacctg gaccccaggc ccacgatgga tggggaccca gacacgccaa     240

agcctgtgag cttcacagtg aaggagacag tgtgccccag gacgacacag cagtcaccag     300

aggattgtga cttcaagaag gacgggctgg tgaagcggtg tatggggaca gtgaccctca     360

accaggccag gggctccttt gacatcagtt gtgataagga taacaagaga tttgccctgc     420

tgggtgattt cttccggaaa tctaaagaga agattggcaa agagtttaaa agaattgtcc     480

agagaatcaa ggatttttg cggaatcttg tacccaggac agagtcctag tgtgtgccct      540

accctggctc aggcttctgg gctctgagaa ataaactatg agagcaattt c              591


<210> SEQ ID NO 28
<211> LENGTH: 167
<212> TYPE: PRT
<213> ORGANISM: Mus musculus

<400> SEQUENCE: 28

Met Ala Gly Leu Trp Lys Thr Phe Val Leu Val Val Ala Leu Ala Val
1               5                   10                  15

Val Ser Cys Glu Ala Leu Arg Gln Leu Arg Tyr Glu Glu Ile Val Asp
            20                  25                  30

Arg Ala Ile Glu Ala Tyr Asn Gln Gly Arg Gln Gly Arg Pro Leu Phe
        35                  40                  45

Arg Leu Leu Ser Ala Thr Pro Pro Ser Ser Gln Asn Pro Ala Thr Asn
    50                  55                  60

Ile Pro Leu Gln Phe Arg Ile Lys Glu Thr Glu Cys Thr Ser Thr Gln
65                  70                  75                  80

Glu Arg Gln Pro Lys Asp Cys Asp Phe Leu Glu Asp Gly Glu Glu Arg
                85                  90                  95

Asn Cys Thr Gly Lys Phe Phe Arg Arg Arg Gln Ser Thr Ser Leu Thr
            100                 105                 110

Leu Thr Cys Asp Arg Asp Cys Ser Arg Glu Asp Thr Gln Glu Thr Ser
        115                 120                 125

Phe Asn Asp Lys Gln Asp Val Ser Glu Lys Glu Lys Phe Glu Asp Val
```

```
    130                 135                 140

Pro Pro His Ile Arg Asn Ile Tyr Glu Asp Ala Lys Tyr Asp Ile Ile
145                 150                 155                 160

Gly Asn Ile Leu Lys Asn Phe
                165


<210> SEQ ID NO 29
<211> LENGTH: 1176
<212> TYPE: DNA
<213> ORGANISM: Mus musculus

<400> SEQUENCE: 29

agtctcaata tcatctacat aaaaggggcc aagagtggta gtgtgtcaga gacaatggca      60

gggctgtgga agacctttgt attggtggtg gccttggctg tggtctcctg tgaggccctt     120

cgacaactaa gatatgagga gattgttgat agagccatag aggcatacaa ccaagggcgg     180

caaggaagac ccctcttccg cctgctaagt gccactccgc cttctagtca gaatcctgct     240

accaatatcc cactccagtt caggattaaa gagacagagt gtacttccac ccaggagaga     300

cagcctaaag actgcgactt cctggaggat ggggaggaga gaaattgcac agggaaattc     360

ttcagaaggc ggcagtcaac ctccctgacc ttgacctgcg acagggattg cagtcgagag     420

gatacccaag aaaccagttt taatgataag caagacgtct ctgaaaagga aaagttcgaa     480

gatgtgcccc ctcacatcag gaacatttat gaagatgcca agtatgatat catcggcaac     540

atcctgaaaa atttctaggg ctggaaagag gagggaggtg ctccctgcat actatgacct     600

cctctttacc tccactaccc atctccccct gctgcattca ggatctgccc ctccttcctg     660

cccttcccag gaacaccccc tctagagtag ctctagctcc taaaacatcc atacctttgt     720

ccatttgctt ccttctgctg ggccttcctg ccttaccctc tatctgaaac ccttattgat     780

tcttcaaggc ccaagttcaa aagtcccctc cagcgggaag cctcctcatt ctcccagagc     840

caaagtcctg cccacatcag ttcactcata atcttcaaac cacattggta ttacctgctg     900

tgtccccagc cagacaaccc tgtatctatt cacagctggg cctcccgggc cagttgcagg     960

tagaatgaat atttcaatga tgtgtccctg gaatcctggg aggacagaac cctgtagact    1020

cctgctctct gcctagtcac tgtgacacca aatgcccctt tacataccca gatcccttaa    1080

tggggatgtg gcaggtgggt gtggtcagat caccttgtga ggcctataag agaggttcaa    1140

taaaaatgct tctgagatta aaaaaaaaaa aaaaaa                              1176


<210> SEQ ID NO 30
<211> LENGTH: 604
<212> TYPE: PRT
<213> ORGANISM: Homo sapiens

<400> SEQUENCE: 30

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80
```

```
Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
    130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
    210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
    290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
    370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
            420                 425                 430

Val Ser Gln Ala Ser Ile Asp Gln Ser Arg Gln Met Lys Tyr Gln Ser
        435                 440                 445

Phe Asn Glu Tyr Arg Lys Arg Phe Met Leu Lys Pro Tyr Glu Ser Phe
    450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
```

```
            500                 505                 510

Ala Pro Phe Ser Leu Lys Gly Leu Met Gly Asn Val Ile Cys Ser Pro
        515                 520                 525

Ala Tyr Trp Lys Pro Ser Thr Phe Gly Gly Glu Val Gly Phe Gln Ile
    530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600


<210> SEQ ID NO 31
<211> LENGTH: 4510
<212> TYPE: DNA
<213> ORGANISM: Homo sapiens

<400> SEQUENCE: 31

aattgtcata cgacttgcag tgagcgtcag gagcacgtcc aggaactcct cagcagcgcc      60

tccttcagct ccacagccag acgccctcag acagcaaagc ctacccccgc gccgcgccct     120

gcccgccgct gcgatgctcg cccgcgccct gctgctgtgc gcggtcctgg cgctcagcca     180

tacagcaaat ccttgctgtt cccacccatg tcaaaaccga ggtgtatgta tgagtgtggg     240

atttgaccag tataagtgcg attgtacccg gacaggattc tatggagaaa actgctcaac     300

accggaattt ttgacaagaa taaaattatt tctgaaaccc actccaaaca cagtgcacta     360

catacttacc cacttcaagg gattttggaa cgttgtgaat aacattccct tccttcgaaa     420

tgcaattatg agttatgtgt tgacatccag atcacatttg attgacagtc caccaactta     480

caatgctgac tatggctaca aaagctggga agccttctct aacctctcct attatactag     540

agcccttcct cctgtgcctg atgattgccc gactcccttg ggtgtcaaag gtaaaaagca     600

gcttcctgat tcaaatgaga ttgtggaaaa attgcttcta agaagaaagt tcatccctga     660

tccccagggc tcaaacatga tgtttgcatt ctttgcccag cacttcacgc atcagttttt     720

caagacagat cataagcgag ggccagcttt caccaacggg ctgggccatg ggtggactt      780

aaatcatatt tacggtgaaa ctctggctag acagcgtaaa ctgcgccttt tcaaggatgg     840

aaaaatgaaa tatcagataa ttgatggaga gatgtatcct cccacagtca aagatactca     900

ggcagagatg atctaccctc ctcaagtccc tgagcatcta cggtttgctg tggggcagga     960

ggtctttggt ctggtgcctg gtctgatgat gtatgccaca atctggctgc gggaacacaa    1020

cagagtatgc gatgtgctta aacaggagca tcctgaatgg ggtgatgagc agttgttcca    1080

gacaagcagg ctaatactga taggagagac tattaagatt gtgattgaag attatgtgca    1140

acacttgagt ggctatcact tcaaactgaa atttgaccca gaactacttt tcaacaaaca    1200

attccagtac caaaatcgta ttgctgctga atttaacacc ctctatcact ggcatcccct    1260

tctgcctgac acctttcaaa ttcatgacca gaaatacaac tatcaacagt ttatctacaa    1320

caactctata ttgctggaac atggaattac ccagtttgtt gaatcattca ccaggcaaat    1380

tgctggcagg gttgctggtg gtaggaatgt tccacccgca gtacagaaag tatcacaggc    1440

ttccattgac cagagcaggc agatgaaata ccagtctttt aatgagtacc gcaaacgctt    1500

tatgctgaag ccctatgaat catttgaaga acttacagga gaaaaggaaa tgtctgcaga    1560
```

```
gttggaagca ctctatggtg acatcgatgc tgtggagctg tatcctgccc ttctggtaga   1620
aaagcctcgg ccagatgcca tctttggtga aaccatggta gaagttggag caccattctc   1680
cttgaaagga cttatgggta atgttatatg ttctcctgcc tactggaagc caagcacttt   1740
tggtggagaa gtgggttttc aaatcatcaa cactgcctca attcagtctc tcatctgcaa   1800
taacgtgaag ggctgtccct ttacttcatt cagtgttcca gatccagagc tcattaaaac   1860
agtcaccatc aatgcaagtt cttcccgctc cggactagat gatatcaatc ccacagtact   1920
actaaaagaa cgttcgactg aactgtagaa gtctaatgat catatttatt tatttatatg   1980
aaccatgtct attaatttaa ttatttaata atatttatat taaactcctt atgttactta   2040
acatcttctg taacagaagt cagtactcct gttgcggaga aaggagtcat acttgtgaag   2100
acttttatgt cactactcta aagattttgc tgttgctgtt aagtttggaa aacagttttt   2160
attctgtttt ataaaccaga gagaaatgag ttttgacgtc tttttacttg aatttcaact   2220
tatattataa gaacgaaagt aaagatgttt gaatacttaa acactgtcac aagatggcaa   2280
aatgctgaaa gtttttacac tgtcgatgtt tccaatgcat cttccatgat gcattagaag   2340
taactaatgt ttgaaatttt aaagtacttt tggttatttt tctgtcatca aacaaaaaca   2400
ggtatcagtg cattattaaa tgaatattta aattagacat taccagtaat ttcatgtcta   2460
ctttttaaaa tcagcaatga aacaataatt tgaaatttct aaattcatag ggtagaatca   2520
cctgtaaaag cttgtttgat ttcttaaagt tattaaactt gtacatatac caaaaagaag   2580
ctgtcttgga tttaaatctg taaaatcagt agaaatttta ctacaattgc ttgttaaaat   2640
attttataag tgatgttcct ttttcaccaa gagtataaac ctttttagtg tgactgttaa   2700
aacttccttt taaatcaaaa tgccaaattt attaaggtgg tggagccact gcagtgttat   2760
cttaaaataa gaatatttg ttgagatatt ccagaatttg tttatatggc tggtaacatg   2820
taaaatctat atcagcaaaa gggtctacct ttaaaataag caataacaaa gaagaaaacc   2880
aaattattgt tcaaatttag gtttaaactt ttgaagcaaa cttttttttta tccttgtgca   2940
ctgcaggcct ggtactcaga ttttgctatg aggttaatga agtaccaagc tgtgcttgaa   3000
taatgatatg ttttctcaga ttttctgttg tacagtttaa tttagcagtc catatcacat   3060
tgcaaaagta gcaatgacct cataaaatac ctcttcaaaa tgcttaaatt catttcacac   3120
attaatttta tctcagtctt gaagccaatt cagtaggtgc attggaatca agcctggcta   3180
cctgcatgct gttccttttc ttttcttctt ttagccattt tgctaagaga cacagtcttc   3240
tcatcacttc gtttctccta ttttgtttta ctagttttaa gatcagagtt cactttcttt   3300
ggactctgcc tatattttct tacctgaact tttgcaagtt ttcaggtaaa cctcagctca   3360
ggactgctat ttagctcctc ttaagaagat taaaagagaa aaaaaaaggc ccttttaaaa   3420
atagtataca cttattttaa gtgaaaagca gagaatttta tttatagcta attttagcta   3480
tctgtaacca agatggatgc aaagaggcta gtgcctcaga gagaactgta cggggtttgt   3540
gactggaaaa agttacgttc ccattctaat taatgccctt tcttatttaa aaacaaaacc   3600
aaatgatatc taagtagttc tcagcaataa taataatgac gataatactt cttttccaca   3660
tctcattgtc actgacattt aatggtactg tatattactt aatttattga agattattat   3720
ttatgtctta ttaggacact atggttataa actgtgttta agcctacaat cattgatttt   3780
tttttgttat gtcacaatca gtatattttc tttggggtta cctctctgaa tattatgtaa   3840
acaatccaaa gaaatgattg tattaagatt tgtgaataaa tttttagaaa tctgattggc   3900
```

```
atattgagat atttaaggtt gaatgtttgt ccttaggata ggcctatgtg ctagcccaca   3960

aagaatattg tctcattagc ctgaatgtgc cataagactg accttttaaa atgttttgag   4020

ggatctgtgg atgcttcgtt aatttgttca gccacaattt attgagaaaa tattctgtgt   4080

caagcactgt gggttttaat atttttaaat caaacgctga ttacagataa tagtatttat   4140

ataaataatt gaaaaaaatt ttcttttggg aagagggaga aaatgaaata aatatcatta   4200

aagataactc aggagaatct tctttacaat tttacgttta gaatgtttaa ggttaagaaa   4260

gaaatagtca atatgcttgt ataaaacact gttcactgtt ttttttaaaa aaaaaacttg   4320

atttgttatt aacattgatc tgctgacaaa acctgggaat ttgggttgtg tatgcgaatg   4380

tttcagtgcc tcagacaaat gtgtatttaa cttatgtaaa agataagtct ggaaataaat   4440

gtctgtttat ttttgtacta tttaaaaatt gacagatctt ttctgaagat aaactttgat   4500

tgtttctata                                                          4510
```

<210> SEQ ID NO 32
<211> LENGTH: 207
<212> TYPE: PRT
<213> ORGANISM: Homo sapiens

<400> SEQUENCE: 32

```
Met Thr Ser Arg Lys Lys Val Leu Leu Lys Val Ile Ile Leu Gly Asp
1               5                   10                  15

Ser Gly Val Gly Lys Thr Ser Leu Met Asn Gln Tyr Val Asn Lys Lys
            20                  25                  30

Phe Ser Asn Gln Tyr Lys Ala Thr Ile Gly Ala Asp Phe Leu Thr Lys
        35                  40                  45

Glu Val Met Val Asp Asp Arg Leu Val Thr Met Gln Ile Trp Asp Thr
    50                  55                  60

Ala Gly Gln Glu Arg Phe Gln Ser Leu Gly Val Ala Phe Tyr Arg Gly
65                  70                  75                  80

Ala Asp Cys Cys Val Leu Val Phe Asp Val Thr Ala Pro Asn Thr Phe
                85                  90                  95

Lys Thr Leu Asp Ser Trp Arg Asp Glu Phe Leu Ile Gln Ala Ser Pro
            100                 105                 110

Arg Asp Pro Glu Asn Phe Pro Phe Val Val Leu Gly Asn Lys Ile Asp
        115                 120                 125

Leu Glu Asn Arg Gln Val Ala Thr Lys Arg Ala Gln Ala Trp Cys Tyr
    130                 135                 140

Ser Lys Asn Asn Ile Pro Tyr Phe Glu Thr Ser Ala Lys Glu Ala Ile
145                 150                 155                 160

Asn Val Glu Gln Ala Phe Gln Thr Ile Ala Arg Asn Ala Leu Lys Gln
                165                 170                 175

Glu Thr Glu Val Glu Leu Tyr Asn Glu Phe Pro Glu Pro Ile Lys Leu
            180                 185                 190

Asp Lys Asn Asp Arg Ala Lys Ala Ser Ala Glu Ser Cys Ser Cys
        195                 200                 205
```

<210> SEQ ID NO 33
<211> LENGTH: 2185
<212> TYPE: DNA
<213> ORGANISM: Homo sapiens

<400> SEQUENCE: 33

```
agtcttggcc ataaagcctg aggcggcggc agcggcggag ttggcggctt ggagagctcg     60
```

```
ggagagttcc ctggaaccag aacttggacc ttctcgcttc tgtcctccgt ttagtctcct    120

cctcggcggg agccctcgcg acgcgcccgg cccggagccc ccagcgcagc ggccgcgttt    180

gaaggatgac ctctaggaag aaagtgttgc tgaaggttat catcctggga gattctggag    240

tcgggaagac atcactcatg aaccagtatg tgaataagaa attcagcaat cagtacaaag    300

ccacaatagg agctgacttt ctgaccaagg aggtgatggt ggatgacagg ctagtcacaa    360

tgcagatatg ggacacagca ggacaggaac ggttccagtc tctcggtgtg gccttctaca    420

gaggtgcaga ctgctgcgtt ctggtatttg atgtgactgc ccccaacaca ttcaaaaccc    480

tagatagctg gagagatgag tttctcatcc aggccagtcc ccgagatcct gaaaacttcc    540

catttgttgt gttgggaaac aagattgacc tcgaaaacag acaagtggcc acaaagcggg    600

cacaggcctg gtgctacagc aaaaacaaca ttccctactt tgagaccagt gccaaggagg    660

ccatcaacgt ggagcaggcg ttccagacga ttgcacggaa tgcacttaag caggaaacgg    720

aggtggagct gtacaacgaa tttcctgaac ctatcaaact ggacaagaat gaccgggcca    780

aggcctcggc agaaagctgc agttgctgag gggcagtga gagttgagca cagagtcctt    840

cacaaaccaa gaacacacgt aggccttcaa cacaattccc ctctcctctt ccaaacaaaa    900

catacattga tctctcacat ccagctgcca aaagaaaacc ccatcaaaca cagttacacc    960

ccacatatct ctcacacaca cacacacacg cacacacaca cacacagatc tgacgtaatc   1020

aaactccagc ccttgcccgt gatggctcct tggggtctgc ctgcccaccc acatgagccc   1080

gcgagtatgg cagcaggaca agccagcggt ggaagtcatt ctgatatgga gttggcattg   1140

gaagcttatt ctttttgttc actggagaga gagagaactg tttacagtta atctgtgtct   1200

aattatctga tttttttat tggtcttgtg gtctttttac cccccctttc ccctccctcc   1260

ttgaaggcta ccccttggga aggctggtgc cccatgcccc attacaggct cacacccagt   1320

ctgatcaggc tgagttttgt atgtatctat ctgttaatgc ttgttacttt taactaatca   1380

gatcttttta cagtatccat ttattatgta atgcttctta gaaaagaatc ttatagtaca   1440

tgttaatata tgcaaccaat taaaatgtat aaattagtgt aagaaattct tggattatgt   1500

gtttaagtcc tgtaatgcag gcctgtaagg tggagggttg aaccctgttt ggattgcaga   1560

gtgttactca gaattgggaa atccagctag cggcagtatt ctgtacagta gacacaagaa   1620

ttatgtacgc cttttatcaa agacttaaga gccaaaaagc ttttcatctc tccaggggga   1680

aaactgtcta gttcccttct gtgtctaaat tttccaaaac gttgatttgc ataatacagt   1740

ggtatgtgca atggataaat tgccgttatt tcaaaaatta aaattctcat tttctttctt   1800

tttttcccc cctgctccac acttcaaaac tcccgttaga tcagcattct actacaagag   1860

tgaaaggaaa accctaacag atctgtccta gtgattttac ctttgttcta gaaggcgctc   1920

ctttcagggt tgtggtattc ttaggttagc ggagcttttt cctcttttcc ccacccatct   1980

ccccaatatt gcccattatt aattaacctc tttctttggt tggaaccctg gcagttctgc   2040

tcccttccta ggatctgccc ctgcattgta gcttgcttaa cggagcactt ctcctttttc   2100

caaaggtcta cattctaggg tgtgggctga gttcttctgt aaagagatga acgcaatgcc   2160

aataaaattg aacaagaaca atgat                                          2185
```

<210> SEQ ID NO 34
<211> LENGTH: 450
<212> TYPE: PRT
<213> ORGANISM: Artificial Sequence
<220> FEATURE:
<223> OTHER INFORMATION: /note="Description of Artificial Sequence:

```
      Anti-IL-22 mAb clone F0025 heavy chain variable domain sequence"

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Val
        35                  40                  45

Gly Trp Ile Asn Pro Tyr Thr Gly Ser Ala Phe Tyr Ala Gln Lys Phe
    50                  55                  60

Arg Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Pro Glu Lys Phe Asp Ser Asp Asp Ser Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Leu Tyr Ser Lys Leu Thr Val
405 410 415

Asp Lys Ser Arg Trp Gln Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 35
<211> LENGTH: 217
<212> TYPE: PRT
<213> ORGANISM: Artificial Sequence
<220> FEATURE:
<223> OTHER INFORMATION: /note="Description of Artificial Sequence: Anti-IL-22 mAb clone F0025 light chain variable domain sequence"

<400> SEQUENCE: 35

Gln Ala Val Leu Thr Gln Pro Pro Ser Val Ser Gly Ala Pro Gly Gln
1 5 10 15

Arg Val Thr Ile Ser Cys Thr Gly Ser Ser Ser Asn Ile Gly Ala Gly
20 25 30

Tyr Gly Val His Trp Tyr Gln Gln Leu Pro Gly Thr Ala Pro Lys Leu
35 40 45

Leu Ile Tyr Gly Asp Ser Asn Arg Pro Ser Gly Val Pro Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Tyr Asp Asn Ser
85 90 95

Leu Ser Gly Tyr Val Phe Gly Gly Gly Thr Gln Leu Thr Val Leu Gly
100 105 110

Gln Pro Lys Ala Ala Pro Ser Val Thr Leu Phe Pro Pro Ser Ser Glu
115 120 125

Glu Leu Gln Ala Asn Lys Ala Thr Leu Val Cys Leu Ile Ser Asp Phe
130 135 140

Tyr Pro Gly Ala Val Thr Val Ala Trp Lys Ala Asp Ser Ser Pro Val
145 150 155 160

Lys Ala Gly Val Glu Thr Thr Thr Pro Ser Lys Gln Ser Asn Asn Lys
165 170 175

Tyr Ala Ala Ser Ser Tyr Leu Ser Leu Thr Pro Glu Gln Trp Lys Ser
180 185 190

His Arg Ser Tyr Ser Cys Gln Val Thr His Glu Gly Ser Thr Val Glu
195 200 205

Lys Thr Val Ala Pro Thr Glu Cys Ser
210 215

METHODS OF TREATING ANEMIA IN MYELODYSPLASTIC SYNDROMES

RELATED APPLICATIONS

This application is a § 371 national-stage application based on PCT/US22/018538, filed Mar. 2, 2022 which claims the benefit of priority from U.S. Provisional Application Ser. No. 63/155,430, filed Mar. 2, 2021; the entire contents of each application are incorporated herein in their entirety by this reference.

SEQUENCE LISTING

The instant application contains a Sequence Listing which has been submitted electronically in ASCII format and is hereby incorporated by reference in its entirety. Said ASCII copy, created on Apr. 27, 2022, is named DFS-31425_SL.txt and is 87,617 bytes in size.

BACKGROUND OF THE INVENTION

Myelodysplastic syndromes (MDS) are heterogeneous hematopoietic stem and progenitor cell neoplasms characterized clinically by bone marrow (BM) failure and resultant cytopenias (Komrokji et al. (2010) *Hematol. Oncol. Clin. North Am.* 24:443-457). MDS are the most commonly diagnosed myeloid neoplasms in the United States (Bejar and Steensma (2014) *Blood* 124(18):2793-2803), with a 3-year survival rate of only 35-45% (Ma (2012) *Am. J. Med.* 125:S2-S5; Rollison et al. (2008) *Blood* 112:45-52). According to the most recent MDS risk assessment tool (Revised International Prognostic Scoring System, IPSS-R), the median time to 25% AML transformation ranged from 10.8 years (low-risk MDS group, LR-MDS) to 0.7 years (high-risk MDS group, HR-MDS) (Greenberg et al. (1997) *Blood* 89:2079-2088; Greenberg et al. (2012) *Blood* 120:2454-2465; Malcovati et al. (2007) *J. Clin. Oncol.* 25:3503-3510). Because the majority of patients at diagnosis are ≥60 years of age (Ma (2012) *Am. J. Med.* 125:S2-S5), most patients are ineligible for BM transplantation due to older age-related comorbidities. Lenalidomide (List et al. (2006) *N. Engl. J. Med.* 355:1456-1465; Fenaux et al. (2011) *Blood* 118:3765-3776; Sekeres et al. (2012) *Blood* 120:4945-4951) and azanucleosides (azacitidine (Silverman et al. (2002) *J. Clin. Oncol.* 20:2429-2440), decitabine (Lubbert et al. (2011) *J. Clin. Oncol.* 29:1987-1996; Steensma et al. (2009) *J. Clin. Oncol.* 27:3842-3848)) remain the only currently approved therapies for treating MDS patients. However, lenalidomide extends survival in LR-MDS patients by only 14-17 months and in the HR-MDS group by 4-6 months. The mean duration of response is ~10-14 months for treatment with azanucleosides (Fenaux et al. (2009) *Lancet Oncol.* 10:223-232; Prebet et al. (2014) *J. Clin. Oncol.* 32:1242-1248). Currently, there are no approved therapies for patients with refractory disease particularly after azanucleoside therapy (Montalban-Bravo and Garcia-Manero (2018) *Am. J. Hematol.* 93:129-147). No new FDA-approved drugs for MDS have emerged in the past decade (DeZern (2015) *Hematol. Am. Soc. Hematol. Educ. Program* 2015:308-316) highlighting the critical need to identify new therapeutic targets that will improve the outlook for MDS patients.

Deletion of chromosome 5q (del(5q)), either isolated or accompanied by additional cytogenetic abnormalities, is the most commonly detected chromosomal abnormality in MDS, reported in 10%-30% of patients (Giagounidis et al. (2006) *Clin. Cancer Res.* 12:5-10; Haase et al. (2007) *Blood* 110:4385-4395; Hofmann et al. (2004) *Hematol J.* 5:1-8; Sole et al. (2000) *Br. J. Haematol.* 108:346-356; Bejar et al. (2011) *J. Clin. Oncol.* 29:504-515). Anemia is the most common hematologic manifestation of MDS, particularly in patients with del(5q) MDS, along with peripheral blood pancytopenia (Komrokji et al. (2013) *Best Pract. Res. Clin. Haematol.* 26:365-375). Previous studies using haploinsufficient 5q gene deletions revealed diminished erythroid progenitors (Kumar et al. (2011) *Blood* 118:4666-4673; Ribezzo et al. (2019) *Leukemia* 33:1759-1772; Schneider et al. (2014) *Cancer Cell* 26:509-520; Schneider et al. (2016) *Nat. Med.* 22:288-297), but the molecular mechanisms underlying this defect remain unclear. The severe anemia in del(5q) MDS patients has been linked to haploinsufficiency of ribosomal proteins such as RPS14 and RPS19 (Ebert et al. (2008) *Nature* 451:335-339; Dutt et al. (2011) *Blood* 117:2567-2576). Some ribosomal protein genes lie outside of 5q33, the most commonly deleted 5q region in MDS. One such gene, right open reading frame kinase 2 (RIOK2), lies at the q15 band on human chromosome 5 (5q15) within the genomic breakpoints observed in del(5q) syndromes (Royer-Pokora et al. (2006) *Cancer Genet. Cytogenet.* 167:66-69; Tang et al. (2015) *Am. J. Clin. Pathol.* 144:78-86). RIOK2, an atypical serine-threonine protein kinase, functions in the synthesis of the 40S ribosomal subunit (Zemp et al. (2009) *J. Cell Biol.* 185:1167-1180).

In addition to the need to improve the outlook for MDS patients in general, there is also a need to improve the diagnosis and treatment of anemia, since various types of anemia, such as those caused or worsened by an inability to produce sufficient red blood cells as in MDS, do not have adequate treatments.

SUMMARY OF THE INVENTION

The present invention is based, at least in part, on the discovery that mice having Riok2 haploinsufficiency exhibit anemia and high T-cell-derived IL-22 production. This anemia phenotype can be ameliorated by downregulating IL-22 signaling, such as by deleting one or both copies of the IL-22 gene or the IL-22 receptor (IL-22RA) gene, and/or by treatment with an anti-IL-22 signaling agent (such as a down-regulator of anti-IL-22, down-regulator of IL22RA, and the like). In accordance with disclosures provided herein, various red blood cell disorders (e.g., anemia, myelodysplastic syndromes, anemia caused by myelodysplastic syndromes, anemia caused by insufficiency of serine/threonine-protein kinase RIOK2, anemia caused by one or more mutations and/or deletions on human chromosome 5 or in an ortholog thereof, macrocytic anemia, Diamond Blackfan anemia, Schwachmann-Diamond syndrome, anemia caused by drugs, such as phenylhydrazine or other stressors of erythroid differentiation, and the like) of a subject can be treated by administering to the subject a down-regulator of IL-22 signaling. Such an administration can treat the red blood cell disorders by promoting differentiation from an erythroid progenitor cell toward a mature red blood cell in the subject. Moreover, it was unexpectedly determined herein that erythroid progenitors express the IL-22 receptor A protein.

Immunobiology of hematologic diseases, such as anemia, is an area of study that is largely under-explored. Thus, therapies targeting immune mediators have not been tested in this realm. Use of anti-IL-22-signaling agents to treat anemia, either as a single agent or in a combinatorial approach with currently existing or experimental therapies, according to the present invention are believed to lead to a prolonged beneficial effect, and can also address the problem of developing resistance to single agent therapies.

Accordingly, in one aspect, a method of treating one or more red blood cell disorders in a subject, the method comprising administering to the subject an effective amount of a down-regulator of interleukin-22 (IL-22) signaling, is provided.

Numerous embodiments are further provided that can be applied to any aspect of the present invention and/or combined with any other embodiment described herein. For example, in one embodiment, the one or more red blood disorders comprise anemia. In another embodiment, the one or more red blood disorders comprise one or more myelodysplastic syndromes (MDS), optionally wherein the one or more MDS are mediated by one or more mutations and/or deletions in the long arm of human chromosome 5, or in an orthologous region of an orthologous chromosome thereof. In still another embodiment, the one or more red blood disorders comprise an insufficiency of serine/threonine-protein kinase RIOK2. In yet another embodiment, the one or more red blood disorders comprise an increase in levels of one or more biomarkers listed in Table 1, optionally wherein the one or more biomarkers is IL-22. In another embodiment, the down-regulator comprises an anti-IL-22 antibody or antigen-binding fragment thereof, an anti-IL-22RA1 antibody or antigen-binding fragment thereof, an anti-IL-10Rbeta antibody or antigen-binding fragment thereof, an agent that inhibits the copy number, amount, and/or activity of at least one biomarker listed in Table 1, or a combination thereof. In still another embodiment, the anti-IL-22 antibody or antigen-binding fragment thereof comprises IL22JOP™ monoclonal antibody, such as fezakinumab. In yet another embodiment, the down-regulator comprises an anti-IL-22RA1 antibody or antigen-binding fragment thereof. In another embodiment, the down-regulator comprises an anti-IL-22RA1/IL-10R2-heterodimer antibody or antigen-binding fragment thereof. In still another embodiment, the down-regulator comprises IL-22 binding protein or a fragment thereof. In yet another embodiment, the down-regulator comprises an antagonist of aryl hydrocarbon receptor, such as stemregenin 1, CH-223191, or 6,2',4'-trimethoxyflavone. In another embodiment, the method further comprises administering to the subject an effective amount of lenalidomide, azacitidine, decitabine, or a combination thereof. In still another embodiment, the method further comprises administering to the subject an effective amount of an erythropoiesis-stimulating agent, such as erythropoietin, epoetin alfa, epoetin beta, epoetin omega, epoetin zeta, IL-9, or darbepoetin alfa.

In another aspect, a method of promoting differentiation of an erythroid progenitor cell toward a mature red blood cell in a subject, the method comprising administering to the subject an effective amount of a down-regulator of interleukin-22 (IL-22) signaling, is provided.

As described above, numerous embodiments are further provided that can be applied to any aspect of the present invention and/or combined with any other embodiment described herein. For example, in one embodiment, the down-regulator comprises an anti-IL-22 antibody or antigen-binding fragment thereof, an anti-IL-22RA1 antibody or antigen-binding fragment thereof, an anti-IL-10Rbeta antibody or antigen-binding fragment thereof, an agent that inhibits the copy number, amount, and/or activity of at least one biomarker listed in Table 1, or a combination thereof. In another embodiment, the anti-IL-22 antibody or antigen-binding fragment thereof comprises IL22JOP™ monoclonal antibody, such as fezakinumab. In still another embodiment, the down-regulator comprises an anti-IL-22RA1 antibody or antigen-binding fragment thereof. In yet another embodiment, the down-regulator comprises an anti-IL-22RA1/IL-10R2-heterodimer antibody or antigen-binding fragment thereof. In another embodiment, the down-regulator comprises IL-22 binding protein or a fragment thereof. In still another embodiment, the down-regulator comprises an antagonist of aryl hydrocarbon receptor, such as stemregenin 1, CH-223191, or 6,2',4'-trimethoxyflavone. In yet another embodiment, the erythroid progenitor is selected from the group consisting of erythroid progenitors of stage RI, RII, RIII, and RIV.

In still another aspect, a method of determining whether a subject afflicted with or at risk for developing an MDS and/or an anemia would benefit from therapy with a down-regulator of IL-22 signaling, the method comprising a) obtaining a biological sample from the subject; b) determining the copy number, amount, and/or activity of at least one biomarker listed in Table 1; c) determining the copy number, amount, and/or activity of the at least one biomarker in a control; and d) comparing the copy number, amount, and/or activity of the at least one biomarker detected in steps b) and c), wherein the presence of, or a significant increase in, the copy number, amount, and/or activity of at least one biomarker listed in Table 1 in the subject sample relative to the control copy number, amount, and/or activity of the at least one biomarker indicates that the subject afflicted with or at risk for developing the MDS and/or the anemia would benefit from therapy with the down-regulator of IL-22 signaling, is provided.

As described above, numerous embodiments are further provided that can be applied to any aspect of the present invention and/or combined with any other embodiment described herein. For example, in one embodiment, the method further comprises recommending, prescribing, or administering the down-regulator of IL-22 signaling if the subject is determined to benefit from the agent. In another embodiment, the method further comprises recommending, prescribing, or administering at least one additional MDS and/or anemia therapy that is administered before, after, or concurrently with the down-regulator of IL-22 signaling. In still another embodiment, the method further comprises recommending, prescribing, or administering cancer therapy other than a down-regulator of IL-22 signaling if the subject is determined not to benefit from the down-regulator of IL-22 signaling. In yet another embodiment, the down-regulator is selected from the group consisting of an anti-IL-22RA1 antibody or antigen-binding fragment thereof, an anti-IL-10Rbeta antibody or antigen-binding fragment thereof, an agent that inhibits the copy number, amount, and/or activity of at least one biomarker listed in Table 1, and combinations thereof. In another embodiment, the control sample comprises cells.

In yet another aspect, A method for predicting the clinical outcome of a subject afflicted with an MDS and/or an anemia to treatment with a down-regulator of IL-22 signaling, the method comprising a) determining the copy number, amount, and/or activity of at least one biomarker listed in Table 1 in a subject sample; b) determining the copy number, amount, and/or activity of the at least one biomarker in a control having a good clinical outcome; and c) comparing the copy number, amount, and/or activity of the at least one biomarker in the subject sample and in the control, wherein the presence of, or a significant increase in, the copy number, amount, and/or activity of at least one biomarker listed in Table 1 in the subject sample as compared to the copy number, amount and/or activity in the control, is an indication that the subject has a favorable clinical outcome, is provided.

In another aspect, a method for monitoring the efficacy of a down-regulator of IL-22 signaling in treating an MDS and/or an anemia in a subject, wherein the subject is administered a therapeutically effective amount of the down-regulator of IL-22 signaling, the method comprising a) detecting in a subject sample at a first point in time the copy number, amount, and/or activity of at least one biomarker listed in Table 1; b) repeating step a) at a subsequent point in time; and c) comparing the amount or activity of at least one biomarker listed in Table 1 detected in steps a) and b) to monitor the progression of the cancer in the subject, wherein the absence of, or a significant decrease in, the copy number, amount, and/or activity of, the at least one biomarker listed in Table 1 in the subject sample as compared to the copy number, amount and/or activity in the control, is an indication that the down-regulator of IL-22 signaling effectively treats the MDS and/or the anemia in the subject.

In still another aspect, a method of assessing the efficacy of an agent that inhibits the copy number, amount, and/or activity of at least one biomarker listed in Table 1 for treating an MDS and/or an anemia in a subject, comprising a) detecting in a sample at a first point in time the copy number, amount, and/or or activity of at least one biomarker listed in Table 1; b) repeating step a) during at least one subsequent point in time after contacting the sample with the agent; and c) comparing the copy number, amount, and/or activity detected in steps a) and b), wherein the absence of, or a significant decrease in, the copy number, amount, and/or activity of, the at least one biomarker listed in Table 1, in the subsequent sample as compared to the copy number, amount, and/or activity in the sample at the first point in time, indicates that the agent effectively treats the MDS and/or the anemia.

As described above, numerous embodiments are further provided that can be applied to any aspect of the present invention and/or combined with any other embodiment described herein. For example, in one embodiment, the subject has undergone treatment, completed treatment, and/or is in remission for the MDS and/or the anemia between the first point in time and the subsequent point in time. In another embodiment, the first and/or at least one subsequent sample is selected from the group consisting of in vitro samples, optionally wherein the in vitro sample comprising cells. In still another embodiment, the first and/or at least one subsequent sample is selected from the group consisting of ex vivo and in vivo samples. In yet another embodiment, the first and/or at least one subsequent sample is a portion of a single sample or pooled samples obtained from the subject. In another embodiment, the sample comprises blood, bone marrow fluid, or Th22 T lymphocytes. In still another embodiment, biomarker mRNA and/or protein are detected. In yet another embodiment, the MDS and/or the anemia is selected from the group consisting of macrocytic anemia, anemia associated with chronic kidney disease (CKD), anemia caused by insufficiency of serine/threonine-protein kinase RIOK2, anemia caused by one or more mutations and/or deletions in human chromosome 5 or in an ortholog thereof, stress-induced anemia, Diamond Blackfan anemia, and Schwachman-Diamond syndrome. In another embodiment, wherein the subject is a mammal, optionally wherein the mammal is a human, a mouse, and/or an animal model of an MDS and/or an anemia.

BRIEF DESCRIPTION OF THE DRAWINGS

FIG. 1A shows the location of RIOK2 on human chromosome 5. FIG. 1B shows expression of Riok2 in mouse BM cells. FIG. 1C shows Riok2 mRNA expression by qPCR in BM cells from Riok2 haploinsufficient mice and Vav1-cre controls. FIG. 1D shows frequency of genotypes indicated on the X-axis among 4 litters from 4 different breeding crosses of the genotypes mentioned. FIG. 1E shows in vivo protein synthesis rates in the indicates cell types from Riok2 haploinsufficient mice and Vav1-cre controls. * p<0.05, **** p<0.0001.

FIG. 2A shows peripheral blood (PB) RBC numbers, hemoglobin (Hb), and hematocrit (HCT) in $Riok2^{fl/+}Vav1^{cre}$ mice in comparison to $Riok2^{+/+}Vav1^{cre}$ controls (n=5/group). FIG. 2B shows frequency of erythroid progenitor populations among viable bone marrow cells in $Riok2^{fl/+}Vav1^{cre}$ mice and $Riok2^{+/+}Vav1^{cre}$ controls (n=5/group). FIG. 2C shows frequency of apoptotic erythroid progenitors among viable bone marrow cells in $Riok2^{fl/+}Vav1^{cre}$ mice and $Riok2^{+/+}Vav1^{cre}$ controls (n=5/group). FIG. 2D shows PB RBC numbers, Hb, and HCT in $Riok2^{fl/+}Vav1^{cre}$ mice and $Riok2^{+/+}Vav1^{cre}$ controls undergoing phenylhydrazine (PhZ)-induced stress erythropoiesis (n=7/group). FIG. 2E shows percentage of monocytes and neutrophils in the PB of $Riok2^{fl/+}Vav1^{cre}$ mice in comparison to $Riok2^{+/+}Vav1^{cre}$ controls (n=5-6/group). FIG. 2F shows percentage of GMPs in the BM of $Riok2^{fl/+}Vav1^{cre}$ mice and $Riok2^{+/+}Vav1^{cre}$ controls (n=3-4/group). FIG. 2G shows percentage CD11b+ cells obtained from Lin-Sca-1+c-kit+ cells from $Riok2^{fl/+}Vav1^{cre}$ mice and $Riok2^{+/+}Vav1^{cre}$ controls cultured in MethoCult™ for 7 days (n=5/group). Unpaired two-tailed t-test (FIGS. 2A-2C and 2E-2G) and 1-way ANOVA with Tukey's correction for multiple comparison (FIG. 2D) used to calculate statistical significance. * p<0.05,  p<0.01. Data are shown as mean±s.e.m and are representative of two (FIGS. 2D and 2F) or three (FIGS. 2A-2C and 2**G) independent experiments.

FIG. 3A shows a gating strategy used for the identification of erythroid progenitors in the BM. FIG. 3B shows results of a cell cycle analysis of erythroid progenitors from Riok2 haploinsufficient mice in comparison to Vav1-cre controls. FIG. 3C shows cdkn1a mRNA expression by qPCR in erythroid progenitors from Riok2 haploinsufficient mice and Vav1-cre controls. FIG. 3D shows a Kaplan-Meier survival curve for Riok2 haploinsufficient mice and Vav1-cre controls subjected to lethal dose of PhZ. FIG. 3E shows PB RBC numbers, Hb, and HCT in mice transplanted with either Riok2 haploinsufficient mice or Vav1-cre BM cells. * p<0.05, ** p<0.01.

FIG. 4A-FIG. 4D show immune activation signatures resulting from quantitative proteomics of Riok2 haploinsufficient progenitors. FIG. 4A shows proteomic analysis of changes in protein expression in erythroid progenitors from Riok2 haploinsufficient mice and Vav1-cre controls. FIG. 4B shows a comparison of upregulated proteins with their respective p-values and log fold-change values in erythroid progenitors from Riok2-haploinsufficient mice and Rps14-haploinsufficient mice with their respective controls. FIG. 4C shows overlap of all the upregulated proteins in each of the dataset with respect to their respective controls. FIG. 4D shows secreted IL-22 levels from in vitro-polarized Th22 cells from Rps14 haploinsufficient mice and Vav1-cre controls. * p<0.05.

5A), IFN-gamma (FIG. 5B), IL-4 (FIG. 5C), IL-5 (FIG. 5D), IL-13 (FIG. 5E), IL-17A (FIG. 5F) and % Foxp3+ cells (FIG. 5G) from in vitro polarized T cells of the indicated genotypes are shown.

Figures 6A, 6B, 6C, 6D:
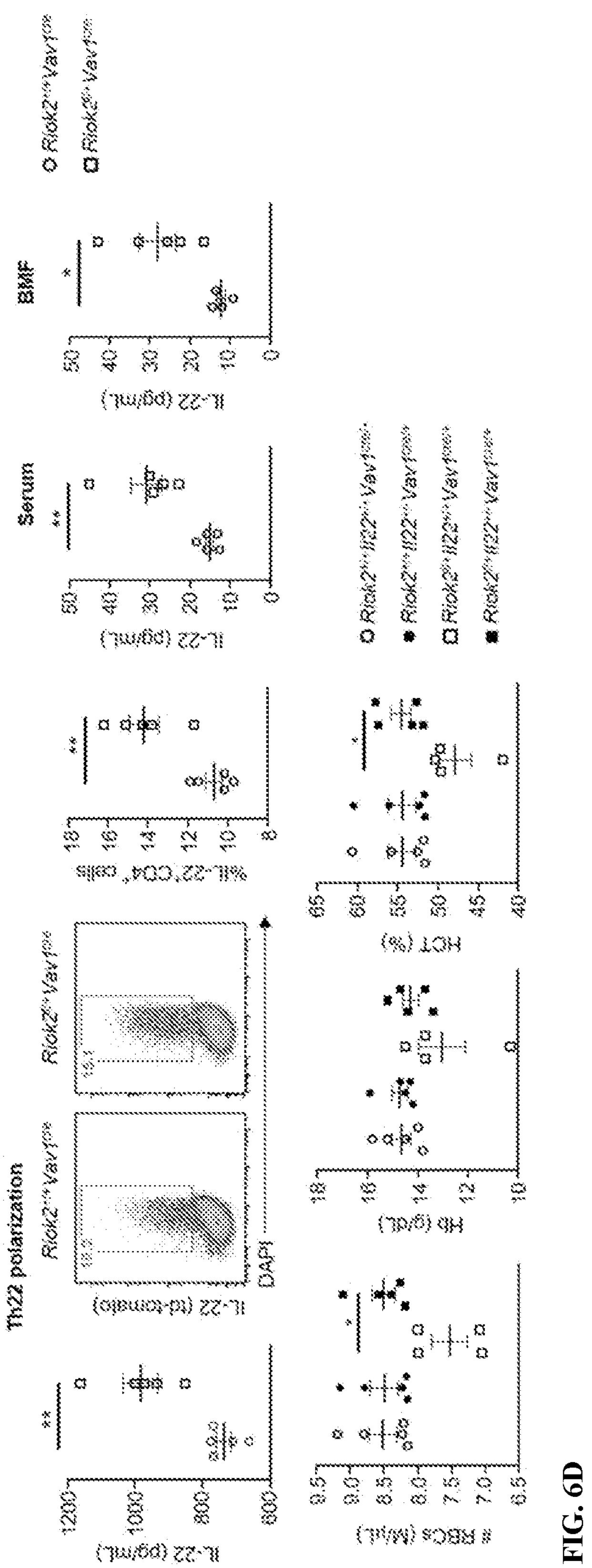
Figures 6E, 6F, 6G:
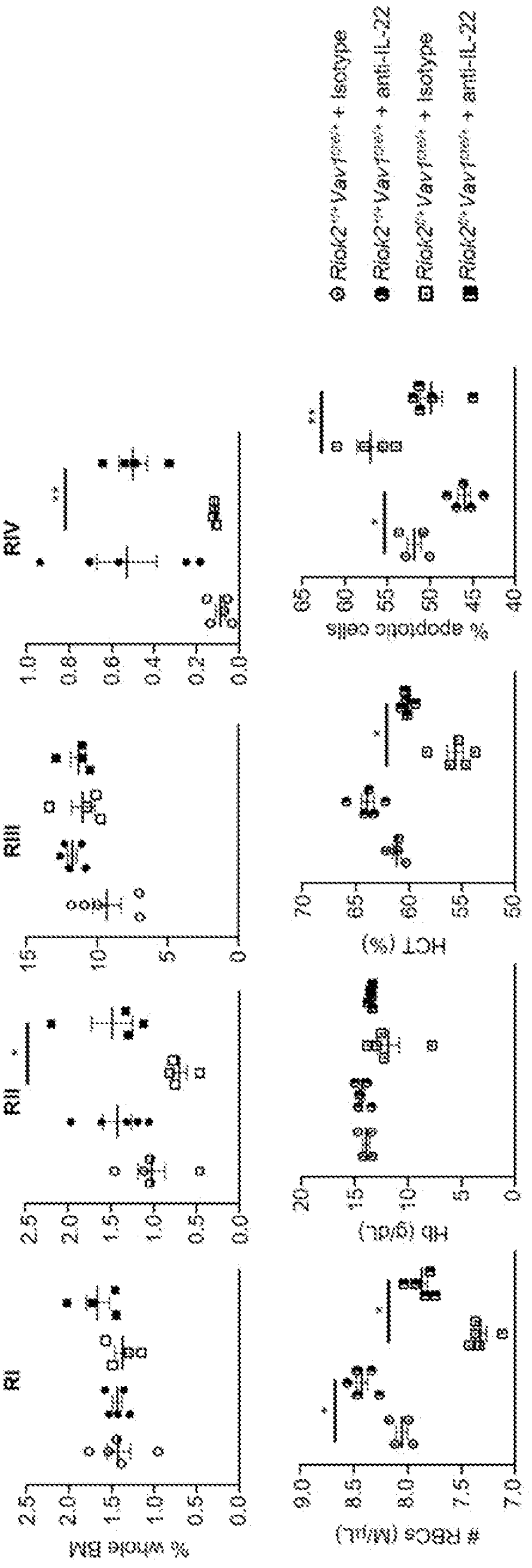

FIG. 6A-FIG. 6G show that Riok2 haploinsufficient T cells secrete increased IL-22 and that IL-22 neutralization alleviates anemia. FIGS. 6A and 6B show secreted IL-22 (FIG. 6A) and percentage of IL-22+CD4+ T cells (FIG. 6B) from in vitro-polarized Th22 cells from Riok2$^{fl/+}$Vav1$^{cre}$ mice and Riok2$^{+/+}$Vav1$^{cre}$ controls (n=5/group). FIG. 6C shows IL-22 levels in the serum (left panel) and bone marrow supernatant (right panel) in Riok2$^{fl/+}$Vav1$^{cre}$ mice and Riok2$^{+/+}$Vav1$^{cre}$ controls (n=5/group). FIG. 6D shows PB RBC numbers, Hb, and HCT in the indicated strains undergoing PhZ-induced stress erythropoiesis (n=4-5/group). FIG. 6E shows frequency of erythroid progenitor populations among viable bone marrow cells in the indicated strains undergoing PhZ-induced stress erythropoiesis (n=4-5/group). FIG. 6F shows PB RBC numbers, Hb, and HCT in Riok2$^{fl/+}$Vav1$^{cre}$ mice and Riok2$^{+/+}$Vav1$^{cre}$ controls undergoing PhZ-induced stress erythropoiesis treated with either an isotype control or anti-IL-22 antibody (n=4-5/group). FIG. 6G shows frequency of apoptotic erythroid progenitors among viable bone marrow cells in Riok2$^{fl/+}$Vav1$^{cre}$ mice and Riok2$^{+/+}$Vav1$^{cre}$ controls undergoing PhZ-induced stress erythropoiesis treated with either an isotype control or anti-IL-22 antibody (n=4-5/group). Unpaired two-tailed t-test (FIG. 6A-FIG. 6C) and 1-way ANOVA with Tukey's correction for multiple comparison (FIG. 6D-FIG. 6G) used to calculate statistical significance. * $p<0.05$, ** $p<0.01$. Data are shown as mean±s.e.m and are representative of two (FIG. 6C and FIG. 6F) or three (FIGS. 6A, 6B, 6D, and 6E) independent experiments.

Figures 7A, 7B, 7C, 7D, 7E:
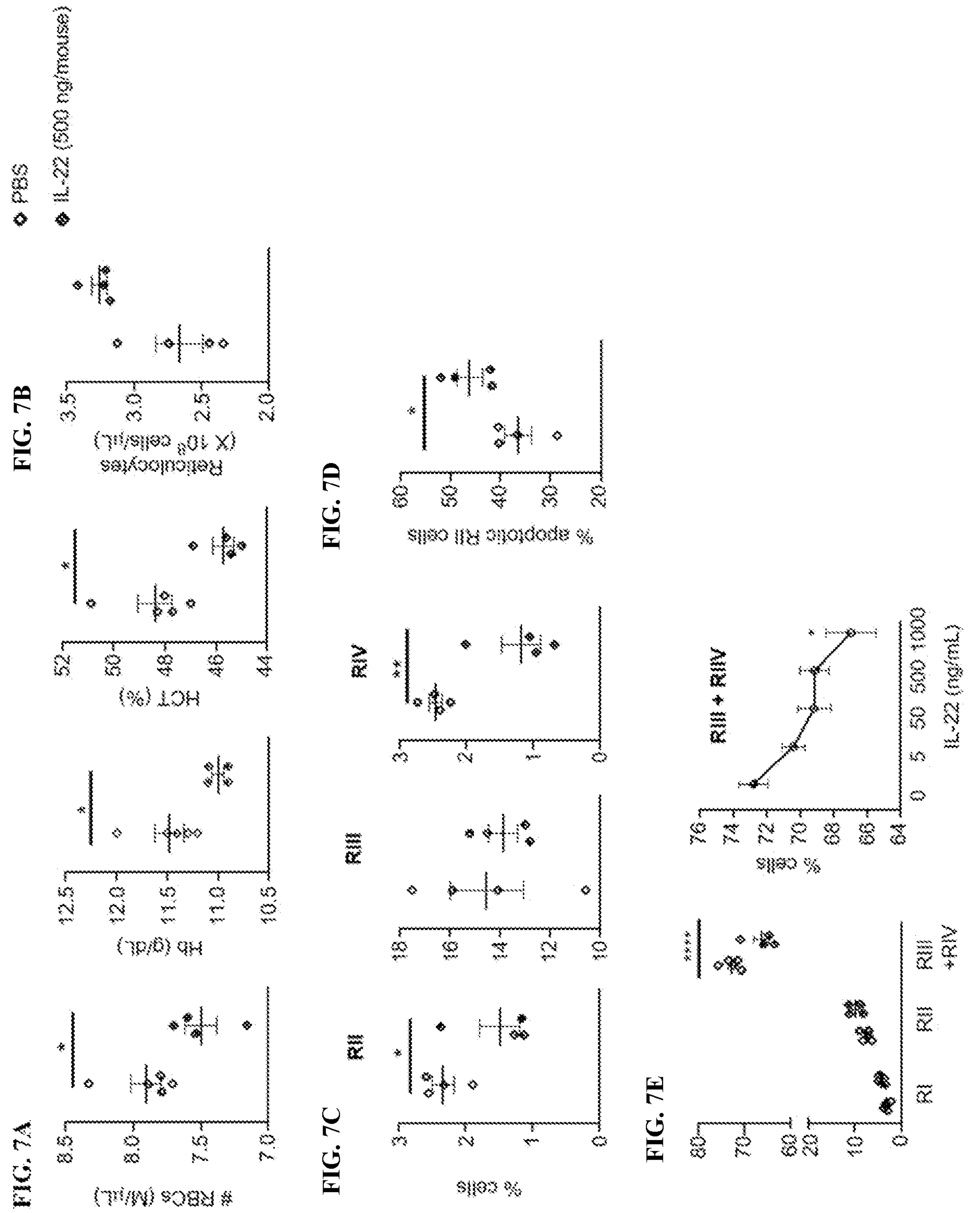
Figure 8A:
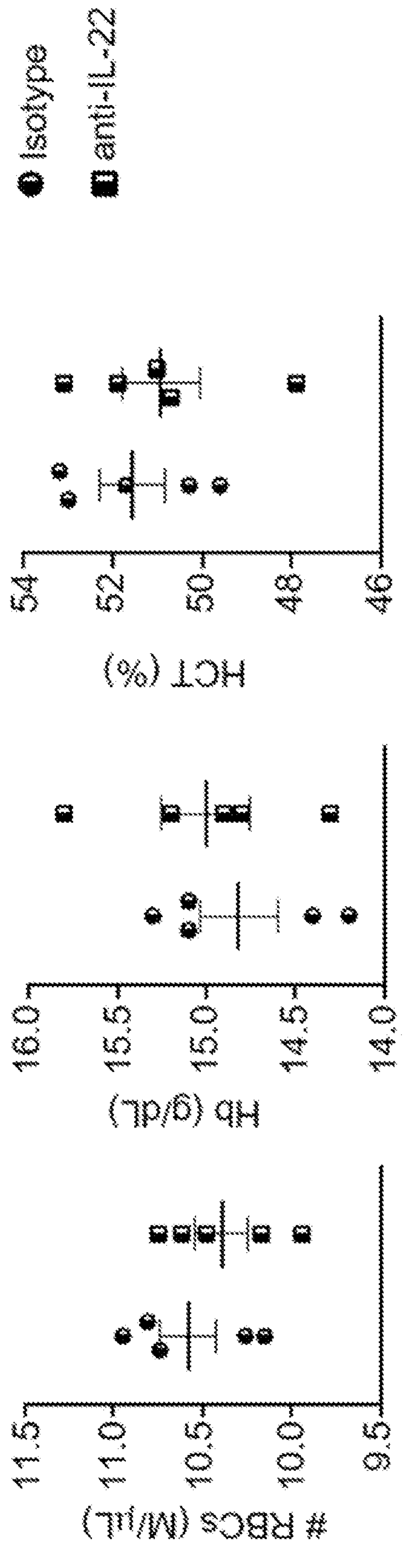
Figure 8B:
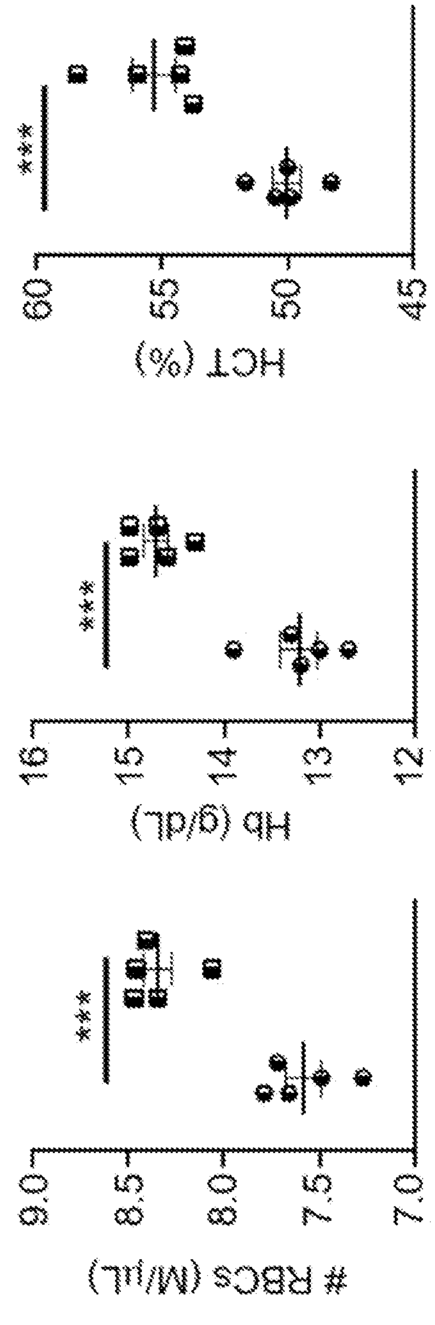

FIG. 7A-FIG. 7E show that recombinant IL-22 exacerbates PhZ-induced anemia in wt mice. FIG. 7A shows PB RBC numbers, Hb, and HCT in wt C57BL/6J mice administered PBS or rIL-22 and subsequently treated with PhZ. FIG. 7B shows PB reticulocytes in mice treated as in FIG. 7A. FIG. 7C shows percentage of RII-RIV erythroid progenitors in the BM of PBS- or rIL-22-treated C57BL/6J mice 7 days after PhZ administration. FIG. 7D shows percentage of apoptotic RII erythroid progenitors in mice treated as in FIG. 7C. FIG. 7E shows an effect of recombinant IL-22 (500 ng/mL) in an in vitro erythropoiesis assay (left panel) and dose-dependent effect of recombinant IL-22 (right panel). * $p<0.05$,  $p<0.01$,  $p<0.0001$ FIG. 8A-FIG. 8B show that IL-22 neutralization alleviates anemia in wt mice undergoing PhZ-induced stress erythropoiesis. FIG. 8A shows PB RBC numbers, Hb, and HCT in naïve wt C57BL/6J mice treated with either an isotype control or anti-IL-22 antibody. FIG. 8B shows PB RBC numbers, Hb, and HCT in wt C57BL/6J mice undergoing PhZ-induced stress erythropoiesis treated with either an isotype control or anti-IL-22 antibody. * $p<0.001$.

Figures 9A, 9B, 9C:
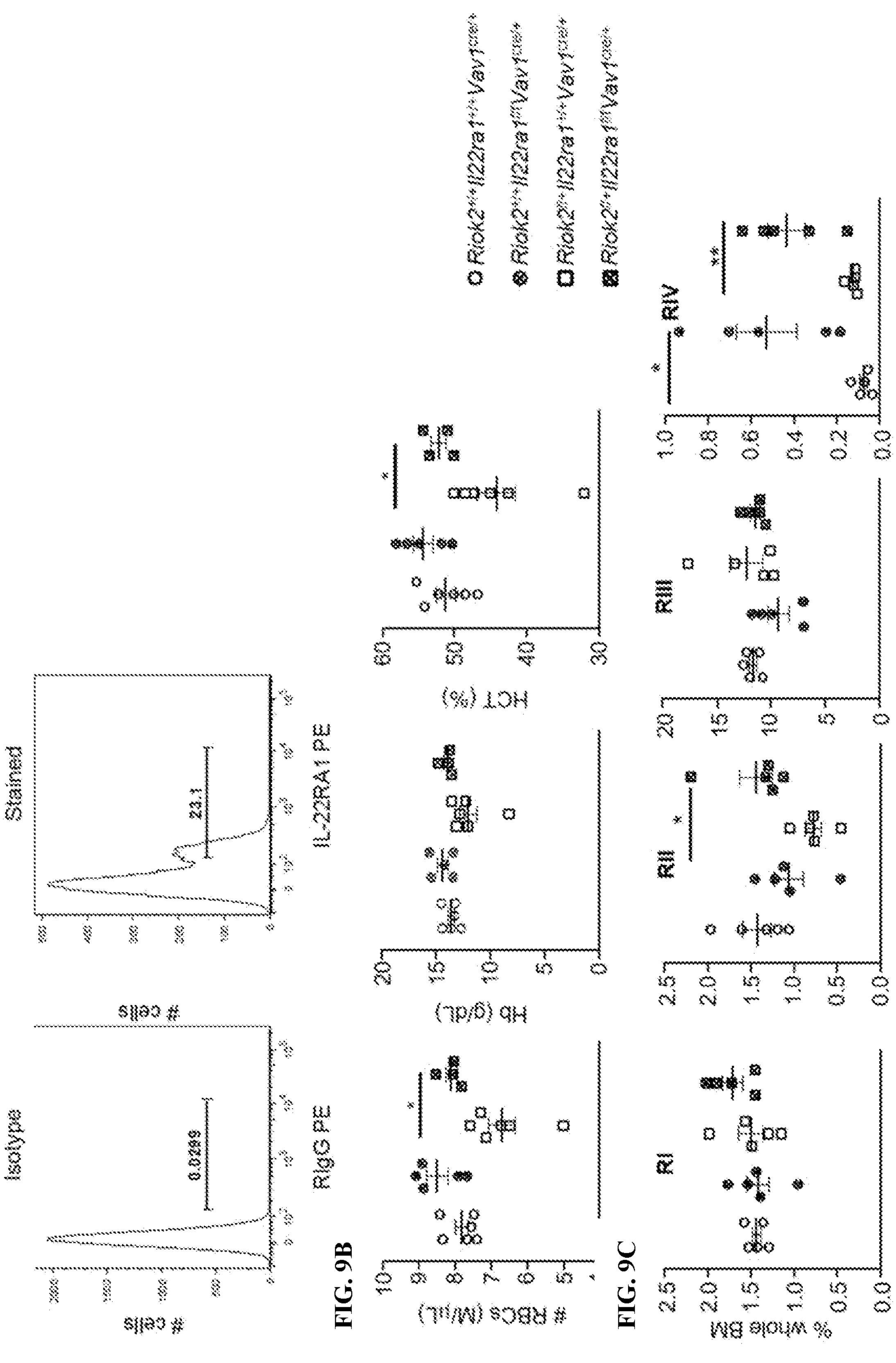
Figure 9D:
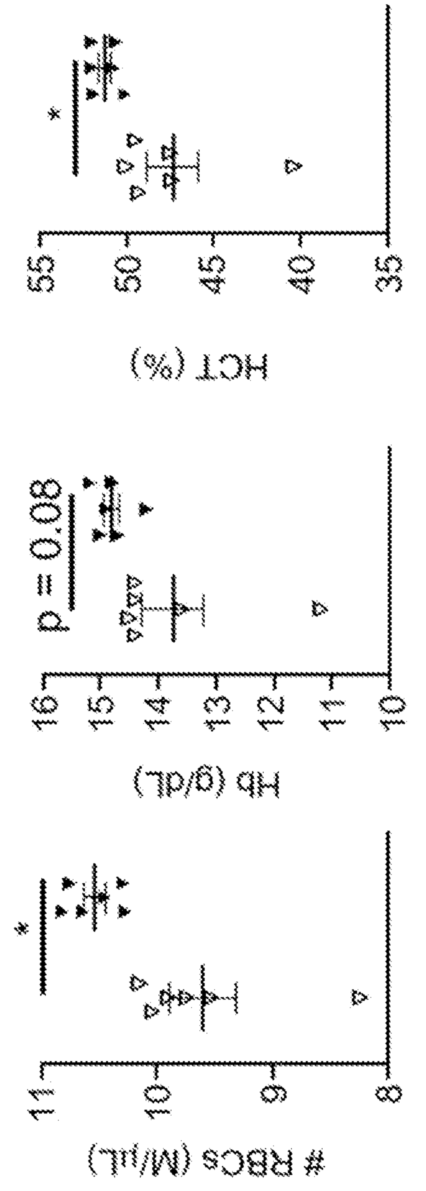
Figure 9E:
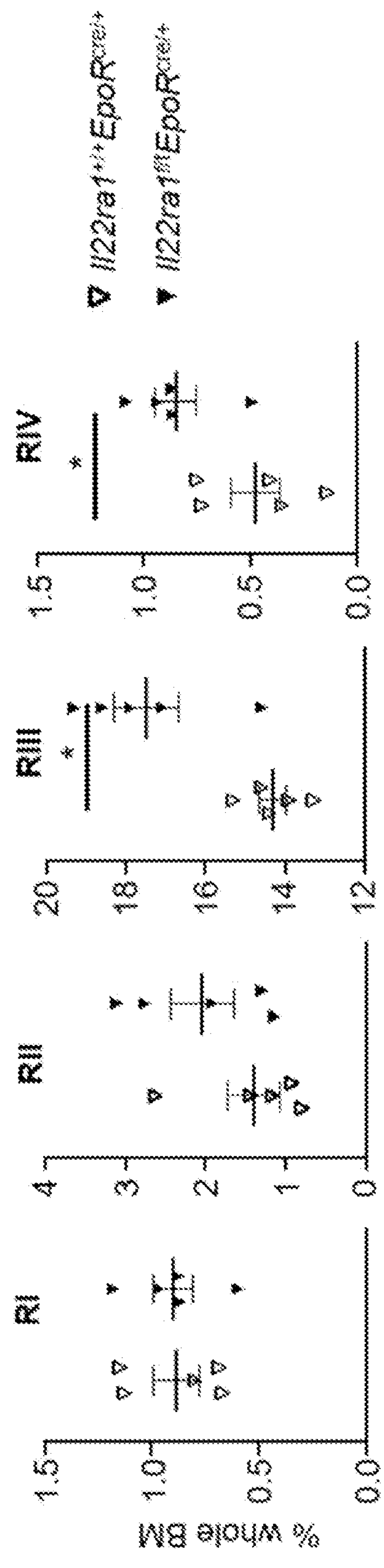

FIG. 9A-FIG. 9E show that genetic deletion of IL-22RA1 alleviates anemia in Riok2 haploinsufficient mice. FIG. 9A shows IL-22RA1 expression on erythroid progenitors in wild-type (wt) mice as assessed by flow cytometry using antibody from Novus Biologicals targeting the extracellular domain of IL-22RA1. FIG. 9B shows PB RBC numbers, Hb, and HCT in the indicated strains undergoing PhZ-induced stress erythropoiesis (n=5-6/group). FIG. 9C shows frequency of erythroid progenitor populations among viable bone marrow cells in the indicated strains undergoing PhZ-induced stress erythropoiesis (n=5/group). FIG. 9D shows PB RBC numbers, Hb, and HCT in the indicated strains undergoing PhZ-induced stress erythropoiesis (n=6/group). FIG. 9E shows frequency of erythroid progenitor populations among viable bone marrow cells in the indicated strains undergoing PhZ-induced stress erythropoiesis (n=5/group). Unpaired two-tailed t-test (FIGS. 9D and 9E and 1-way ANOVA with Tukey's correction for multiple comparison (FIGS. 9B and 9C) used to calculate statistical significance. * $p<0.05$. Data are shown as mean±s.e.m and are representative of two (FIGS. 9D and 9E) or three (FIG. 9A-9C) independent experiments. The presence of the IL-22RA1 receptor on erythroid progenitors has not been previously discovered and is an important component of the use of IL-22 signaling blockade.

Figures 10A, 10B, 10C:
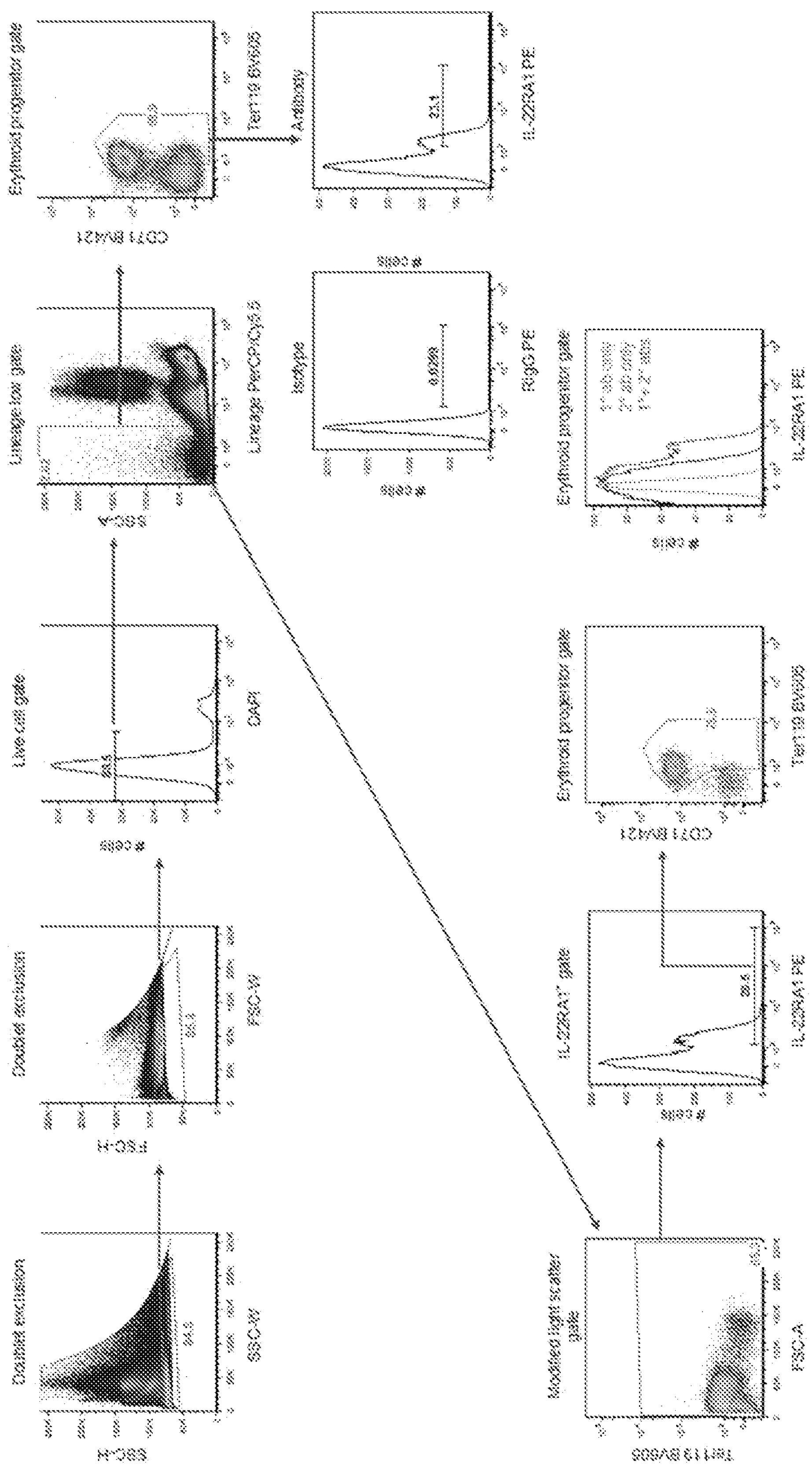

FIG. 10A-FIG. 10C show that erythroid progenitors express IL-22RA1. FIG. 10A shows a gating strategy employed for assessing IL-22RA1 expression by erythroid progenitors. FIG. 10B shows a gating strategy to show that majority of IL-22RA1+ cells in the mouse BM are erythroid progenitors. FIG. 10C shows IL-22RA1 expression on erythroid progenitors assessed using flow cytometry and a second antibody targeting a different epitope.

Figures 11A, 11B, 11C, 11D:
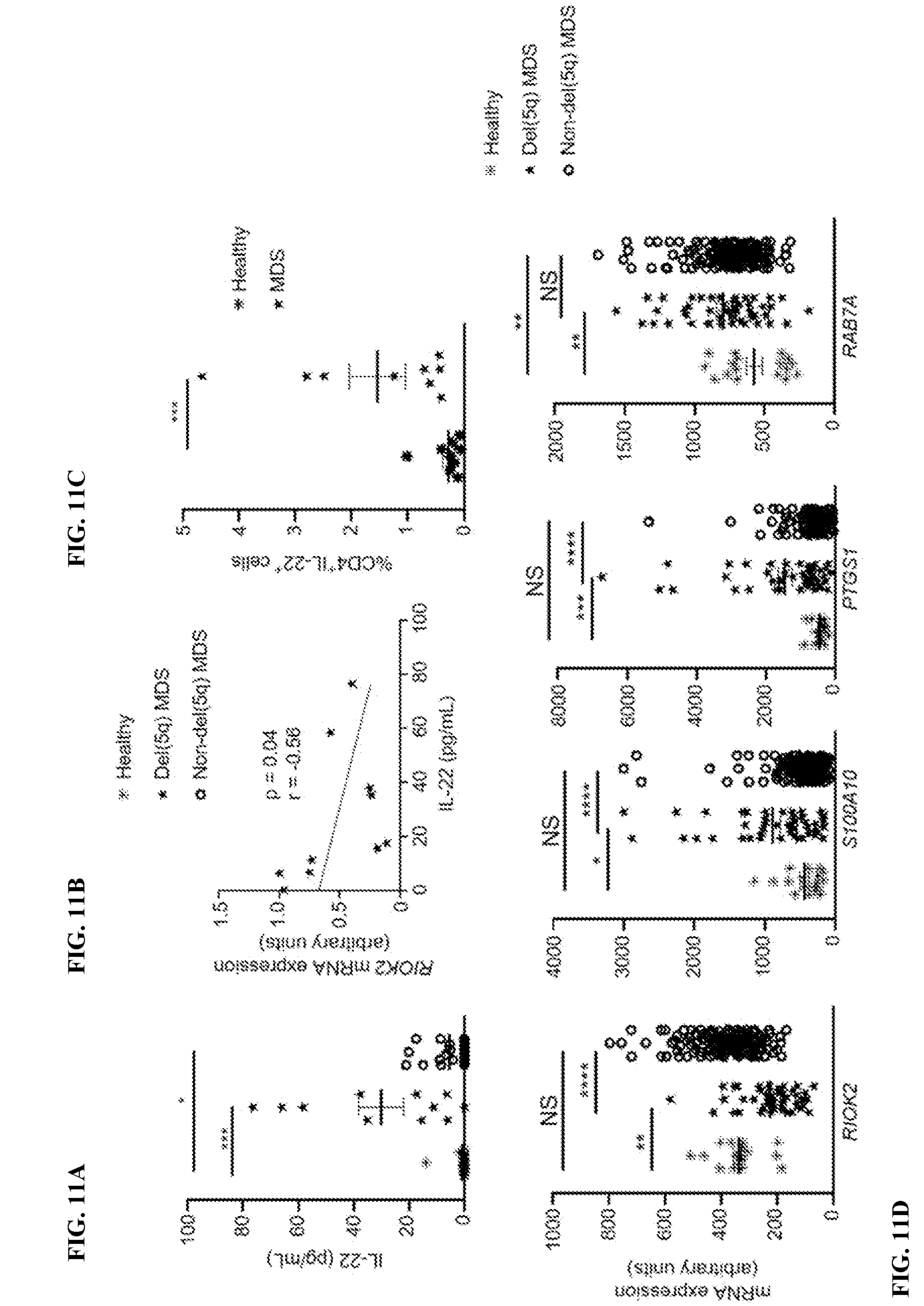
Figure 11E:
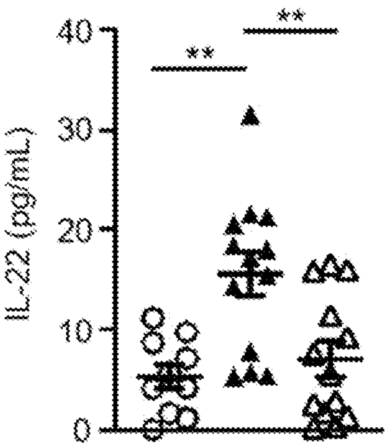
Figure 11F:
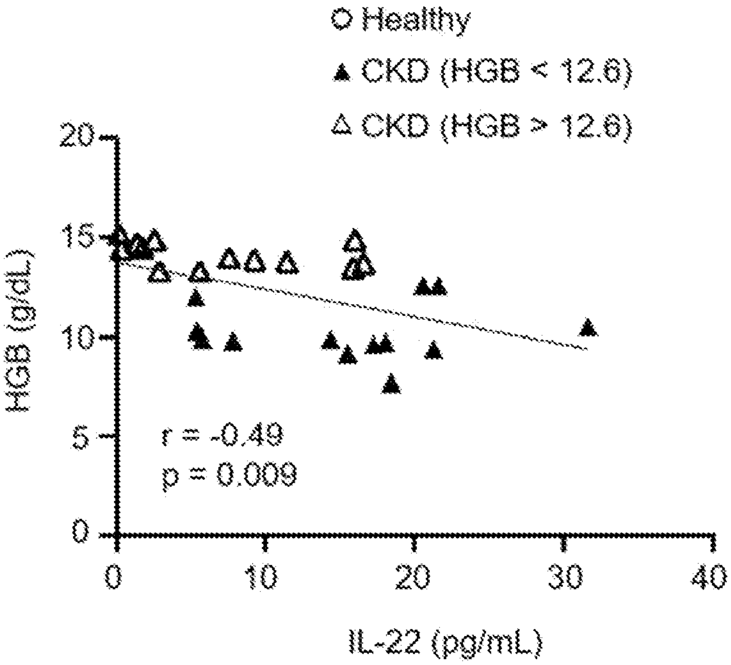

FIG. 11A-FIG. 11F shows that MDS patients exhibit increased IL-22 levels and IL-22 associated signature. FIG. 11A shows IL-22 concentration in the BM fluid of healthy controls and del(5q) and nondel(5q) MDS patients. FIG. 11B shows correlation between RIOK2 mRNA and IL-22 concentration in the del(5q) cohort shown in FIG. 11A. FIG. 11C shows frequency of IL-22 producing CD4 T cells in the PB of healthy controls and MDS patients. FIG. 11D shows expression of IL-22 signature genes in CD34+ cells from healthy controls and del(5q) and nondel(5q) MDS patients. FIG. 11E shows plasma IL-22 concentration in healthy subjects and CKD patients with or without secondary anemia. FIG. 11F shows correlation between IL-22 concentration and hemoglobin levels in CKD patients shown in FIG. 11E. r denotes Pearson correlation coefficient. Unpaired two-tailed t-test (FIG. 11C) and 1-way ANOVA with Tukey's correction for multiple comparison (FIGS. 11A and 11D) used to calculate statistical significance. * $p<0.05$,  $p<0.01$, * $p<0.001$, **** $p<0.0001$.

Figure 12:
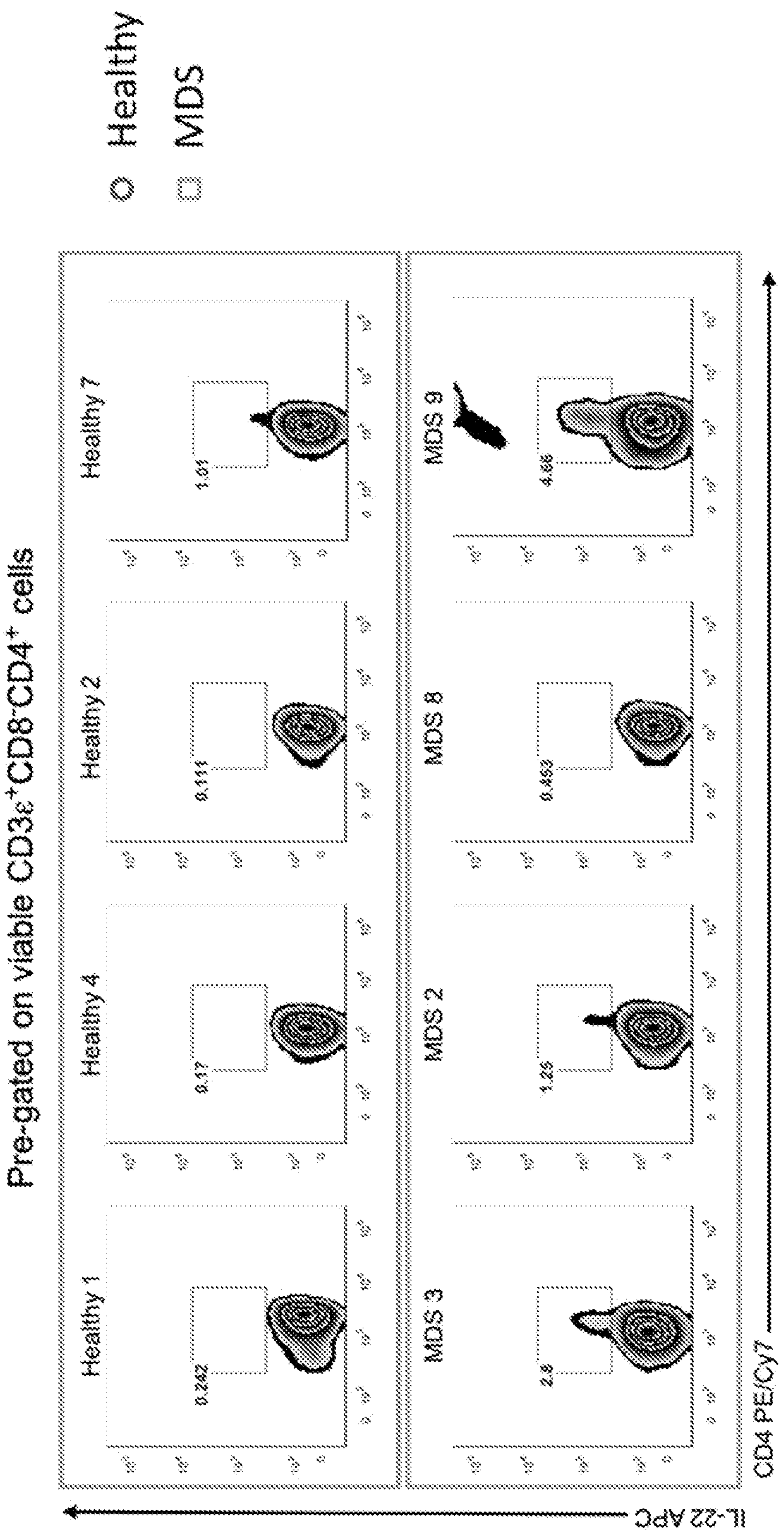

FIG. 12 shows increased frequency of IL-22+CD4+ cells in MDS subjects. The figure shows frequency of CD4+IL-22+ cells among total PBMCs in the peripheral blood of MDS patients and healthy subjects.

Figure 13:
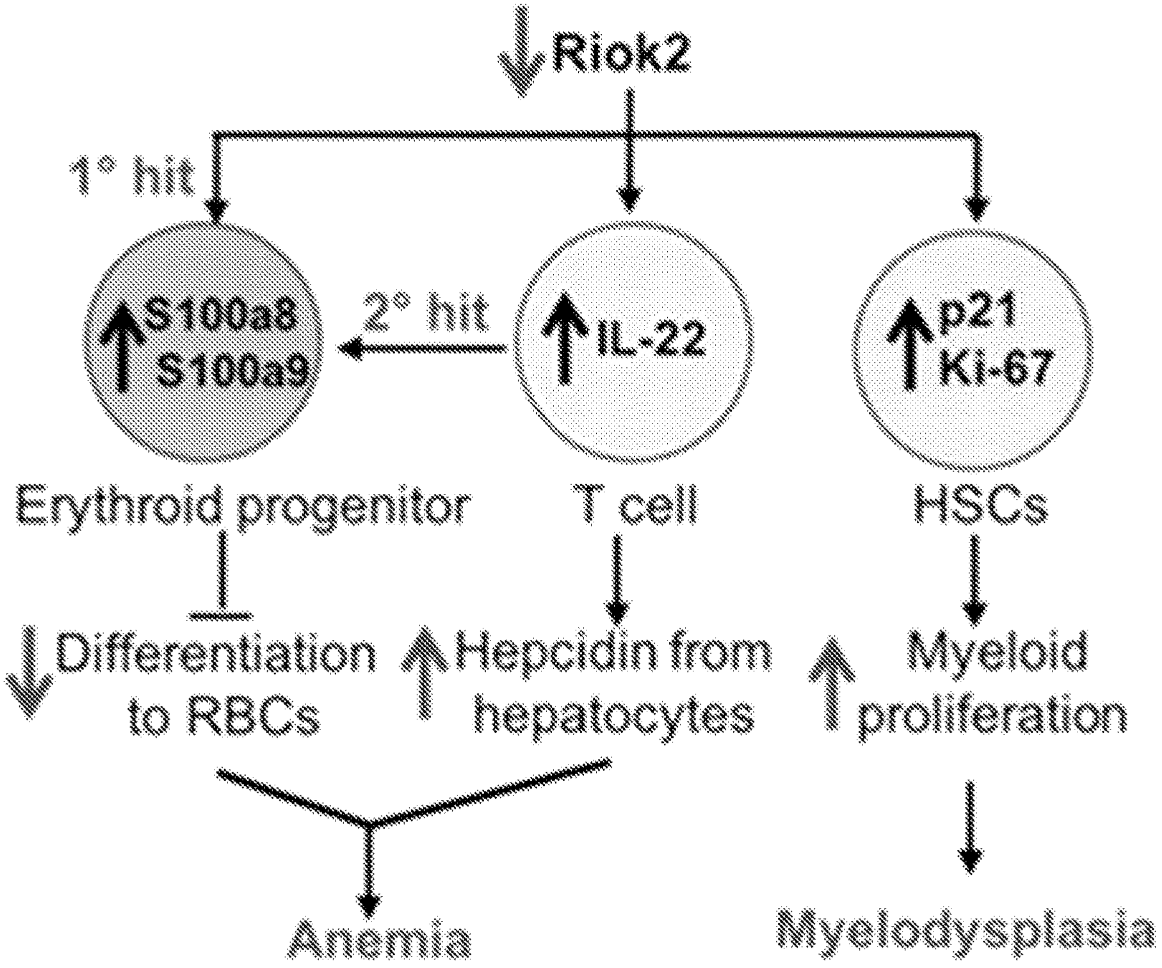

FIG. 13 is a chart showing some of the functions of IL-22 in progenitor and immune cells.

Figure 14A:
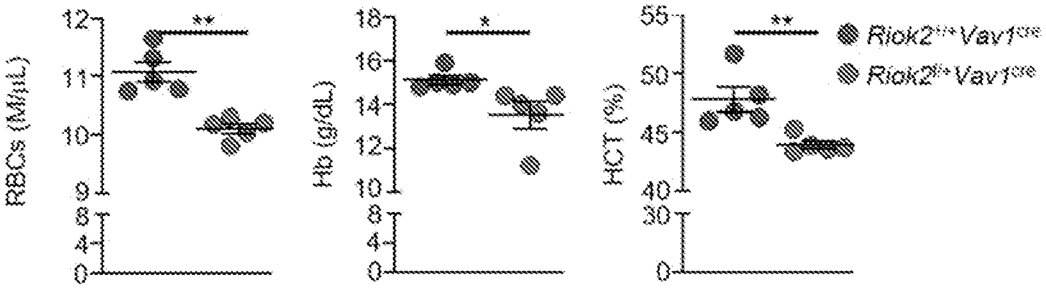
Figure 14B:
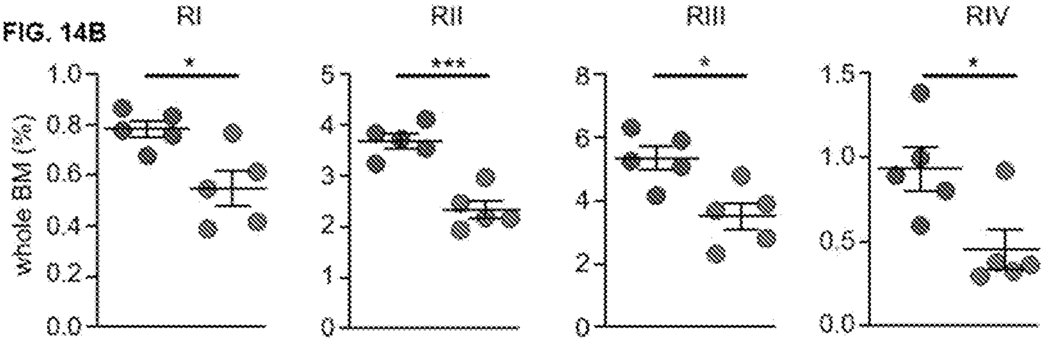
Figure 14C:
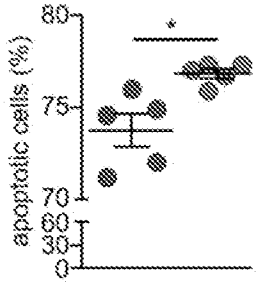
Figure 14D:
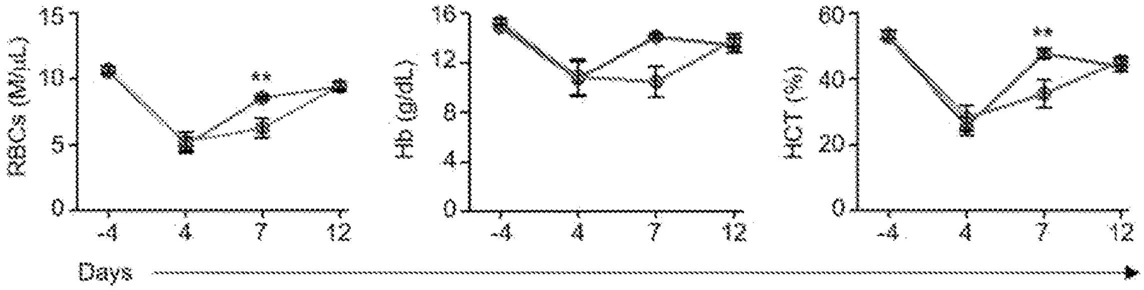
Figure 14E:
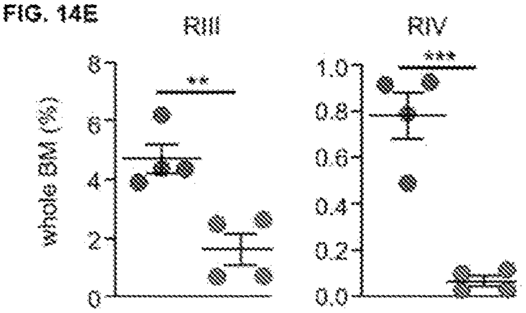
Figure 14F:
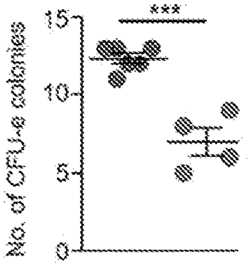
Figure 14G:
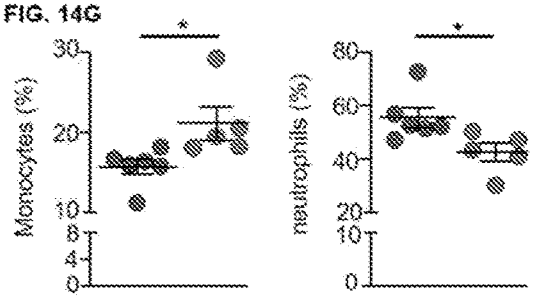
Figure 14H:
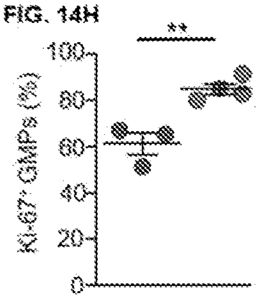
Figure 14I:
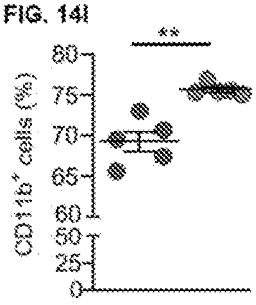

FIG. 14A-FIG. 14I show that Riok2 haploinsufficient (Riok2$^{fl/+}$Vav1$^{cre}$) mice display anemia and myeloproliferation. FIG. 14A shows peripheral blood (PB) RBC numbers, hemoglobin (Hb), and hematocrit (HCT) in Riok2$^{fl/+}$Vav1$^{cre}$ mice in comparison to Riok2$^{+/+}$Vav1$^{cre}$ controls (n=5/group). FIG. 14B shows frequency of erythroid progenitor/precursor populations among viable bone marrow (BM) cells in Riok2$^{fl/+}$Vav1$^{cre}$ mice and Riok2$^{+/+}$Vav1$^{cre}$ controls (n=5/group). FIG. 14C shows frequency of apoptotic erythroid precursors among viable BM cells in Riok2$^{fl/+}$Vav1$^{cre}$ mice and Riok2$^{+/+}$Vav1$^{cre}$ controls (n=5/group). FIG. 14D shows PB RBC numbers, Hb, and HCT in Riok2$^{fl/+}$Vav mice and Riok2$^{+/+}$Vav1$^{cre}$ controls undergoing phenylhydrazine (PhZ)-induced stress erythropoiesis (n=7/group). FIG. 14E shows frequency of RIII and RIV erythroid precursor populations among viable BM cells in Riok2$^{fl/+}$Vav1$^{cre}$ mice and Riok2$^{+/+}$Vav1$^{cre}$ controls day 6 after PhZ treatment (n=4/group). FIG. 14F shows number of CFU-e colonies in Epo-containing MethoCult assay using Lin$^{-}$c-kit$^{+}$CD71$^{+}$ cells from Riok2$^{fl/+}$Vav1$^{cre}$ mice (n=4) in comparison to Riok2$^{+/+}$Vav1$^{cre}$ controls (n=6). FIG. 14G shows percentage of monocytes (CD11b$^{+}$Ly6G$^{-}$Ly6C$^{hi}$) and neutrophils ($CD11b^+Ly6G^+$) in the PB of $Riok2^{f/+}Vav1^{cre}$ mice (n=6) in comparison to $Riok2^{+/+}Vav1^{cre}$ controls (n=5). FIG. 14H shows Percentage of $Ki\text{-}67^+$ granulocyte-macrophage progenitors (GMPs) in the BM of $Riok2^{f/+}Vav1^{cre}$ mice (n=3) and $Riok2^{+/+}Vav1^{cre}$ controls (n=4). FIG. 14I shows Percentage of $CD11b^+$ cells obtained from $Lin^-Sca\text{-}1^+c\text{-}kit+$ BM cells from $Riok2^{f/+}Vav1^{cre}$ mice and $Riok2^{+/+}Vav1^{cre}$ controls cultured in MethoCult for 7 days (n=5/group). Unpaired two-tailed t-test (FIG. 14A to C, E to I) and 1-way ANOVA with Tukey's correction for multiple comparisons (FIG. 14D) used to calculate statistical significance. * p<0.05,  p<0.01, * p<0.001. Data are shown as mean±s.e.m and are representative of two (FIG. 14C, D, F-H) or three (FIG. 14A, B, E, I) independent experiments.

Figure 15A:
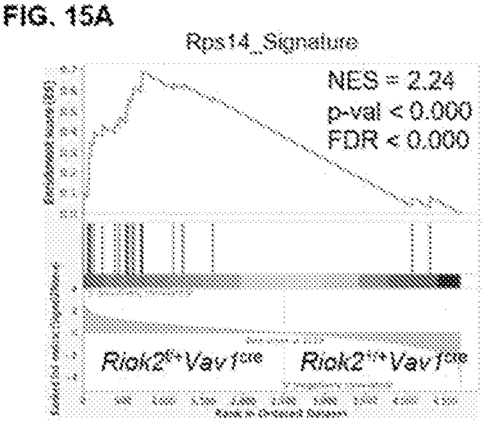
Figure 15B:
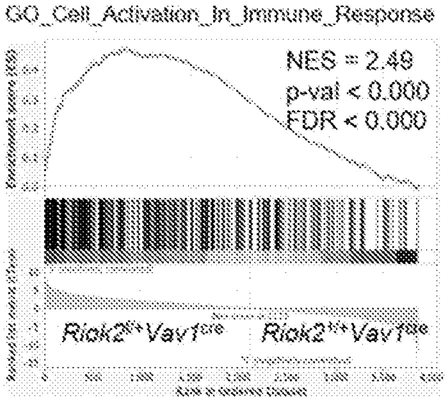
Figure 15C:
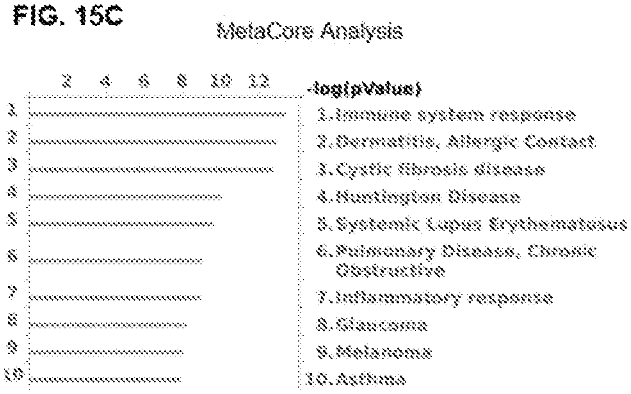
Figure 15D:
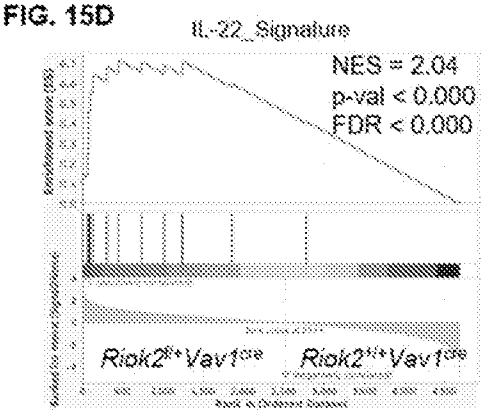

FIG. 15A-FIG. 15D show quantitative proteomics of Riok2 haploinsufficient erythroid precursors reveals immune activation signatures. FIG. 15A to C show GSEA performed on proteomics data shown in FIG. 4A to reveal similarity with Rps14 haploinsufficient data (FIG. 15A), activation of immune response (FIG. 15B) and enrichment of IL-22 signature genes (FIG. 15C). NES=Normalized enrichment score, FDR=False discovery rate. FIG. 15D shows MetaCore analysis of the Riok2 proteomics dataset shown in FIG. 4A. Two sample moderated t-test with multiple hypothesis corrections used to calculate the statistical significance in FIG. 4B.

Figure 16A:
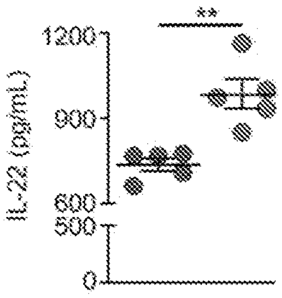
Figure 16B:
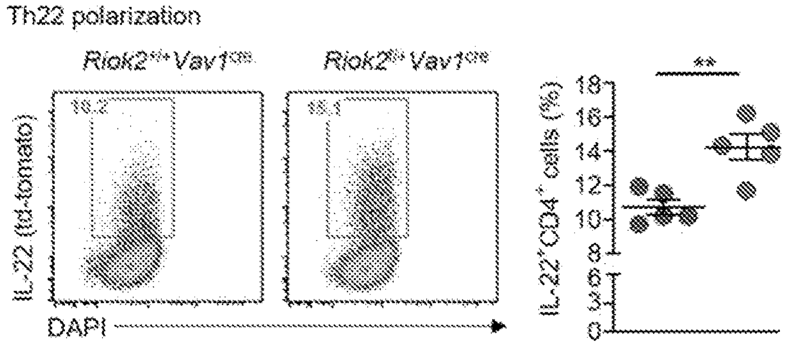
Figure 16C:
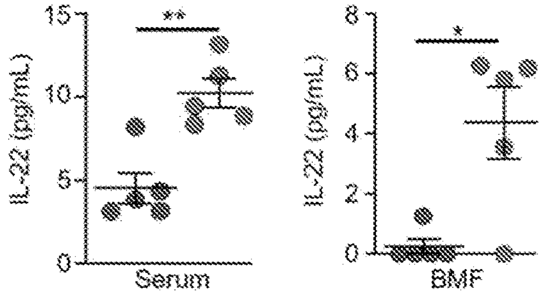
Figure 16D:
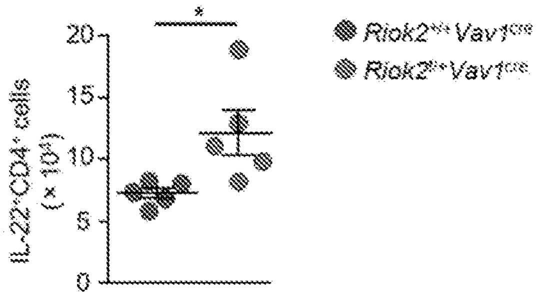
Figure 16E:
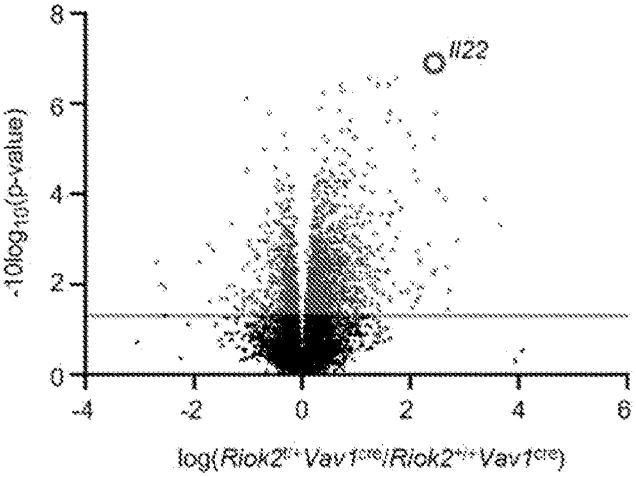
Figure 16F:
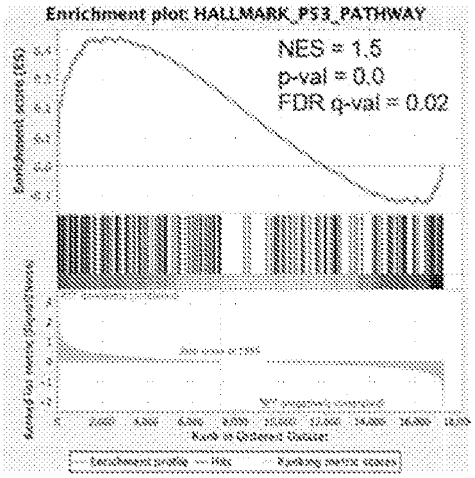
Figure 16G:
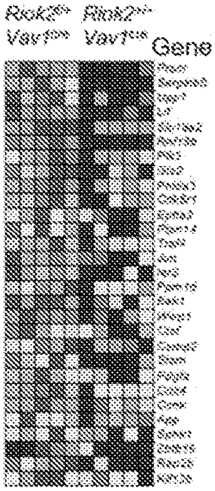
Figure 16H:
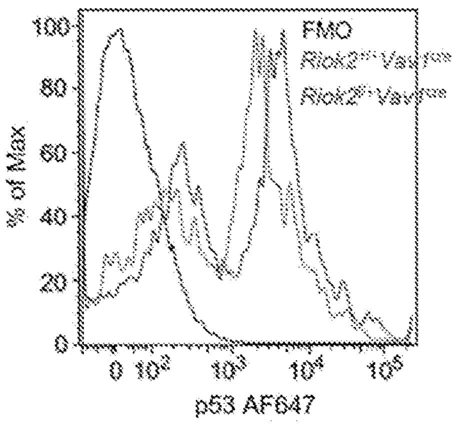
Figure 16I:
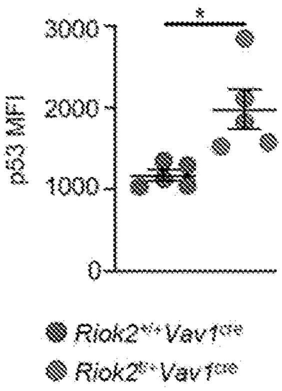
Figure 16J:
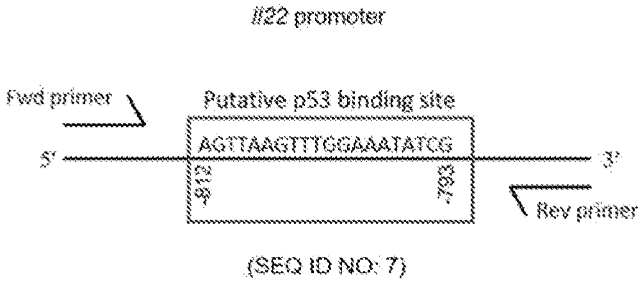
Figure 16K:
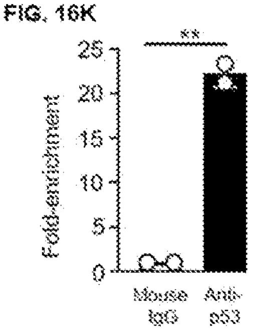
Figure 16L:
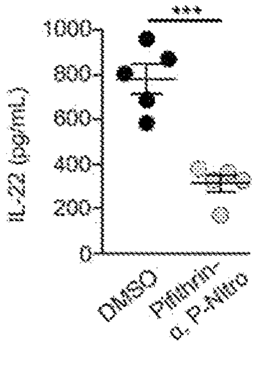
Figure 16M:
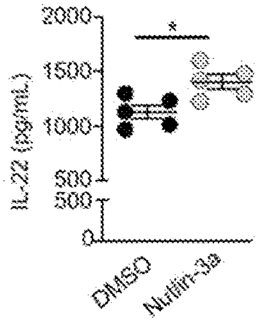
Figure 16N:
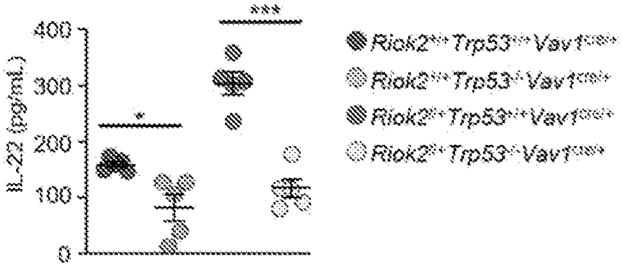

FIG. 16A-FIG. 16N show Riok2 haploinsufficiency-driven p53 upregulation drives increased IL-22. FIG. 16A shows secreted IL-22 and FIG. 16B shows percentage of $IL\text{-}22^+CD4^+$ T cells from in vitro polarized $T_H22$ cells from $Riok2^{f/+}Vav1^{cre}$ mice and $Riok2^{+/+}Vav1^{cre}$ controls (n=5/group). FIG. 16C shows IL-22 levels in the serum (left) and bone marrow fluid (BMF) (right) in $Riok2^{f/+}Vav1^{cre}$ mice and $Riok2^{+/+}Vav1^{cre}$ controls (n=5/group). FIG. 16D shows number of $IL\text{-}22^+CD4^+$ cells in the spleens of $Riok2^{f/+}Vav1^{cre}$ mice and $Riok2^{+/+}Vav1^{cre}$ controls (n=5/group). FIG. 16E shows Volcano plot showing transcriptomic changes in purified $IL\text{-}22^+$ cells from $Riok2^{f/+}Vav1^{cre}$ mice in comparison to $Riok2^{+/+}Vav1^{cre}$ controls. n=5/group. FIG. 16F shows GSEA analysis showing activation of the p53 pathway in $IL\text{-}22^+$ cells from $Riok2^{f/+}Vav1^{cre}$ mice in comparison to $Riok2^{+/+}Vav1^{cre}$ controls. FIG. 16G shows Snapshot of differentially expressed genes in the p53 pathway shown in (FIG. 16F) in $Riok2^{f/+}Vav1^{cre}$ and $Riok2^{+/+}Vav1^{cre}$ mice. FIG. 16H shows flow cytometry plot showing p53 expression in in vitro polarized $T_H22$ cells from $Riok2^{f/+}Vav1^{cre}$ and $Riok2^{+/+}Vav1^{cre}$ controls. FIG. 16I shows graphical representation of data shown in (FIG. 16H). n=5/group. FIG. 16J shows predicted p53 binding site in the Il22 promoter region. SEQ ID NO: 7. AGTTAAGTTTGGAAATATCG. FIG. 16K shows chromatin immunoprecipitation showing p53 occupancy at the Il22 promoter in T cells. n=2 independent experiments. FIG. 16I shows secreted IL-22 from wt $T_H22$ cells cultured in the presence or absence of p53 inhibitor, pifithrin-α, p-nitro (1 μM). n=5 mice/group. FIG. 16M shows secreted IL-22 from WT $T_H22$ cells cultured in the presence or absence of p53 activator, Nutlin-3 (100 nM). n=4 mice/group. FIG. 16N shows secreted IL-22 from in vitro polarized $T_H22$ cells from the indicated strains. n=5/group. Unpaired two-tailed t-test (FIG. 16A to D, I, K-M) and 1-way ANOVA with Tukey's correction for multiple comparison (n) used to calculate statistical significance. * p<0.05,  p<0.01, * p<0.001. Data are shown as mean±s.e.m and are representative of two (FIG. 16C-D, H, I, K-N) or three (FIG. 16A, B) independent experiments. Data in (FIG. 16K) is represented as mean±s.d. and is pooled from two independent experiments.

Figure 17A:
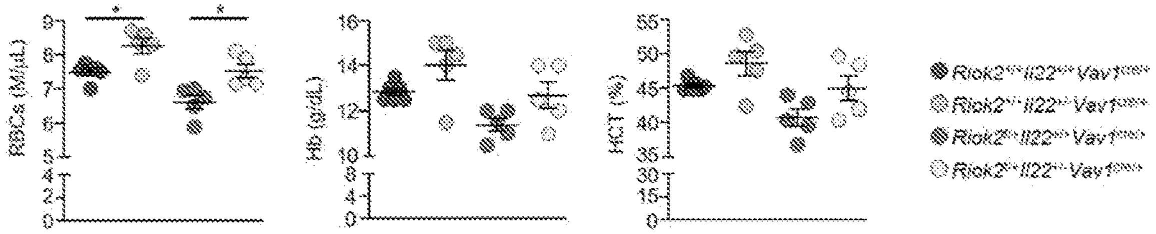
Figure 17B:
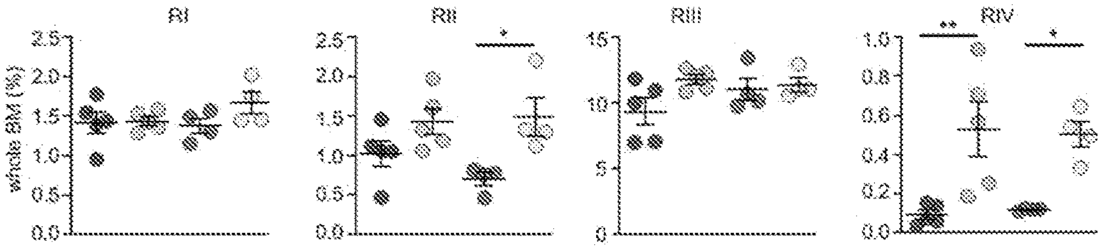
Figure 17C:
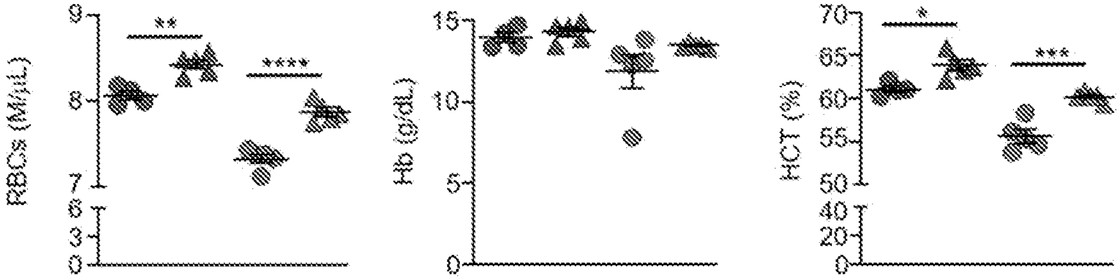
Figure 17D:
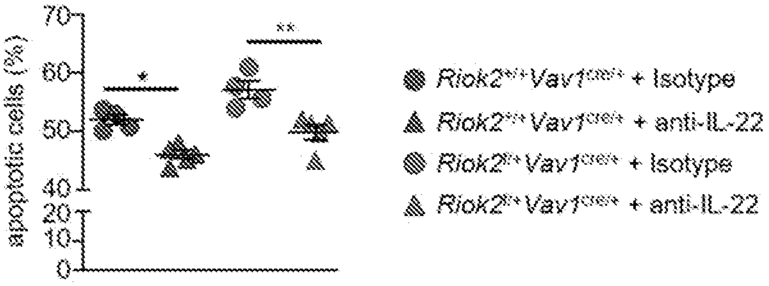

FIG. 17A-FIG. 17D show IL-22 neutralization alleviates stress-induced anemia in Riok2 sufficient and haploinsufficient mice. FIG. 17A shows PB RBC numbers, Hb, and HCT in the indicated strains undergoing PhZ-induced stress erythropoiesis. n=6,5,5, and 5 mice for $Riok2^{+/+}Il22^{+/+}Vav1^{cre}$, $Riok2^{+/+}Il22^{+/+}Vav1^{cre}$, $Riok2^{f/+}Il22^{+/+}Vav1^{cre}$, $Riok2^{f/+}Il22^{+/-}Vav1^{cre}$ respectively. FIG. 17B shows frequency of erythroid progenitor/precursor populations among viable BM cells in the indicated strains undergoing PhZ-induced stress erythropoiesis (n=4-5/group). FIG. 17C shows PB RBC numbers, Hb, and HCT in $Riok2^{f/+}Vav1^{cre}$ mice and $Riok2^{+/+}Vav1^{cre}$ controls undergoing PhZ-induced stress erythropoiesis treated with either an isotype control or anti-IL-22 antibody (n=4-5/group). FIG. 17D shows frequency of apoptotic erythroid precursors among viable BM cells in $Riok2^{f/+}Vav1^{cre}$ mice and $Riok2^{+/+}Vav1^{cre}$ controls undergoing PhZ-induced stress erythropoiesis treated with either an isotype control or anti-IL-22 antibody. n=4,5,4, and 5 mice for isotype-treated $Riok2^{+/+}Vav1^{cre}$, anti-IL-22-treated $Riok2^{+/+}Vav1^{cre}$, isotype-treated $Riok2^{f/+}Vav1^{cre}$, and anti-IL-22-treated $Riok2^{f/+}Vav1^{cre}$ mice, respectively. 1-way ANOVA with Tukey's correction for multiple comparison (FIG. 17A to D) used to calculate statistical significance. * p<0.05,  p<0.01, * p<0.001, ** p<0.0001. Data are shown as mean±s.e.m and are representative of two (FIG. 17C, D) or three (FIG. 17**A, B) independent experiments.

Figure 18A:
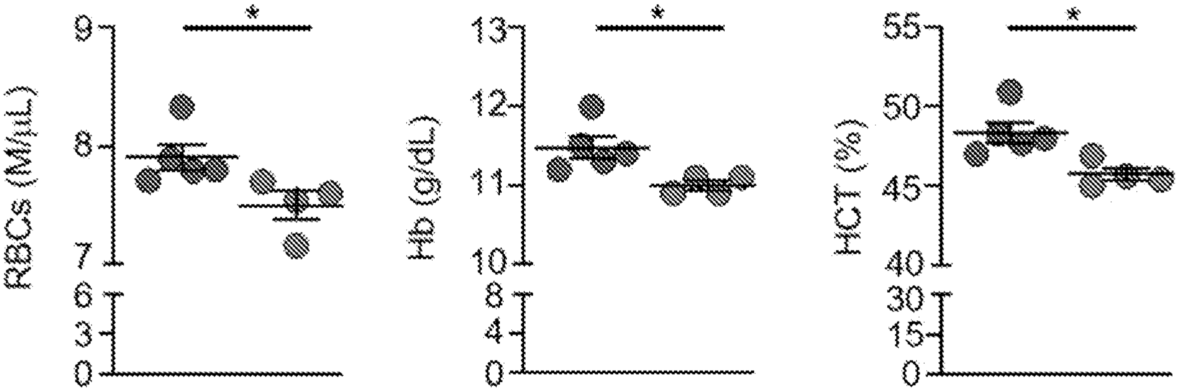
Figure 18B:
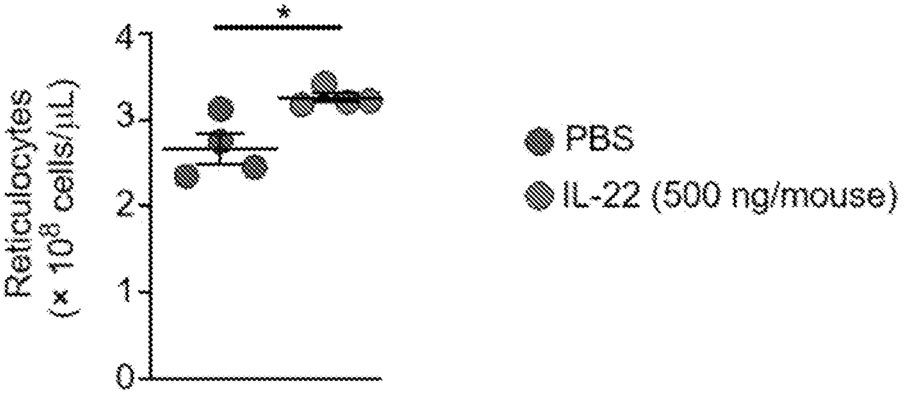
Figure 18C:
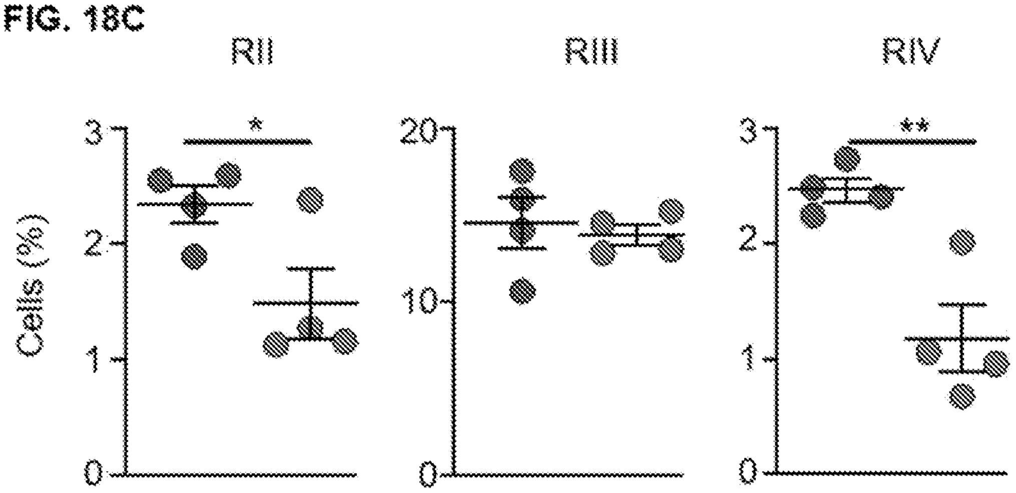
Figure 18D:
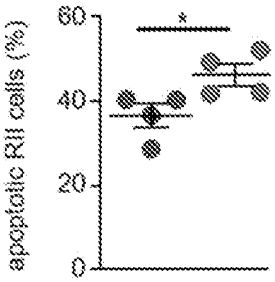
Figure 18E:
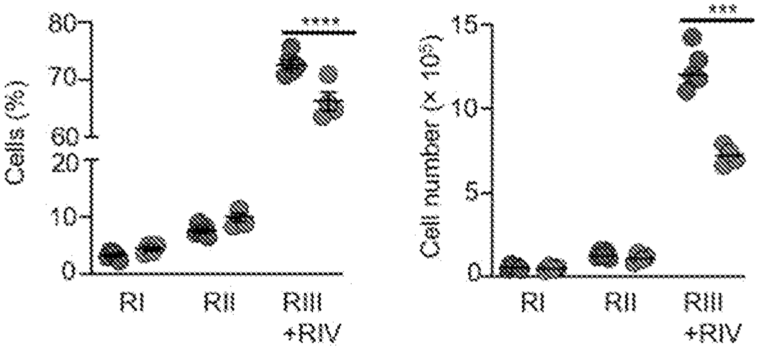
Figure 18F:
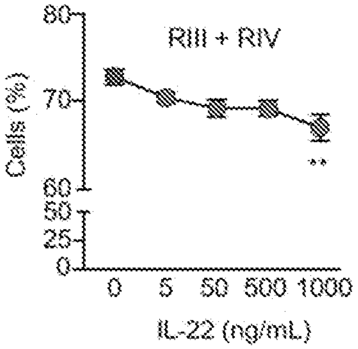
Figure 18G:
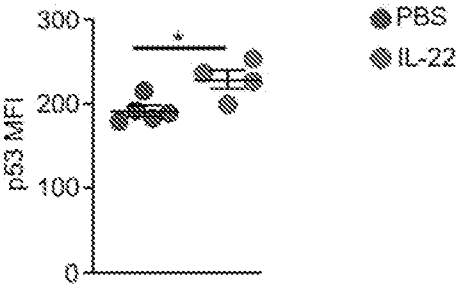

FIG. 18A-FIG. 18G show recombinant IL-22 exacerbates PhZ-induced anemia in wt mice. FIG. 18A shows PB RBC numbers, Hb, and HCT in wt C57BL/6J mice administered PBS (n=5) or rIL-22 (n=4) and subsequently treated with PhZ. n=4-5 mice/group. FIG. 18B shows PB reticulocytes in mice treated as in (FIG. 18A). n=4 mice/group. FIG. 18C shows percentage of RII-RIV erythroid precursors in the BM of PBS- or rIL-22-treated C57BL/6J mice 7 days after PhZ administration. n=4 mice/group. FIG. 18D shows percentage of apoptotic RH erythroid precursors in mice treated as in (FIG. 18C). n=4 mice/group. FIG. 18D shows effect of recombinant IL-22 (500 ng/mL) on the frequency (left) and cell number (right) in an in vitro erythropoiesis assay and FIG. 18F shows dose dependent effect of recombinant IL-22. n=5 and 4 for PBS and IL-22 groups, respectively. FIG. 18G shows p53 expression in in in vitro erythropoiesis culture treated with rIL-22 or PBS. n=5 and 4 mice for PBS and IL-22 groups, respectively. Data are shown as mean±s.e.m and are representative of three (FIG. 18A, B) or two (FIG. 18C to G) independent experiments. Unpaired two-tailed t-test (FIG. 18A to D, G), multiple unpaired two-tailed t-tests with Holm-Sidak method (FIG. 18E) and 1-way ANOVA with Tukey's correction for multiple comparisons (FIG. 18F) used to calculate statistical significance. * p<0.05,  p<0.01, * p<0.001, **** p<0.0001.

Figures 19A, 19B, 19C:
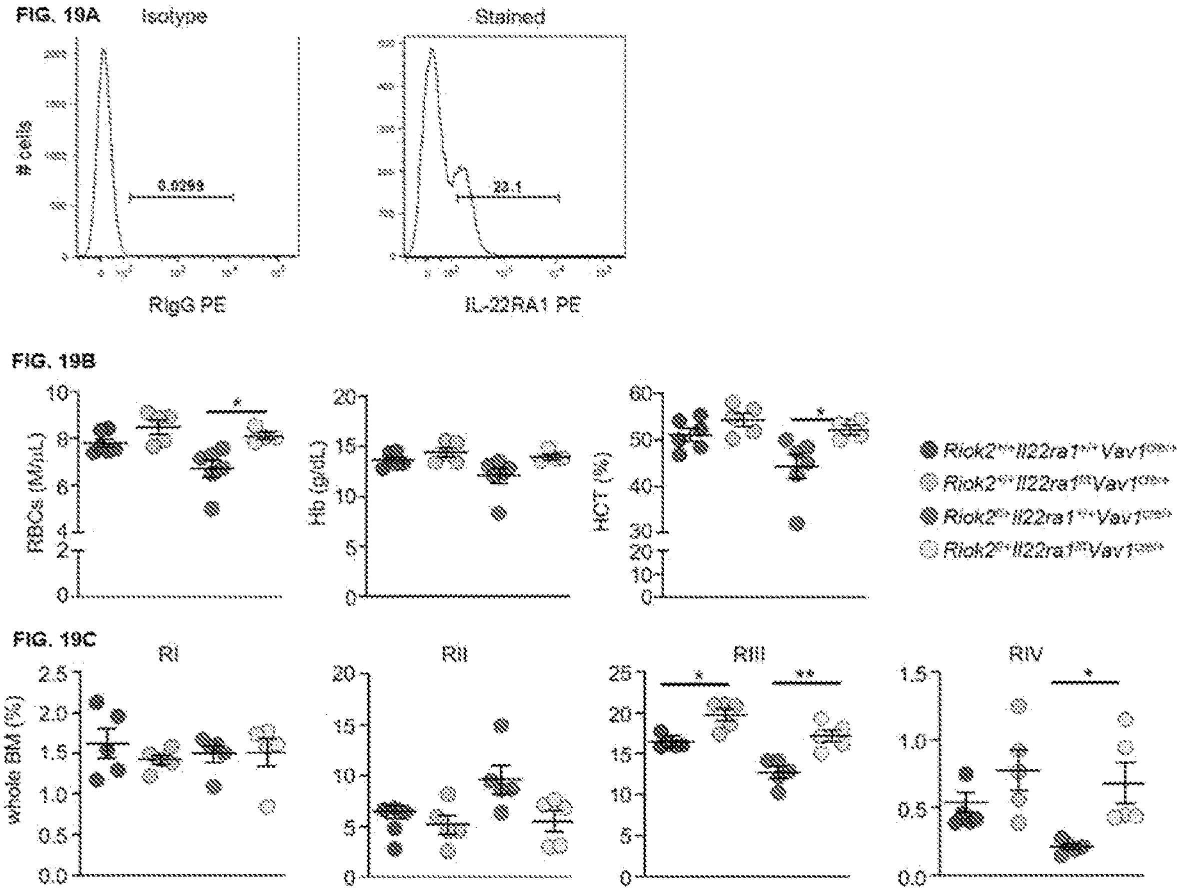
Figure 19D:
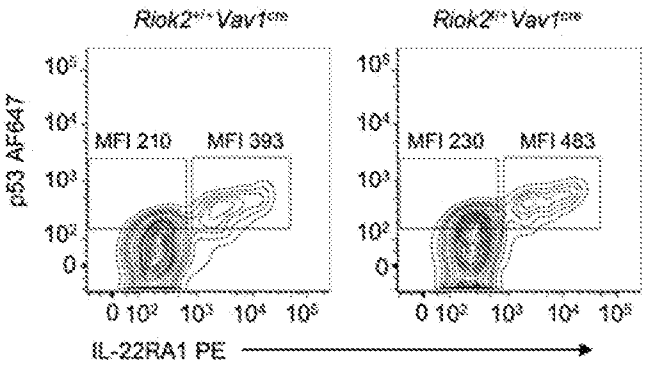
Figure 19E:
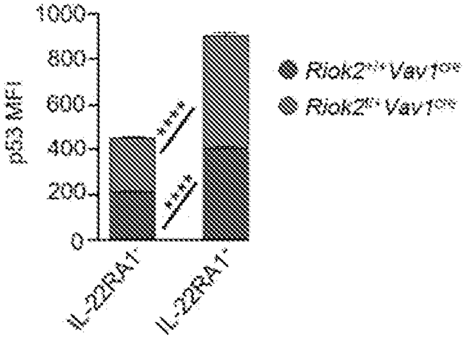
Figure 19F:
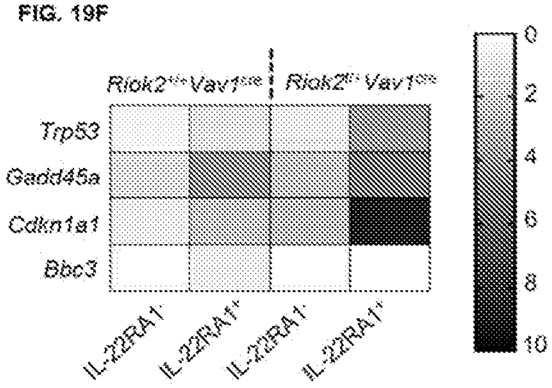
Figure 19G:
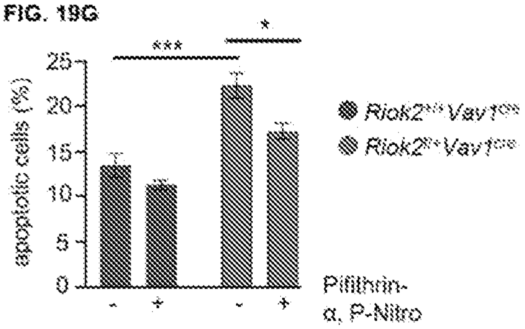

FIG. 19A-FIG. 19G show genetic deletion of Il22ra1 alleviates anemia in Riok2 haploinsufficient mice. FIG. 19A shows IL-22RA1 expression on BM erythroid precursors in wild-type (WT) mice assessed by flow cytometry using antibody from Novus Biologicals targeting the extracellular domain of IL-22RA1. FIG. 19B shows PB RBC numbers, Hb, and HCT in the indicated strains undergoing PhZ-induced stress erythropoiesis. n=6,5,6, and 4 mice for $Riok2^{+/+}Il22r1a^{+/+}Vav1^{cre}$, $Riok2^{+/+}Il22ra1^{f/f}Vav1^{cre}$, $Riok2^{f/+}Il22ra1^{+/+}Vav1^{cre}$, $Riok2^{f/+}Il22ra1^{f/f}Vav1^{cre}$, respectively. FIG. 19C shows frequency of erythroid progenitor/precursor populations among viable BM cells in the indicated strains undergoing PhZ-induced stress erythropoiesis (n=5/group). FIG. 19D shows flow cytometry plots showing p53 expression in $IL\text{-}22RA1^+$ and $IL\text{-}22RA1^-$ erythroid precursors in Riok2$^{f/+}$Vav1$^{cre}$ mice and Riok2$^{+/+}$Vav1$^{cre}$ controls. n=5/group. FIG. 19E shows graphical representation of data shown in (FIG. 19D). FIG. 19F shows gene expression of Trp53 (p53) and listed p53 target genes in IL-22RA1$^{+}$ and IL-22RA1$^{-}$ erythroid precursors from Riok2$^{f/+}$Vav1$^{cre}$ and Riok2$^{+/+}$Vav1$^{cre}$ mice assessed by qRT-PCR. n=3/group. FIG. 19G shows frequency of apoptotic cells (assessed by flow cytometry) with (n=4) or without (n=5) p53 inhibitor, pifithrin-α, p-nitro (1 μM), in an in vitro erythropoiesis assay using Lin$^{-}$ BM cells from Riok2$^{f/+}$ Vav1$^{cre}$ and Riok2$^{+/+}$Vav1$^{cre}$ mice. 2-way ANOVA with Tukey's correction for multiple comparisons (FIGS. 19E, G) and 1-way ANOVA with Tukey's correction for multiple comparison (FIGS. 19B, C) used to calculate statistical significance. * $p<0.05$,  $p<0.01$, * $p<0.001$, ** $p<0.0001$. Data are shown as mean±s.e.m and are representative of two (FIG. 19D-G) or three (FIG. 19**A to C) independent experiments.

Figure 20A:
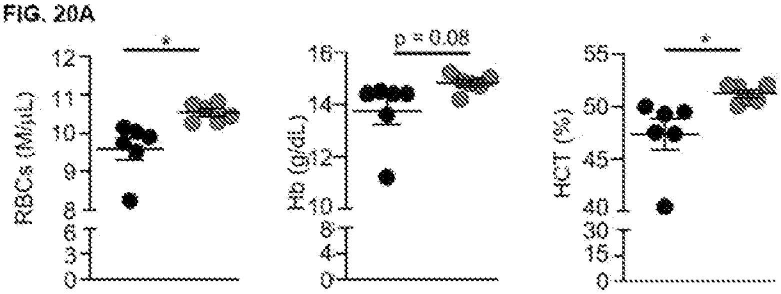
Figure 20B:
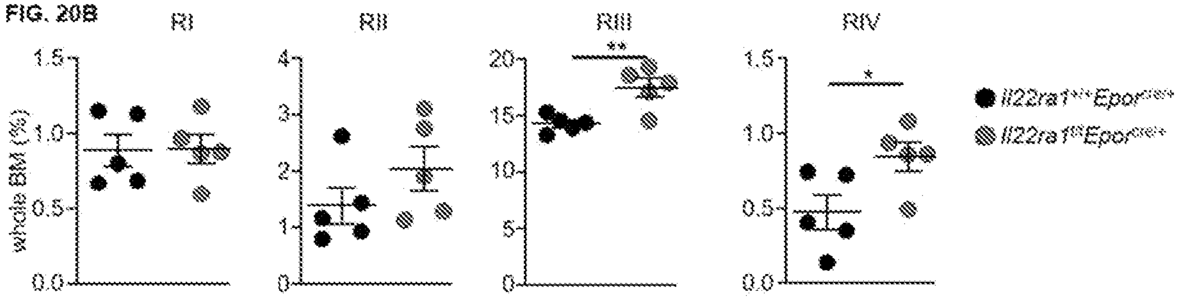
Figure 20C:
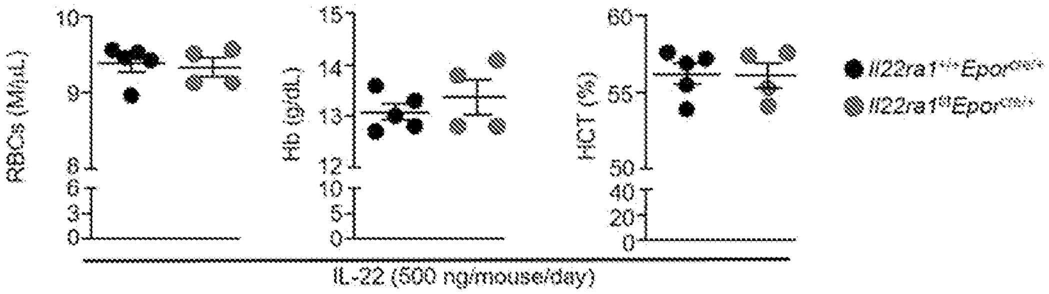

FIG. 20A-FIG. 20C show erythroid-specific deletion of IL-22RA1 alleviates stress-induced anemia. FIG. 20A shows PB RBC numbers, Hb, and HCT in the indicated strains undergoing PhZ-induced stress erythropoiesis (n=6/group). FIG. 20B shows frequency of erythroid progenitor/precursor populations among viable BM cells in the indicated strains undergoing PhZ-induced stress erythropoiesis (n=5/group). FIG. 20C shows PB RBC numbers, Hb, and HCT in Il22ra1$^{+/+}$Epor$^{cre}$ (n=5) and Il22ra1$^{fl/fl}$Epor$^{cre}$ (n=4) mice administered rIL-22 and subsequently treated with PhZ. n=4-5 mice/group. Unpaired two-tailed t-test (FIG. 20A-C) used to calculate statistical significance. * $p<0.05$, * $p<0.001$. Data are shown as mean±s.e.m and are representative of two (FIG. 20**A-C) independent experiments.

Figure 21A:
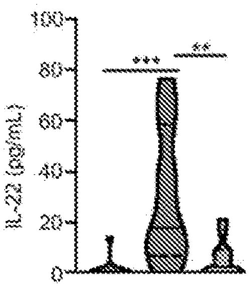
Figure 21B:
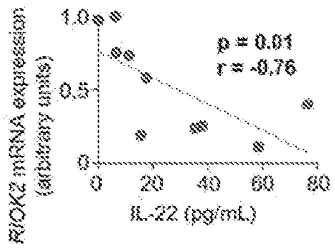
Figure 21C:
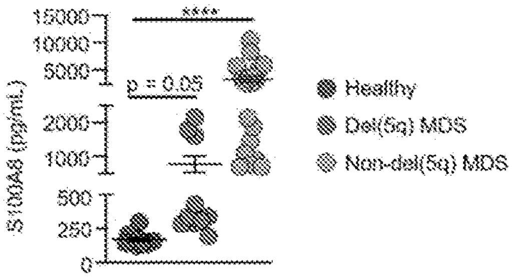
Figure 21D:
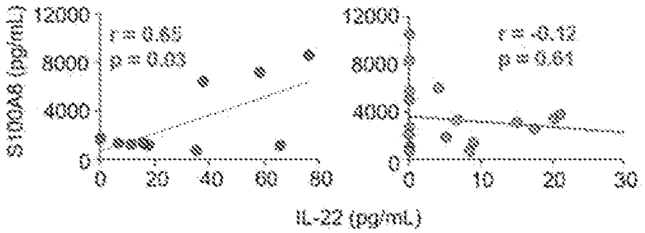
Figure 21E:
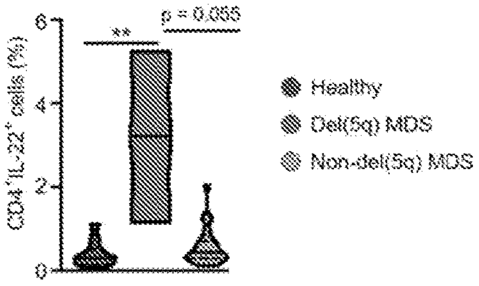
Figure 21F:
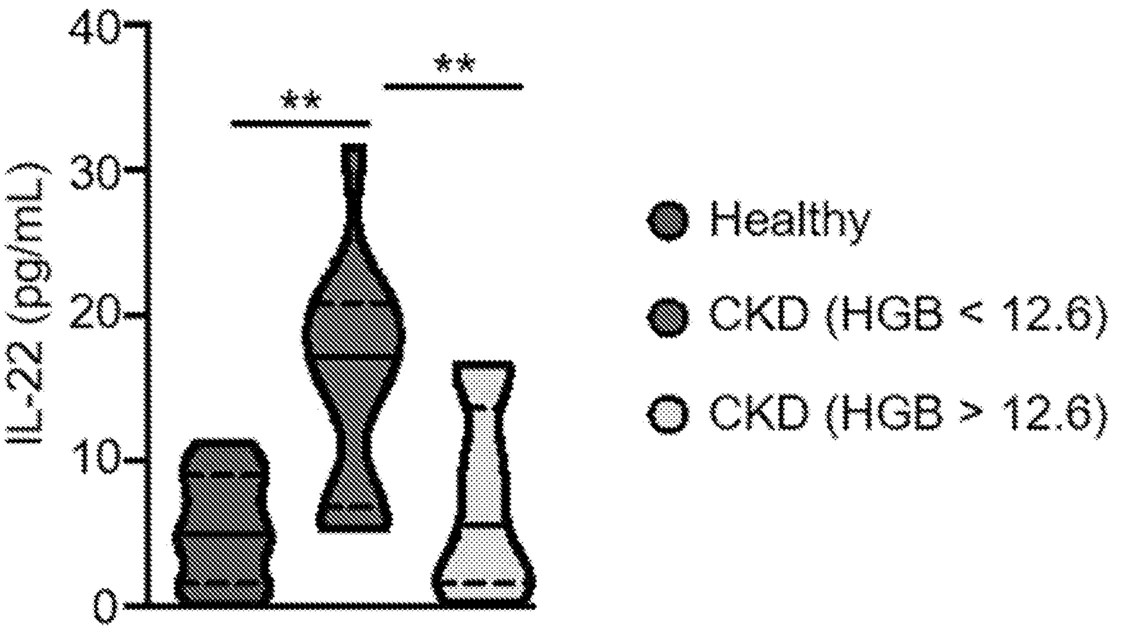
Figure 21G:
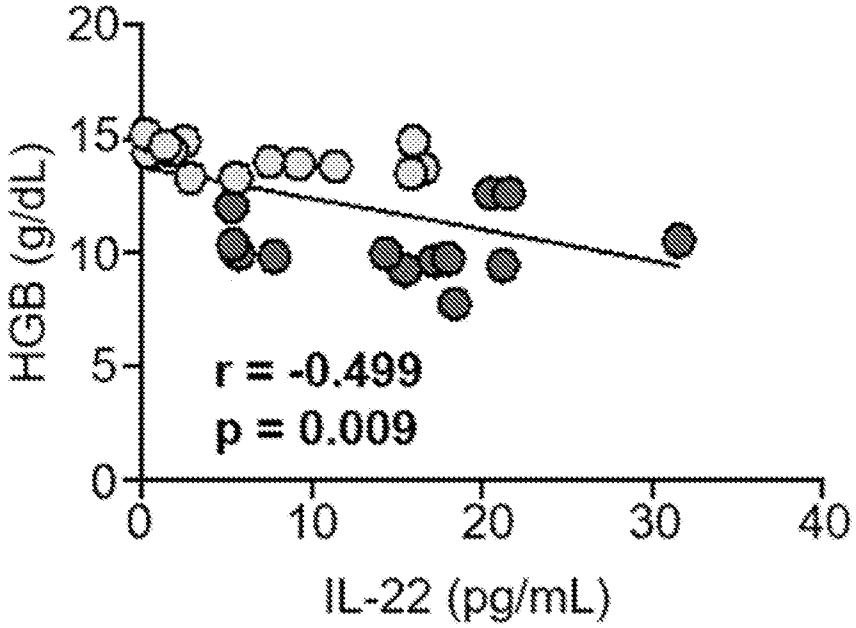

FIG. 21A-FIG. 21G show MDS patients exhibit increased IL-22 levels and IL-22 associated signature. FIG. 21A shows IL-22 concentration in the BM fluid of healthy controls (n=12), del(5q) MDS (n=11), and non-del(5q) MDS (n=22) patients. FIG. 21B shows correlation between RIOK2 mRNA and BM IL-22 concentration in the del(5q) cohort shown in (a), n=10. FIG. 21C shows S100A8 concentration in the samples shown in (a). n=11, 10, and 19 for healthy, del(5q) MDS, and non-del(5q) MDS, respectively. FIG. 21D shows correlation between IL-22 concentration and S100A8 concentration in BM fluid of del(5q) (left, n=10) and non-del(5q) (right, n=19) samples. FIG. 21E shows frequency of IL-22 producing CD4$^{+}$ T cells in the PB of healthy controls (n=11), del(5q) (n=3) and non-del(5q) (n=24) MDS patients. FIG. 21F shows plasma IL-22 concentration in healthy subjects (n=10) and chronic kidney disease (CKD) patients with (n=13) or without (n=13) secondary anemia. FIG. 21G shows correlation between plasma IL-22 concentration and hemoglobin (HGB) in CKD patients with (n=13) or without (n=13) anemia. Kruskal-Wallis test with Dunn's correction for multiple comparisons (FIG. 21A to C, E), 1-way ANOVA with Tukey's correction for multiple comparisons (FIG. 21F) used to calculate statistical significance. Pearson correlation co-efficient (FIG. 21B, D, G), used to calculate statistical significance and correlation coefficient.  $p<0.01$, * $p<0.001$, ** $p<0.0001$. Data are shown as mean±s.e.m (FIG. 21C). Solid lines represent median and dashed lines represent quartiles (FIG. 21**A, E, F).

Figure 22A:
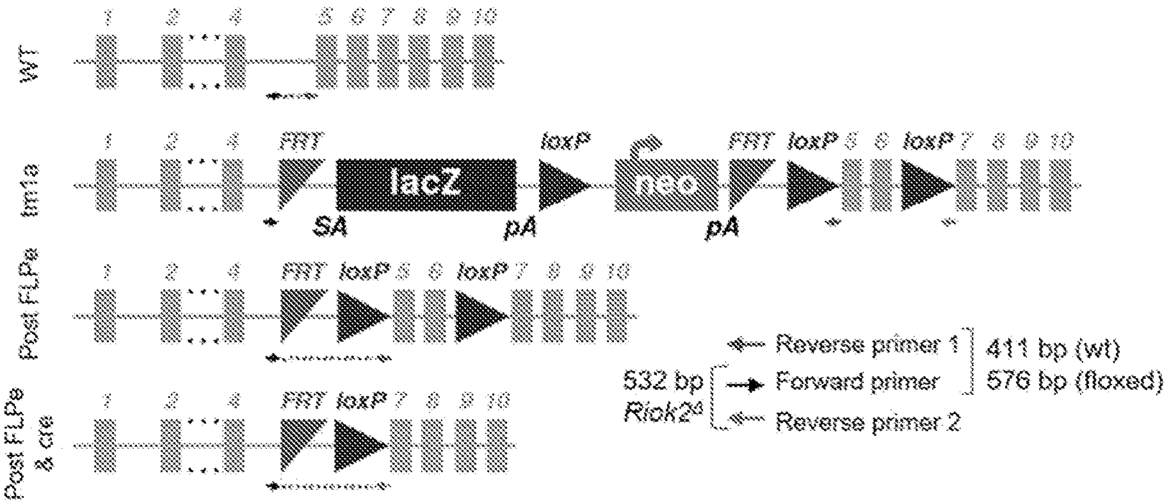
Figure 22B:
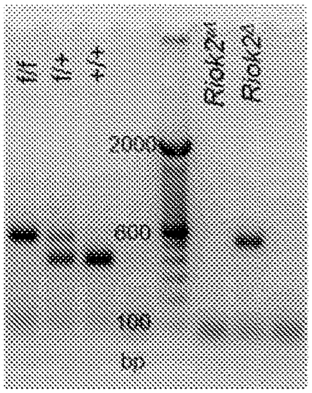
Figure 22C:
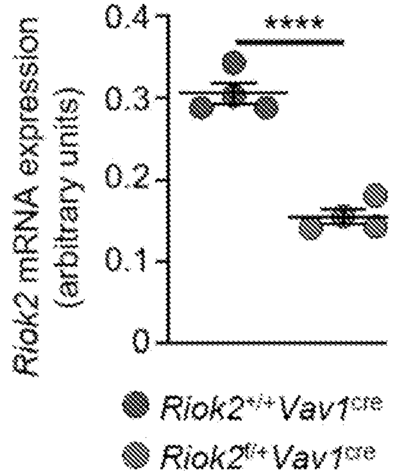
Figure 22D:
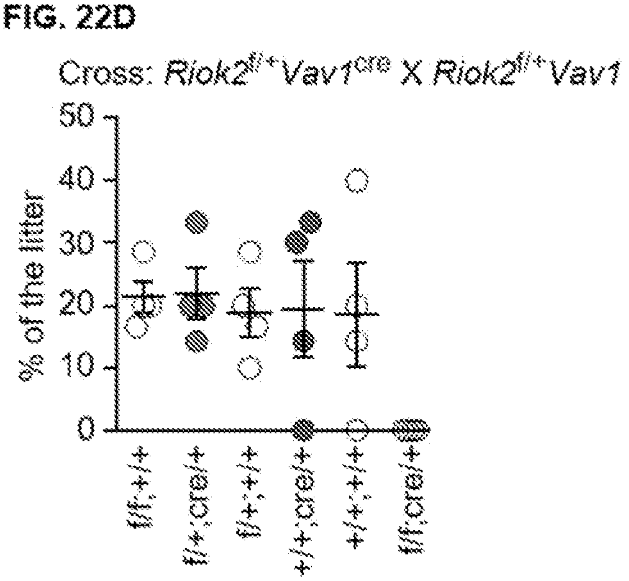
Figure 22E:
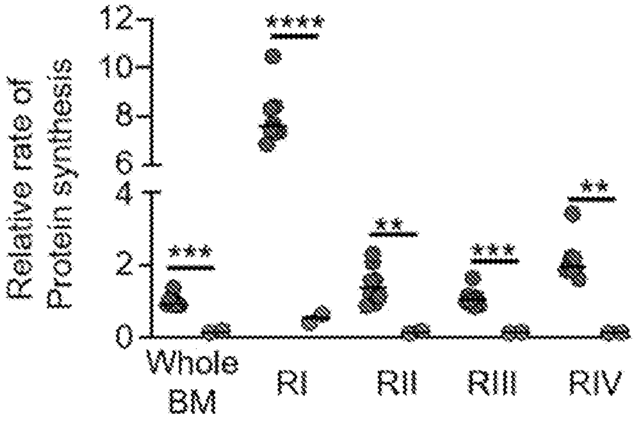

FIG. 22A-FIG. 22E show localization and expression of Riok2. FIG. 22A shows schematic representation of the Riok2$^{tm1a(KOMP)Wtsi}$ allele and generation of Riok2 foxed mice. FIG. 22B shows agarose gel showing genotyping of Riok2 foxed mice. Riok2$^{\Delta}$ indicates deletion of Riok2. No band expected in the Riok2$^{wt}$ lane. FIG. 22C shows Riok2 mRNA expression by qRT-PCR in BM cells from Riok2 haploinsufficient mice and Vav1$^{cre}$ controls. n=5 mice/group. FIG. 22D shows frequency of the genotypes indicated on the X-axis among 4 litters from 4 different breeding crosses of the genotypes mentioned. FIG. 22E shows in vivo protein synthesis rates in the indicated cell types from Riok2 haploinsufficient mice (n=2) and Vav1$^{cre}$ controls (n=8). Unpaired two-tailed t-test (FIG. 22C), multiple unpaired two-tailed t-tests with Holm-Sidak method (FIG. 22E) used to calculate statistical significance. Data are shown as mean±s.e.m (FIG. 22C, D) or mean±s.d. (FIG. 22E) and are representative of two (FIG. 22C, E) or four (FIG. 22B, D) independent experiments.  $p<0.01$, * $p<0.001$, **** $p<0.0001$.

Figure 23A:
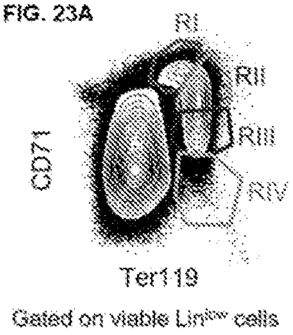
Figure 23B:
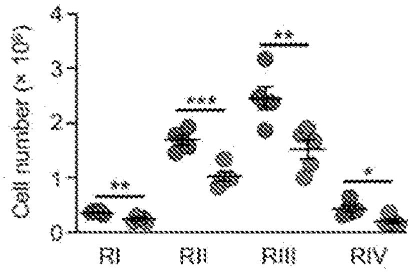
Figure 23C:
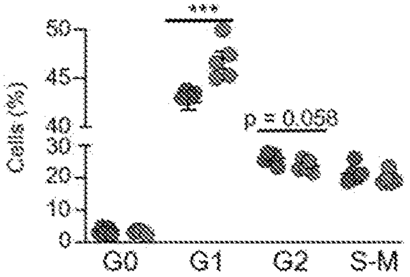
Figure 23D:
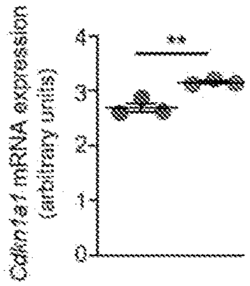
Figure 23E:
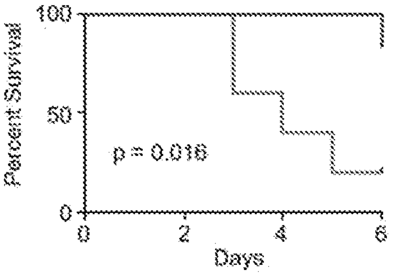
Figure 23E:
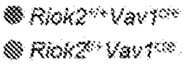
Figure 23F:
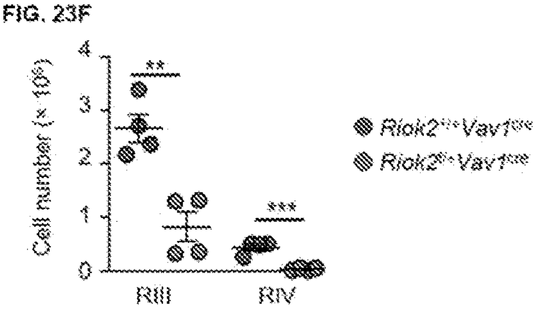
Figure 23G:
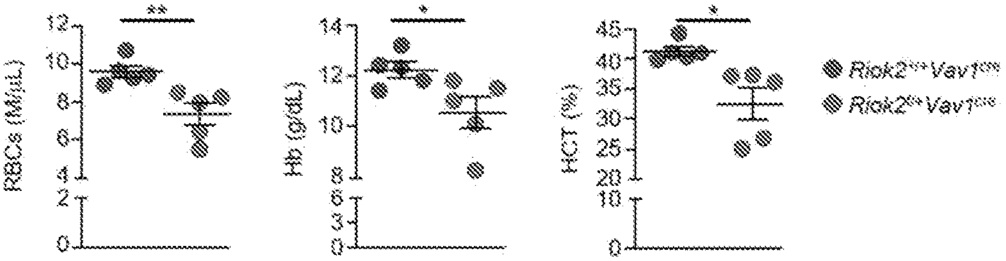
Figure 23H:
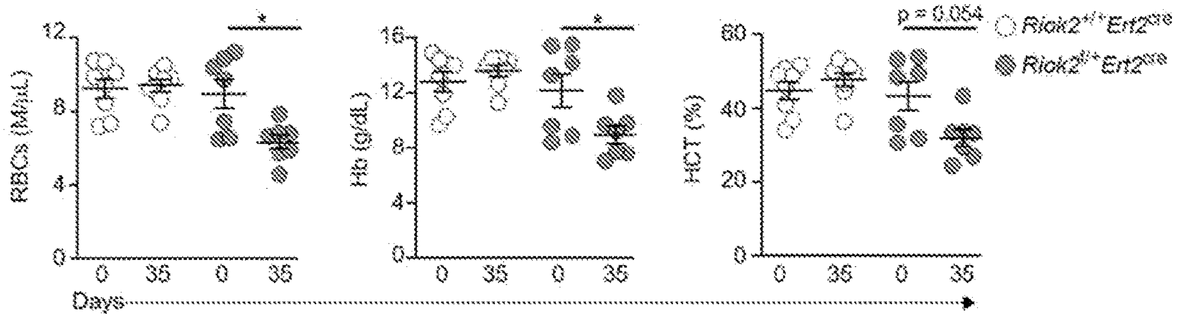
Figure 23I:
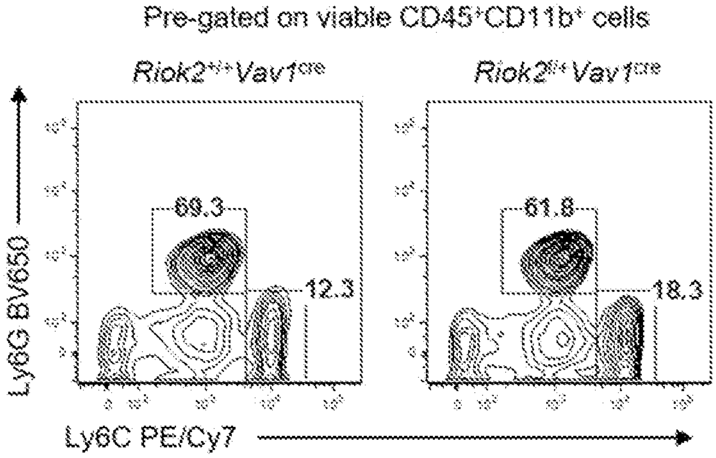
Figure 23J:
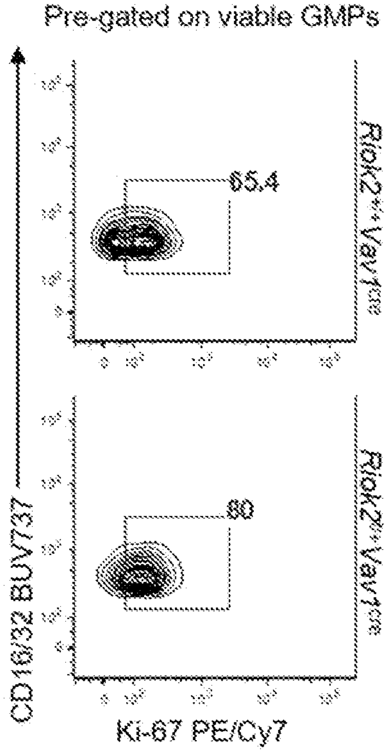
Figure 23K:
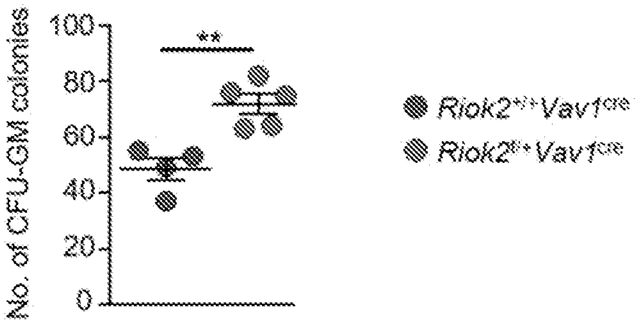

FIG. 23A-FIG. 23K further show that Riok2 haploinsufficient mice display anemia and myeloproliferation. FIG. 23A shows gating strategy used for the identification of erythroid progenitor/precursor cells in the BM. FIG. 23B shows Number of erythroid progenitor populations among viable BM cells in Riok2$^{f/+}$Vav1$^{cre}$ mice and Riok2$^{+/+}$ Vav1$^{cre}$ controls. n=5/group. FIG. 23C shows cell cycle analysis of erythroid progenitor/precursor cells from Riok2 haploinsufficient mice in comparison to Vav1$^{cre}$ controls. n=5 mice/group. FIG. 23D shows Cdkn1a mRNA expression by qRT-PCR in erythroid progenitors from Riok2 haploinsufficient mice and Vav1$^{cre}$ controls. n=3 mice/group. FIG. 23E shows Kaplan-Meier survival curve for Riok2 haploinsufficient mice and Vav1$^{cre}$ controls subjected to lethal dose of PhZ. FIG. 23F shows number of RIII and RIV erythroid precursor populations among viable BM cells in Riok2$^{f/+}$Vav1$^{cre}$ mice and Riok2$^{+/+}$Vav1$^{cre}$ controls day 6 after PhZ treatment. n=4/group. FIG. 23G shows PB RBC numbers, Hb, and HCT in mice transplanted with either Riok2 haploinsufficient mice or Vav1$^{cre}$ BM cells. n=5 mice/group. FIG. 23H shows PB RBC numbers, Hb, and HCT in mice with tamoxifen-inducible deletion of Riok2. Tamoxifen administered on days 3-7. n=8 and 7 for Riok2$^{+/+}$ Ert2$^{cre}$ and Riok2$^{f/+}$Ert2$^{cre}$ mice, respectively. FIG. 23I shows representative flow cytometry plots showing frequency of monocytes (CD11b$^{+}$Ly6G$^{-}$Ly6C$^{hi}$) and neutrophils (CD11b$^{+}$Ly6G$^{+}$) in the PB of Riok2$^{f/+}$Vav1$^{cre}$ and Riok2$^{+/+}$Vav1$^{cre}$ mice. FIG. 23J shows representative flow cytometry plots showing Ki-67$^{+}$ GMPs in the BM of Riok2$^{f/+}$Vav1$^{cre}$ and Riok2$^{+/+}$Vav1$^{cre}$ mice. FIG. 23K shows number of CFU-GM colonies in MethoCult from Lin$^{-}$Sca-1$^{+}$c-kit$^{+}$ BM cells from Riok2$^{f/+}$Vav1$^{cre}$ mice (n=5) and Riok2$^{+/+}$Vav1$^{cre}$ controls (n=4) after a 7-day culture period. n=4-5/group. Multiple unpaired two-tailed t-tests with Holm-Sidak method (FIG. 23B, C), unpaired two-tailed t-test (FIG. 23D, F, G, K), log-rank test (FIG. 23E), and 2-way ANOVA with Sidak's correction for multiple comparisons (FIG. 23H) used to calculate statistical significance. Data are shown as mean±s.e.m and are representative of two (FIG. 23B to K) independent experiments. * $p<0.05$,  $p<0.01$, * $p<0.001$.

Figure 24A:
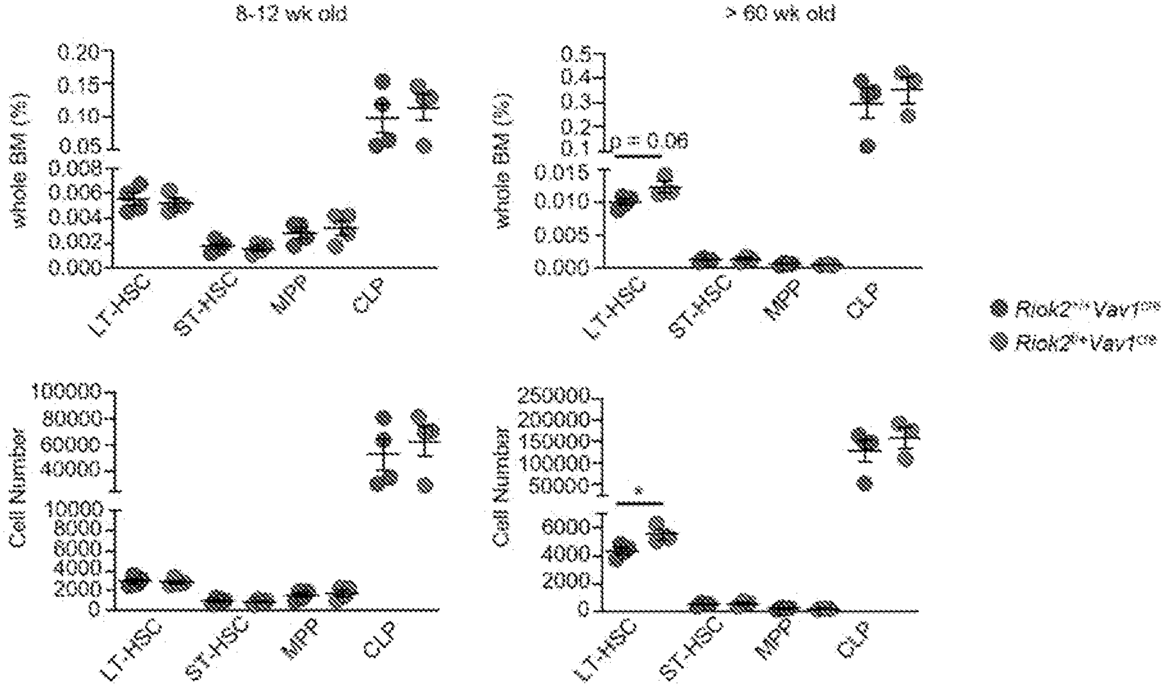
Figure 24B:
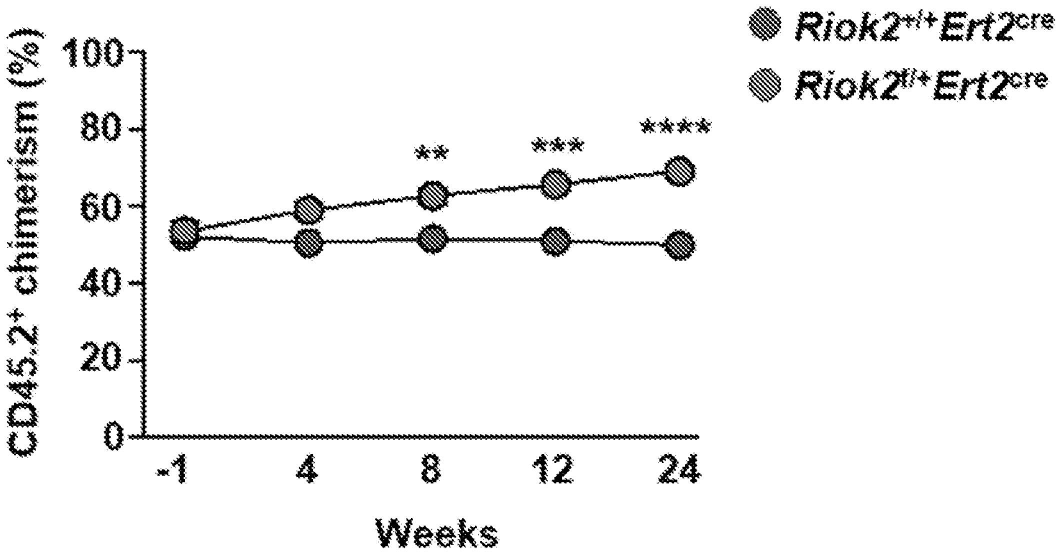
Figure 24C:
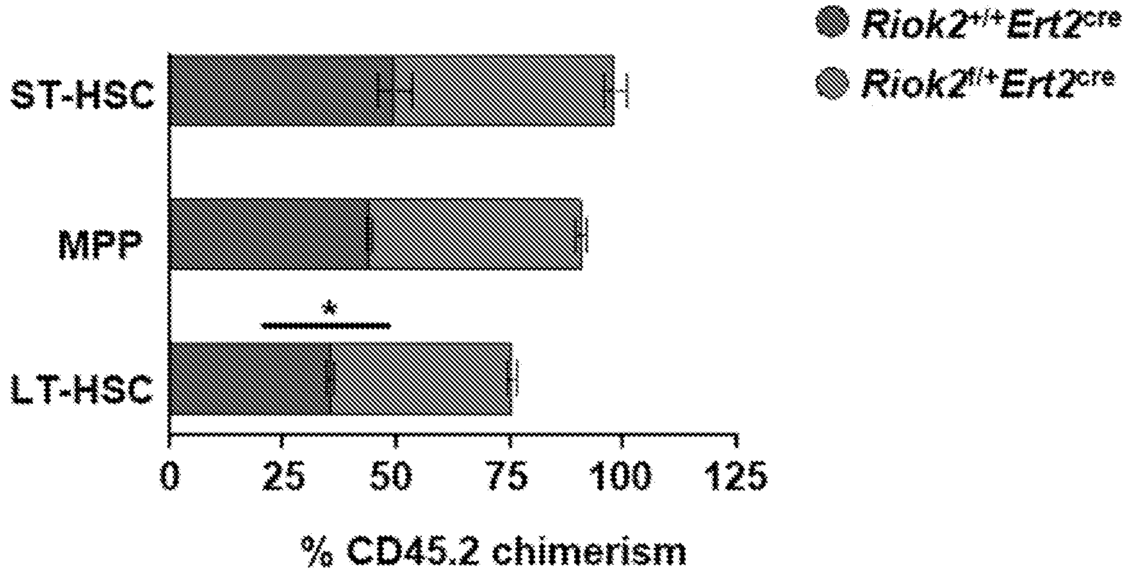

FIG. 24A-FIG. 24C show that Riok2 haploinsufficiency alters early hematopoietic progenitors in an age-dependent fashion. FIG. 24A shows frequency and number of indicated cell types in the bone marrow of Riok2$^{f/+}$Vav1$^{cre}$ and Riok2$^{+/+}$Vav1$^{cre}$ mice. n=4/group. LT-HSC=long term hematopoietic stem cells, ST-HSC=short term hematopoietic stem cells, MPP=multipotent progenitors, CLP=common lymphoid progenitors. FIG. 24B shows % CD45.2 (donor) chimerism in PB from competitive BM transplant with CD45.1 recipient cells. Time point '−1' reflects first bleeding 4 weeks after transplantation and one day before tamoxifen induced deletion of Riok2. Donor (CD45.2) chimerism of the HSC compartment in the BM of competitive transplantation experiments. n=5/group. FIG. 24C shows frequency of donor (CD45.2$^+$) early hematopoietic progenitors 24 weeks after tamoxifen treatment in a competitive transplantation assay as described in (FIG. 24B). n=5 and 4 for Riok2$^{+/+}$Ert2$^{cre}$ and Riok2$^{fl/+}$Ert2$^{cre}$ mice, respectively. Unpaired two-tailed t-test (FIG. 24A, C) and 2-way ANOVA with Sidak's multiple comparison test (FIG. 24B) used to calculate statistical significance. Data are shown as mean±s.e.m and are representative of two (FIG. 24A-C) independent experiments. * p<0.05,  p<0.01, * p<0.001, **** p<0.0001.

Figures 25A, 25B, 25C:
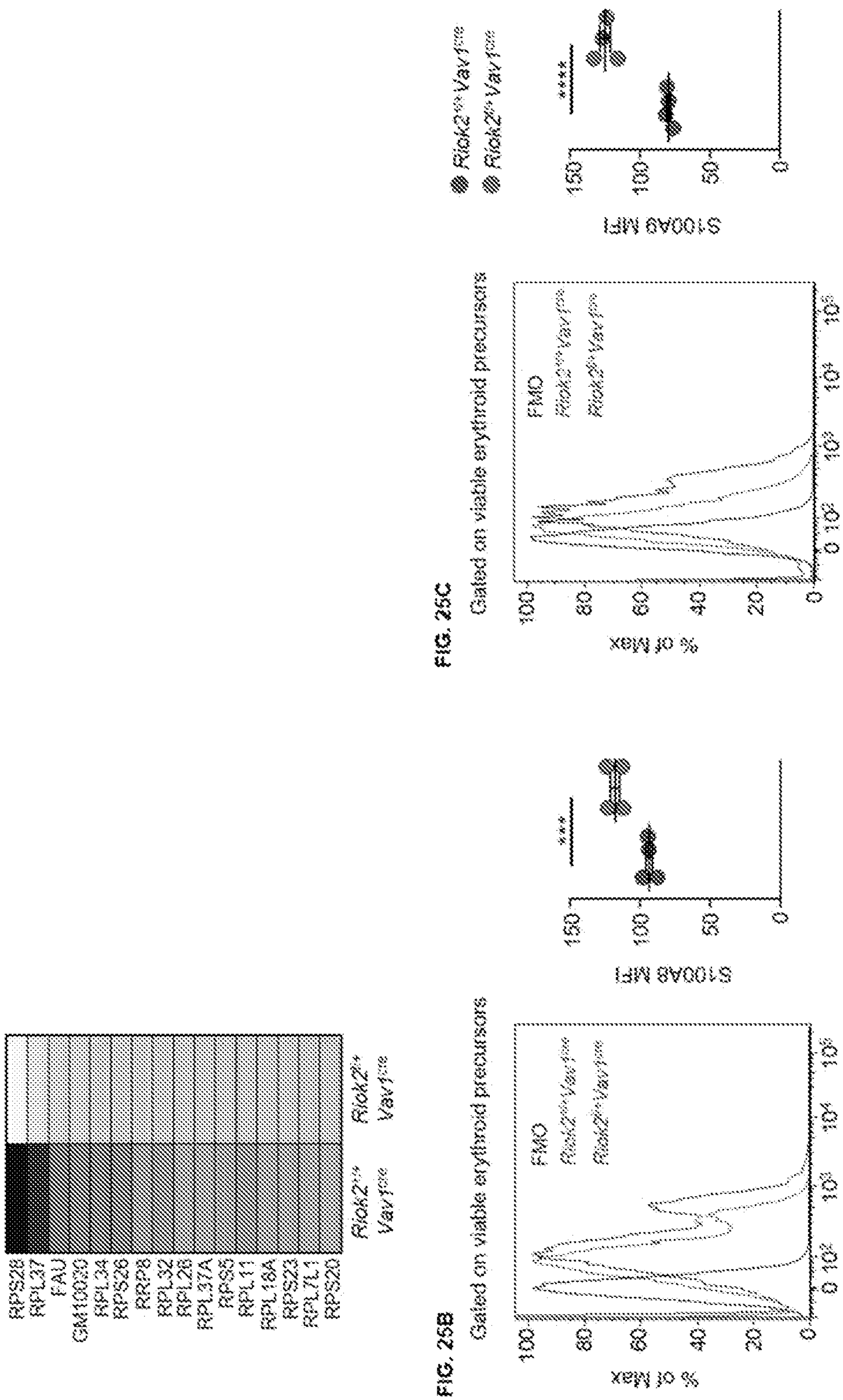
Figure 25D:
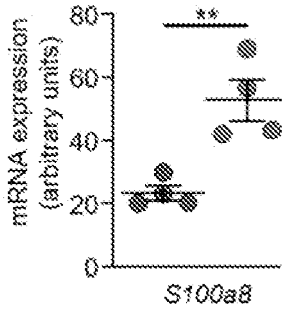
Figure 25E:
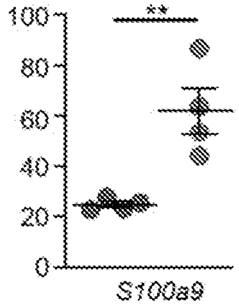
Figure 25F:
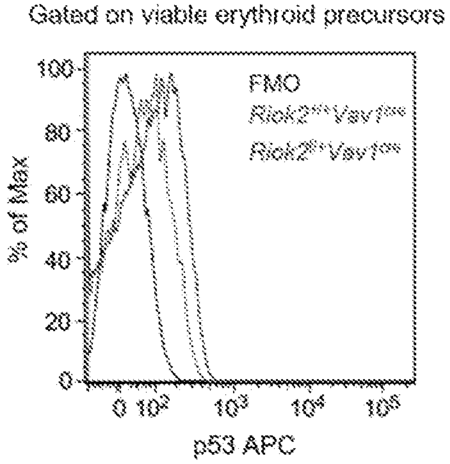
Figure 25G:
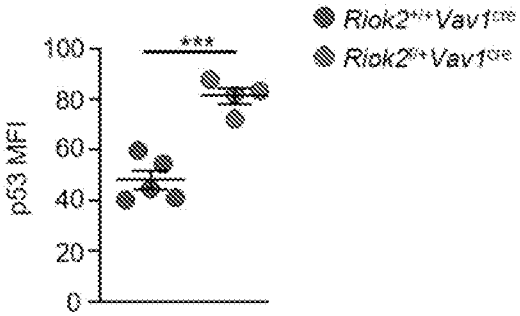

FIG. 25A-FIG. 25G show that Riok2 haploinsufficient erythroid precursors express increased S100 proteins. FIG. 25A shows expression of ribosomal proteins quantified by proteomics in Riok2$^{fl/+}$Vav1$^{cre}$ and Riok2$^{+/+}$Vav1$^{cre}$ erythroid precursors. S100A8 (FIG. 25B) and S100A9 (FIG. 25C) expression assessed by flow cytometry in BM erythroid precursors from Riok2$^{fl/+}$Vav1$^{cre}$ and Riok2$^{+/+}$Vav1$^{cre}$ mice. n=4 mice/group. FIGS. 25D and E show S100a8 and S100a9 mRNA expression in erythroid precursors isolated from Riok2$^{fl/+}$Vav1$^{cre}$ and Riok2$^{+/+}$Vav1$^{cre}$ mice. n=4 mice/group. FIG. 25F shows p53 expression assessed by flow cytometry in BM erythroid precursors from Riok2$^{fl/+}$Vav1$^{cre}$ and Riok2$^{+/+}$Vav1$^{cre}$ mice. FIG. 25G shows graphical representation of data shown in (FIG. 25E). n=5 mice/group. Data are shown as mean±s.e.m and are representative of two (FIG. 25B to G) independent experiments. Unpaired two-tailed t-test (FIG. 25B to G) used to calculate statistical significance.  p<0.01, * p<0.001, **** p<0.0001.

Figure 26A:
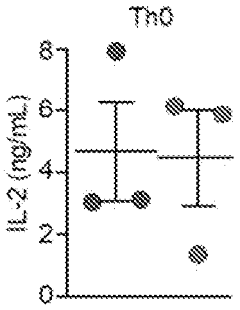
Figure 26B:
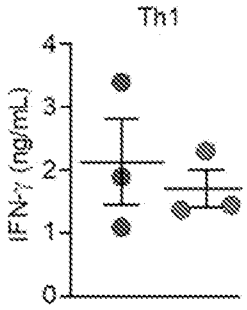
Figure 26C:
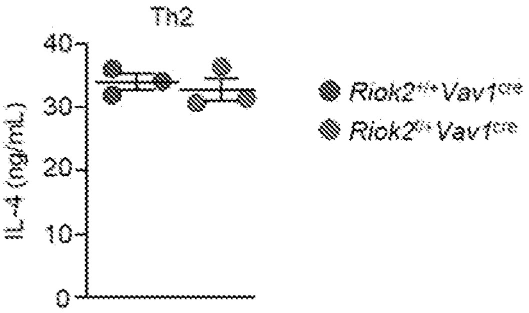
Figure 26D:
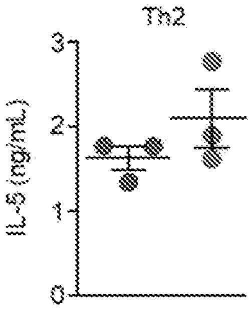
Figure 26E:
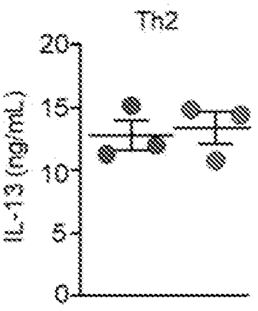
Figure 26F:
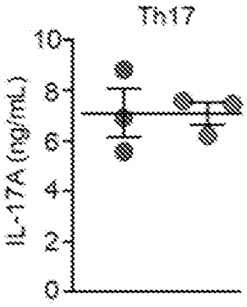
Figure 26G:
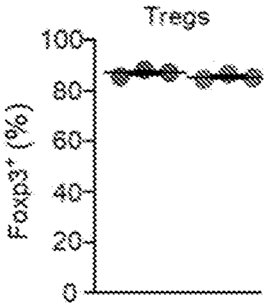
Figure 26H:
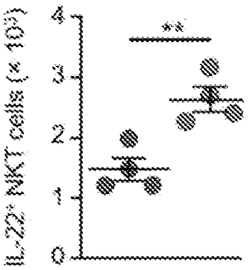
Figure 26I:
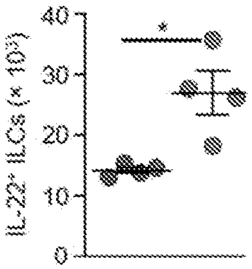
Figure 26J:
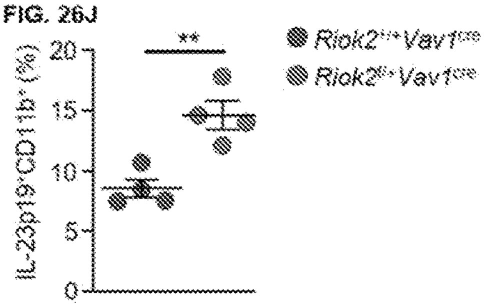
Figure 26K:
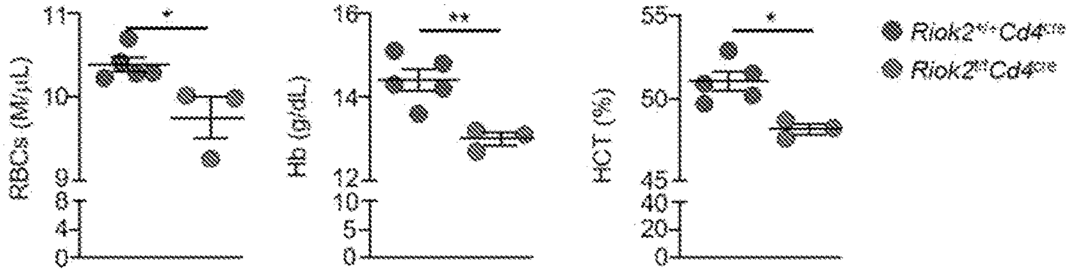
Figure 26L:
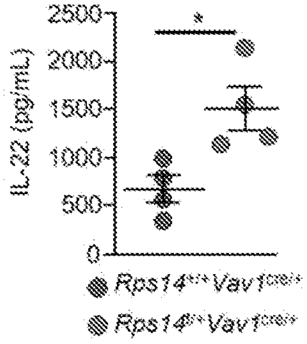
Figure 26M:
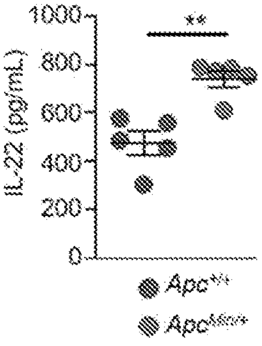
Figure 26N:
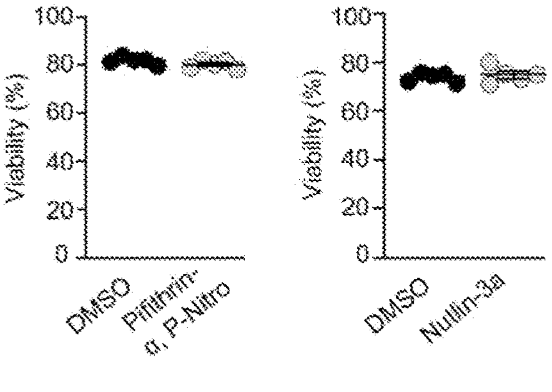

FIG. 26A-FIG. 26N show that expression of lineage-associated T cell cytokines is comparable between Riok2 haploinsufficient and sufficient T cells. FIG. 26A to G show concentration of IL-2 (FIG. 26A), IFN-γ (FIG. 26B), IL-4 (FIG. 26C), IL-5 (FIG. 26D), IL-13 (FIG. 26E), IL-17A (FIG. 26F) and frequency of Foxp3$^+$ cells (FIG. 26G) from in vitro polarized T cells of the indicated genotypes. n=3 mice/group. FIG. 26H to I show number of IL-22$^+$ NKT cells (FIG. 26H) and ILCs (FIG. 26I) in the spleens of Riok2$^{fl/+}$Vav1$^{cre}$ mice and Riok2$^{+/+}$Vav1$^{cre}$ controls (n=4/group). FIG. 26J shows frequency of IL_23p19$^+$ DCs in Riok2$^{fl/+}$Vav1$^{cre}$ mice and Riok2$^{+/+}$Vav1$^{cre}$ controls. n=4 mice/group. FIG. 26K shows PB RBC numbers, Hb, and HCT in Riok2 f Cd4$^{cre}$ mice (n=3) in comparison to Riok2$^{+/+}$Cd4$^{cre}$ controls (n=5). FIG. 26L shows secreted IL-22 from in vitro polarized $T_H$22 cells from Rps14 haploinsufficient mice and Vav1$^{cre}$ controls. n=4 mice/group. FIG. 26M shows secreted IL-22 from in vitro polarized $T_H$22 cells from Apc$^{Min}$ mice and littermate controls. n=4 mice/group. FIG. 26N shows viable cells (expressed as percentage of total cells in culture) for the indicated treatments assessed by flow cytometry. n=5 mice/group. Data are shown as mean±s.e.m and are representative of two (FIG. 26A to N) independent experiments. Unpaired two-tailed t-test FIG. 26A to N) used to calculate statistical significance. * p<0.05, ** p<0.01.

FIG. 27A-FIG. 27D show that neutralization of IL-22 signaling increases number of erythroid precursors. FIG. 27A to D show number of RI-RIV erythroid populations among viable BM cells in the indicated strains undergoing PhZ-induced stress erythropoiesis. For (FIG. 27A), n=5,5,4, and 4 for Riok2$^{+/+}$Il22$^{+/+}$Vav1$^{cre}$, Riok2$^{+/+}$Il22$^{+/+}$Vav1$^{cre}$, Riok2$^{fl/+}$Il22$^{+/+}$Vav1$^{cre}$, Riok2$^{fl/+}$Il22$^{fl/-}$Vav1$^{cre}$ respectively. For (FIG. 27D), n=5/group. Data are shown as mean±s.e.m and are representative of three (FIG. 27A, C) or two (FIG. 27B, D) independent experiments. 1-way ANOVA with Tukey's correction (FIG. 27A, C) or unpaired two-tailed t-test (FIG. 27B, D) used to calculate statistical significance. * p<0.05, ** p<0.01.

Figure 28A:
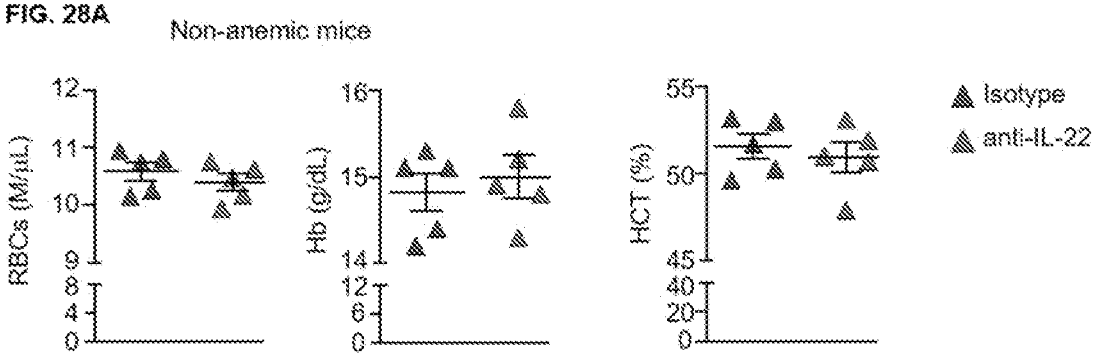
Figure 28B:
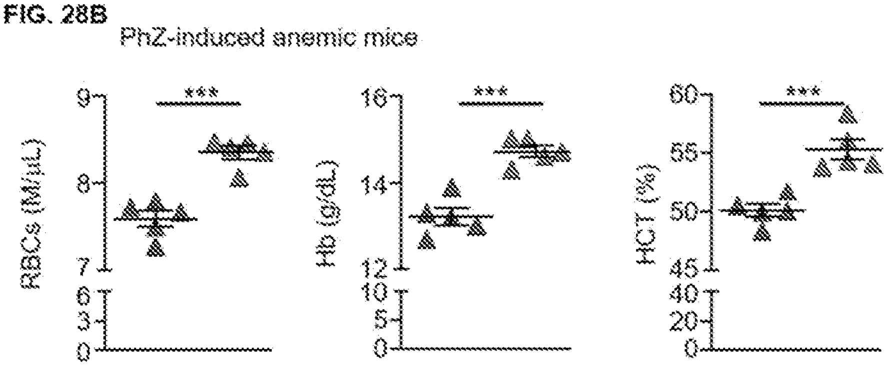
Figure 28C:
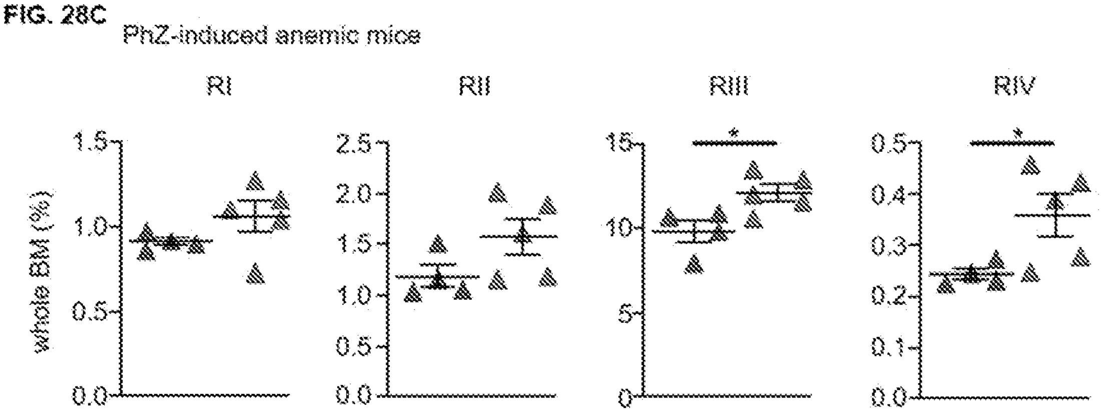

FIG. 28A-FIG. 28C show that IL-22 neutralization alleviates anemia in wt mice undergoing PhZ-induced stress erythropoiesis. FIG. 28A shows PB RBC numbers, Hb, and HCT in naïve wt C57BL/6J mice treated with isotype control (Rat IgG2aκ, 50 mg/mouse) or anti-IL-22 antibody (50 mg/mouse). n=5 mice/group. FIG. 28B shows PB RBC numbers, Hb, and HCT in wt C57BL/6J mice undergoing PhZ-induced stress erythropoiesis treated with isotype control or anti-IL-22 antibody. n=5 mice/group. FIG. 28C shows Percentage of RI-RIV erythroid precursors in the BM of mice treated as in (FIG. 28B). n=4 and 5 for Il22ra1$^{+/+}$Epor$^{cre}$ and Il22ra1$^{fl/fl}$Epor$^{cre}$ mice, respectively. Data are shown as mean±s.e.m and are representative of three (FIG. 28A, B) or two (FIG. 28C) independent experiments. Unpaired two-tailed t-test (FIG. 28A to C) used to calculate statistical significance. * p<0.05, *** p<0.001.

Figures 29A, 29B, 29C, 29D:
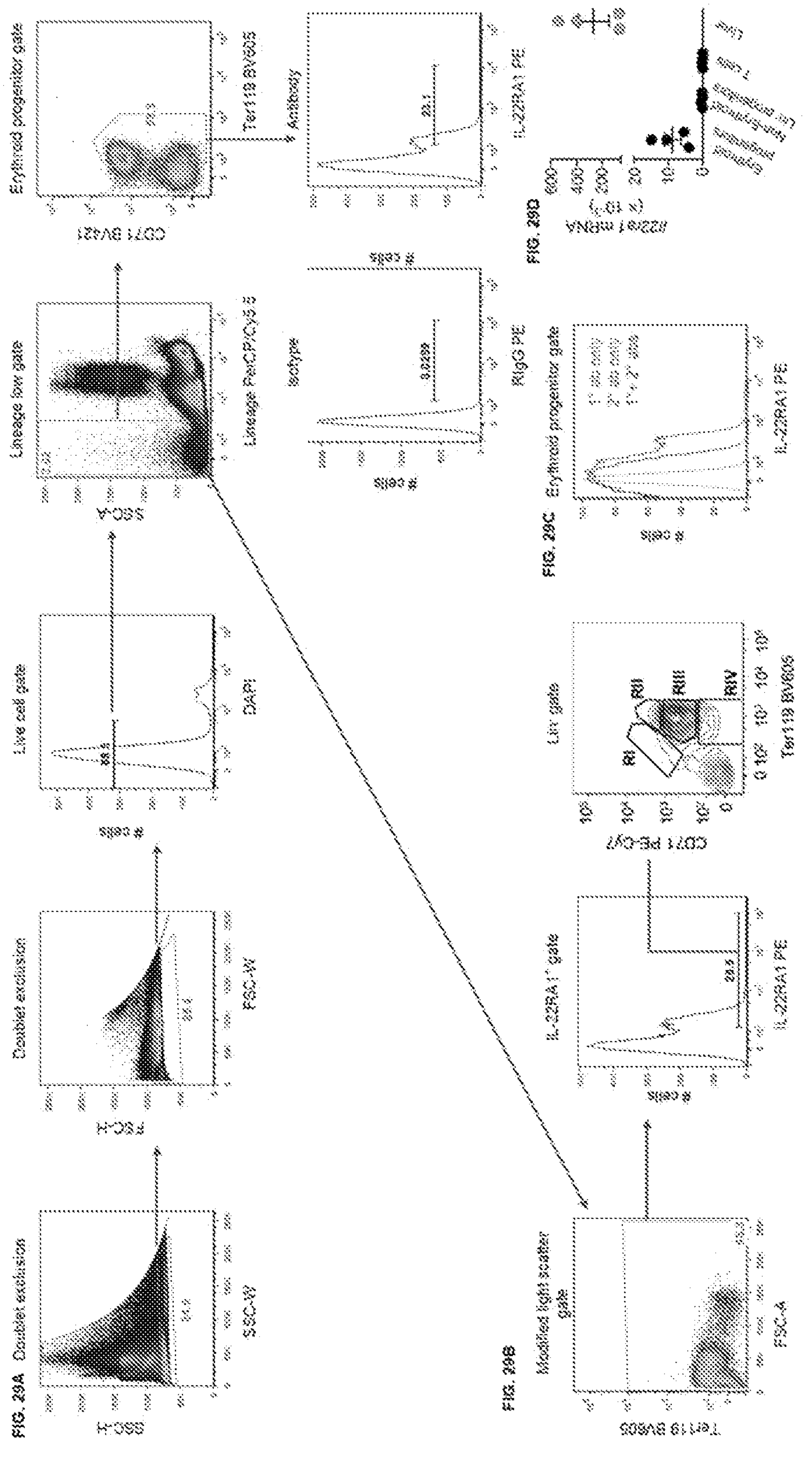

FIG. 29A-FIG. 29D show that erythroid precursors express IL-22RA1. FIG. 29A shows gating strategy employed for assessing IL-22RA1 expression on erythroid precursors. FIG. 29B shows gating strategy to show that majority of IL-22RA1$^+$ cells in the mouse BM are erythroid precursors. FIG. 29C shows IL-22RA1 expression on erythroid precursors assessed using flow cytometry and a second antibody targeting a different epitope of IL-22RA1. FIG. 29D shows Il22ra1 mRNA expression in the indicated cell types assessed by qRT-PCR. T cells and liver represent negative and positive controls, respectively. n=4 mice/group. Data are shown as mean±s.e.m (FIG. 29D) and are representative of three (FIG. 29A to C) or two (FIG. 29D) independent experiments.

Figure 30A:
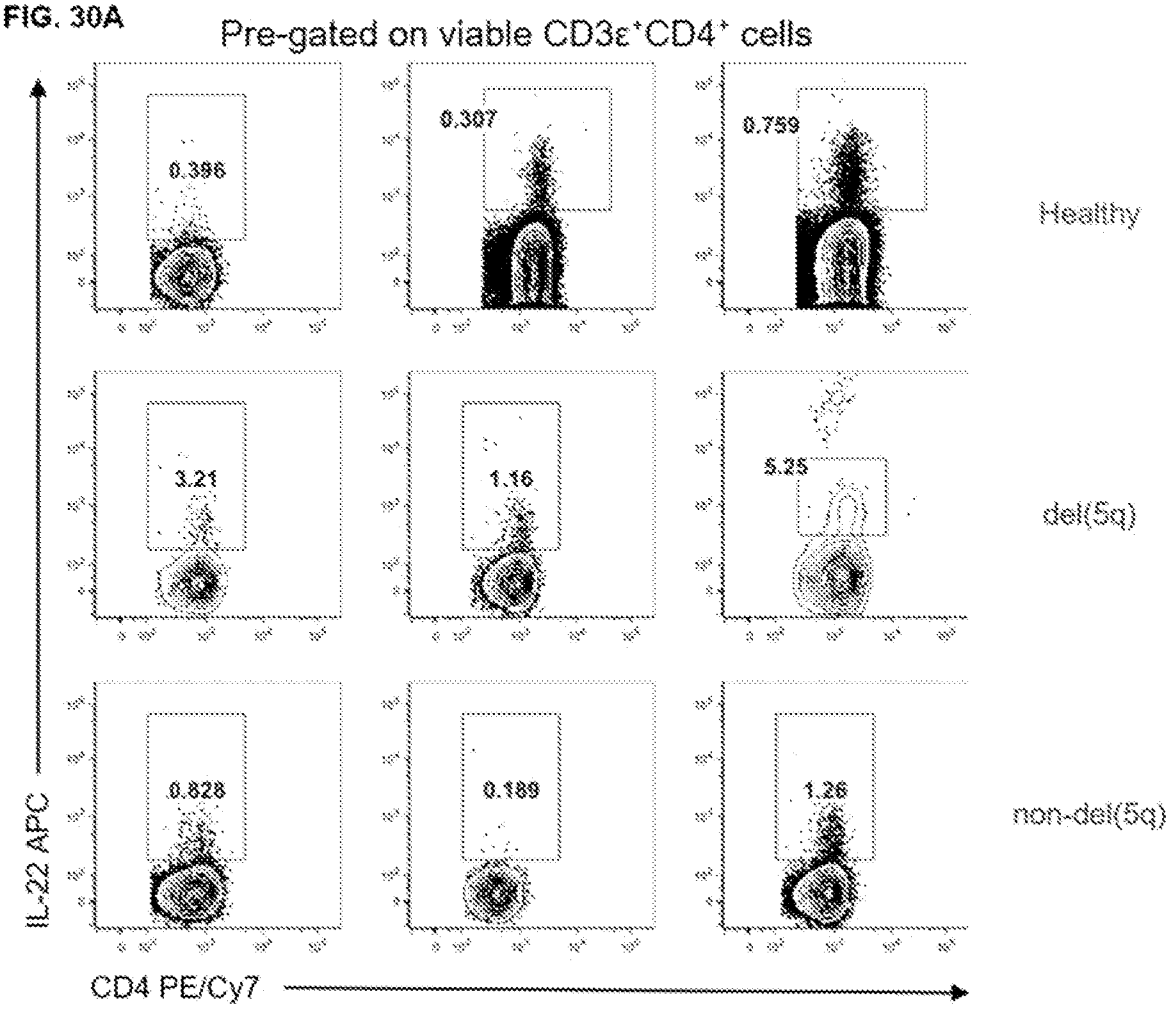
Figure 30B:
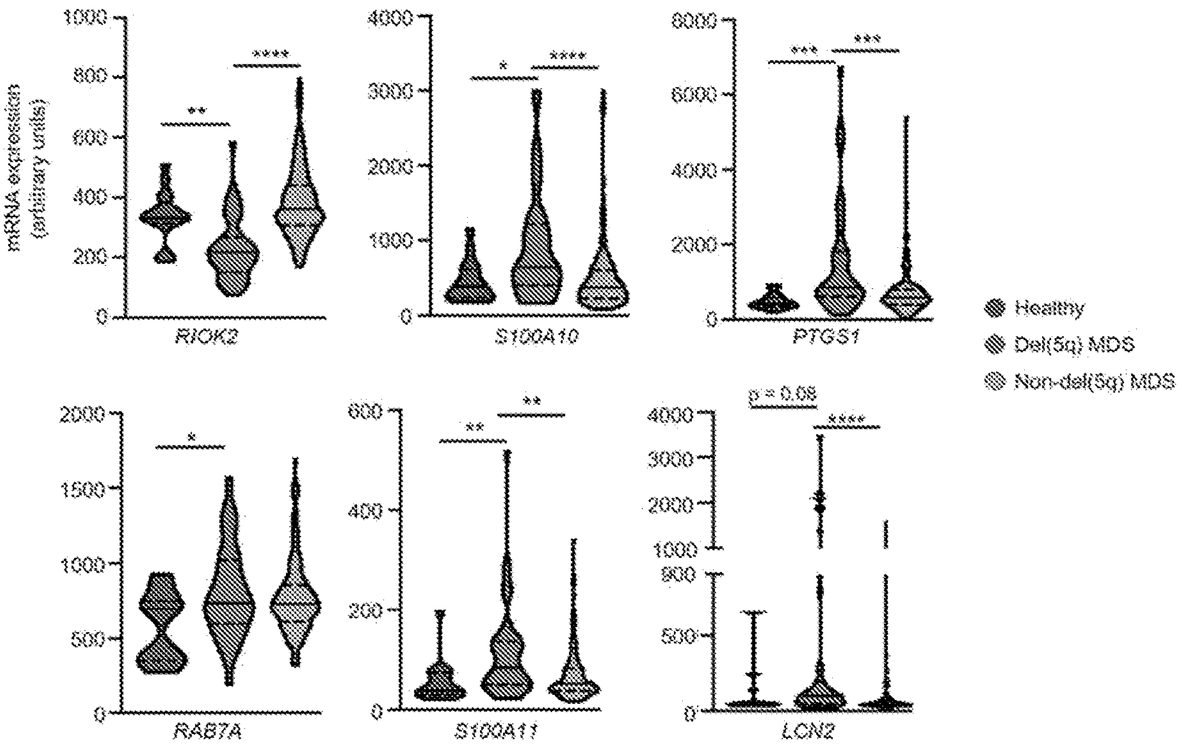

FIG. 30A-FIG. 30B show increased IL-22 and its signature genes in del(5q) MDS subjects IL-22. FIG. 30A shows representative flow cytometry plots showing frequency of CD4$^+$IL-22$^+$ cells among total PBMCs in the peripheral blood of MDS patients and healthy subjects. Pre-gated on viable CD3e$^+$CD4$^+$ cells. Cumulative data shown in FIG. 25E. FIG. 30B shows expression of indicated IL-22 signature genes in CD34$^+$ cells from healthy controls and del(5q) and non-del(5q) MDS patients. n=17, 47, and 136 for healthy, del(5q) MDS, and non-del(5q) MDS, respectively. Kruskal-Wallis test with Dunn's correction for multiple comparisons (FIG. 30B) used to calculate statistical significance * p<0.05,  p<0.01, * p<0.001, ** p<0.0001. Solid lines represent median and dashed lines represent quartiles (FIG. 30**B).

Figure 31A:
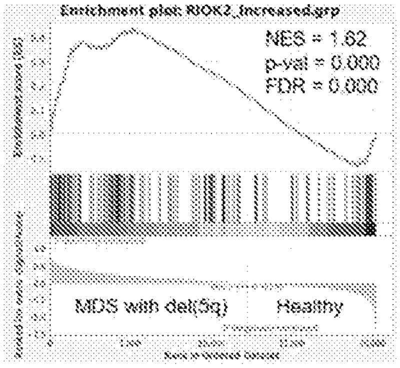
Figure 31B:
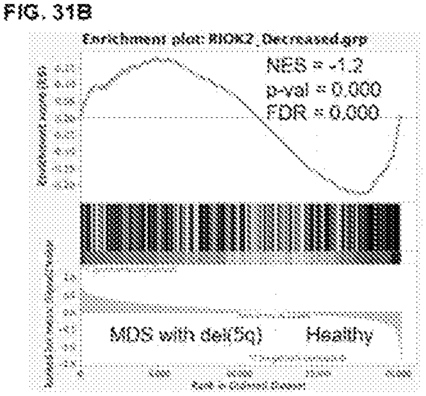
Figure 31C:
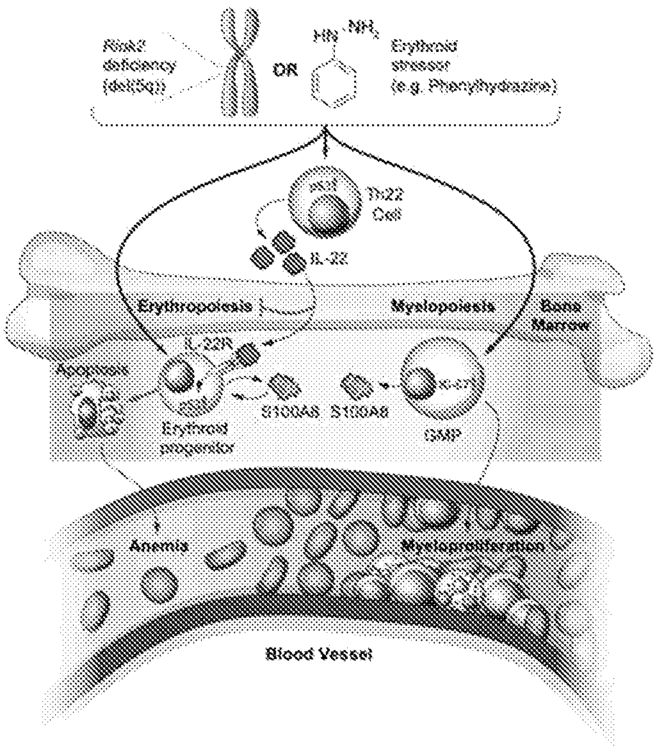

FIG. 31A-FIG. 31C show that Riok2 haploinsufficiency recapitulates del(5q) MDS transcriptional changes. FIG. 31A to B show GSEA enrichment plots comparing proteins up-regulated (FIG. 31A) and down-regulated (FIG. 31B) upon Riok2 haploinsufficiency to the transcriptional changes seen in del(5q) MDS. FIG. 31C shows schematic of mechanism underlying Riok2 haploinsufficiency-induced, IL-22-induced anemia.

Figure 32A:
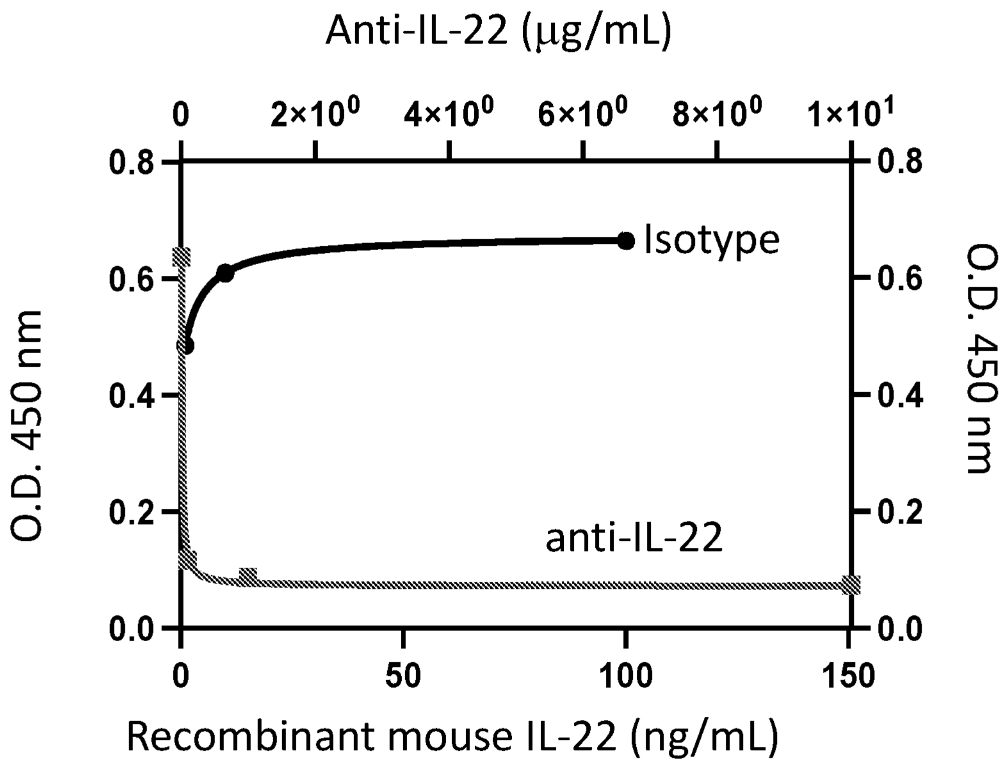
Figure 32B:
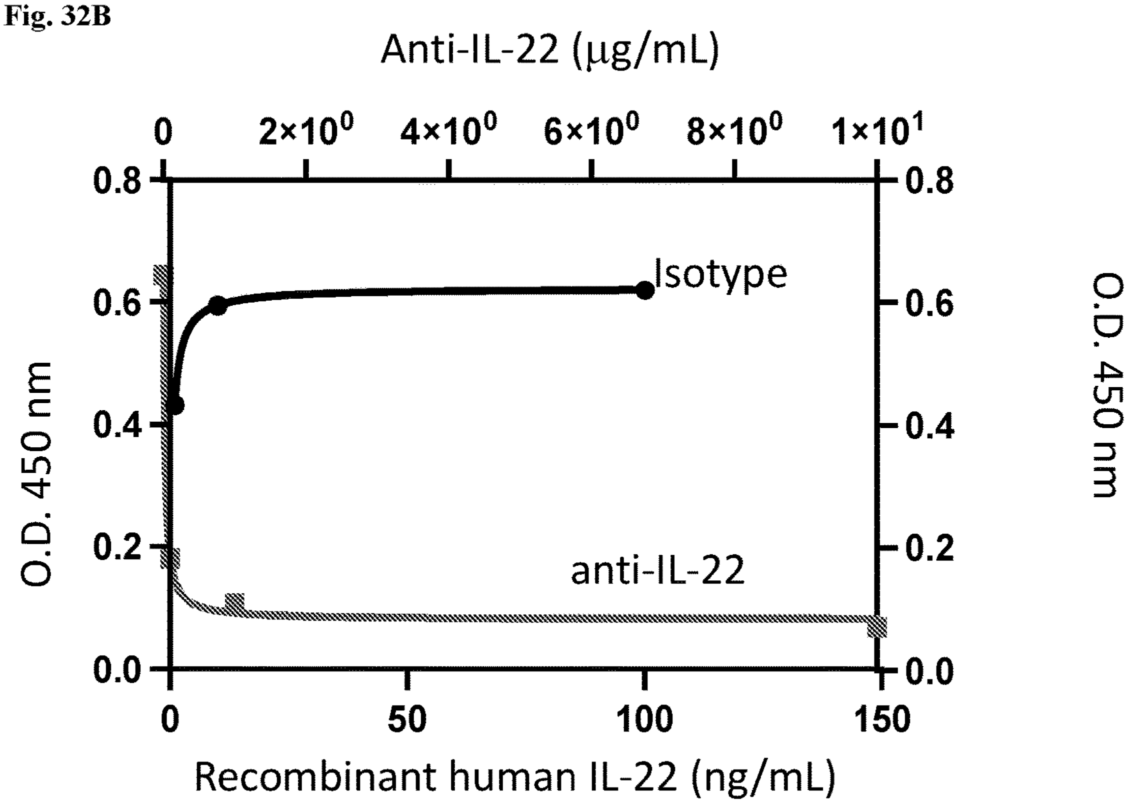

FIG. 32A-FIG. 32B show that anti-IL-22 inhibits recombinant IL-22-induced IL-10 production. FIG. 32A and FIG. 32B show COLO-205 cells stimulated with recombinant mouse IL-22 (FIG. 32A) and recombinant human IL-22 (FIG. 32B) in the presence of anti-IL-22 or matching isotype. After 24 hours, cell free-supernatant was collected and subjected to IL-10 quantification by ELISA.

Figure 33:
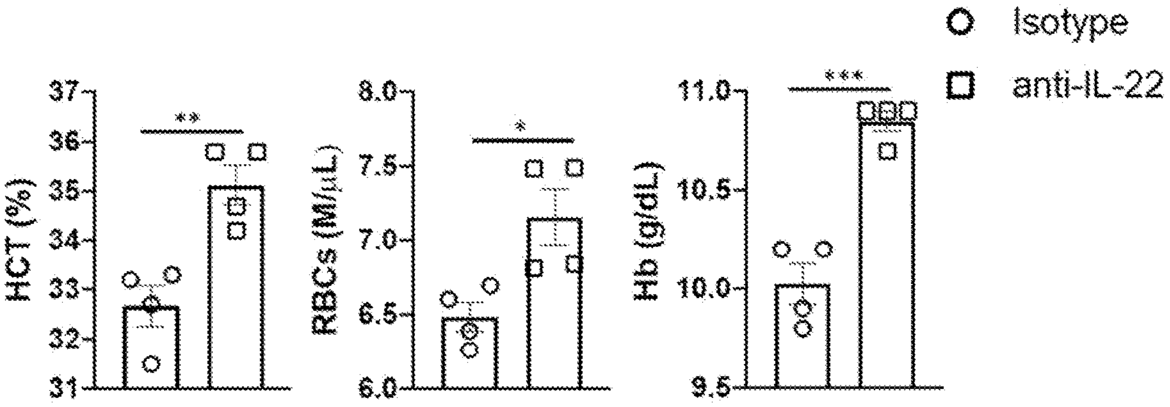

FIG. 33 shows that IL-22 neutralization with anti-IL-22 antibody alleviates anemia in wild type (wt) mice undergoing PhZ-induced stress erythropoiesis. FIG. 33 shows PB RBC numbers, Hb, and HCT in wt C57BL/6J mice undergoing PhZ-induced stress erythropoiesis treated with either an isotype control or anti-IL-22. * $p<0.05$,  $p<0.01$, * $p<0.001$.

For any figure showing a bar histogram, curve, or other data associated with a legend, the bars, curve, or other data presented from left to right for each indication correspond directly and in order to the boxes from top to bottom of the legend.

DETAILED DESCRIPTION OF THE INVENTION

The present invention is based, at least in part, on the discovery that down-regulators of IL-22 signaling can treat red blood cell disorders, such as anemia. In particular, it is described herein that hematopoietic cell-specific haploinsufficient deletion of Riok2 (Riok2$^{f/+}$Vav1$^{cre}$) leads to reduced erythroid progenitor frequency due to increased apoptosis and cell cycle arrest leading to anemia. Quantitative proteomics of Riok2$^{f/+}$ Vav1$^{cre}$ erythroid progenitors identified elevated expression of multiple antimicrobial and alarmin proteins, an indication of immune system activation. An exclusive increase in IL-22 secretion from Riok2$^{f/+}$Vav1$^{cre}$ CD4$^{+}$ T cells after polarization towards different T cell lineages was observed. In addition and unexpectedly, it was discovered that the IL-22 receptor, IL-22RA1, is present on erythroid progenitor cells. Genetic blockade of IL-22 signaling by deletion of Il22 or Il22ra1 alleviated anemia in Riok2$^{f/+}$Vav1$^{cre}$ mice. Additionally, erythroid cell-specific deletion of Il22ra1 in Riok2 sufficient phenylhydrazine-treated mice led to increased erythroid progenitor frequency and peripheral blood RBCs confirming a function of IL-22 signaling in stress-induced erythropoiesis. Further, treatment with a neutralizing monoclonal IL-22 antibody alleviated phenylhydrazine-driven anemia not only in Riok2$^{f/+}$ Vav1$^{cre}$ mice but also in wild-type mice indicating a broader role for targeting IL-22 in disorders with defective erythropoiesis. Levels of IL-22 and its downstream signaling effectors were increased in two independent cohorts of MDS patients and in a published large-scale sequencing study (Pellagatti et al. (2010) *Leukemia* 24:756-764) of CD34$^{+}$ cells from MDS patients. Moreover, patients with anemia secondary to chronic kidney disease (CKD) were also demonstrated herein to have elevated levels of IL-22 as compared to CKD patients with normal hematocrits. The results described herein demonstrate an unexpected role for IL-22 signaling in erythroid differentiation and provides therapeutic opportunities for reversing anemias, including stress-induced anemias, and MDS disorders. Down-regulators of IL-22 not only act against an increase of hepcidin from hepatocytes, but can promote differentiation of erythroid progenitors to red blood cells. These effects of down-regulators of IL-22 are useful for diagnosing, prognosing, and treating a variety of red blood cell disorders, such as anemia, since the effects include increasing the number of red blood cells in a subject.

Accordingly, the present invention provides methods of treating one or more red blood cell disorders (e.g., anemia) in a subject by administering to the subject an effective amount of a down-regulator of IL-22 signaling. The present invention also provides methods of promoting differentiation from an erythroid progenitor cell toward a mature red blood cell in a subject by administering to the subject an effective amount of a down-regulator of IL-22 signaling.

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a sample, as compared to the expression level or copy number of the biomarker nucleic acid in a control sample. The term "altered amount" of a biomarker also includes an increased or decreased protein level of a biomarker protein in a sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 10%, 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered activity" of a biomarker refers to an activity of the biomarker which is increased or decreased in a disease state, e.g., in a sample from a subject having MDS and/or an anemia, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

The term "administering" is intended to include modes and routes of administration which allow an agent to perform its intended function. Examples of routes of administration for treatment of a body which can be used include injection (subcutaneous, intravenous, parenterally, intraperitoneally, intrathecal, etc.), oral, inhalation, and transdermal routes. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, murine, chimeric, humanized, and human antibodies and multi-specific antibodies, as well as fragments and derivatives of all of the foregoing, which fragments and derivatives have at least an antigenic binding site. Antibody derivatives may comprise a protein or chemical moiety conjugated to an antibody.

In addition, intrabodies are well-known antigen-binding molecules having the characteristic of antibodies, but that are capable of being expressed within cells in order to bind and/or inhibit intracellular targets of interest (Chen et al. (1994) *Human Gene Ther.* 5:595-601). Methods are well-known in the art for adapting antibodies to target (e.g., inhibit) intracellular moieties, such as the use of single-chain antibodies (scFvs), modification of immunoglobulin VL domains for hyperstability, modification of antibodies to resist the reducing intracellular environment, generating fusion proteins that increase intracellular stability and/or modulate intracellular localization, and the like. Intracellular antibodies can also be introduced and expressed in one or more cells, tissues or organs of a multicellular organism, for example for prophylactic and/or therapeutic purposes (e.g., as a gene therapy) (see, at least PCT Publs. WO 08/020079, WO 94/02610, WO 95/22618, and WO 03/014960; U.S. Pat. No. 7,004,940; Cattaneo and Biocca (1997) *Intracellular Antibodies: Development and Applications* (Landes and Springer-Verlag publs.); Kontermann (2004) *Methods* 34:163-170; Cohen et al. (1998) *Oncogene* 17:2445-2456; Auf der Maur et al. (2001) *FEBS Lett.* 508:407-412; Shaki-Loewenstein et al. (2005) *J. Immunol. Meth.* 303:19-39).

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P. et al. (1993) *Proc. Natl. Acad. Sci. USA* 90:6444-6448; Poljak, R. J. et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M. et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M. et al. (1994) *Mol. Immunol.* 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts. In addition, antibodies can be "humanized," which includes antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies encompassed by the present invention may include amino acid residues not encoded by human germline immunoglobulin sequences (e.g., mutations introduced by random or site-specific mutagenesis in vitro or by somatic mutation in vivo), for example in the CDRs. The term "humanized antibody," as used herein, also includes antibodies in which CDR sequences derived from the germline of another mammalian species, such as a mouse, have been grafted onto human framework sequences.

A "blocking" antibody is one which inhibits or reduces at least one biological activity of the antigen(s) it binds. In certain embodiments, the blocking antibodies or fragments thereof described herein substantially or completely inhibit a given biological activity of the antigen(s). Blocking antibodies are alternatively referred to herein with the prefix "anti" with respect to a target of them (e.g., anti-IL-22 for an antibody that binds to IL-22 and down-regulates IL-22 signaling).

An "antagonist" is one which attenuates, decreases, or inhibits at least one biological activity of at least one protein, such as a receptor (e.g., AHR), described herein. In certain embodiments, the antagonist described herein substantially or completely attenuates or inhibits a given biological activity of at least one protein described herein.

Any one of the antibodies or fragments thereof disclosed herein may bind specifically to any one of the amino acid sequences disclosed in Table 1.

The term "biomarker" refers to a measurable entity of the present invention that has been determined to be indicative of elevated and/or activated IL-22 signaling. Representative, non-limiting examples are described herein, such as IL-22 itself (e.g., increased IL-22 mRNA or protein levels in a body fluid, such as blood, bone marrow fluid, peripheral blood Th22 T lymphocytes), and/or IL-22 pathway member, such as increased levels of alarmins (e.g., S100A8, S100A9, S100 A10, S100A11, Stat3 phosphorylation), IL-22 receptor (such as IL-22RA1, IL-10Rbeta, and heterodimers thereof), and other pathway members like Camp, Ngp, Ptgs2, Rab7A, and the like in a body fluid. Moreover, IL-22 itself is indicative of IL-22 signaling, such as blood, bone marrow fluid, peripheral blood Th22 T lymphocytes. IL-22 activation is downstream of the arylhydrocarbon receptor, which is also a relevant biomarker. Biomarkers can include, without limitation, nucleic acids and proteins, including those shown in the Tables, the Examples, the Figures, and otherwise described herein. As described herein, any relevant characteristic of a biomarker can be used, such as the copy number, amount, activity, location, modification (e.g., phosphorylation), and the like.

TABLE 1

Representative biomarkers useful according to methods encompassed by the present invention; exemplary amino acid and nucleic acid sequences of such biomarkers disclosed below.

| Biomarker | Accession Numbers (Protein) | Accession Numbers (cDNA; mRNA) |
|---|---|---|
| IL-22 | NP_065386.1 | NM_020525.5 |
| IL-22 receptor, including IL-22RA1, and heterodimers thereof | AAG22073.1 | AF286095.1 |
| IL-10Rbeta, and heterodimers thereof | NP_000619.3 | NM_000628.5 |
| Arylhydrocarbon receptor | NP_001612.1 | NM_001621.5 |
| S100A8 | NP_002955.2 | NM_002964.5 |
| | NP_001306125.1 | NM_001319196.1 |
| | NP_001306126.1 | NM_001319197.1 |
| | NP_001306127.1 | NM_001319198.2 |
| | NP_001306130.1 | NM_001319201.2 |
| S100A9 | NP_002956.1 | NM_002965.4 |
| S100A10 | NP_002957.1 | NM_002966.3 |
| S100A11 | NP_005611.1 | NM_005620.2 |
| Phosphorylated Stat3 | NP_644805.1 | NM_139276.3 |
| | NP_003141.2 | NM_003150.4 |
| | NP_998827.1 | NM_213662.2 |
| | NP_001356441.1 | NM_001369512.1 |
| | NP_001356442.1 | NM_001369513.1 |
| | NP_001356443.1 | NM_001369514.1 |
| | NP_001356446.1 | NM_001369516.1 |
| | NP_001371913.1 | NM_001369517.1 |
| | NP_001371914.1 | NM_001369518.1 |
| | NP_001371915.1 | NM_001369519.1 |
| | NP_001371916.1 | NM_001369520.1 |
| | NP_001371917.1 | NM_001384984.1 |
| | NP_001371918.1 | NM_001384985.1 |
| | NP_001371919.1 | NM_001384986.1 |
| | NP_001371920.1 | NM_001384987.1 |
| | NP_001371921.1 | NM_001384988.1 |
| | NP_001371922.1 | NM_001384989.1 |
| | XP_016880462.1 | NM_001384990.1 |
| | XP_024306664.1 | NM_001384991.1 |
| | | NM_001384992.1 |
| | | NM_001384993.1 |
| | | XM_017024973.2 |
| | | XM_024450896.1 |
| Camp | NP_004336.4 | NM_004345.5 |
| Ngp | NP_032720.2 | NM_008694.2 |
| Ptgs2 | NP_000954.1 | NM_000963.4 |
| Rab7A | NP_004628.4 | NM_004637.6 |

SEQ ID NO: 8 Human Amino Acid Sequence IL-22 (NP_065386.1)
MAALQKSVSSFLMGTLATSCLLLLALLVQGGAAAPISSHCRLDKSNFQQPYITNRTFMLAKEASLADNNT

DVRLIGEKLFHGVSMSERCYLMKQVLNFTLEEVLFPQSDRFQPYMQEVVPFLARLSNRLSTCHIEGDDLH

IQRNVQKLKDTVKKLGESGEIKAIGELDLLFMSLRNACI

SEQ ID NO: 9 Human Nucleic Acid cDNA/mRNA Sequence IL-22 (NM_020525.5)
ACAAGCAGAATCTTCAGAACAGGTTCTCCTTCCCCAGTCACCAGTTGCTCGAGTTAGAATTGTCTGCAAT

GGCCGCCCTGCAGAAATCTGTGAGCTCTTTCCTTATGGGGACCCTGGCCACCAGCTGCCTCCTTCTCTTG

GCCCTCTTGGTACAGGGAGGAGCAGCTGCGCCCATCAGCTCCCACTGCAGGCTTGACAAGTCCAACTTCC

AGCAGCCCTATATCACCAACCGCACCTTCATGCTGGCTAAGGAGGCTAGCTTGGCTGATAACAACACAGA

CGTTCGTCTCATTGGGGAGAAACTGTTCCACGGAGTCAGTATGAGTGAGCGCTGCTATCTGATGAAGCAG

GTGCTGAACTTCACCCTTGAAGAAGTGCTGTTCCCTCAATCTGATAGGTTCCAGCCTTATATGCAGGAGG

TGGTGCCCTTCCTGGCCAGGCTCAGCAACAGGCTAAGCACATGTCATATTGAAGGTGATGACCTGCATAT

CCAGAGGAATGTGCAAAAGCTGAAGGACACAGTGAAAAAGCTTGGAGAGAGTGGAGAGATCAAAGCAATT

GGAGAACTGGATTTGCTGTTTATGTCTCTGAGAAATGCCTGCATTTGACCAGAGCAAAGCTGAAAAATGA

ATAACTAACCCCCTTTCCCTGCTAGAAATAACAATTAGATGCCCCAAAGCGATTTTTTTTAACCAAAAGG

AAGATGGGAAGCCAAACTCCATCATGATGGGTGGATTCCAAATGAACCCCTGCGTTAGTTACAAAGGAAA

CCAATGCCACTTTTGTTTATAAGACCAGAAGGTAGACTTTCTAAGCATAGATATTTATTGATAACATTTC

ATTGTAACTGGTGTTCTATACACAGAAAACAATTTATTTTTTAAATAATTGTCTTTTTCCATAAAAAAGA

TTACTTTCCATTCCTTTAGGGGAAAAAACCCCTAAATAGCTTCATGTTTCCATAATCAGTACTTTATATT

TATAAATGTATTTATTATTATTATAAGACTGCATTTTATTTATATCATTTTATTAATATGGATTTATTTA

TAGAAACATCATTCGATATTGCTACTTGAGTGTAAGGCTAATATTGATATTTATGACAATAATTATAGAG

CTATAACATGTTTATTTGACCTCAATAAACACTTGGATATCCTAA

SEQ ID NO: 10: Human Amino Acid Sequence IL-22 Receptor (AAG22073.1)
MRTLLTILTVGSLAAHAPEDPSDLLQHVKFQSSNFENILTWDSGPEGTPDTVYSIEYKTYGERDWVAKKG

CQRITRKSCNLTVETGNLTELYYARVTAVSAGGRSATKMTDRFSSLQHTTLKPPDVTCISKVRSIQMIVH

PTPTPIRAGDGHRLTLEDIFHDLFYHLELQVNRTYQMHLGGKQREYEFFGLTPDTEFLGTIMICVPTWAK

ESAPYMCRVKTLPDRTWTYSFSGAFLFSMGFLVAVLCYLSYRYVTKPPAPPNSLNVQRVLTFQPLRFIQE

HVLIPVEDLSGPSSLAQPVQYSQIRVSGPREPAGAPQRHSLSEITYLGQPDISILQPSNVPPPQILSPLS

YAPNAAPEVGPPSYAPQVTPEAQFPFYAPQAISKVQPSSYAPQATPDSWPPSYGVCMEGSGKDSPTGTLS

SPKHLRPKGQLQKEPPAGSCMLGGLSLQEVTSLAMEESQEAKSLHQPLGICTDRTSDPNVLHSGEEGTPQ

YLKGQLPLLSSVQIEGHPMSLPLQPPSGPCSPSDQGPSPWGLLESLVCPKDEAKSPAPETSDLEQPTELD

SLFRGLALTVQWES

SEQ ID NO: 11: Human Nucleic Acid cDNA/mRNA Sequence IL-22 Receptor (AF286095.1)
GGGAGGGCTCTGTGCCAGCCCCGATGAGGACGCTGCTGACCATCTTGACTGTGGGATCCCTGGCTGCTCA

CGCCCCTGAGGACCCCTCGGATCTGCTCCAGCACGTGAAATTCCAGTCCAGCAACTTTGAAAACATCCTG

ACGTGGGACAGCGGGCCAGAGGGCACCCCAGACACGGTCTACAGCATCGAGTATAAGACGTACGGAGAGA

GGGACTGGGTGGCAAAGAAGGGCTGTCAGCGGATCACCCGGAAGTCCTGCAACCTGACGGTGGAGACGGG

CAACCTCACGGAGCTCTACTATGCCAGGGTCACCGCTGTCAGTGCGGGAGGCCGGTCAGCCACCAAGATG

ACTGACAGGTTCAGCTCTCTGCAGCACACTACCCTCAAGCCACCTGATGTGACCTGTATCTCCAAAGTGA

GATCGATTCAGATGATTGTTCATCCTACCCCCACGCCAATCCGTGCAGGCGATGGCCACCGGCTAACCCT

GGAAGACATCTTCCATGACCTGTTCTACCACTTAGAGCTCCAGGTCAACCGCACCTACCAAATGCACCTT

GGAGGGAAGCAGAGAGAATATGAGTTCTTCGGCCTGACCCCTGACACAGAGTTCCTTGGCACCATCATGA

-continued

TTTGCGTTCCCACCTGGGCCAAGGAGAGTGCCCCCTACATGTGCCGAGTGAAGACACTGCCAGACCGGAC

ATGGACCTACTCCTTCTCCGGAGCCTTCCTGTTCTCCATGGGCTTCCTCGTCGCAGTACTCTGCTACCTG

AGCTACAGATATGTCACCAAGCCGCCTGCACCTCCCAACTCCCTGAACGTCCAGCGAGTCCTGACTTTCC

AGCCGCTGCGCTTCATCCAGGAGCACGTCCTGATCCCTGTCTTTGACCTCAGCGGCCCCAGCAGTCTGGC

CCAGCCTGTCCAGTACTCCCAGATCAGGGTGTCTGGACCCAGGGAGCCCGCAGGAGCTCCACAGCGGCAT

AGCCTGTCCGAGATCACCTACTTAGGGCAGCCAGACATCTCCATCCTCCAGCCCTCCAACGTGCCACCTC

CCCAGATCCTCTCCCCACTGTCCTATGCCCCAAACGCTGCCCCTGAGGTCGGGCCCCCATCCTATGCACC

TCAGGTGACCCCCGAAGCTCAATTCCCATTCTACGCCCCACAGGCCATCTCTAAGGTCCAGCCTTCCTCC

TATGCCCCTCAAGCCACTCCGGACAGCTGGCCTCCCTCCTATGGGGTATGCATGGAAGGTTCTGGCAAAG

ACTCCCCCACTGGGACACTTTCTAGTCCTAAACACCTTAGGCCTAAAGGTCAGCTTCAGAAAGAGCCACC

AGCTGGAAGCTGCATGTTAGGTGGCCTTTCTCTGCAGGAGGTGACCTCCTTGGCTATGGAGGAATCCCAA

GAAGCAAAATCATTGCACCAGCCCCTGGGGATTTGCACAGACAGAACATCTGACCCAAATGTGCTACACA

GTGGGGAGGAAGGGACACCACAGTACCTAAAGGGCCAGCTCCCCCTCCTCTCCTCAGTCCAGATCGAGGG

CCACCCCATGTCCCTCCCTTTGCAACCTCCTTCCGGTCCATGTTCCCCCTCGGACCAAGGTCCAAGTCCC

TGGGGCCTGCTGGAGTCCCTTGTGTGTCCCAAGGATGAAGCCAAGAGCCCAGCCCCTGAGACCTCAGACC

TGGAGCAGCCCACAGAACTGGATTCTCTTTTCAGAGGCCTGGCCCTGACTGTGCAGTGGGAGTCCTGAGG

GGAATGGGAAAGGCTTGGTGCTTCCTCCCTGTCCCTACCCAGTGTCACATCCTTGGCTGTCAATCCCATG

CCTGCCCATGCCACACACTCTGCGATCTGGCCTCAGACGGGTGCCCTTGAGAGAAGCAGAGGGAGTGGCA

TGCAGGGCCCCTGCCATGGGTGCGCTCCTCACCGGAACAAAGCAGCATGATAAGGACTGCAGCGGGGGAG

CTCTGGGGAGCAGCTTGTGTAGACAAGCGCGTGCTCGCTGAGCCCTGCAAGGCAGAAATGACAGTGCAAG

GAGGAAATGCAGGGAAACTCCCGAGGTCCAGAGCCCCACCTCCTAACACCATGGATTCAAAGTGCTCAGG

GAATTTGCCTCTCCTTGCCCCATTCCTGGCCAGTTTCACAATCTAGCTCGACAGAGCATGAGGCCCCTGC

CTCTTCTGTCATTGTTCAAAGGTGGGAAGAGAGCCTGGAAAAGAACCAGGCCTGGAAAAGAACCAGAAGG

AGGCTGGGCAGAACCAGAACAACCTGCACTTCTGCCAAGGCCAGGGCCAGCAGGACGGCAGGACTCTAGG

GAGGGGTGTGGCCTGCAGCTCATTCCCAGCCAGGGCAACTGCCTGACGTTGCACGATTTCAGCTTCATTC

CTCTGATAGAACAAAGCGAAATGCAGGTCCACCAGGGAGGGAGACACACAAGCCTTTTCTGCAGGCAGGA

GTTTCAGACCCTATCCTGAGAATGGGGTTTGAAAGGAAGGTGAGGGCTGTGGCCCCTGGACGGGTACAAT

AACACACTGTACTGATGTCACAACTTTGCAAGCTCTGCCTTGGGTTCAGCCCATCTGGGCTCAAATTCCA

GCCTCACCACTCACAAGCTGTGTGACTTCAAACAAATGAAATCAGTGCCCAGAACCTCGGTTTCCTCATC

TGTAATGTGGGGATCATAACACCTACCTCATGGAGTTGTGGTGAAGATGAAATGAAGTCATGTCTTTAAA

GTGCTTAATAGTGCCTGGTACATGGGCAGTGCCCAATAAACGGTAGCTATTTAAAAAAAAAAAAA

SEQ ID NO: 12: Human Amino Acid Sequence IL-10 Receptor Beta (NP_000619.3)
MAWSLGSWLGGCLLVSALGMVPPPENVRMNSVNFKNILQWESPAFAKGNLTFTAQYLSYRIFQDKCMNTTLTE

CDFSSLSKYGDHTLRVRAEFADEHSDWVNITFCPVDDTIIGPPGMQVEVLADSLHMRFLAPKIENEYETWTMK

NVYNSWTYNVQYWKNGTDEKFQITPQYDFEVLRNLEPWTTYCVQVRGFLPDRNKAGEWSEPVCEQTTHDETVP

SWMVAVILMASVFMVCLALLGCFALLWCVYKKTKYAFSPRNSLPQHLKEFLGHPHHNTLLFFSFPLSDENDVE

DKLSVIAEDSESGKQNPGDSCSLGTPPGQGPQS

SEQ ID NO: 13: Human Nucleic Acid cDNA/mRNA Sequence IL-10 Receptor Beta (NM_000628.5)
ATCTCCGCTGGTTCCCGGAAGCCGCCGCGGACAAGCTCTCCCGGGCGCGGGCGGGGGTCGTGTGCTTGGAGGA

AGCCGCGGAACCCCCAGCGTCCGTCCATGGCGTGGAGCCTTGGGAGCTGGCTGGGTGGCTGCCTGCTGGTGTC

AGCATTGGGAATGGTACCACCTCCCGAAAATGTCAGAATGAATTCTGTTAATTTCAAGAACATTCTACAGTGG

-continued

GAGTCACCTGCTTTTGCCAAAGGGAACCTGACTTTCACAGCTCAGTACCTAAGTTATAGGATATTCCAAGATA

AATGCATGAATACTACCTTGACGGAATGTGATTTCTCAAGTCTTTCCAAGTATGGTGACCACACCTTGAGAGT

CAGGGCTGAATTTGCAGATGAGCATTCAGACTGGGTAAACATCACCTTCTGTCCTGTGGATGACACCATTATT

GGACCCCCTGGAATGCAAGTAGAAGTACTTGCTGATTCTTTACATATGCGTTTCTTAGCCCCTAAAATTGAGA

ATGAATACGAAACTTGGACTATGAAGAATGTGTATAACTCATGGACTTATAATGTGCAATACTGGAAAAACGG

TACTGATGAAAAGTTTCAAATTACTCCCCAGTATGACTTTGAGGTCCTCAGAAACCTGGAGCCATGGACAACT

TATTGTGTTCAAGTTCGAGGGTTTCTTCCTGATCGGAACAAAGCTGGGGAATGGAGTGAGCCTGTCTGTGAGC

AAACAACCCATGACGAAACGGTCCCCTCCTGGATGGTGGCCGTCATCCTCATGGCCTCGGTCTTCATGGTCTG

CCTGGCACTCCTCGGCTGCTTCGCCTTGCTGTGGTGCGTTTACAAGAAGACAAAGTACGCCTTCTCCCCTAGG

AATTCTCTTCCACAGCACCTGAAAGAGTTTTTGGGCCATCCTCATCATAACACACTTCTGTTTTTCTCCTTTC

CATTGTCGGATGAGAATGATGTTTTTGACAAGCTAAGTGTCATTGCAGAAGACTCTGAGAGCGGCAAGCAGAA

TCCTGGTGACAGCTGCAGCCTCGGGACCCCGCCTGGGCAGGGGCCCCAAAGCTAGGCTCTGAGAAGGAAACAC

ACTCGGCTGGGCACAGTGACGTACTCCATCTCACATCTGCCTCAGTGAGGGATCAGGGCAGCAAACAAGGGCC

AAGACCATCTGAGCCAGCCCCACATCTAGAACTCCCAGACCCTGGACTTAGCCACCAGAGAGCTACATTTTAA

AGGCTGTCTTGGCAAAAATACTCCATTTGGGAACTCACTGCCTTATAAAGGCTTTCATGATGTTTTCAGAAGT

TGGCCACTGAGAGTGTAATTTTCAGCCTTTTATATCACTAAAATAAGATCATGTTTTAATTGTGAGAAACAGG

GCCGAGCACAGTGGCTCACGCCTGTAATACCAGCACCTTAGAGGTCGAGGCAGGCGGATCACTTGAGGTCAGG

AGTTCAAGACCAGCCTGGCCAATATGGTGAAACCCAGTCTCTACTAAAAATACAAAAATTAGCTAGGCATGAT

GGCGCATGCCTATAATCCCAGCTACTCGAGTGCCTGAGGCAGGAGAATTGCATGAACCCGGGAGGAGGAGGAG

GAGGTTGCAGTGAGCCGAGATAGCGGCACTGCACTCCAGCCTGGGTGACAAAGTGAGACTCCATCTCAAAAAA

AAAAAAAAAAAAAATTGTGAGAAACAGAAATACTTAAAATGAGGAATAAGAATGGAGATGTTACATCTGGTAG

ATGTAACATTCTACCAGATTATGGATGGACTGATCTGAAAATCGACCTCAACTCAAGGGTGGTCAGCTCAATG

CTACACAGAGCACGGACTTTTGGATTCTTTGCAGTACTTTGAATTTATTTTTCTACCTATATATGTTTTATAT

GCTGCTGGTGCTCCATTAAAGTTTTACTCTGTGTTGCACTATA

SEQ ID NO: 14 Human Amino Acid Sequence Arylhydrocarbon receptor (NP_001612.1)

MNSSSANITYASRKRRKPVQKTVKPIPAEGIKSNPSKRHRDRINTELDRLASLLPFPQDVINKLDKLSVL

RLSVSYLRAKSFFDVALKSSPTERNGGQDNCRAANFREGLNLQEGEFLLQALNGFVLVVTTDALVFYASS

TIQDYLGFQQSDVIHQSVYELIHTEDRAEFQRQLHWALNPSQCTESGQGIEEATGLPQTVVCYNPDQIPP

ENSPLMERCFICRLRCLLDNSSGFLAMNFQGKLKYLHGQKKKGKDGSILPPQLALFAIATPLQPPSILEI

RTKNFIFRTKHKLDFTPIGCDAKGRIVLGYTEAELCTRGSGYQFIHAADMLYCAESHIRMIKTGESGMIV

FRLLTKNNRWTWVQSNARLLYKNGRPDYIIVTQRPLTDEEGTEHLRKRNTKLPFMFTTGEAVLYEATNPF

PAIMDPLPLRTKNGTSGKDSATTSTLSKDSLNPSSLLAAMMQQDESIYLYPASSTSSTAPFENNFFNESM

NECRNWQDNTAPMGNDTILKHEQIDQPQDVNSFAGGHPGLFQDSKNSDLYSIMKNLGIDFEDIRHMQNEK

FFRNDFSGEVDERDIDLTDEILTYVQDSLSKSPFIPSDYQQQQSLALNSSCMVQEHLHLEQQQQHHQKQV

VVEPQQQLCQKMKHMQVNGMFENWNSNQFVPFNCPQQDPQQYNVFTDLHGISQEFPYKSEMDSMPYTQNF

ISCNQPVLPQHSKCTELDYPMGSFEPSPYPTTSSLEDFVTCLQLPENQKHGLNPQSAIITPQTCYAGAVS

MYQCQPEPQHTHVGQMQYNPVLPGQQAFLNKFQNGVLNETYPAELNNINNTQTTTHLQPLHHPSEARPFP

DLTSSGFL

SEQ ID NO: 15 Human Nucleic Acid cDNA/mRNA Sequence Arylhydrocarbon receptor (NM_001621.5)

AGTGGCTGGGGAGTCCCGTCGACGCTCTGTTCCGAGAGCGTGCCCCGGACCGCCAGCTCAGAACAGGGGC

AGCCGTGTAGCCGAACGGAAGCTGGGAGCAGCCGGGACTGGTGGCCCGCGCCCGAGCTCCGCAGGCGGGA

-continued

AGCACCCTGGATTTAGGAAGTCCCGGGAGCAGCGCGGCGGCACCTCCCTCACCCAAGGGGCCGCGGCGAC

GGTCACGGGGCGCGGCGCCACCGTGAGCGACCCAGGCCAGGATTCTAAATAGACGGCCCAGGCTCCTCCT

CCGCCCGGGCCGCCTCACCTGCGGGCATTGCCGCGCCGCCTCCGCCGGTGTAGACGGCACCTGCGCCGCC

TTGCTCGCGGGTCTCCGCCCCTCGCCCACCCTCACTGCGCCAGGCCCAGGCAGCTCACCTGTACTGGCGC

GGGCTGCGGAAGCCTGCGTGAGCCGAGGCGTTGAGGCGCGGCGCCCACGCCACTGTCCCGAGAGGACGCA

GGTGGAGCGGGCGCGGCTTCGCGGAACCCGGCGCCGGCCGCCGCAGTGGTCCCAGCCTACACCGGGTTCC

GGGGACCCGGCCGCCAGTGCCCGGGGAGTAGCCGCCGCCGTCGGCTGGGCACCATGAACAGCAGCAGCGC

CAACATCACCTACGCCAGTCGCAAGCGGCGGAAGCCGGTGCAGAAAACAGTAAAGCCAATCCCAGCTGAA

GGAATCAAGTCAAATCCTTCCAAGCGGCATAGAGACCGACTTAATACAGAGTTGGACCGTTTGGCTAGCC

TGCTGCCTTTCCCACAAGATGTTATTAATAAGTTGGACAAACTTTCAGTTCTTAGGCTCAGCGTCAGTTA

CCTGAGAGCCAAGAGCTTCTTTGATGTTGCATTAAAATCCTCCCCTACTGAAAGAAACGGAGGCCAGGAT

AACTGTAGAGCAGCAAATTTCAGAGAAGGCCTGAACTTACAAGAAGGAGAATTCTTATTACAGGCTCTGA

ATGGCTTTGTATTAGTTGTCACTACAGATGCTTTGGTCTTTTATGCTTCTTCTACTATACAAGATTATCT

AGGGTTTCAGCAGTCTGATGTCATACATCAGAGTGTATATGAACTTATCCATACCGAAGACCGAGCTGAA

TTTCAGCGTCAGCTACACTGGGCATTAAATCCTTCTCAGTGTACAGAGTCTGGACAAGGAATTGAAGAAG

CCACTGGTCTCCCCCAGACAGTAGTCTGTTATAACCCAGACCAGATTCCTCCAGAAAACTCTCCTTTAAT

GGAGAGGTGCTTCATATGTCGTCTAAGGTGTCTGCTGGATAATTCATCTGGTTTTCTGGCAATGAATTTC

CAAGGGAAGTTAAAGTATCTTCATGGACAGAAAAAGAAAGGGAAAGATGGATCAATACTTCCACCTCAGT

TGGCTTTGTTTGCGATAGCTACTCCACTTCAGCCACCATCCATACTTGAAATCCGGACCAAAAATTTTAT

CTTTAGAACCAAACACAAACTAGACTTCACACCTATTGGTTGTGATGCCAAAGGAAGAATTGTTTTAGGA

TATACTGAAGCAGAGCTGTGCACGAGAGGCTCAGGTTATCAGTTTATTCATGCAGCTGATATGCTTTATT

GTGCCGAGTCCCATATCCGAATGATTAAGACTGGAGAAAGTGGCATGATAGTTTTCCGGCTTCTTACAAA

AAACAACCGATGGACTTGGGTCCAGTCTAATGCACGCCTGCTTTATAAAAATGGAAGACCAGATTATATC

ATTGTAACTCAGAGACCACTAACAGATGAGGAAGGAACAGAGCATTTACGAAAACGAAATACGAAGTTGC

CTTTTATGTTTACCACTGGAGAAGCTGTGTTGTATGAGGCAACCAACCCTTTTCCTGCCATAATGGATCC

CTTACCACTAAGGACTAAAAATGGCACTAGTGGAAAAGACTCTGCTACCACATCCACTCTAAGCAAGGAC

TCTCTCAATCCTAGTTCCCTCCTGGCTGCCATGATGCAACAAGATGAGTCTATTTATCTCTATCCTGCTT

CAAGTACTTCAAGTACTGCACCTTTTGAAAACAACTTTTTCAACGAATCTATGAATGAATGCAGAAATTG

GCAAGATAATACTGCACCGATGGGAAATGATACTATCCTGAAACATGAGCAAATTGACCAGCCTCAGGAT

GTGAACTCATTTGCTGGAGGTCACCCAGGGCTCTTTCAAGATAGTAAAAACAGTGACTTGTACAGCATAA

TGAAAAACCTAGGCATTGATTTTGAAGACATCAGACACATGCAGAATGAAAAATTTTTCAGAAATGATTT

TTCTGGTGAGGTTGACTTCAGAGACATTGACTTAACGGATGAAATCCTGACGTATGTCCAAGATTCTTTA

AGTAAGTCTCCCTTCATACCTTCAGATTATCAACAGCAACAGTCCTTGGCTCTGAACTCAAGCTGTATGG

TACAGGAACACCTACATCTAGAACAGCAACAGCAACATCACCAAAAGCAAGTAGTAGTGGAGCCACAGCA

ACAGCTGTGTCAGAAGATGAAGCACATGCAAGTTAATGGCATGTTTGAAAATTGGAACTCTAACCAATTC

GTGCCTTTCAATTGTCCACAGCAAGACCCACAACAATATAATGTCTTTACAGACTTACATGGGATCAGTC

AAGAGTTCCCCTACAAATCTGAAATGGATTCTATGCCTTATACACAGAACTTTATTTCCTGTAATCAGCC

TGTATTACCACAACATTCCAAATGTACAGAGCTGGACTACCCTATGGGGAGTTTTGAACCATCCCCATAC

CCCACTACTTCTAGTTTAGAAGATTTTGTCACTTGTTTACAACTTCCTGAAAACCAAAAGCATGGATTAA

ATCCACAGTCAGCCATAATAACTCCTCAGACATGTTATGCTGGGGCCGTGTCGATGTATCAGTGCCAGCC

-continued

AGAACCTCAGCACACCCACGTGGGTCAGATGCAGTACAATCCAGTACTGCCAGGCCAACAGGCATTTTTA

AACAAGTTTCAGAATGGAGTTTTAAATGAAACATATCCAGCTGAATTAAATAACATAAATAACACTCAGA

CTACCACACATCTTCAGCCACTTCATCATCCGTCAGAAGCCAGACCTTTTCCTGATTTGACATCCAGTGG

ATTCCTGTAATTCCAAGCCCAATTTTGACCCTGGTTTTTGGATTAAATTAGTTTGTGAAGGATTATGGAA

AAATAAAACTGTCACTGTTGGACGTCAGCAAGTTCACATGGAGGCATTGATGCATGCTATTCACAATTAT

TCCAAACCAAATTTTAATTTTTGCTTTTAGAAAAGGGAGTTTAAAAATGGTATCAAAATTACATATACTA

CAGTCAAGATAGAAAGGGTGCTGCCACGGAGTGGTGAGGTACCGTCTACATTTCACATTATTCTGGGCAC

CACAAAATATACAAAACTTTATCAGGGAAACTAAGATTCTTTTAAATTAGAAAATATTCTCTATTTGAAT

TATTTCTGTCACAGTAAAAATAAAATACTTTGAGTTTTGAGCTACTGGATTCTTATTAGTTCCCCAAATA

CAAAGTTAGAGAACTAAACTAGTTTTTCCTATCATGTTAACCTCTGCTTTTATCTCAGATGTTAAAATAA

ATGGTTTGGTGCTTTTTATAAAAAGATAATCTCAGTGCTTTCCTCCTTCACTGTTTCATCTAAGTGCCTC

ACATTTTTTTCTACCTATAACACTCTAGGATGTATATTTTATATAAAGTATTCTTTTTCTTTTTTAAATT

AATATCTTTCTGCACACAAATATTATTTGTGTTTCCTAAATCCAACCATTTTCATTAATTCAGGCATATT

TTAACTCCACTGCTTACCTACTTTCTTCAGGTAAAGGGCAAATAATGATCGAAAAAATAATTATTTATTA

CATAATTTAGTTGTTTCTAGACTATAAATGTTGCTATGTGCCTTATGTTGAAAAAATTTAAAAGTAAAAT

GTCTTTCCAAATTATTTCTTAATTATTATAAAAATATTAAGACAATAGCACTTAAATTCCTCAACAGTGT

TTTCAGAAGAAATAAATATACCACTCTTTACCTTTATTGATATCTCCATGATGATAGTTGAATGTTGCAA

TGTGAAAAATCTGCTGTTAACTGCAACCTTGTTTATTAAATTGCAAGAAGCTTTATTTCTAGCTTTTTAA

TTAAGCAAAGCACCCATTTCAATGTGTATAAATTGTCTTTAAAAACTGTTTTAGACCTATAATCCTTGAT

AATATATTGTGTTGACTTTATAAATTTCGCTTCTTAGAACAGTGGAAACTATGTGTTTTTCTCATATTTG

AGGAGTGTTAAGATTGCAGATAGCAAGGTTTGGTGCAAAGTATTGTAATGAGTGAATTGAATGGTGCATT

GTATAGATATAATGAACAAAATTATTTGTAAGATATTTGCAGTTTTTCATTTTAAAAAGTCCATACCTTA

TATATGCACTTAATTTGTTGGGGCTTTACATACTTTATCAATGTGTCTTTCTAAGAAATCAAGTAATGAA

TCCAACTGCTTAAAGTTGGTATTAATAAAAAGACAACCACATAGTTCGTTTACCTTCAAACTTTAGGTTT

TTTTAATGATATACTGATCTTCATTACCAATAGGCAAATTAATCACCCTACCAACTTTACTGTCCTAACA

TGGTTTAAAAGAAAAAATGACACCATCTTTTATTCTTTTTTTTTTTTTTTTTGAGAGAGAGTCTTACTC

TGCCGCCCAAACTGGAGTGCAGTGGCACAATCTTGGCTCACTGCAACCTCTACCTCCTGGGTTCAAGTGA

TTCTCTTGCCTCAGCCTCCCGAGTTGCTGGGATTACAGGCATGTGCCACCATGCCCAGCTAATTTTTGTA

TTTTTAGTAGAAACGGGTTTCACCATGTTGGCCAGACTGGTCTCAAACTCCTGACCTCAGGTGAGCCTCC

CACCTTGGCCTCCCAAAGTGCTGGGATTACAGGCGTGAGCCACTGCATTCAGCTCTTCTTTTCTTTAGAT

ATGAGAGCTGAAGAGCTTAGACACATTTTGCATGTATTATTTGAAAATCTGATGGAATCCCAAACTGAGA

TGTATTAAAATACAATTTTTGGCCGGGTGCAGTGGCTCACGCCTGTAATCCCAGCACTTGGGGAGGGCGA

GGAGGGTGGATCACGAGGTCAAGAGATGGAGACCATCCTGACCAACATGGTGAAACCCTGTCTCTACTAA

AAATACAGAAATTAGCTGGGCATGGTGGCGTGAGCCTGTAGTCCTAGCTACTCAGGAGGCTGAGGCAGGA

GAATAGCCTGAACCTGGGAATCGGAGGTTGCAGAGCCAAGATCGCCCCACTGCACTCCAGCCTGGCAATA

GACCGAGACTCCGTCTCCAAAAAAAAAAAAAAATACAATTTTTATTTCTTTTACTTTTTTTAGTAAGTTAA

TGTATATAAAAATGGCTTCGGACAAAATATCTCTGAGTTCTGTGTATTTTCAGTCAAAACTTTAAACCTG

TAGAATCAATTTAAGTGTTGGAAAAAAATTTGTCTGAAACATTTCATAATTTGTTTCCAGCATGAGGTATC

TAAGGATTTAGACCAGAGGTCTAGATTAATACTCTATTTTTACATTTAAACCTTTTATTATAAGTCTTAC

ATAAACCATTTTTGTTACTCTCTTCCACATGTTACTGGATAAATTGTTTAGTGGAAAATAGGCTTTTTAA

TCATGAATATGATGACAATCAGTTATACAGTTATAAAATTAAAAGTTTGAAAAGCAATATTGTATATTTT

-continued

TATCTATATAAAATAACTAAAATGTATCTAAGAATAATAAAATCACGTTAAACCAAATACACGTTTGTCT

GTATTGTTAAGTGCCAAACAAAGGATACTTAGTGCACTGCTACATTGTGGGATTTATTTCTAGATGATGT

GCACATCTAAGGATATGGATGTGTCTAATTTAGTCTTTTCCTGTACCAGGTTTTTCTTACAATACCTGAA

GACTTACCAGTATTCTAGTGTATTATGAAGCTTTCAACATTACTATGCACAAACTAGTGTTTTTCGATGT

TACTAAATTTTAGGTAAATGCTTTCATGGCTTTTTTCTTCAAAATGTTACTGCTTACATATATCATGCAT

AGATTTTTGCTTAAAGTATGATTTATAATATCCTCATTATCAAAGTTGTATACAATAATATATAATAAAA

SEQ ID NO: 16 Human Amino Acid Sequence S100A8 (NP_001306125.1)
MSLVSCLSEDLKVLFFRWGKSVGIMLTELEKALNSIIDVYHKYSLIKGNFHAVYRDDLKKLLETECPQYI

RKKGADVWFKELDINTDGAVNFQEFLILVIKMGVAAHKKSHEESHKE

SEQ ID NO: 17 Human Nucleic Acid cDNA/mRNA Sequence S100A8 (NM_001319196.1)
GAGAAACCAGAGACTGTAGCAACTCTGGCAGGGAGAAGCTGTCTCTGATGGCCTGAAGCTGTGGGCAGCT

GGCCAAGCCTAACCGCTATAAAAAGGAGCTGCCTCTCAGCCCTGCATGTCTCTTGTCAGCTGTCTTTCAG

AAGACCTGAAGGTTCTGTTTTTCAGGTGGGGCAAGTCCGTGGGCATCATGTTGACCGAGCTGGAGAAAGC

CTTGAACTCTATCATCGACGTCTACCACAAGTACTCCCTGATAAAGGGGAATTTCCATGCCGTCTACAGG

GATGACCTGAAGAAATTGCTAGAGACCGAGTGTCCTCAGTATATCAGGAAAAAGGGTGCAGACGTCTGGT

TCAAAGAGTTGGATATCAACACTGATGGTGCAGTTAACTTCCAGGAGTTCCTCATTCTGGTGATAAAGAT

GGGCGTGGCAGCCCACAAAAAAAGCCATGAAGAAAGCCACAAAGAGTAGCTGAGTTACTGGGCCCAGAGG

CTGGGCCCCTGGACATGTACCTGCAGAATAATAAAGTCATCAATACCTCAAAAAAAAAA

SEQ ID NO: 18 Human Amino Acid Sequence S100A9 (NP_002956.1)
MTCKMSQLERNIETIINTFHQYSVKLGHPDTLNQGEFKELVRKDLQNFLKKENKNEKVIEHIMEDLDTNA

DKQLSFEEFIMLMARLTWASHEKMHEGDEGPGHHHKPGLGEGTP

SEQ ID NO: 19 Human Nucleic Acid cDNA/mRNA Sequence S100A9 (NM_002965.4)
AAACACTCTGTGTGGCTCCTCGGCTTTGACAGAGTGCAAGACGATGACTTGCAAAATGTCGCAGCTGGAA

CGCAACATAGAGACCATCATCAACACCTTCCACCAATACTCTGTGAAGCTGGGGCACCCAGACACCCTGA

ACCAGGGGGAATTCAAAGAGCTGGTGCGAAAAGATCTGCAAAATTTTCTCAAGAAGGAGAATAAGAATGA

AAAGGTCATAGAACACATCATGGAGGACCTGGACACAAATGCAGACAAGCAGCTGAGCTTCGAGGAGTTC

ATCATGCTGATGGCGAGGCTAACCTGGGCCTCCCACGAGAAGATGCACGAGGGTGACGAGGGCCCTGGCC

ACCACCATAAGCCAGGCCTCGGGGAGGGCACCCCCTAAGACCACAGTGGCCAAGATCACAGTGGCCACGG

CCACGGCCACAGTCATGGTGGCCACGGCCACAGCCACTAATCAGGAGGCCAGGCCACCCTGCCTCTACCC

AACCAGGGCCCCGGGGCCTGTTATGTCAAACTGTCTTGGCTGTGGGGCTAGGGGCTGGGGCCAAATAAAG

TCTCTTCCTCCAA

SEQ ID NO: 20 Human Amino Acid Sequence S100A10 (NP_002957.1)
MPSQMEHAMETMMFTFHKFAGDKGYLTKEDLRVLMEKEFPGFLENQKDPLAVDKIMKDLDQCRDGKVGFQ

SFFSLIAGLTIACNDYFVVHMKQKGKK

SEQ ID NO: 21 Human Nucleic Acid cDNA/mRNA Sequence S100A10 (NM_002966.3)
ACCCACCCGCCGCACGTACTAAGGAAGGCGCACAGCCCGCCGCGCTCGCCTCTCCGCCCCGCGTCCAGCT

CGCCCAGCTCGCCCAGCGTCCGCCGCGCCTCGGCCAAGGCTTCAACGGACCACACCAAAATGCCATCTCA

AATGGAACACGCCATGGAAACCATGATGTTTACATTTCACAAATTCGCTGGGGATAAAGGCTACTTAACA

AAGGAGGACCTGAGAGTACTCATGGAAAAGGAGTTCCCTGGATTTTTGGAAAATCAAAAAGACCCTCTGG

CTGTGGACAAAATAATGAAGGACCTGGACCAGTGTAGAGATGGCAAAGTGGGCTTCCAGAGCTTCTTTTC

CCTAATTGCGGGCCTCACCATTGCATGCAATGACTATTTTGTAGTACACATGAAGCAGAAGGGAAAGAAG

TAGGCAGAAATGAGCAGTTCGCTCCTCCCTGATAAGAGTTGTCCCAAAGGGTCGCTTAAGGAATCTGCCC

CACAGCTTCCCCCATAGAAGGATTTCATGAGCAGATCAGGACACTTAGCAAATGTAAAAATAAAATCTAA

-continued

CTCTCATTTGACAAGCAGAGAAAGAAAAGTTAAATACCAGATAAGCTTTTGATTTTTGTATTGTTTGCAT

CCCCTTGCCCTCAATAAATAAAGTTCTTTTTTAGTTCCAAA

SEQ ID NO: 22 Human Amino Acid Sequence S100A11 (NP_005611.1)
MAKISSPTETERCIESLIAVFQKYAGKDGYNYTLSKTEFLSFMNTELAAFTKNQKDPGVLDRMMKKLDTN

SDGQLDFSEFLNLIGGLAMACHDSFLKAVPSQKRT

SEQ ID NO: 23 Human Nucleic Acid cDNA/mRNA Sequence S100A11 (NM_005620.2)
GAGGAGAGGCTCCAGACCCGCACGCCGCGCGCACAGAGCTCTCAGCGCCGCTCCCAGCCACAGCCTCCCG

CGCCTCGCTCAGCTCCAACATGGCAAAAATCTCCAGCCCTACAGAGACTGAGCGGTGCATCGAGTCCCTG

ATTGCTGTCTTCCAGAAGTATGCTGGAAAGGATGGTTATAACTACACTCTCTCCAAGACAGAGTTCCTAA

GCTTCATGAATACAGAACTAGCTGCCTTCACAAAGAACCAGAAGGACCCTGGTGTCCTTGACCGCATGAT

GAAGAAACTGGACACCAACAGTGATGGTCAGCTAGATTTCTCAGAATTTCTTAATCTGATTGGTGGCCTA

GCTATGGCTTGCCATGACTCCTTCCTCAAGGCTGTCCCTTCCCAGAAGCGGACCTGAGGACCCCTTGGCC

CTGGCCTTCAAACCCACCCCCTTTCCTTCCAGCCTTTCTGTCATCATCTCCACAGCCCACCCATCCCCTG

AGCACACTAACCACCTCATGCAGGCCCCACCTGCCAATAGTAATAAAGCAATGTCACTTTTTTAAAACAT

GAA

SEQ ID NO: 24 Human Amino Acid Sequence *Homo sapiens* signal transducer and activator of transcription 3 (STAT3) (NP_644805.1)
MAQWNQLQQLDTRYLEQLHQLYSDSFPMELRQFLAPWIESQDWAYAASKESHATLVFHNLLGEIDQQYSR

FLQESNVLYQHNLRRIKQFLQSRYLEKPMEIARIVARCLWEESRLLQTAATAAQQGGQANHPTAAVVTEK

QQMLEQHLQDVRKRVQDLEQKMKVVENLQDDFDFNYKTLKSQGDMQDLNGNNQSVTRQKMQQLEQMLTAL

DQMRRSIVSELAGLLSAMEYVQKTLTDEELADWKRRQQIACIGGPPNICLDRLENWITSLAESQLQTRQQ

IKKLEELQQKVSYKGDPIVQHRPMLEERIVELFRNLMKSAFVVERQPCMPMHPDRPLVIKTGVQFTTKVR

LLVKFPELNYQLKIKVCIDKDSGDVAALRGSRKFNILGTNTKVMNMEESNNGSLSAEFKHLTLREQRCGN

GGRANCDASLIVTEELHLITFETEVYHQGLKIDLETHSLPVVVISNICQMPNAWASILWYNMLTNNPKNV

NFFTKPPIGTWDQVAEVLSWQFSSTTKRGLSIEQLTTLAEKLLGPGVNYSGCQITWAKFCKENMAGKGFS

FWVWLDNIIDLVKKYILALWNEGYIMGFISKERERAILSTKPPGTFLLRFSESSKEGGVTFTWVEKDISG

KTQIQSVEPYTKQQLNNMSFAEIIMGYKIMDATNILVSPLVYLYPDIPKEEAFGKYCRPESQEHPEADPG

SAAPYLKTKFICVTPTTCSNTIDLPMSPRTLDSLMQFGNNGEGAEPSAGGQFESLTFDMELTSECATSPM

SEQ ID NO: 25 Human Nucleic Acid cDNA/mRNA Sequence *Homo sapiens* signal transducer and activator of transcription 3 (STAT3), transcript variant 1, cDNA/mRNA (NM_139276.3)
GTCGCAGCCGAGGGAACAAGCCCCAACCGGATCCTGGACAGGCACCCCGGCTTGGCGCTGTCTCTCCCCC

TCGGCTCGGAGAGGCCCTTCGGCCTGAGGGAGCCTCGCCGCCCGTCCCCGGCACACGCGCAGCCCCGGCC

TCTCGGCCTCTGCCGGAGAAACAGTTGGGACCCCTGATTTTAGCAGGATGGCCCAATGGAATCAGCTACA

GCAGCTTGACACACGGTACCTGGAGCAGCTCCATCAGCTCTACAGTGACAGCTTCCCAATGGAGCTGCGG

CAGTTTCTGGCCCCTTGGATTGAGAGTCAAGATTGGGCATATGCGGCCAGCAAAGAATCACATGCCACTT

TGGTGTTTCATAATCTCCTGGGAGAGATTGACCAGCAGTATAGCCGCTTCCTGCAAGAGTCGAATGTTCT

CTATCAGCACAATCTACGAAGAATCAAGCAGTTTCTTCAGAGCAGGTATCTTGAGAAGCCAATGGAGATT

GCCCGGATTGTGGCCCGGTGCCTGTGGGAAGAATCACGCCTTCTACAGACTGCAGCCACTGCGGCCCAGC

AAGGGGGCCAGGCCAACCACCCCACAGCAGCCGTGGTGACGGAGAAGCAGCAGATGCTGGAGCAGCACCT

TCAGGATGTCCGGAAGAGAGTGCAGGATCTAGAACAGAAAATGAAAGTGGTAGAGAATCTCCAGGATGAC

TTTGATTTCAACTATAAAACCCTCAAGAGTCAAGGAGACATGCAAGATCTGAATGGAAACAACCAGTCAG

TGACCAGGCAGAAGATGCAGCAGCTGGAACAGATGCTCACTGCGCTGGACCAGATGCGGAGAAGCATCGT

GAGTGAGCTGGCGGGGCTTTTGTCAGCGATGGAGTACGTGCAGAAAACTCTCACGGACGAGGAGCTGGCT

-continued

GACTGGAAGAGGCGGCAACAGATTGCCTGCATTGGAGGCCCGCCCAACATCTGCCTAGATCGGCTAGAAA

ACTGGATAACGTCATTAGCAGAATCTCAACTTCAGACCCGTCAACAAATTAAGAAACTGGAGGAGTTGCA

GCAAAAAGTTTCCTACAAAGGGGACCCCATTGTACAGCACCGGCCGATGCTGGAGGAGAGAATCGTGGAG

CTGTTTAGAAACTTAATGAAAAGTGCCTTTGTGGTGGAGCGGCAGCCCTGCATGCCCATGCATCCTGACC

GGCCCCTCGTCATCAAGACCGGCGTCCAGTTCACTACTAAAGTCAGGTTGCTGGTCAAATTCCCTGAGTT

GAATTATCAGCTTAAAATTAAAGTGTGCATTGACAAAGACTCTGGGGACGTTGCAGCTCTCAGAGGATCC

CGGAAATTTAACATTCTGGGCACAAACACAAAAGTGATGAACATGGAAGAATCCAACAACGGCAGCCTCT

CTGCAGAATTCAAACACTTGACCCTGAGGGAGCAGAGATGTGGGAATGGGGGCCGAGCCAATTGTGATGC

TTCCCTGATTGTGACTGAGGAGCTGCACCTGATCACCTTTGAGACCGAGGTGTATCACCAAGGCCTCAAG

ATTGACCTAGAGACCCACTCCTTGCCAGTTGTGGTGATCTCCAACATCTGTCAGATGCCAAATGCCTGGG

CGTCCATCCTGTGGTACAACATGCTGACCAACAATCCCAAGAATGTAAACTTTTTTACCAAGCCCCCAAT

TGGAACCTGGGATCAAGTGGCCGAGGTCCTGAGCTGGCAGTTCTCCTCCACCACCAAGCGAGGACTGAGC

ATCGAGCAGCTGACTACACTGGCAGAGAAACTCTTGGGACCTGGTGTGAATTATTCAGGGTGTCAGATCA

CATGGGCTAAATTTTGCAAAGAAAACATGGCTGGCAAGGGCTTCTCCTTCTGGGTCTGGCTGGACAATAT

CATTGACCTTGTGAAAAAGTACATCCTGGCCCTTTGGAACGAAGGGTACATCATGGGCTTTATCAGTAAG

GAGCGGGAGCGGGCCATCTTGAGCACTAAGCCTCCAGGCACCTTCCTGCTAAGATTCAGTGAAAGCAGCA

AAGAAGGAGGCGTCACTTTCACTTGGGTGGAGAAGGACATCAGCGGTAAGACCCAGATCCAGTCCGTGGA

ACCATACACAAAGCAGCAGCTGAACAACATGTCATTTGCTGAAATCATCATGGGCTATAAGATCATGGAT

GCTACCAATATCCTGGTGTCTCCACTGGTCTATCTCTATCCTGACATTCCCAAGGAGGAGGCATTCGGAA

AGTATTGTCGGCCAGAGAGCCAGGAGCATCCTGAAGCTGACCCAGGTAGCGCTGCCCCATACCTGAAGAC

CAAGTTTATCTGTGTGACACCAACGACCTGCAGCAATACCATTGACCTGCCGATGTCCCCCCGCACTTTA

GATTCATTGATGCAGTTTGGAAATAATGGTGAAGGTGCTGAACCCTCAGCAGGAGGGCAGTTTGAGTCCC

TCACCTTTGACATGGAGTTGACCTCGGAGTGCGCTACCTCCCCCATGTGAGGAGCTGAGAACGGAAGCTG

CAGAAAGATACGACTGAGGCGCCTACCTGCATTCTGCCACCCCTCACACAGCCAAACCCCAGATCATCTG

AAACTACTAACTTTGTGGTTCCAGATTTTTTTTAATCTCCTACTTCTGCTATCTTTGAGCAATCTGGGCA

CTTTTAAAAATAGAGAAATGAGTGAATGTGGGTGATCTGCTTTTATCTAAATGCAAATAAGGATGTGTTC

TCTGAGACCCATGATCAGGGGATGTGGCGGGGGGTGGCTAGAGGGAGAAAAAGGAAATGTCTTGTGTTGT

TTTGTTCCCCTGCCCTCCTTTCTCAGCAGCTTTTTGTTATTGTTGTTGTTGTTCTTAGACAAGTGCCTCC

TGGTGCCTGCGGCATCCTTCTGCCTGTTTCTGTAAGCAAATGCCACAGGCCACCTATAGCTACATACTCC

TGGCATTGCACTTTTTAACCTTGCTGACATCCAAATAGAAGATAGGACTATCTAAGCCCTAGGTTTCTTT

TTAAATTAAGAAATAATAACAATTAAAGGGCAAAAAACACTGTATCAGCATAGCCTTTCTGTATTTAAGA

AACTTAAGCAGCCGGGCATGGTGGCTCACGCCTGTAATCCCAGCACTTTGGGAGGCCGAGGCGGATCATA

AGGTCAGGAGATCAAGACCATCCTGGCTAACACGGTGAAACCCCGTCTCTACTAAAAGTACAAAAAATTA

GCTGGGTGTGGTGGTGGGCGCCTGTAGTCCCAGCTACTCGGGAGGCTGAGGCAGGAGAATCGCTTGAACC

TGAGAGGCGGAGGTTGCAGTGAGCCAAAATTGCACCACTGCACACTGCACTCCATCCTGGGCGACAGTCT

GAGACTCTGTCTCAAAAAAAAAAAAAAAAAAAAAGAAACTTCAGTTAACAGCCTCCTTGGTGCTTTAAGCA

TTCAGCTTCCTTCAGGCTGGTAATTTATATAATCCCTGAAACGGGCTTCAGGTCAAACCCTTAAGACATC

TGAAGCTGCAACCTGGCCTTTGGTGTTGAAATAGGAAGGTTTAAGGAGAATCTAAGCATTTTAGACTTTT

TTTTATAAATAGACTTATTTTCCTTTGTAATGTATTGGCCTTTTAGTGAGTAAGGCTGGGCAGAGGGTGC

TTACAACCTTGACTCCCTTTCTCCCTGGACTTGATCTGCTGTTTCAGAGGCTAGGTTGTTTCTGTGGGTG

-continued

CCTTATCAGGGCTGGGATACTTCTGATTCTGGCTTCCTTCCTGCCCCACCCTCCCGACCCCAGTCCCCCT

GATCCTGCTAGAGGCATGTCTCCTTGCGTGTCTAAAGGTCCCTCATCCTGTTTGTTTTAGGAATCCTGGT

CTCAGGACCTCATGGAAGAAGAGGGGGAGAGAGTTACAGGTTGGACATGATGCACACTATGGGGCCCCAG

CGACGTGTCTGGTTGAGCTCAGGGAATATGGTTCTTAGCCAGTTTCTTGGTGATATCCAGTGGCACTTGT

AATGGCGTCTTCATTCAGTTCATGCAGGGCAAAGGCTTACTGATAAACTTGAGTCTGCCCTCGTATGAGG

GTGTATACCTGGCCTCCCTCTGAGGCTGGTGACTCCTCCCTGCTGGGGCCCCACAGGTGAGGCAGAACAG

CTAGAGGGCCTCCCCGCCTGCCCGCCTTGGCTGGCTAGCTCGCCTCTCCTGTGCGTATGGGAACACCTAG

CACGTGCTGGATGGGCTGCCTCTGACTCAGAGGCATGGCCGGATTTGGCAACTCAAAACCACCTTGCCTC

AGCTGATCAGAGTTTCTGTGGAATTCTGTTTGTTAAATCAAATTAGCTGGTCTCTGAATTAAGGGGGAGA

CGACCTTCTCTAAGATGAACAGGGTTCGCCCCAGTCCTCCTGCCTGGAGACAGTTGATGTGTCATGCAGA

GCTCTTACTTCTCCAGCAACACTCTTCAGTACATAATAAGCTTAACTGATAAACAGAATATTTAGAAAGG

TGAGACTTGGGCTTACCATTGGGTTTAAATCATAGGGACCTAGGGCGAGGGTTCAGGGCTTCTCTGGAGC

AGATATTGTCAAGTTCATGGCCTTAGGTAGCATGTATCTGGTCTTAACTCTGATTGTAGCAAAAGTTCTG

AGAGGAGCTGAGCCCTGTTGTGGCCCATTAAAGAACAGGGTCCTCAGGCCCTGCCCGCTTCCTGTCCACT

GCCCCCTCCCCATCCCCAGCCCAGCCGAGGGAATCCCGTGGGTTGCTTACCTACCTATAAGGTGGTTTAT

AAGCTGCTGTCCTGGCCACTGCATTCAAATTCCAATGTGTACTTCATAGTGTAAAAATTTATATTATTGT

GAGGTTTTTTGTCTTTTTTTTTTTTTTTTTTTTTTTGGTATATTGCTGTATCTACTTTAACTTCCAGAAAT

AAACGTTATATAGGAACCGTC

SEQ ID NO: 26 Human Amino Acid Sequence cathelicidin antimicrobial peptide preproprotein (STAT3 (NP_004336.4)
MKTQRDGHSLGRWSLVLLLLGLVMPLAIIAQVLSYKEAVLRAIDGINQRSSDANLYRLLDLDPRPTMDGD

PDTPKPVSFTVKETVCPRTTQQSPEDCDFKKDGLVKRCMGTVTLNQARGSFDISCDKDNKRFALLGDFFR

KSKEKIGKEFKRIVQRIKDFLRNLVPRTES

SEQ ID NO: 27 Human Nucleic Acid cDNA/mRNA Sequence cathelicidin antimicrobial peptide (CAMP), mRNA (NM_004345.5)
AGGCAGACATGGGGACCATGAAGACCCAAAGGGATGGCCACTCCCTGGGGCGGTGGTCACTGGTGCTCCT

GCTGCTGGGCCTGGTGATGCCTCTGGCCATCATTGCCCAGGTCCTCAGCTACAAGGAAGCTGTGCTTCGT

GCTATAGATGGCATCAACCAGCGGTCCTCGGATGCTAACCTCTACCGCCTCCTGGACCTGGACCCCAGGC

CCACGATGGATGGGGACCCAGACACGCCAAAGCCTGTGAGCTTCACAGTGAAGGAGACAGTGTGCCCCAG

GACGACACAGCAGTCACCAGAGGATTGTGACTTCAAGAAGGACGGGCTGGTGAAGCGGTGTATGGGGACA

GTGACCCTCAACCAGGCCAGGGGCTCCTTTGACATCAGTTGTGATAAGGATAACAAGAGATTTGCCCTGC

TGGGTGATTTCTTCCGGAAATCTAAAGAGAAGATTGGCAAAGAGTTTAAAAGAATTGTCCAGAGAATCAA

GGATTTTTTGCGGAATCTTGTACCCAGGACAGAGTCCTAGTGTGTGCCCTACCCTGGCTCAGGCTTCTGG

GCTCTGAGAAATAAACTATGAGAGCAATTTC

SEQ ID NO: 28 Human Amino Acid Sequence neutrophilic granule protein [Mus musculus] (ngp) (NP_032720.2)
MAGLWKTFVLVVALAVVSCEALPQLRYERIVDRAIEAYNQGRQGRPIFRLLSATPPSSONPATNIPLQER

IKETECTSTOEROPKDCDFLEDGEERNCTGKFERRROSTSLTLTCDRDCSREDTOETSENDKQDVSEKEK

FEDVPPHIRNIYEDAKYDIIGNILKNF

SEQ ID NO: 29 Human Nucleic Acid cDNA/mRNA Sequence neutrophilic granule protein [Mus musculus] (ngp), mRNA (NM_008694.2)
AGTCTCAATATCATCTACATAAAAGGGGCCAAGAGTGGTAGTGTGTCAGAGACAATGGCAGGGCTGTGGA

AGACCTTTGTATTGGTGGTGGCCTTGGCTGTGGTCTCCTGTGAGGCCCTTCGACAACTAAGATATGAGGA

GATTGTTGATAGAGCCATAGAGGCATACAACCAAGGGCGGCAAGGAAGACCCCTCTTCCGCCTGCTAAGT

GCCACTCCGCCTTCTAGTCAGAATCCTGCTACCAATATCCCACTCCAGTTCAGGATTAAAGAGACAGAGT

-continued

GTACTTCCACCCAGGAGAGACAGCCTAAAGACTGCGACTTCCTGGAGGATGGGGAGGAGAGAAATTGCAC

AGGGAAATTCTTCAGAAGGCGGCAGTCAACCTCCCTGACCTTGACCTGCGACAGGGATTGCAGTCGAGAG

GATACCCAAGAAACCAGTTTTAATGATAAGCAAGACGTCTCTGAAAAGGAAAAGTTCGAAGATGTGCCCC

CTCACATCAGGAACATTTATGAAGATGCCAAGTATGATATCATCGGCAACATCCTGAAAAATTTCTAGGG

CTGGAAAGAGGAGGGAGGTGCTCCCTGCATACTATGACCTCCTCTTTACCTCCACTACCCATCTCCCCCT

GCTGCATTCAGGATCTGCCCCTCCTTCCTGCCCTTCCCAGGAACACCCCCTCTAGAGTAGCTCTAGCTCC

TAAAACATCCATACCTTIGTCCATTTGCTTCCTTCTGCTGGGCCTTCCTGCCTTACCCTCTATCTGAAAC

CCTTATTGATTCTTCAAGGCCCAAGTTCAAAAGTCCCCTCCAGCGGGAAGCCTCCTCATTCTCCCAGAGC

CAAAGTCCTGCCCACATCAGTTCACTCATAATCTTCAAACCACATTGGTATTACCTGCTGTGTCCCCAGC

CAGACAACCCTGTATCTATTCACAGCTGGGCCTCCCGGGCCAGTTGCAGGTAGAATGAATATTTCAATGA

TGTGTCCCTGGAATCCTGGGAGGACAGAACCCTGTAGACTCCTGCTCTCTGCCTAGTCACTGTGACACCA

AATGCCCCTTTACATACCCAGATCCCTTAATGGGGATGTGGCAGGTGGGTGTGGTCAGATCACCTTGTGA

GGCCTATAAGAGAGGTTCAATAAAAATGCTTCTGAGATTAAAAAAAAAAAAAAAAA

SEQ ID NO: 30 Human Amino Acid Sequence prostaglandin G/H synthase 2 precursor (NP_000954.1)
MLARALLLCAVLALSHTANPCCSHPCQNRGVCMSVGFDQYKCDCTRTGFYGENCSTPEFLTRIKLFLKPT

PNTVHYILTHFKGFWNVVNNIPFLRNAIMSYVLTSRSHLIDSPPTYNADYGYKSWEAFSNLSYYTRALPP

VPDDCPTPLGVKGKKQLPDSNEIVEKLLLRRKFIPDPQGSNMMFAFFAQHFTHQFFKTDHKRGPAFTNGL

GHGVDLNHIYGETLARQRKLRLFKDGKMKYQIIDGEMYPPTVKDTQAEMIYPPQVPEHLRFAVGQEVFGL

VPGLMMYATIWLREHNRVCDVLKQEHPEWGDEQLFQTSRLILIGETIKIVIEDYVQHLSGYHFKLKFDPE

LLFNKQFQYQNRIAAEFNTLYHWHPLLPDTFQIHDQKYNYQQFIYNNSILLEHGITQFVESFTRQIAGRV

AGGRNVPPAVQKVSQASIDQSRQMKYQSFNEYRKRFMLKPYESFEELTGEKEMSAELEALYGDIDAVELY

PALLVEKPRPDAIFGETMVEVGAPFSLKGLMGNVICSPAYWKPSTFGGEVGFQIINTASIQSLICNNVKG

CPFTSFSVPDPELIKTVTINASSSRSGLDDINPTVLLKERSTEL

SEQ ID NO: 31 Human Nucleic Acid cDNA/mRNA Sequence prostaglandin G/H synthase 2 precursor (NM_000963.4)
AATTGTCATACGACTTGCAGTGAGCGTCAGGAGCACGTCCAGGAACTCCTCAGCAGCGCCTCCTTCAGCT

CCACAGCCAGACGCCCTCAGACAGCAAAGCCTACCCCCGCGCCGCGCCCTGCCCGCCGCTGCGATGCTCG

CCCGCGCCCTGCTGCTGTGCGCGGTCCTGGCGCTCAGCCATACAGCAAATCCTTGCTGTTCCCACCCATG

TCAAAACCGAGGTGTATGTATGAGTGTGGGATTTGACCAGTATAAGTGCGATTGTACCCGGACAGGATTC

TATGGAGAAAACTGCTCAACACCGGAATTTTTGACAAGAATAAAATTATTTCTGAAACCCACTCCAAACA

CAGTGCACTACATACTTACCCACTTCAAGGGATTTTGGAACGTTGTGAATAACATTCCCTTCCTTCGAAA

TGCAATTATGAGTTATGTGTTGACATCCAGATCACATTTGATTGACAGTCCACCAACTTACAATGCTGAC

TATGGCTACAAAAGCTGGGAAGCCTTCTCTAACCTCTCCTATTATACTAGAGCCCTTCCTCCTGTGCCTG

ATGATTGCCCGACTCCCTTGGGTGTCAAAGGTAAAAAGCAGCTTCCTGATTCAAATGAGATTGTGGAAAA

ATTGCTTCTAAGAAGAAAGTTCATCCCTGATCCCCAGGGCTCAAACATGATGTTTGCATTCTTTGCCCAG

CACTTCACGCATCAGTTTTTCAAGACAGATCATAAGCGAGGGCCAGCTTTCACCAACGGGCTGGGCCATG

GGGTGGACTTAAATCATATTTACGGTGAAACTCTGGCTAGACAGCGTAAACTGCGCCTTTTCAAGGATGG

AAAAATGAAATATCAGATAATTGATGGAGAGATGTATCCTCCCACAGTCAAAGATACTCAGGCAGAGATG

ATCTACCCTCCTCAAGTCCCTGAGCATCTACGGTTTGCTGTGGGGCAGGAGGTCTTTGGTCTGGTGCCTG

GTCTGATGATGTATGCCACAATCTGGCTGCGGGAACACAACAGAGTATGCGATGTGCTTAAACAGGAGCA

TCCTGAATGGGGTGATGAGCAGTTGTTCCAGACAAGCAGGCTAATACTGATAGGAGAGACTATTAAGATT

-continued

GTGATTGAAGATTATGTGCAACACTTGAGTGGCTATCACTTCAAACTGAAATTTGACCCAGAACTACTTT

TCAACAAACAATTCCAGTACCAAAATCGTATTGCTGCTGAATTTAACACCCTCTATCACTGGCATCCCCT

TCTGCCTGACACCTTTCAAATTCATGACCAGAAATACAACTATCAACAGTTTATCTACAACAACTCTATA

TTGCTGGAACATGGAATTACCCAGTTTGTTGAATCATTCACCAGGCAAATTGCTGGCAGGGTTGCTGGTG

GTAGGAATGTTCCACCCGCAGTACAGAAAGTATCACAGGCTTCCATTGACCAGAGCAGGCAGATGAAATA

CCAGTCTTTTAATGAGTACCGCAAACGCTTTATGCTGAAGCCCTATGAATCATTTGAAGAACTTACAGGA

GAAAAGGAAATGTCTGCAGAGTTGGAAGCACTCTATGGTGACATCGATGCTGTGGAGCTGTATCCTGCCC

TTCTGGTAGAAAAGCCTCGGCCAGATGCCATCTTTGGTGAAACCATGGTAGAAGTTGGAGCACCATTCTC

CTTGAAAGGACTTATGGGTAATGTTATATGTTCTCCTGCCTACTGGAAGCCAAGCACTTTTGGTGGAGAA

GTGGGTTTTCAAATCATCAACACTGCCTCAATTCAGTCTCTCATCTGCAATAACGTGAAGGGCTGTCCCT

TTACTTCATTCAGTGTTCCAGATCCAGAGCTCATTAAAACAGTCACCATCAATGCAAGTTCTTCCCGCTC

CGGACTAGATGATATCAATCCCACAGTACTACTAAAAGAACGTTCGACTGAACTGTAGAAGTCTAATGAT

CATATTTATTTATTTATATGAACCATGTCTATTAATTTAATTATTTAATAATATTTATATTAAACTCCTT

ATGTTACTTAACATCTTCTGTAACAGAAGTCAGTACTCCTGTTGCGGAGAAAGGAGTCATACTTGTGAAG

ACTTTTATGTCACTACTCTAAAGATTTTGCTGTTGCTGTTAAGTTTGGAAAACAGTTTTTATTCTGTTTT

ATAAACCAGAGAGAAATGAGTTTTGACGTCTTTTTACTTGAATTTCAACTTATATTATAAGAACGAAAGT

AAAGATGTTTGAATACTTAAACACTGTCACAAGATGGCAAAATGCTGAAAGTTTTTACACTGTCGATGTT

TCCAATGCATCTTCCATGATGCATTAGAAGTAACTAATGTTTGAAATTTTAAAGTACTTTTGGTTATTTT

TCTGTCATCAAACAAAAACAGGTATCAGTGCATTATTAAATGAATATTTAAATTAGACATTACCAGTAAT

TTCATGTCTACTTTTTAAAATCAGCAATGAAACAATAATTTGAAATTTCTAAATTCATAGGGTAGAATCA

CCTGTAAAAGCTTGTTTGATTTCTTAAAGTTATTAAACTTGTACATATACCAAAAAGAAGCTGTCTTGGA

TTTAAATCTGTAAAATCAGTAGAAATTTTACTACAATTGCTTGTTAAAATATTTTATAAGTGATGTTCCT

TTTTCACCAAGAGTATAAACCTTTTTAGTGTGACTGTTAAAACTTCCTTTTAAATCAAAATGCCAAATTT

ATTAAGGTGGTGGAGCCACTGCAGTGTTATCTTAAAATAAGAATATTTTGTTGAGATATTCCAGAATTTG

TTTATATGGCTGGTAACATGTAAAATCTATATCAGCAAAAGGGTCTACCTTTAAAATAAGCAATAACAAA

GAAGAAAACCAAATTATTGTTCAAATTTAGGTTTAAACTTTTGAAGCAAACTTTTTTTTATCCTTGTGCA

CTGCAGGCCTGGTACTCAGATTTTGCTATGAGGTTAATGAAGTACCAAGCTGTGCTTGAATAATGATATG

TTTTCTCAGATTTTCTGTTGTACAGTTTAATTTAGCAGTCCATATCACATTGCAAAAGTAGCAATGACCT

CATAAAATACCTCTTCAAAATGCTTAAATTCATTTCACACATTAATTTTATCTCAGTCTTGAAGCCAATT

CAGTAGGTGCATTGGAATCAAGCCTGGCTACCTGCATGCTGTTCCTTTTCTTTTCTTCTTTTAGCCATTT

TGCTAAGAGACACAGTCTTCTCATCACTTCGTTTCTCCTATTTTGTTTTACTAGTTTTAAGATCAGAGTT

CACTTTCTTTGGACTCTGCCTATATTTTCTTACCTGAACTTTTGCAAGTTTTCAGGTAAACCTCAGCTCA

GGACTGCTATTTAGCTCCTCTTAAGAAGATTAAAAGAGAAAAAAAAAGGCCCTTTTAAAAATAGTATACA

CTTATTTTAAGTGAAAAGCAGAGAATTTTATTTATAGCTAATTTTAGCTATCTGTAACCAAGATGGATGC

AAAGAGGCTAGTGCCTCAGAGAGAACTGTACGGGGTTTGTGACTGGAAAAAGTTACGTTCCCATTCTAAT

TAATGCCCTTTCTTATTTAAAAACAAAACCAAATGATATCTAAGTAGTTCTCAGCAATAATAATAATGAC

GATAATACTTCTTTTCCACATCTCATTGTCACTGACATTTAATGGTACTGTATATTACTTAATTTATTGA

AGATTATTATTTATGTCTTATTAGGACACTATGGTTATAAACTGTGTTTAAGCCTACAATCATTGATTTT

TTTTTGTTATGTCACAATCAGTATATTTTCTTTGGGGTTACCTCTCTGAATATTATGTAAACAATCCAAA

GAAATGATTGTATTAAGATTTGTGAATAAATTTTTAGAAATCTGATTGGCATATTGAGATATTTAAGGTT

GAATGTTTGTCCTTAGGATAGGCCTATGTGCTAGCCCACAAAGAATATTGTCTCATTAGCCTGAATGTGC

-continued

CATAAGACTGACCTTTTAAAATGTTTTGAGGGATCTGTGGATGCTTCGTTAATTTGTTCAGCCACAATTT

ATTGAGAAAATATTCTGTGTCAAGCACTGTGGGTTTTAATATTTTTAAATCAAACGCTGATTACAGATAA

TAGTATTTATATAAATAATTGAAAAAAATTTTCTTTTGGGAAGAGGGAGAAAATGAAATAAATATCATTA

AAGATAACTCAGGAGAATCTTCTTTACAATTTTACGTTTAGAATGTTTAAGGTTAAGAAAGAAATAGTCA

ATATGCTTGTATAAAACACTGTTCACTGTTTTTTTAAAAAAAAAACTTGATTTGTTATTAACATTGATC

TGCTGACAAAACCTGGGAATTTGGGTTGTGTATGCGAATGTTTCAGTGCCTCAGACAAATGTGTATTTAA

CTTATGTAAAAGATAAGTCTGGAAATAAATGTCTGTTTATTTTTGTACTATTTAAAAATTGACAGATCTT

TTCTGAAGATAAACTTTGATTGTTTCTATA

SEQ ID NO: 32 Human Amino Acid Sequence ras-related protein Rab-7a (NP_004628.4)
MTSRKKVLLKVIILGDSGVGKTSLMNQYVNKKFSNQYKATIGADFLTKEVMVDDRLVTMQIWDTAGQERF

QSLGVAFYRGADCCVLVFDVTAPNTFKTLDSWRDEFLIQASPRDPENFPFVVLGNKIDLENRQVATKRAQ

AWCYSKNNIPYFETSAKEAINVEQAFQTIARNALKQETEVELYNEFPEPIKLDKNDRAKASAESCSC

SEQ ID NO: 33 Human Nucleic Acid cDNA/mRNA Sequence ras-related protein Rab-7a (NM_004637.6)
AGTCTTGGCCATAAAGCCTGAGGCGGCGGCAGCGGCGGAGTTGGCGGCTTGGAGAGCTCGGGAGAGTTCC

CTGGAACCAGAACTTGGACCTTCTCGCTTCTGTCCTCCGTTTAGTCTCCTCCTCGGCGGGAGCCCTCGCG

ACGCGCCCGGCCCGGAGCCCCCAGCGCAGCGGCCGCGTTTGAAGGATGACCTCTAGGAAGAAAGTGTTGC

TGAAGGTTATCATCCTGGGAGATTCTGGAGTCGGGAAGACATCACTCATGAACCAGTATGTGAATAAGAA

ATTCAGCAATCAGTACAAAGCCACAATAGGAGCTGACTTTCTGACCAAGGAGGTGATGGTGGATGACAGG

CTAGTCACAATGCAGATATGGGACACAGCAGGACAGGAACGGTTCCAGTCTCTCGGTGTGGCCTTCTACA

GAGGTGCAGACTGCTGCGTTCTGGTATTTGATGTGACTGCCCCCAACACATTCAAAACCCTAGATAGCTG

GAGAGATGAGTTTCTCATCCAGGCCAGTCCCCGAGATCCTGAAAACTTCCCATTTGTTGTGTTGGGAAAC

AAGATTGACCTCGAAAACAGACAAGTGGCCACAAAGCGGGCACAGGCCTGGTGCTACAGCAAAAACAACA

TTCCCTACTTTGAGACCAGTGCCAAGGAGGCCATCAACGTGGAGCAGGCGTTCCAGACGATTGCACGGAA

TGCACTTAAGCAGGAAACGGAGGTGGAGCTGTACAACGAATTTCCTGAACCTATCAAACTGGACAAGAAT

GACCGGGCCAAGGCCTCGGCAGAAAGCTGCAGTTGCTGAGGGGGCAGTGAGAGTTGAGCACAGAGTCCTT

CACAAACCAAGAACACACGTAGGCCTTCAACACAATTCCCCTCTCCTCTTCCAAACAAAACATACATTGA

TCTCTCACATCCAGCTGCCAAAAGAAAACCCCATCAAACACAGTTACACCCCACATATCTCTCACACACA

CACACACACGCACACACACACACACAGATCTGACGTAATCAAACTCCAGCCCTTGCCCGTGATGGCTCCT

TGGGGTCTGCCTGCCCACCCACATGAGCCCGCGAGTATGGCAGCAGGACAAGCCAGCGGTGGAAGTCATT

CTGATATGGAGTTGGCATTGGAAGCTTATTCTTTTTGTTCACTGGAGAGAGAGAGAACTGTTTACAGTTA

ATCTGTGTCTAATTATCTGATTTTTTTTATTGGTCTTGTGGTCTTTTTACCCCCCCTTTCCCCTCCCTCC

TTGAAGGCTACCCCTTGGGAAGGCTGGTGCCCCATGCCCCATTACAGGCTCACACCCAGTCTGATCAGGC

TGAGTTTTGTATGTATCTATCTGTTAATGCTTGTTACTTTTAACTAATCAGATCTTTTTACAGTATCCAT

TTATTATGTAATGCTTCTTAGAAAAGAATCTTATAGTACATGTTAATATATGCAACCAATTAAAATGTAT

AAATTAGTGTAAGAAATTCTTGGATTATGTGTTTAAGTCCTGTAATGCAGGCCTGTAAGGTGGAGGGTTG

AACCCTGTTTGGATTGCAGAGTGTTACTCAGAATTGGGAAATCCAGCTAGCGGCAGTATTCTGTACAGTA

GACACAAGAATTATGTACGCCTTTTATCAAAGACTTAAGAGCCAAAAAGCTTTTCATCTCTCCAGGGGGA

AAACTGTCTAGTTCCCTTCTGTGTCTAAATTTTCCAAAACGTTGATTTGCATAATACAGTGGTATGTGCA

ATGGATAAATTGCCGTTATTTCAAAAATTAAAATTCTCATTTTCTTTCTTTTTTTTCCCCCCTGCTCCAC

ACTTCAAAACTCCCGTTAGATCAGCATTCTACTACAAGAGTGAAAGGAAAACCCTAACAGATCTGTCCTA

-continued

```
GTGATTTTACCTTTGTTCTAGAAGGCGCTCCTTTCAGGGTTGTGGTATTCTTAGGTTAGCGGAGCTTTTT

CCTCTTTTCCCCACCCATCTCCCCAATATTGCCCATTATTAATTAACCTCTTTCTTTGGTTGGAACCCTG

GCAGTTCTGCTCCCTTCCTAGGATCTGCCCCTGCATTGTAGCTTGCTTAACGGAGCACTTCTCCTTTTTC

CAAAGGTCTACATTCTAGGGTGTGGGCTGAGTTCTTCTGTAAAGAGATGAACGCAATGCCAATAAAATTG

AACAAGAACAATGAT
```

In some embodiments, an agent disclosed herein or a down-regulator of IL-22 signaling includes any agent that specific binds to or decreases the activity or level of any one of the biomarkers listed in Table 1.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

As used herein, the phrase "conjoint administration" refers to any form of administration of two or more different therapeutic agents such that the second agent is administered while the previously administered therapeutic agent is still effective in the body (e.g., the two agents are simultaneously effective in the subject, which may include synergistic effects of the two agents). For example, the different therapeutic agents can be administered either in the same formulation or in separate formulations, either concomitantly or sequentially. In certain embodiments, the different therapeutic agents can be administered within about one hour, about 12 hours, about 24 hours, about 36 hours, about 48 hours, about 72 hours, or about a week of one another. Thus, a subject who receives such treatment can benefit from a combined effect of different therapeutic agents.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control patient (can be stored sample or previous sample measurement) with a known outcome; normal tissue or cells isolated from a subject, such as a normal subject or a subject with an MDS and/or an anemia, cultured primary cells/tissues isolated from a subject, such as a normal subject or a subject with an MDS and/or an anemia, adjacent normal cells/tissues obtained from the same organ or body location of a normal subject or a subject with an MDS and/or an anemia, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, reduced anemia for one, two, three, four years, etc.) or receiving a certain treatment (for example, standard of care therapy). It will be understood by those of skill in the art that such control samples and reference standard expression product levels can be used in combination as controls in the methods of the present invention. In one embodiment, the control may comprise normal or an MDS and/or an anemia cell/tissue sample. In another preferred embodiment, the control may comprise an expression level for a set of patients, such as a set of patients, or for a set of patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells or cells from subjects treated with combination therapy. In another embodiment, the control may also comprise a measured value for example, average level of expression of a particular gene in a population compared to the level of expression of a housekeeping gene in the same population. Such a population may comprise normal subjects, subjects having an MDS and/or an anemia who have not undergone any treatment (i.e., treatment naive), or subjects having an MDS and/or an anemia undergoing standard of care therapy. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all subjects in a cohort having an MDS and/or an anemia. In one embodiment a control expression product level is established wherein higher or lower levels of expression product relative to, for instance, a particular percentile, are used as the basis for predicting outcome. In another preferred embodiment, a control expression product level is established using expression product levels from control subjects with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with an MDS and/or an anemia, or from a corresponding non-affected tissue in the same afflicted subject.

The term "diagnosing" includes the use of the methods, systems, and code of the present invention to determine a level of IL-22 signaling in an individual, cell population, tissue, and the like. The term also includes methods, systems, and code for assessing the level of disease activity in an individual.

The term "down-regulate" includes the decrease, limitation, or blockage, of, for example a particular action, function, or interaction. In some embodiments, IL-22 signaling is "down-regulated" if at least one effect of IL-22 signaling is alleviated, terminated, slowed, or prevented. Similarly, a "down-regulator" of IL-22 signaling is an agent (e.g., a therapeutic agent) that down-regulates IL-22 signaling. The terms "promote" and "up-regulate" have the opposite meaning as compared to "down-regulate."

A molecule is "fixed" or "affixed" to a substrate if it is covalently or non-covalently associated with the substrate such that the substrate can be rinsed with a fluid (e.g., standard saline citrate, pH 7.4) without a substantial fraction of the molecule dissociating from the substrate.

The term "mode of administration" includes any approach of contacting a desired target (e.g., cells, a subject) with a desired agent (e.g., a therapeutic agent). The route of administration, as used herein, is a particular form of the mode of administration, and it specifically covers the routes by which agents are administered to a subject or by which biophysical agents are contacted with a biological material.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as modulation of one or more biomarkers described herein, and/or evaluate the disease state. A pre-determined biomarker amount and/or activity measurement(s) may be determined in populations of patients with or without an MDS and/or an anemia. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionally conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn and Cullen (2002) *J. Virol.* 76:9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. "Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA). In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having an MDS and/or an anemia, to inhibit expression of a biomarker gene which is overexpressed in an MDS and/or an anemia, and thereby treat, prevent, or inhibit the MDS and/or the anemia.

siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

RNAi agent disclosed herein may target any one of the nucleic acids listed in Table 1. In some embodiments, any one of the RNAi agents may be complementary to any one of the nucleic acid sequences in Table 1.

The term "sample" used for detecting or determining the presence or level of at least one biomarker is typically brain tissue, cerebrospinal fluid, whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "subject" refers to any healthy animal, mammal or human, or any animal, mammal or human afflicted with a red blood cell disorder. The term "subject" is interchangeable with "patient."

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human.

The terms "therapeutically-effective amount" and "effective amount" as used herein means that amount of a compound, material, or composition comprising a compound encompassed by the present invention which is effective for producing some desired therapeutic effect in at least a sub-population of cells in an animal at a reasonable benefit/risk ratio applicable to any medical treatment. Toxicity and therapeutic efficacy of subject compounds can be determined by standard pharmaceutical procedures in cell cultures or experimental animals, e.g., for determining the $LD_{50}$ and the $ED_{50}$.

Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to administration of a suitable control agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to administration of a suitable control agent.

II. Subjects

In some embodiments, the subject is a mammal (e.g., mouse, rat, primate, non-human mammal, domestic animal, such as a dog, cat, cow, horse, and the like), and is preferably a human. In other embodiments, the subject is an animal model of a red blood cell disorder. In some embodiments, the subject is not limited to animals or humans with genetic mutation in Riok2 or other ribosomal or non-ribosomal protein mutations. For example, anti-IL-22 treatment of wild type (wt) mice undergoing acute anemia was determined herein to increase peripheral blood red blood cells as compared to mice treated with an isotype antibody.

In addition, cells can be used according to the methods described herein, whether in vitro, ex vivo, or in vivo, such as cells from such subjects. In some embodiments, the cells are a collection of erythroid progenitors and/or erythroid progenitors defined according to developmental stage (e.g., I, II, III, and IV, expression of biomarkers of interest such as IL-22 or an IL-22 receptor like IL-22RA1, IL-10Rbeta, and heterodimers thereof, and combinations thereof).

In some embodiments encompassed by the methods of the present invention, the subject has not undergone treatment, such as with lenalidomide, azacitidine, decitabine, or an erythropoiesis-stimulating agent. In other embodiments, the subject has undergone treatment, such as with lenalidomide, azacitidine, decitabine, or an erythropoiesis-stimulating agent.

The methods encompassed by the present invention can be used across many different red blood cell disorders in subjects such as those described herein. The red blood cell disorders that can be treated with the disclosed methods include myelodysplastic syndromes (MDS) and anemias, such as, without limitation, anemia caused by insufficiency of serine/threonine-protein kinase RIOK2, anemia caused by mutations or deletions on human chromosome 5, macrocytic anemia, anemia associated with increased levels of IL-22, chronic kidney disease (CKD), stress-induced anemia, Diamond Blackfan anemia, and Shwachman-Diamond syndrome.

The ordinarily skilled artisan will appreciate from the results of a wide variety of experimental models described herein that the methods encompassed by the present invention apply generally to a subject having an MDS and/or an anemia, such as those indicating increased IL-22 signaling and/or activation, and are not limited to individuals having particular genetic mutations. In some particular embodiments, subjects have an MDS and/or an anemia defined according to a genetic mutation, such as a del(5q)-mediated MDS. In some embodiments, MDS/anemia patients have increased IL-22 levels in serum, plasma, Th22 T lymphocytes, or bone marrow fluid.

The methods encompassed by the present invention can be used to stratify subjects and/or determine responsiveness of subjects described herein to IL-22 signaling pathway modulation.

III. Therapeutic Agents

In some embodiments, the agents used are therapeutic agents that are down-regulators of IL-22 signaling. These agents can block or neutralize, at least to some extent, the biological activity or function of IL-22 or the biological activity or function of an IL-22 receptor.

In some embodiments, the down-regulator of IL-22 signaling is an antibody (or an antigen-binding fragment thereof) that binds to IL-22. Recombinant IL-22 is available from multiple vendors including PeproTech (Cat #AF-210-22-250UG), and various antibodies can be generated against IL-22 using IL-22 (or a fragment thereof) as the antigen. In addition, certain anti-IL-22 antibodies are already commercially available. For example, a human/mouse anti-IL-22 neutralizing antibody is available from Thermo Fisher Scientific (Cat #16-7222-85).

Structural information for IL-22, its receptor, and the IL22/IL22R1 receptor-ligand complex is well-known in the art (Nagem et al. (2002) *Structure* 10(8):1051-62; Xu et al. (2005) *Acta Crystallogr D Biol Crystallogr.* 61 (Pt 7):942-50; Bleicher et al. (2008) *FEBS Lett.* 582(20):2985-92; Jones et al. (2008) *Structure* 16(9):1333-44), such that structure-function relationships between agents that block or neutralize IL-22, including anti-IL-22 agents and anti-IL-22 receptor agents, and the mechanism of action are well-known in the art (see, for example, human IL-22 crystal structure information at PubMed identifier PMID 12176383 and PMID 15983417, as well as human IL-22/IL22-R1 complex crystal structure information at PubMed identifier PMID 18675809 and PMID 18599299). Structure-function relationships among non-human orthologs of IL-22 and IL-22 receptor are similarly well-known in the art. Mouse and human IL-22 share 78% protein sequence identity. Mouse and human IL22ra1 share 72% protein sequence identity. IL-22BP shares a 34% sequence identity with the extracellular region of IL-22RA1.

The term "down-regulator of IL-22 signaling or signaling pathway" includes any natural or non-natural agent prepared, synthesized, manufactured, and/or purified by humans that is capable of reducing, inhibiting, blocking, preventing, and/or that inhibits the IL-22 signaling pathway, including inhibition of IL-22 polypeptide (and its fragments, domains, and/or motifs thereof, discussed herein) directly. In one embodiment, such inhibitors may reduce or inhibit the binding/interaction between IL-22 and its substrates or other binding partners. In another embodiment, such inhibitors may reduce or inhibit an upstream and/or downstream member of the IL-22 signaling pathway. In still another embodiment, such inhibitors may increase or promote the turnover rate, reduce or inhibit the expression and/or the stability (e.g., the half-life) of IL-22, resulting in at least a decrease in IL-22 levels and/or activity. Such inhibitors may be any molecule, including but not limited to small molecule compounds, antibodies or intrabodies, RNA interfering (RNAi) agents (including at least siRNAs, shRNAs, microRNAs (miRNAs), piwi, and other well-known agents). Such inhibitors may be specific to IL-22 or also inhibit at least one IL-22 signaling pathway member. RNA interference agents for IL-22 polypeptides are well-known and commercially available (e.g., human or mouse shRNA (Cat. #TL303948, TR502849, TL303948V, etc.) products, siRNA products (Cat. #SR323991, SR404300, etc.), and human or mouse gene knockout kit via CRISPR (Cat. #KN409995, KN209995, etc.) from Origene (Rockville, MD), siRNA/shRNA products (Cat. #sc-39664, sc-39665, etc.) and human or mouse gene knockout kit via CRISPR (Cat. #sc-403228) from Santa Cruz Biotechnology (Dallas, Texas), and siRNA/shRNA products (Cat. #ABIN5784850, ABIN5784849, etc.) from Genomics Online (Limerick, PA). Methods for detection, purification, and/or inhibition of IL-22 (e.g., by anti-IL-22 antibodies) are also well-known and commercially available (e.g., multiple anti-IL-22 antibodies from Origene (Cat. #PP1224B1, TA326688, TA328247, TA337159, TA338422, PP1226, TA328506, TA328507, etc.), Novus Biologicals (Littleton, CO, Cat. #AF582, AF782, NBP2-27339, NB100-737, MAB582, MAB7821, NBP2-31215, NBP2-11699, NBP2-41245, MAB7822, NBP2-27322, NBP2-27360, MAP782, MAP5821, NBP2-27320, NBP2-27321, MAB7822R, NB100-733, NB100-738, H00050616-D01P, etc.), abcam (Cambridge, MA, Cat. #ab18498, ab203211, ab134035, ab227033, ab263954, ab18564, ab181007, ab109819, ab267467, ab267789, ab228687, ab96341, ab133545, ab211756, ab18566, ab84033, ab84225, ab174534, ab193813, ab90937, ab222646, ab222645, ab206858, ab5984, ab18568, ab211675, ab167213, ab232925, ab5982, ab98917, etc.), patent literature (e.g., U.S. Pat. No. 7,901,684), and the like). IL-22 knockout human cell lines are also well-known and available at Horizon (Cambridge, UK, Cat. #HZGHC50626). Reagents and kits for assaying IL-22 are well-known in the art (see, for example SMC™ Human IL-22 High Sensitivity Immunoassay Kit; EMD Millipore, product #03-0162-00).

Similarly, compositions for modulation (e.g., down-regulation), as well as detection and purification of IL-22 signaling pathway members, such as IL-22RA1, alarmins (e.g., S100A8, S100A9, S100 A10, phosphorylated Stat3, etc.), Camp, Ngp, and the like, are also well-known in the art. For example, RNA interference agents for IL-22RA1 polypeptides are well-known and commercially available (e.g., human or mouse shRNA (Cat. #TL303947V, TR303947, TR506901, TL506901V, etc.) products, siRNA products (Cat. #SR324794, SR417732, etc.), and human or mouse gene knockout kit via CRISPR (Cat. #KN406447, KN206447, etc.) from Origene (Rockville, MD), siRNA/shRNA products (Cat. #sc-146217, sc-88174, etc.) and human or mouse gene knockout kit via CRISPR (Cat. #sc-404104, etc.) from Santa Cruz Biotechnology (Dallas, Texas), and siRNA/shRNA products (Cat. #ABIN4120152, ABIN4163636, ABIN4120153, ABIN4163637, ABIN5353047, ABIN5353048, ABIN5353045, ABIN5353044, ABIN3401988, ABIN3430223, ABIN3396755, ABIN3818550, ABIN4013677, ABIN4013676, ABIN3818551, etc.) from Genomics Online (Limerick, PA). Methods for detection, purification, and/or inhibition of IL-22RA1 (e.g., by anti-IL-22RA1 antibodies) are also well-known and commercially available (e.g., multiple anti-IL-22RA1 antibodies from Origene (Cat. #AP07312PU-N, TA306082, TA306086, TA322224, TA322225, TA338469, TA338470, etc.), Novus Biologicals (Littleton, CO, Cat. #MAB42941, MAB2770, NBP1-76724, AF2770, MAB4294, AF4294, NB100-740, etc.), Antibodies-Online (Limerick, PA, Cat. #ABIN2783836, ABIN2783835, ABIN4899326, ABIN4899325, ABIN4895922, ABIN6742083, ABIN4895924, ABIN4324949, ABIN748178, ABIN6743529, etc.), and the like). IL-22 knockout human cell lines are also well-known and available at Horizon (Cambridge, UK, Cat. #HZGHC58985).

In some embodiments, the down-regulator of IL-22 signaling includes IL22JOP™ monoclonal antibody, fezakinumab, or a combination thereof.

In some embodiments, the down-regulator of IL-22 signaling includes an antibody (or an antigen-binding fragment thereof) directed against IL-22RA1. In certain embodiments, the down-regulator of IL-22 signaling includes an antibody (or an antigen-binding fragment thereof) directed against IL-22RA1/IL-10R2-heterodimer.

In certain embodiments, the down-regulator of IL-22 signaling includes IL-22 binding protein (IL-22BP) or a fragment of IL-22BP that can bind IL-22 and down-regulate its signaling.

In some embodiments, the down-regulator of IL-22 signaling includes an antagonist of aryl hydrocarbon receptor (AHR). For example, such a down-regulator can include stemregenin 1, CH-223191, or 6,2',4'-trimethoxyflavone.

In some embodiments, an agent disclosed herein or a down-regulator of IL-22 signaling includes any agent that specific binds to or decreases the activity or level of any one of the biomarkers listed in Table 1.

In certain embodiments, the down-regulator of IL-22 signaling can be conjointly administered (e.g., separately or together, at different times or at the same time) with another therapeutic agent. Such therapeutic agents for a combination therapy include lenalidomide, azacitidine, decitabine, or a combination thereof. Such therapeutic agents for a combination therapy also include erythropoiesis-stimulating agents, such as erythropoietin, epoetin alfa, epoetin beta, epoetin omega, epoetin zeta, darbepoetin alfa, or a combination thereof. In some embodiments, lenalidomide, azacitidine, or decitabine is not conjointly administered with one of the erythropoiesis-stimulating agents, for example if the two are contraindicated.

IV. Therapeutic Methods

One aspect encompassed by the present invention pertains to methods of treating one or more red blood cell disorders in a subject. Such methods include administering to the subject an effective amount of a down-regulator of interleukin-22 (IL-22) signaling.

As an example, a method of treating anemia in a subject, according to some of the disclosed embodiments herein, includes administering to the subject fezakinumab.

Another aspect encompassed by the present invention pertains to methods of promoting differentiation from an erythroid progenitor cell toward a mature red blood cell in a subject. Such methods include administering to the subject an effective amount of a down-regulator of interleukin-22 (IL-22) signaling.

As an example, in a method according to some of the disclosed embodiments herein, fezakinumab is administered to a subject, after which erythroid progenitor cells classified as RI differentiate toward mature red blood cells (e.g., by first differentiating into erythroid progenitor cells classified as RII).

In connection with the therapeutic methods described above, an aspect encompassed by the present invention relates to methods of selecting a subject for treatment with a down-regulator of interleukin-22 (IL-22) signaling. Such a method includes determining that a subject has a chromosome 5 that comprises a mutation in its long arm; and selecting the subject for treatment with a down-regulator of IL-22 signaling.

The mutation for these methods can be any mutation that has been or is associated with MDS or another red blood cell disorder, such as anemia. For example, the mutation can include deletions in the q33.1, q33.2, q33.3 regions of human chromosome 5. In addition, the mutation can include a deletion in q15 region of human chromosome 5. In particular, the mutation can be a mutation in the RIOK2 gene. In some embodiments, the mutation results in an I245T mutation in the RIOK2 protein, defined with respect to SEQ ID NO: 1 provided as follows.

```
| Q9BVS4|RIOK2_HUMAN Serine/threonine-protein
kinase RIOK2
                                    SEQ ID NO: 1
MGKVNVAKLRYMSRDDFRVLTAVEMGMKNHEIVPGSLIASIASLKHGGCN

KVLRELVKHKLIAWERTKTVQGYRLTNAGYDYLALKTLSSRQVVESVGNQ

MGVGKESDIYIVANEEGQQFALKLHRLGRTSFRNLKNKRDYHKHRHNVSW

LYLSRLSAMKEFAYMKALYERKFPVPKPIDYNRHAVVMELINGYPLCQIH

HVEDPASVYDEAMELIVKLANHGLIHGDFNEFNLILDESDHITMIDFPQM

VSTSHPNAEWYFDRDVKCIKDFFMKRFSYESELFPTFKDIRREDTLDVEV

SASGYTKEMQADDELLHPLGPDDKNIETKEGSEFSFSDGEVAEKAEVYGS

ENESERNCLEESEGCYCRSSGDPEQIKEDSLSEESADARSFEMTEFNQAL
```

-continued

```
EEIKGQVVENNSVTEFSEEKNRTENYNRQDGQRVQGGVPAGSDEYEDECP

HLIALSSLNREFRPERDEENVGAMNQYRTRTLSITSSGSAVSCSTIPPEL

VKQKVKRQLTKQQKSAVRRRLQKGEANIFTKQRRENMQNIKSSLEAASFW

GE
```

The I245T mutation or any of the other mutations can be identified by sequencing (e.g., via high-throughput DNA sequencing) a nucleic acid from the subject.

Similar chromosomal regions, mutations, and the like are well-known in orthologs of non-human mammals, such as mice, and are contemplated for use according to the present invention.

The therapeutic methods described herein can also be used in a variety of in vitro and in vivo applications, such as in analyzing cellular models of an MDS and/or an anemia, without treating a subject. Such methods involved contacting a cell, such as an erythroid progenitor, with a modulatory agent described herein.

V. Further Uses and Methods Encompassed by the Present Invention

The methods and compositions described herein can be used in a variety of screening, diagnostic, and prognostic applications in addition to therapeutic applications. In any method described herein, such as a diagnostic method, prognostic method, therapeutic method, or combination thereof, all steps of the method can be performed by a single actor or, alternatively, by more than one actor. For example, diagnosis can be performed directly by the actor providing therapeutic treatment. Alternatively, a person providing a therapeutic agent can request that a diagnostic assay be performed. The diagnostician and/or the therapeutic interventionist can interpret the diagnostic assay results to determine a therapeutic strategy. Similarly, such alternative processes can apply to other assays, such as prognostic assays.

a. Screening Methods

One aspect of the present invention relates to screening assays, including non-cell-based assays and animal model assays. In one embodiment, the assays provide a method for identifying whether an agent is useful for treating an MDS and/or an anemia condition, such as by identifying agents that modulate an IL-22 signaling pathway inhibitor (e.g., one or more biomarkers listed in Table 1).

In one embodiment, the present invention relates to assays for screening test agents which bind to, or modulate the biological activity of, at least one biomarker described herein (e.g., in the Tables, Figures, Examples, or otherwise in the specification). In one embodiment, a method for identifying such an agent entails determining the ability of the agent to modulate, e.g. inhibit, the at least one biomarker described herein.

In one embodiment, an assay is a cell-free or cell-based assay, comprising contacting at least one biomarker described herein, with a test agent, and determining the ability of the test agent to modulate (e.g., inhibit) the activity of the biomarker, such as by measuring direct binding of substrates or by measuring indirect parameters as described below, and optionally further determining the effect on treating an MDS and/or an anemia.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}I$, $^{35}S$, $^{14}C$ or $^{3}H$, either directly or indirectly, and the radioisotope detected by direct counting of radioemission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies described herein can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further encompasses novel agents identified by the above-described screening assays. Accordingly, it is within the scope of the present invention to further use an agent identified as described herein, such as in an appropriate animal model. For example, an agent identified as described herein can be used in an animal model to determine the efficacy, toxicity, or side effects of treatment with such an agent. Alternatively, an agent, such as an antibody, identified as described herein can be used in an animal model to determine the mechanism of action of such an agent.

b. Diagnostic and Predictive Medicine

The present invention also pertains to the field of predictive medicine in which diagnostic assays, prognostic assays, and monitoring clinical trials are used for prognostic (predictive) purposes to thereby stratify subject populations and/or treat an individual prophylactically. Accordingly, one aspect of the present invention relates to diagnostic assays for determining the amount and/or activity level of a biomarker described herein in the context of a biological sample (e.g., blood, serum, cells, or tissue) to thereby determine whether an individual afflicted with an MDS and/or an anemia is likely to respond to biomarker inhibitor treatments. Such assays can be used for prognostic or predictive purpose alone or can be coupled with a therapeutic intervention to thereby prophylactically treat an individual prior to the onset or after recurrence of a disorder characterized by or associated with biomarker polypeptide, nucleic acid expression or activity. The ordinarily skilled artisan will appreciate that any method can use one or more (e.g., combinations) of biomarkers described herein, such as those in the Tables, Figures, Examples, and otherwise described in the specification.

Another aspect of the present invention pertains to monitoring the influence of agents (e.g., drugs, compounds, and small nucleic acid-based molecules) on the expression or activity of a biomarker described herein. These and other agents are described in further detail in the following sections.

The ordinarily skilled artisan will also appreciate that, in certain embodiments, the methods of the present invention may implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from tissue of interest. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods encompassed by the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the tissue of a subject not afflicted with an MDS and/or an anemia and/or profiles generated from population-based distributions of informative loci of interest in relevant populations of the same species can be stored and later compared to that of a sample derived from tissue of instructed, such as tissue suspected of being relevant to an MDS and/or an anemia of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

As an additional aspect encompassed by the present invention, methods of detecting a level of interleukin-22 (IL-22) signaling are disclosed. Such methods include determining an expression level of one or more biomarkers listed in Table 1. For example, S100A8, an IL-22 target gene, contributes to the dyserythropoiesis seen in anemia and MDS. S100A8 and other biomarkers listed in the Tables, Figures, Examples, and otherwise described in the specification can be used as a measure of functional inhibition of IL-22 signaling.

Prognostic assay methods are also provided that may be used to identify subjects having or at risk of developing an MDS and/or an anemia that is likely or unlikely to be responsive to a modulator of IL-22 signaling. Assays described herein, such as the preceding diagnostic assays or the following assays, can be utilized to identify a subject having or at risk of developing a disorder associated with a dysregulation of the amount or activity of at least one biomarker described herein, such as in an MDS and/or an anemia. Alternatively, the prognostic assays can be utilized to identify a subject having or at risk for developing a disorder associated with a dysregulation of at least one biomarker described herein, such as in an MDS and/or an anemia. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

The present invention provides, in part, methods, systems, and code for accurately classifying whether a biological sample is associated with an MDS and/or an anemia that is likely to respond to a modulator (e.g., inhibitor) of IL-22 pathway signaling. In some embodiments, the present invention is useful for classifying a sample (e.g., from a subject) as associated with or at risk for responding to or not responding to IL-22 pathway signaling modulation (e.g., inhibition) using a statistical algorithm and/or empirical data (e.g., the amount or activity of a biomarker described herein, such as in the Tables, Figures, Examples, and otherwise described in the specification).

An exemplary method for detecting the amount or activity of a biomarker described herein, and thus useful for classifying whether a sample (e.g., a sample from a subject having an MDS and/or an anemia or an in vitro model of an MDS and/or an anemia) is likely or unlikely to respond to IL-22 pathway signaling modulation (e.g., inhibition) involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely responder or non-responder with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of ordinary skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., a hematologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have an MDS and/or an anemia of interest or a sample that is susceptible to biomarker inhibitor treatment), a biological sample from the subject during remission, or a biological sample timepoint during treatment for the condition.

c. Clinical Efficacy

Similarly, clinical efficacy can be measured by any method known in the art. For example, the benefit from a therapy with an agent that down-regulates IL-22 signaling, alone or in combination with a another agent, such as lenalidomide, azacitidine, decitabine, or an erythropoiesis-stimulating agent (e.g., erythropoietin, epoetin alfa, epoetin beta, epoetin omega, epoetin zeta, darbepoetin alfa, IL-9), relates to an increase in the level of healthy red blood cells so that adequate oxygen can be carried to the tissues of the subject. As another example, the benefit from an anti-IL-22 therapy can relate to the level of red blood cells in the blood (e.g., hematocrit) or the level of hemoglobin in the blood, both of which can be measured as part of a routine complete blood count.

The benefit from using agents encompassed by the present invention can be determined by measuring the level of cytotoxicity in a biological material. The benefit from using agents encompassed by the present invention can be assessed by measuring transcription profiles, viability curves, microscopic images, biosynthetic activity levels, redox levels, and the like. The benefit from using agents encompassed by the present invention can also be determined by measuring the presence and severity of side effects from the anti-IL-22 treatment such as autoimmune or allergic sequelae. IL-22 signaling normally function to maintain epithelial integrity in lungs, skin and GI tract, induction of antibacterial proteins, protection against cellular damage, liver progenitor cell proliferation In some embodiments, clinical efficacy of the therapeutic treatments described herein can be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular therapeutic regimen is at least 25%, 30%, 35%, 40%, 45%, 50%, 55%, 60%, 65%, 70%, 75%, 80%, 85%, or more.

Additional criteria for evaluating the response to therapies are related to "survival," which includes all of the following: survival until mortality, also known as overall survival (wherein said mortality can be either irrespective of cause or tumor related); "recurrence-free survival" (wherein the term recurrence shall include both localized and distant recurrence); disease free survival. The length of said survival can be calculated by reference to a defined start point (e.g., time of diagnosis or start of treatment) and end point (e.g., death, recurrence). In addition, criteria for efficacy of treatment can be expanded to include response to therapy, probability of survival, and probability of recurrence.

For example, in order to determine appropriate threshold values, a particular anti-IL-22 therapeutic regimen can be administered to a population of subjects and the outcome can be correlated to biomarker measurements detailed previously that were determined prior to administration of any therapy. The outcome measurement can be pathologic response to therapy. Alternatively, outcome measures, such as overall survival and disease-free survival can be monitored over a period of time for subjects following therapies for whom biomarker measurement values are known as detailed previously. In certain embodiments, the same doses of therapy agents, if any, are administered to each subject. In related embodiments, the doses administered are standard doses known in the art for those agents used in therapies. The period of time for which subjects are monitored can vary. For example, subjects can be monitored for at least 2, 4, 6, 8, 10, 12, 14, 16, 18, 20, 25, 30, 35, 40, 45, 50, 55, or 60 months.

d. Biomarker Analyses

Methods analyzing biomarkers encompassed by the present invention may be performed according to well-known techniques in the art. In some embodiments, biomarker amount and/or activity measurement(s) in a sample from a subject is compared to a predetermined control (standard) sample. The sample from the subject is typically from a diseased tissue. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement (s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment (e.g., based on the number of genomic mutations and/or the number of genomic mutations causing non-functional proteins for DNA repair genes), evaluate a response to a modulator (e.g., an inhibitor) of one or more biomarkers listed in Table 1 and/or evaluate a response to a modulator (e.g., an inhibitor) of one or more biomarkers listed in Table 1. A pre-determined biomarker amount and/or activity measurement(s) may be determined in populations of patients with or without an MDS and/or an anemia. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of therapy for an MDS and/or an anemia. Post-treatment biomarker measurement can be made at any time after initiation of therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of therapy, and even longer toward indefinitely for continued monitoring.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. In a preferred embodiment, the subject and/or control sample is selected from the group consisting of cells, cell lines, histological slides, paraffin embedded tissues, biopsies, whole blood, serum, plasma, buccal scrape, saliva, cerebrospinal fluid, urine, stool, and bone marrow. In another preferred embodiment, the subject and/or control sample is selected from the group consisting of whole blood, serum, plasma, bone marrow fluid, and/or Th22 T lymphocytes in peripheral blood.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CLEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CLEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

i. Methods for Detection of Copy Number

Methods of evaluating the copy number of a biomarker nucleic acid are well-known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of inhibitors of one or more biomarkers listed in Table 1 and immunotherapy combination treatments.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well-known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radioisotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well-known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol.* 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR)). In a quantitative amplification, the amount of amplification product will be proportional to the amount of template in the original sample. Comparison to appropriate controls, e.g. healthy tissue, provides a measure of the copy number.

Methods of "quantitative" amplification are well-known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

ii. Methods for Detection of Biomarker Nucleic Acid Expression

Biomarker expression may be assessed by any of a wide variety of well-known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+ RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, NY).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) *Proc. Natl. Acad. Sci. U.S.A.* 86: 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well-known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety).

Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

iii. Methods for Detection of Biomarker Protein Expression

The activity or level of a biomarker protein can be detected and/or quantified by detecting or quantifying the expressed polypeptide. The polypeptide can be detected and quantified by any of a number of means well-known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of an MDS and/or an anemia to modulators (e.g., inhibitors) of the IL-22 signaling pathway. Any method known in the art for detecting polypeptides can be used. Such methods include, but are not limited to, immunodiffusion, immunoelectrophoresis, radioimmunoassay (RIA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and RIA procedures may be conducted such that a desired biomarker protein standard is labeled (with a radioisotope such as $^{125}I$ or $^{35}S$, or an assayable enzyme, such as horseradish peroxidase or alkaline phosphatase), and, together with the unlabeled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker protein antibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabeling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MM. For X-radiographic techniques, suitable markers include any radioisotope that emits detectable radiation but that is not overtly harmful to the subject, such as barium or cesium, for example. Suitable markers for NMR and MM generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$ M, $10^{-7}$ M, $10^{-8}$ M, $10^{-9}$ M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

iv. Methods for Detection of Biomarker Structural Alterations

The following illustrative methods can be used to identify the presence of a structural alteration in a biomarker nucleic acid and/or biomarker polypeptide molecule in order to, for example, identify STUB1, UBQLN1, HSP90B1, or other biomarkers used in the immunotherapies described herein that are overexpressed, overfunctional, and the like.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well-known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

VI. Administration of Agents

The agents encompassed by the present invention (e.g., down-regulators of IL-22) are administered to subjects in a biologically compatible form suitable for pharmaceutical administration in vivo, to enhance their effects. By "biologically compatible form suitable for administration in vivo" is meant a form to be administered in which any toxic effects are outweighed by the therapeutic effects. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition encompassed by the present invention is defined as an amount effective, at dosages and for periods of time necessary, to achieve the desired result. For example, a therapeutically active amount of an agent can vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

Agents encompassed by the present invention can be administered either alone or in combination with an additional therapy. In the combination therapy, a down-regulator of IL-22 encompassed by the present invention and another agent, such as lenalidomide, azacitidine, decitabine, or an erythropoiesis-stimulating agent (e.g., erythropoietin, epoetin alfa, epoetin beta, epoetin omega, epoetin zeta, darbepoetin alfa) can be delivered to the same or different cells and can be delivered at the same or different times. The agents encompassed by the present invention can be incorporated into pharmaceutical compositions suitable for administration. Such compositions can comprise one or more agents or one or more molecules that result in the production of such one or more agents (e.g., a nucleic acid that results in production of an antigen-binding fragment of an anti-IL-22 antibody) and a pharmaceutically acceptable carrier.

The therapeutic agents described herein can be administered using a mode or route of administration that delivers them to the particular locations in the body where IL-22 or IL-22RA1 expression can increase in red blood cell disorders, such as the kidney, liver, lung, gastrointestinal tract, brain, thymus skin, or pancreas.

The therapeutic agents described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which can inactivate the compound. For example, for administration of agents, by other than parenteral administration, it can be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, nonionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

As described in detail below, the pharmaceutical compositions encompassed by the present invention can be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intra-vaginally or intra-rectally, for example, as a pessary, cream or foam; or (5) aerosol, for example, as an aqueous aerosol, liposomal preparation or solid particles containing the compound.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods encompassed by the present invention can contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods encompassed by the present invention include those suitable for oral, nasal, topical (including buccal and sublingual), rectal, vaginal, aerosol and/or parenteral administration. The formulations can conveniently be presented in unit dosage form and can be prepared by any methods well-known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound can also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered peptide or peptidomimetic moistened with an inert liquid diluent.

Tablets, and other solid dosage forms, such as dragees, capsules, pills and granules, can optionally be scored or prepared with coatings and shells, such as enteric coatings and other coatings well-known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions, which can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration can be presented as a suppository, which can be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component can be mixed under sterile conditions with a pharmaceutically-acceptable carrier, and with any preservatives, buffers, or propellants which can be required.

The ointments, pastes, creams and gels can contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agents disclosed herein can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions encompassed by the present invention suitable for parenteral administration comprise one or more therapeutic agents in combination with one or more pharmaceutically-acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers which can be employed in the pharmaceutical compositions encompassed by the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution, which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents encompassed by the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in pharmaceutical compositions encompassed by the present invention can be determined by the methods encompassed by the present invention to obtain an amount of the active ingredient, which is effective to achieve the desired therapeutic response for a particular subject, composition, and mode of administration, without being toxic to the subject.

The nucleic acid molecules encompassed by the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

In one embodiment, an agent encompassed by the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment can increase or decrease over the course of a particular treatment. Changes in dosage can result from the results of diagnostic assays.

EXAMPLES

Example 1: Materials and Methods for Examples 2-5 a. Flow Cytometry and Cell Isolation

Whole bone marrow (BM) cells were isolated by crushing hind leg bones (femur and tibia) with mortar and pestle in staining buffer (PBS, Corning) supplemented with 2% heat inactivated fetal bovine serum (FBS, Atlanta Biologicals) and EDTA (GIBCO)). Whole bone marrow was lysed with 1× Pharm Lyse™ (BD Biosciences) for 90 seconds, and the reaction was terminated by adding an excess of staining buffer. Cells were labeled with fluorochrome-conjugated antibodies in staining buffer for 30 minutes at 4° C. For flow cytometric analysis, cells were incubated with combinations of fluorochrome-conjugated antibodies to the following cell surface markers: CD3 (17A2), CD5 (53-7.3), CD11b (M1/70), Gr1 (RB6-8C5), B220 (RA3-6B2), Ter119 (TER119), CD71 (C2), ckit (2B8), Sca1 (D7), CD16/32 (93), CD150 (TC15-12F12.2), CD48 (HM48-1). For sorting of lineage-negative cells, lineage markers included CD3, CD5, CD11b, Gr1 and Ter119. For sorting of erythroid progenitor cells, the lineage cocktail did not include Ter119. All reagents were acquired from BD Biosciences, Thermo Fisher Scientific, Novus Biologicals, R&D Biosystems, Tonbo Biosciences, or BioLegend. Identification of apoptotic cells was carried out using the Annexin V Apoptosis Detection Kit (BioLegend). Intracytoplasmic and intranuclear staining was performed using Foxp3/Transcription Factor Staining Kit (eBioscience). To increase the sorting efficiency, whole bone marrow samples were lineage-depleted using magnetic microbeads (Miltenyi Biotec) and autoMACS® Pro magnetic separator (Miltenyi Biotec). Cell sorting was performed on a FACSAria® flow cytometer (BD Biosciences), data acquisition was performed on a BD Fortessa™ X-20 instrument equipped with 5 lasers (BD Biosciences). Data were analyzed by FlowJo (Tree Star) version 9 software. Flow analyses were performed on viable cells by exclusion of dead cells using either DAPI or a fixable viability dye (Tonbo Biosciences).

b. In Vivo Measurement of Protein Synthesis

One hundred mL of a 20 mM solution of 0-Propargyl-Puromycin (OP-Puro; BioMol) was injected intraperitoneally in mice and mice were then rested for 1 hour (1 h). Mice injected with PBS were used as controls. BM was harvested after 1 h and stained with antibodies against cell surface markers, washed to remove excess unbound antibodies, fixed in 1% paraformaldehyde, and permeabilized in PBS with 3% fetal bovine serum and 0.1% saponin. The azide-alkyne cyclo-addition was performed using the Click-iT™ Cell Reaction Buffer Kit (Thermo Fisher Scientific) and azide conjugated to Alexa Fluor 647® (Thermo Fisher Scientific) at 5 μM final concentration for 30 minutes. Cells were washed twice and analyzed by flow cytometry.

c. Methylcellulose Assay

Cells at a population of 1,000-2,500 BM c-kit$^+$ cells were sorted and plated in semi-solid methylcellulose culture medium (M3434, StemCell Technologies) and incubated at 37° C. in a humidified atmosphere for 7-10 days. At the end of the incubation period, each well was triturated with staining buffer to collect cells. Collected cells were then processed for flow cytometry as described above.

d. Phenylhydrazine Treatment

Phenylhydrazine (PhZ) was purchased from Sigma and injected intraperitoneally on 2 consecutive days (days 0 and 1) at a dose of 25 mg/kg. Peripheral blood was collected 3-4 days before the start of treatment and at day 4, 7 and 11. PhZ treatment experiments were carried out in 8-16 week-old mice.

e. T Cell Polarization

Single cell suspensions of mouse spleens were prepared by pressing tissue through a 70 μm cell strainer followed by red blood cell lysis using Pharm Lyse™ (BD Biosciences). Total splenic CD4+ T cells were isolated using CD4 T cell isolation kit (Miltenyi Biotec). Enriched CD4 T cells were then incubated with fluorochrome-conjugated antibodies to CD4, CD8, CD25, CD62L, and CD44 to purify naïve CD4 T cells using fluorescence activated cell sorting (FACS). In the presence of 1 μg/mL plate-bound anti-CD3ε and soluble 1 μg/mL anti-CD28, T cell polarizations were carried out in IMDM supplemented with 10% FBS, 2 mM L-glutamine, 100 mg/mL penicillin-streptomycin, HEPES, non-essential amino acids, 100 μM β-mercaptoethanol, and sodium pyruvate as follows—Th1 (20 ng/mL IL-12, 10 μg/mL anti-IL-4), Th2 (20 ng/mL IL-4, 10 μg/mL anti-IFN-γ), Th17 (30 ng/mL IL-6, 20 ng/mL IL-23, 20 ng/mL IL-1b, 10 μg/mL anti-IL-4, 10 μg/mL anti-IFN-γ), Tregs (1 ng/mL TGF-β, 10 μg/mL anti-IL-4, 10 μg/mL anti-IFN-γ), and Th22 (1 ng/mL TGF-β, 30 ng/mL IL-6, 20 ng/mL IL-23, 20 ng/mL IL-1b, 10 μg/mL anti-IL-4, 10 μg/mL anti-IFN-γ, 200 nM FICZ).

f. IL-22 Neutralization and Reconstitution.

Monoclonal anti-IL-22 (Clone IL22JOP) blocking antibody and isotype control IgG2a (Clone eBR2a) were purchased from Thermo Fisher Scientific. Mice were administered anti-IL-22 (50 μg/mouse) or isotype intraperitoneally every 48 h until the conclusion of the experiment. For recombinant IL-22 treatment, mice were injected with recombinant IL-22 (500 ng/mouse; PeproTech) intraperitoneally every 24 h until the conclusion of the experiment.

g. Cytokine Quantitation

IL-22 in human samples was quantified using SMC™ Human IL-22 High Sensitivity Immunoassay Kit (EMD Millipore, 03-0162-00) according to manufacturers' instructions. The assay was read on a SMCxPro™ (EMD Millipore) instrument. The lower limit of quantification (LLOQ) of this immunoassay is 0.1 pg/mL. IL-22 in mouse samples was quantified using ELISA MAX™ Deluxe Set Mouse IL-22 (BioLegend, 436304). The LLOQ of this immunoassay is 3.9 pg/mL. Concentration of lineage-associated cytokines in cell culture supernatants of polarized T cells were quantified using a custom-made ProcartaPlex™ assay (Thermo Fisher Scientific) acquired on a Luminex® platform.

h. Statistical Tests

Data are presented as mean±s.e.m. Comparison of two groups was performed using unpaired two-tailed t-test, assuming normal distribution. For multiple group comparison, analysis of variance (ANOVA) with post hoc Tukey's correction was applied. Statistical analyses were performed using GraphPad Prism 8.0 (GraphPad Software Inc., San Diego, CA). A p-value of less than 0.05 was considered significant.

Figure 1A:
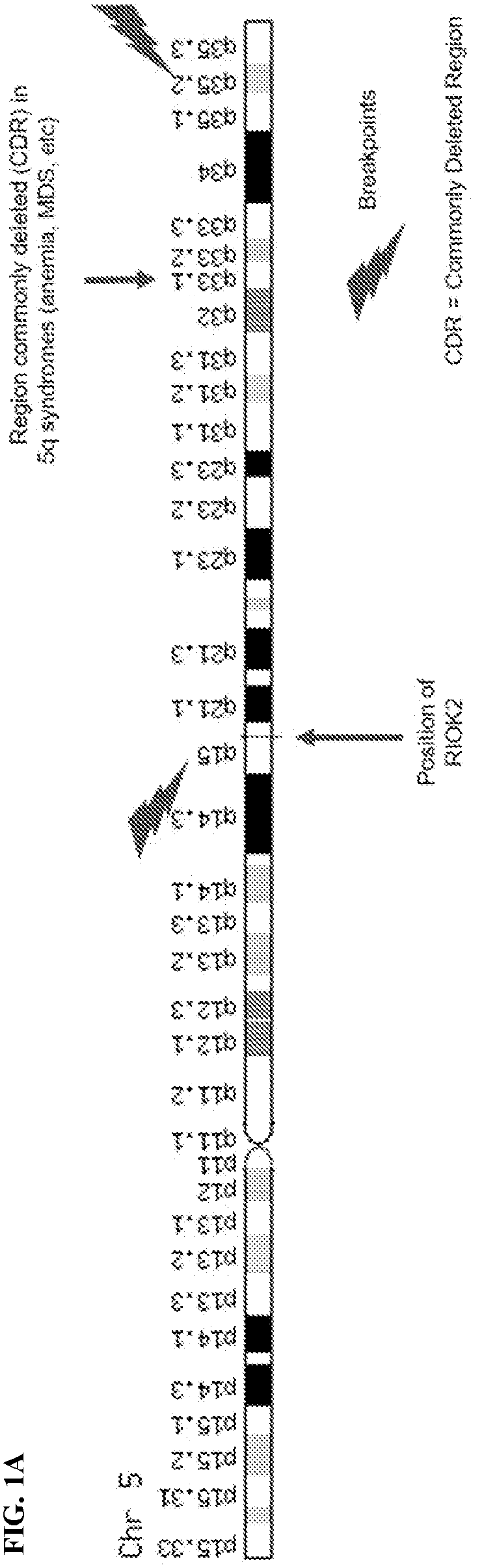
FIG. 1A-FIG. 1E show localization and expression of Riok2.
Figure 1B:
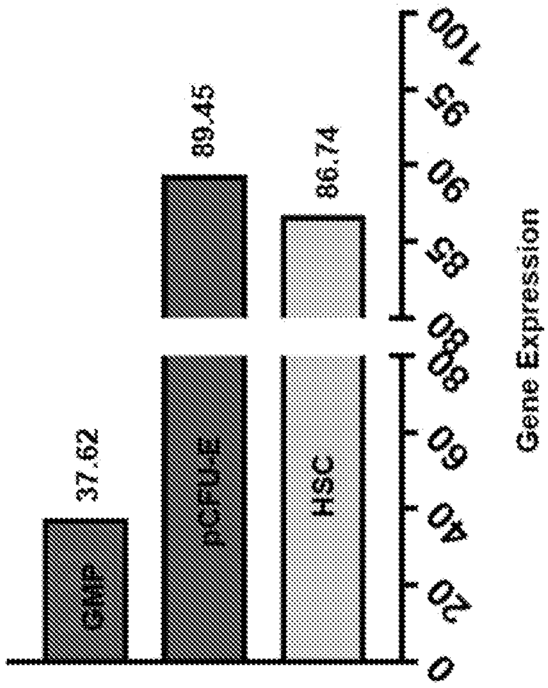
Figure 1C:
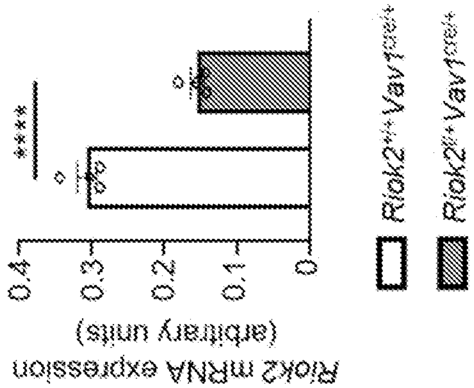
Figure 1E:
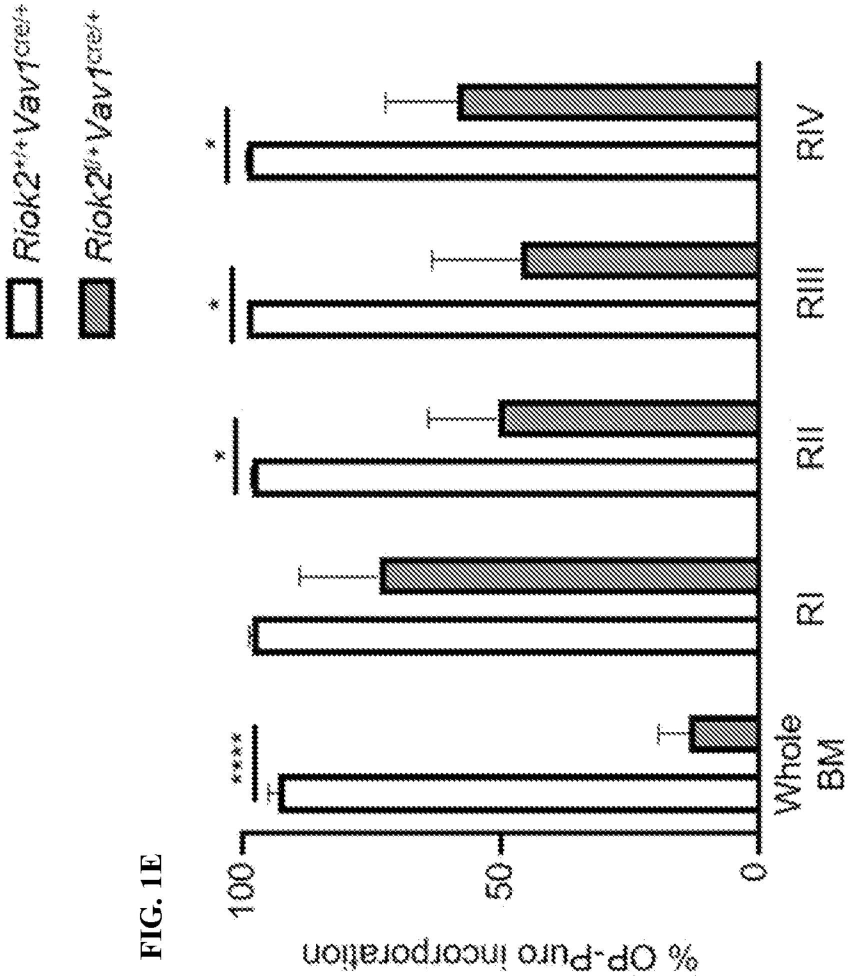
Figure 1D:
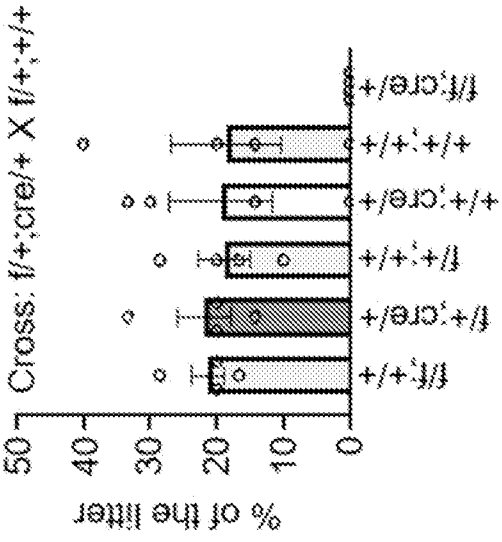

Example 2: Riok2 Haploinsufficiency Blocks Erythroid Differentiation Leading to Anemia T cells lacking the endoplasmic reticulum stress transcription factor Xbp1 have reduced Riok2 expression (Song et al. (2018) *Nature* 562:423-428). RIOK2 lies on the long arm of chromosome 5q (5q15) in the human genome, between the breakpoints (5q13-5q35), which are known to occur in del(5q) syndromes, such as (del(5q)) myelodysplastic syndromes (MDS) (FIG. 1A). Studies in yeast (Ferreira-Cerca et al. (2012) *Nat. Struct. Mol. Biol.* 19:1316-1323) and human (Zemp et al. (2009) *J. Cell. Biol.* 185:1167-1180) cancer cell lines have shown that Riok2 plays an indispensable role in the maturation of the pre-40S ribosomal complex. GEXC analysis revealed that in mouse bone marrow (BM), Riok2 expression is highest in pCFU-E (primitive colony-forming-unit erythroid) cells, indicating that Riok2 may be involved in maintaining red blood cell (RBC) output (FIG. 1B). To further study the role of Riok2 in hematopoiesis, Vav1-Cre+ transgenic floxed Riok2 (Riok2$^{f/+}$Vav1$^{cre}$) mice were generated in which the Cre recombinase is under the control of the hematopoietic cell-specific Vav1 promoter. Riok2 expression in hematopoietic cells from Riok2$^{f/+}$ Vav1$^{cre}$ mice was approximately 50% compared to those from Vav1-Cre$^+$controls (FIG. 1C). Interestingly, no Vav1-Cre foxed Riok2 homozygous knockout mice were recovered (FIG. 1D), indicating embryonic lethality from complete hematopoietic deletion of Riok2. However, Vav1 Cre Riok2 f/+ mice were viable with approximately 50% Riok2 expression levels in hematopoietic cells compared to that of Vav1-Cre$^+$ controls (FIG. 1C). As is seen with other ribosomal protein haploinsufficiency mouse models (Schneider et al. (2016) Nat. Med. 22:288-297), BM cells from Riok2$^{f/+}$ Vav1$^{cre}$ mice showed reduced nascent protein synthesis in vivo compared to Vav1-cre controls (FIG. 1D), which is consistent with Riok2's role in maturation of the pre-40S ribosome. A recent study showed that ribosomal protein deficiency-mediated reduced protein synthesis significantly affects erythropoiesis over myelopoiesis (Khajuria et al. (2018) *Cell* 173:90-103).

Figures 2A, 2B, 2C:
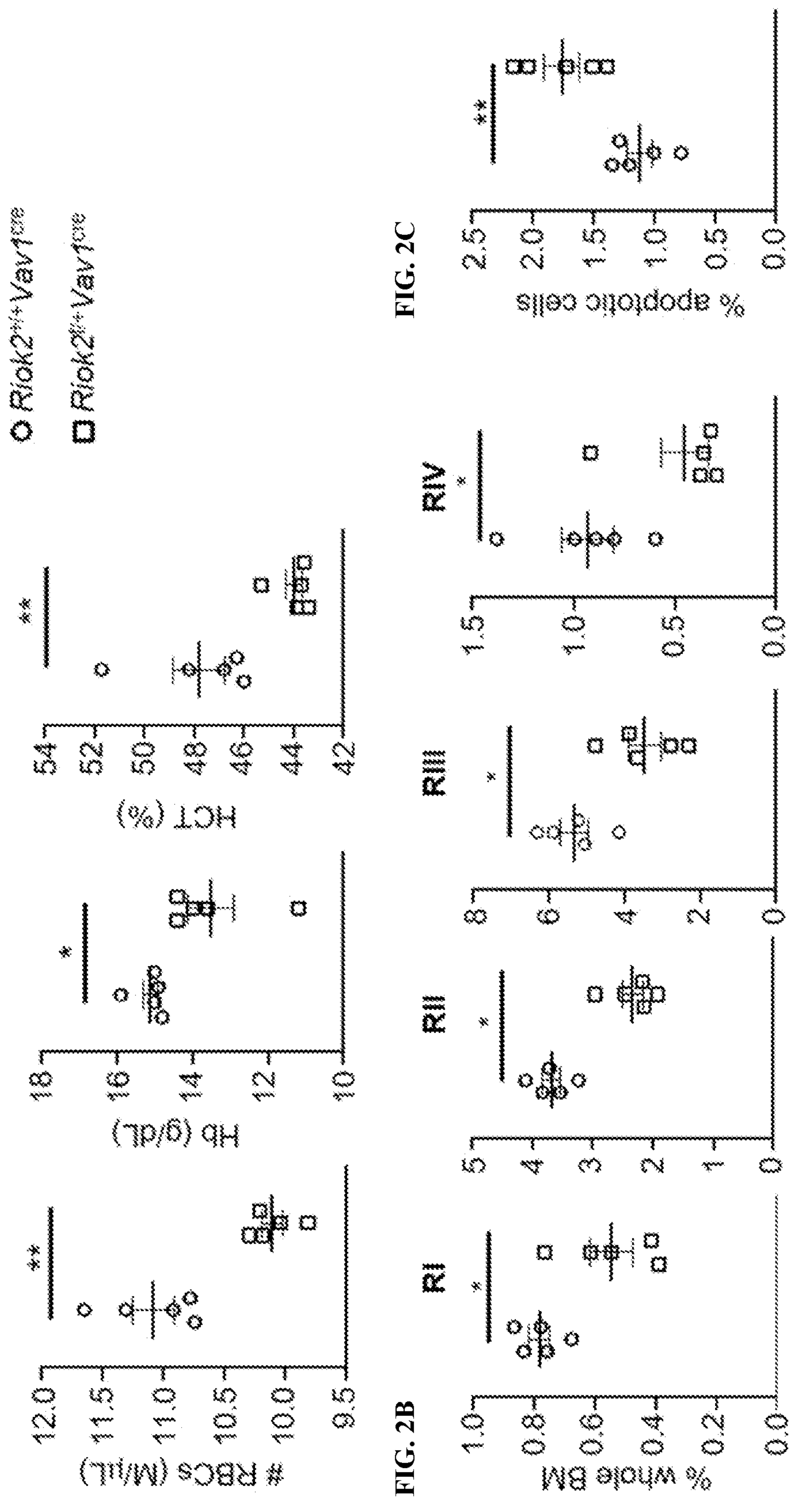
FIG. 2A-FIG. 2G show that Riok2 haploinsufficient ($Riok2^{fl/+}Vav1^{cre}$) mice display anemia and myeloproliferation.
Figure 3A:
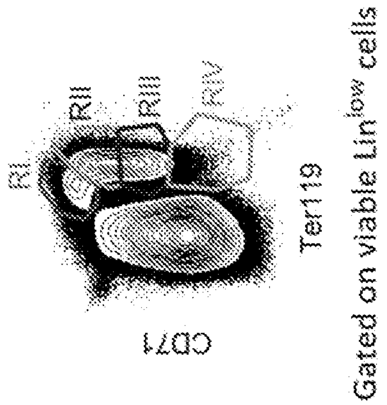
FIG. 3A-FIG. 3E further show that Riok2 haploinsufficient mice display anemia.
Figure 3B:
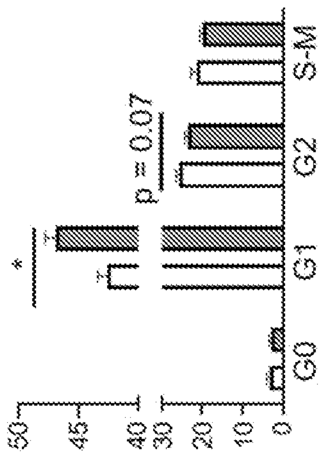
Figure 3C:
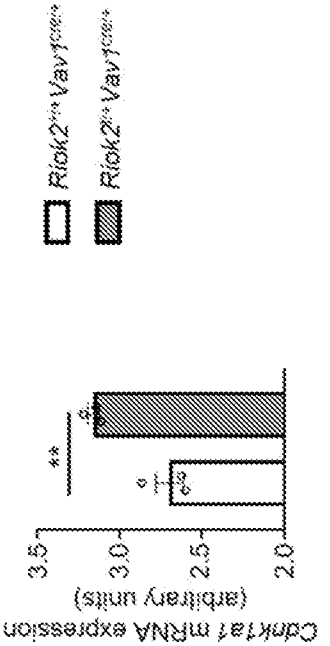

Consistent with the high expression of Riok2 in pCFU-e cells in the BM, mice with heterozygous deletion of Riok2 in hematopoietic cells (Riok2$^{f/+}$Vav1$^{cre}$) displayed anemia with reduced peripheral blood red blood cell (RBC) numbers, hemoglobin (Hb), and hematocrit (HCT) (FIG. 2A). It was next determined whether Riok2 haploinsufficiency-mediated anemia was secondary to a defect in erythroid development in the BM. The states of erythropoiesis (referred to herein as RI, RII, RIII and RIV) were characterized by flow cytometry by using the expression of Ter119 and CD71 (FIG. 3A). Riok2f Vav1$^{cre}$ mice had impaired erythropoiesis in the BM (FIG. 2B). Moreover, Riok2 haploinsufficiency led to increased apoptosis in erythroid progenitors as compared to controls (FIG. 2C), Additionally, Riok2$^{f/+}$Vav1$^{cre}$ erythroid progenitors showed a decrease in cell quiescence with cell cycle block at the GI stage (FIG. 313). A block in cell cycle is driven by a group of proteins known as cyclin-dependent kinase inhibitors (CM). The expression of p21 (a CM encoded by Cdkn1a) was increased in erythroid progenitors from Riok2$^{f/+}$Vav1$^{cre}$ mice compared to Riok2$^{+/+}$Vav1$^{cre}$ controls (FIG. 3C).

Figure 2D:
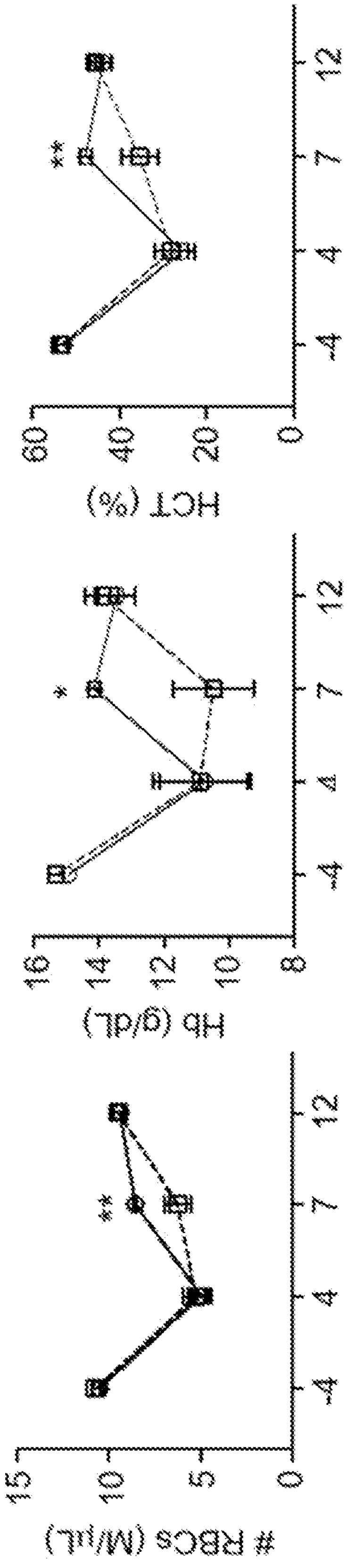
Figure 3D:
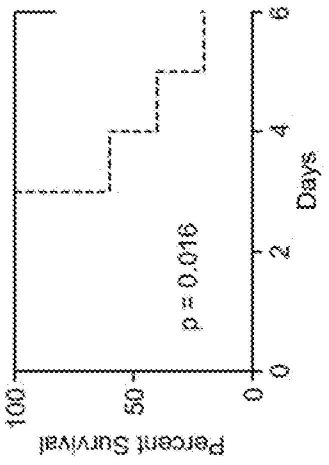
Figure 3E:
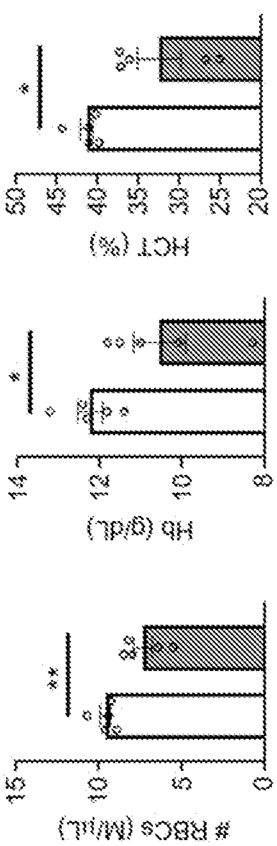

In addition, the effect of Riok2 haploinsufficiency on stress-induced erythropoiesis was determined by analyzing mice in which hemolysis was induced by non-lethal phenylhydrazine treatment (25 mg/kg on days 0 and 1). After acute hemolytic stress, Riok2$^{f/+}$Vav1$^{cre}$ mice developed more severe anemia and had a delayed RBC recovery response, as compared to Riok2$^{+/+}$ Vav1$^{cre}$ control mice (FIG. 2D). Riok2P Vav1$^{cre}$ mice succumbed faster to a lethal dose of phenylhydrazine (35 Ing/kg on days 0 and 1) as compared to Vav1-cre controls (FIG. 3D). To determine whether Riok2 haploinsufficiency in BM cells drives anemia, bone marrow (BM) chimeras were generated. Wild-type (WT) mice transplanted with Riok2$^{f/+}$Vav1$^{cre}$ whole BM developed anemia as compared to Riok2$^{+/+}$ Vav1$^{cre}$ BM transplanted WT mice (FIG. 3E).

Figure 2E:
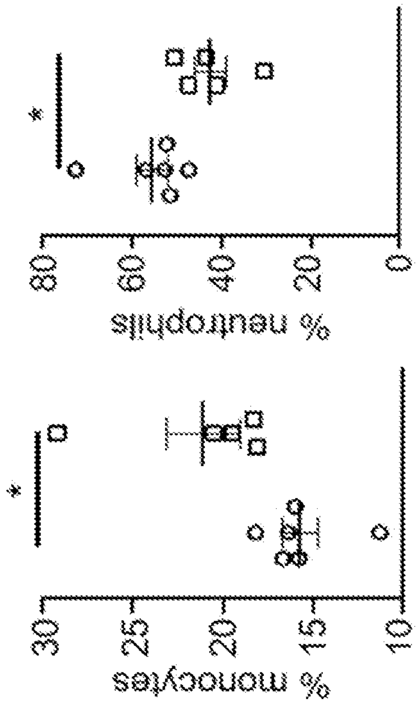
Figure 2F:
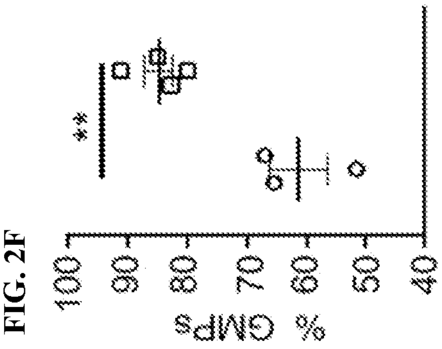
Figure 2G:
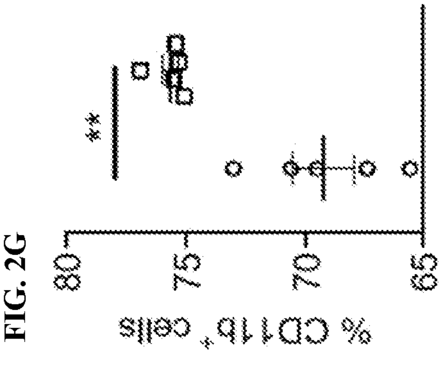

In addition to the reduction in RBC numbers in peripheral blood (PB) from Riok2$^{f/+}$Vav1" mice, an increased percentage of monocytes (monocytosis) and decreased percentage of neutrophils (neutropenia) compared to controls was also observed (FIG. 2E). Granulocyte macrophage progenitors (GNPs) in the BM give rise to PB myeloid cells. The percentage of BM GMPs was increased in Riok2$^{f/+}$Vav1" mice as compared to Riok2$^{+/+}$Vav1$^{cre}$ controls (FIG. 2F). To analyze the effect of Riok2 haploinsufficiency on myelopoiesis in the absence of in vivo compensatory mechanisms, LSK (lineage-Sca-1+Kit+) cells from the BM of Riok2$^{f/+}$Vav1$^{cre}$ and Riok2$^{+/+}$Vav1$^{cre}$ controls were cultured in a MethoCult™ assay supplemented with growth factors (IL-6, IL-3, and SCF, but devoid of erythropoietin). LSKs from Riok2$^{f/+}$Vav1$^{cre}$ mice gave rise to an increased percentage of CD11b+ myeloid cells suggesting a cell-intrinsic myeloproliferative effect due to Riok2 haploinsufficiency (FIG. 2G).

Example 3: Riok2 Haploinsufficiency Induces Increased Levels of Immune-Related Proteins in Erythroid Progenitors To elucidate a mechanism for the erythroid differentiation defect observed in Riok2$^{f/+}$Vav1$^{cre}$ mice, quantitative proteomic analysis of purified erythroid progenitors using mass spectrometry was performed. Riok2 haploinsufficiency led to upregulation of 564 distinct proteins (adjusted p-value of <0.05) in erythroid progenitors compared to those from Vav1-cre controls (FIG. 4A). Interestingly, the most highly upregulated proteins in the dataset correlated significantly (p-val: $1.66\times10^{-16}$) with those observed upon haploinsufficiency of Rps14 (Schneider et al. (2016) *Nat. Med.* 22:288-297), another component of the 40S ribosomal complex (FIG. 4B). Fourteen of the total 26 upregulated proteins in the Rps14 dataset were also upregulated in the Riok2 haploinsufficient dataset, revealing a largely common proteomic signature on deletion of distinct ribosomal proteins (FIG. 4C).

In Riok2$^{f/+}$Vav1$^{cre}$ erythroid progenitor cells, the upregulated proteins with the highest fold-change (S100A8, S100A9 Camp, Ngp, and the like) are proteins with known immune functions, such as antimicrobial defense. This indicated a possible role for the immune system in driving the proteomic changes seen in the Riok2 haploinsufficient erythroid progenitors. To assess if Riok2 haploinsufficiency leads to changes in immune cell function, naïve T cells from Riok2$^{f/+}$Vav1$^{cre}$ mice and Riok2$^{+/+}$Vav1$^{cre}$ controls were subjected to in vitro polarization towards known T cell lineages (Th1 Th2, Th17, Th22, and Tregs). Secretion of IL-2, IFN-gamma, IL-13, IL-17A, and the frequency of Foxp3±Tregs was comparable between Riok2$^{f/+}$Vav1$^{cre}$ and Riok2$^{+/+}$Vav1$^{cre}$ T cells (FIG. 5A-5G). However, an exclusive increase in IL-22 secretion from Riok2$^{f/+}$Vav1$^{cre}$ naïve T cells polarized towards the Th22 lineage was observed (FIG. 6A, left panel). The frequency of IL-22±CD4+ T cells was also higher in Riok2$^{f/+}$Vav1$^{cre}$ Th22 cultures as compared to Vav1-cre control Th22 cultures (FIG. 6A, right panel). The concentration of IL-22 in the serum and BM fluid of Riok2$^{f/+}$Vav1$^{cre}$ mice was also significantly higher as compared to Vav1-cre controls (FIG. 6B). Rps14 haploinsufficient Th22 cells also secreted elevated levels of IL-22 compared to Vav1-cre control Th22. cells (FIG. 4D).

Phenylhydrazine (PhZ) administration to wild-type (C57BL/6J, C57) mice treated intraperitoneally with rIL-22 led to decreased PB RBCs, Mb, and HCT owing to decreased BM erythroid progenitor cells (FIGS. 7A and 7C). Recombinant IL-22 led to an increase in apoptosis of erythroid progenitors (FIG. 7D). It also led to an increase in PB and BM reticulocytes as an indication of increased erythropoiesis under stress (FIG. 7B). Recombinant IL-22 also dose-dependently decreased terminal erythropoiesis in an in vitro erythropoiesis assay (FIG. 7E).

Example 4: Neutralization of IL-22 Signaling Alleviates Anemia in Riok2 Haploinsufficient Mice and Increases Red Blood Cell (RBC) Numbers in Wild-Type Mice Mice harboring a compound genetic deletion of IL-22 on the Riok2 haploinsufficient background (Riok2$^{f/+}$Il22$^{+/-}$ Vav1$^{cre}$) exhibited increased numbers of PB RBCs and HCT compared to IL-22 sufficient Riok2 haploinsufficient mice on day 7 after two treatments with 25 mg/kg PhZ treatment (FIG. 6C). Interestingly, an increase in PB RBCs in Riok2-sufficient mice heterozygous for IL-22 deletion (Riok2$^{+/+}$ Il22$^{+/-}$) as compared to Riok2-sufficient IL-22 sufficient mice (Riok2$^{+/+}$Il22$^{+/+}$) was observed. Next, it was assessed whether the increase in PB RBCs in Riok2$^{+/-}$Il22$^{+/+}$ mice was due to increased erythropoiesis in the BM of these mice. An increase in RII and RIV erythroid progenitors in Riok2$^{+/-}$Il22$^{+/-}$ as compared to Riok2$^{+/-}$Il22$^{+/+}$ mice was observed (FIG. 6D). Using a neutralizing IL-22 antibody in vivo, a similar anti-anemic effect on PB RBCs and HCT in Riok2$^{f/+}$Vav1$^{cre}$ mice, as well as Riok2 sufficient (Riok2$^{+/+}$ Vav1$^{cre}$) mice undergoing PhZ-induced anemia, was observed (FIG. 6E). Unexpectedly, IL-22 neutralization also reduced the frequency of apoptotic erythroid progenitors in both Riok2-sufficient, as well as Riok2$^{f/+}$Vav1$^{cre}$, mice (FIG. 6F). These data indicate that IL-22 neutralization reverses anemia, at least in part, by reducing apoptosis of erythroid progenitors. Recently, dampening IL-22 signaling in intestinal epithelial stem cells was shown to reduce apoptosis (Gronke et al. (2019) *Nature* 566:249-253). The effect of IL-22 deficiency (genetic as well as antibody-mediated) in alleviating anemia in genetically wild-type mice indicates a role for IL-22 in reversing anemia regardless of ribosomal haploinsufficiency. Accordingly, treatment of C57BL/6J mice undergoing PhZ-induced anemia with anti-IL-22 antibody significantly increased PB RBCs, Hb, and HCT compared to isotype antibody-treated mice (FIG. 8B). Of note, PB RBCs, Hb, and HCT did not differ in healthy, non-anemic wt mice injected with anti-IL-22 versus isotype matched antibodies (FIG. 8A).

IL-22 signals through a cell surface heterodimeric receptor composed of IL-10Rbeta and IL-22RA1 (encoded by Il22ra1) (Kotenko et al. (2001) *J. Biol. Chem.* 276:2725-2732). IL-22RA1 expression has been reported to be restricted to cells of non-hematopoietic origin (e.g., epithelial cells and mesenchymal cells) (Wolk et al. (2004) *Immunity* 21:241-254), However, it was unexpectedly discovered herein that erythroid progenitors in the BM also express IL-22RA1 (FIG. 4A and FIG. 10A). Moreover, it was observed that the majority of the IL-22RA1-expressing cells in the BM were erythroid progenitors (FIG. 10B). Using a second anti-IL-22RA1 antibody (targeting a different epitope than the antibody used in FIG. 9A), the presence of IL-22RA1 on erythroid progenitors was confirmed (FIG. 10C).

Deletion of IL-22RA1 in Riok2-haploinsufficient mice (Riok2$^{f/+}$Il22ra1$^{f/f}$Vav1$^{cre/+}$) led to improvement in PB RBCs, Hb, and HCT as compared to IL-22RA1-sufficient Riok2-haploinsufficient mice (Riok2$^{f/+}$Il22ra1$^{+/+}$Vav1$^{cre/+}$) (FIG. 9B). This improvement could be attributed to the increase in RH and RIV erythroid progenitors in the BM of Riok2$^{f/+}$Il22ra1$^{f/f}$Vav1$^{cre/+}$ mice (FIG. 9C). Erythroid cell-specific deletion of IL-22RA1 (using cre recombinase expressed under the erythropoietin receptor (EpoR) promoter) also increased numbers of PB RBCs and HCT (FIG. 9D) due to the increase in RIII and RIV erythroid progenitors in the BM (FIG. 9E). These data reinforce the notion that IL-22 signaling plays a role in regulating erythroid development regardless of ribosomal haploinsufficiency. Thus, using three different approaches to neutralize IL-22 signaling, it is demonstrated herein that IL-22 plays an important role in inducing anemia by directly regulating erythropoiesis.

Example 5: IL-22 and its Downstream Targets are Increased in del(5q) MDS Patients It was next assessed whether IL-22 expression is increased in human disorders that display dyserythropoiesis due to ribosomal protein haploinsufficiency. A significant increase in IL-22 levels in the BM fluid (BMF) of del(5q) MDS patients as compared to BMF from healthy controls was observed. A small but significant increase in IL-22 was also observed in non-del(5q) MDS patients (FIG. 11A). Interestingly, a strong negative correlation between cellular RIOK2 mRNA expression and BMF IL-22 level was evident in the del(5q) MDS cohort (FIG. 11B) indicating that a decrease in Riok2 expression is associated with increased IL-22 expression. The frequency of CD4+ T cells producing IL-22 among freshly isolated PBMCs was significantly higher in MDS patients compared to healthy controls (FIGS. 11C and 12).

An independent analysis of a large-scale microarray sequencing dataset of CD34$^{+}$ cells performed herein from normal, del(5q), non-del(5q) MDS subjects showed that RIOK2 mRNA was significantly decreased in the del(5q) MDS cohort (78% (37/47)). Interestingly, expression of known IL-22 target genes, such as S100A10, S100A1 I, PTGS2, and RAB7A was specifically increased in the del (5q) MDS cohort compared to both the healthy control and non-del(5q) groups (FIG. 11D).

Anemia is a common feature seen in chronic kidney disease (CKD) patients and is associated with poor outcomes. Anemia of CKD is resistant to erythropoiesis-stimulating agents (ESAs) in 10-20% of the patients (KDOQI (2006) *Am. J. Kidney Dis.* 47:S11-S15) suggesting that pathogenic mechanisms other than erythropoietin deficiency are at play. An increase in IL-22 concentration in the plasma of CKD patients with secondary anemia compared to healthy controls and CKD patients without anemia was determined herein (FIG. 1E) Plasma IL-22 levels negatively correlated with hemoglobin concentration in CKD patients indicating a function for IL-2.2 in driving anemia occurrence in CKD. Thus, the results provided herein demonstrate that IL-22 overexpression is partly responsible for very common anemias, like the anemia observed in patients with chronic kidney disease.

Del(5q), either isolated or accompanied by additional cytogenetic abnormalities, is the most commonly detected chromosomal abnormality in MDS, reported in ~15% of patients. Anemia is the most common hematologic manifestation of MDS, particularly in patients with del(5q) MDS. The severe anemia in del(5q) MDS patients has been linked to haploinsufficiency of ribosomal proteins such as RPS14 (Schneider et al. (2016) *Nat. Med.* 22:288-297) and RPS19 (Dutt et al. (2011) *Blood* 117:2567-2576). Genes lying outside of the 5q region most commonly deleted (5q33) have also been implicated in MDS (Lane et al. (2010) *Blood* 115:3489-3497; Sebert et al. (2019) *Blood* 134:1441-1444). While much research has focused on the effect of such gene deletions or mutations in hematopoietic stem cells and lineage-committed progenitors, the Immunobiology underlying this MDS subtype has remained largely unexplored, thus impeding development of immune-targeted therapies. With the exception of the TNF-alpha inhibitor, etanercept (Maciejewski et al. (2002) *Br. J. Haematol.* 117:119-126), which proved to be ineffective, no other therapies against immune cell-derived cytokines have been tested in MDS patients.

Based on the results described herein, two critical functions have been identified for an understudied kinase, Riok2, that synergize to induce dyserythropoiesis and anemia. The primary effect of Riok2 loss in erythroid progenitors is the intrinsic block in erythroid differentiation owing to its indispensable role in the maturation of the pre-40S ribosomal complex leading to increased apoptosis and cell cycle arrest. The secondary effect of Riok2 loss is the extrinsic induction of the erythropoiesis-suppressive cytokine, IL-22, in T cells, which then directly activates IL-22RA signaling in erythroid progenitors. The data described herein reveal a novel molecular link between haploinsufficiency of a ribosomal protein and induction of erythropoiesis-suppressive cytokine IL-22. While IL-22 has been shown to modulate RBC production by controlling the expression of iron-chelating proteins, such as hepcidin (Smith et al. (2013) *J. Immunol.* 191:1845-1855) and haptoglobin (Sakamoto et al. (2017) *Sci. Immunol.* 2:eaai8371), the results described herein elucidate a novel role for IL-22 in directly regulating erythropoiesis in the BM. Using banked and fresh MDS patient samples, it was also demonstrated that IL-22 is elevated in BMF and T cells of MDS patients.

IL-22 is known to play a pathogenic role in some autoimmune diseases (Cai et al. (2013) *PLoS One* 8:e59009; Ikeuchi et al. (2005) *Arthritis Rheum.* 52:1037-1046; Yamamoto-Furusho et al. (2010) *Inflamm. Bowel Dis.* 16:1823). Interestingly, autoimmune diseases, such as colitis, Behcet's disease, and arthritis, are common in MDS patients, with features of autoimmunity observed in up to 10% of patients (Dalamaga et al. (2010) *J. Eur. Acad. Dermatol. Venereol.* 22:543-548; Lee et al. (2016)*Medicine* (*Baltimore*) 95:e3091). Based on the results described herein, it is believed that IL-22 accounts both for the onset of MDS and autoimmunity in this subset of patients. Low-level exposure to benzene, a hydrocarbon, has been associated with an increased risk of MDS (Schnatter et al. (2012) *J. Natl. Cancer Inst.* 104:1724-1737). Hydrocarbons are known ligands for Ahr, the transcription factor that controls IL-22 production in T cells (Monteleone et al. (2011) *Gastroenterology* 141:237-248). Stemregenin 1, an Ahr antagonist, was shown to promote the ex vivo expansion of human HSCs, with the highest fold expansion seen in the erythroid lineage (Boitano et al. (2010) *Science* 329:1345-1348).

More importantly, evidence is provided herein that neutralization of IL-22 signaling effectively treats MDS and anemias, such as stress-induced anemias and the anemia of CKD, diseases that are very much in need of new therapeutic approaches. Ideally, IL-22-based therapeutics may be used not only as monotherapy, but also in conjunction with already existing therapeutics, such as erythropoietin, lenalidomide and azacytidine, which unfortunately presently provide only an average 3- to 5-year window of survival.

Example 6: Effects of IL-22 Neutralization on Riok2 Haploinsufficiency to Alleviate Anemia and Aberrant Myelopoiesis As described herein, in a model of ribosomal protein (Riok2) haploinsufficiency (Riok2$^{+/-}$)-induced anemia and myelodysplasia, an increased IL-22 secretion from T cells as compared to normal wild-type (wt, Riok2$^{+/+}$) T cells was observed. Additionally, a compound genetic deletion of IL-22 on the Riok2 haploinsufficient background (Riok2$^{+/-}$Il22$^{+/+}$) partially reversed the anemia seen in IL-22 sufficient Riok2 haploinsufficient (Riok2$^{+/-}$IL22$^{+/+}$) mice. Moreover, wt mice undergoing phenylhydrazine-induced acute anemia treated with an anti-IL-22 neutralizing antibody repopulated their peripheral blood RBCs faster than isotype-treated controls. Similarly, anti-IL-22 mAb treatment of Riok2$^{+/-}$ mice partially reversed the anemia in these mice as compared to isotype-treated controls. It was further found that IL-22 levels are increased in the bone marrow fluid (BMF) of MDS patients as compared to healthy controls. Based on these data, disclosed herein are methods of using agents that downregulate IL-22 signaling (e.g., a neutralizing antibody against IL-22) to alleviate the red blood cell deficit seen in anemia and MDS patients.

The MDS-like phenotype in Riok2$^{+/-}$ mice described herein indicated that RIOK2 deletions or inactivating mutations exist in a subclass of MDS patients (with or without del(5q)). Accordingly, a RIOK2 mutation (I245T) was identified in an aplastic anemia patient that acts as a dominant negative to inhibit erythropoiesis. Additionally, independent analysis of a publicly available microarray dataset of MDS patients (Pellagatti et al. (2010) *Leukemia* 24(4):756-764) showed significant reduction in RIOK2 mRNA in del(5q) MDS patients as compared to healthy controls and to non-del(5q) MDS patients.

The IL-22 receptor, IL-22RA1, is specifically expressed on structural cells and cells of non-hematopoietic origin. It has been determined herein for the first time that erythroid progenitors in the bone marrow express IL-22RA1. Using an erythroid specific-cre recombinase (erythropoietin receptor-cre, EpoR-cre), IL-22RA1 was deleted on erythroid progenitor cells. Mice lacking IL-22RA1 on erythroid cells had significantly higher peripheral blood RBC numbers and hematocrit as compared to the cre alone controls. Thus, using an alternative approach of neutralizing IL-22 signaling in erythroid origin cells, it was proved herein that IL-22 signaling leads to inhibition of erythropoiesis. Based on these data, anti-IL22RA1 blocking antibodies can be used in alleviating red blood cell deficit seen in anemia and MDS.

IL-22RA1, apart from dimerizing with IL-10R2 to form the IL-22RA1/IL-10R2 heterodimer, also couples with IL-20R2 to form a signaling receptor for IL-24. IL-24 has been implicated in anti-tumor functions. Thus, to specifically target IL-22 and not IL-24 signaling via its receptor, antibodies against the IL-22RA1/IL-10R2 heterodimer can be beneficial. An alternative approach to the anti-IL-22 antibody approach is to use recombinant IL-22 binding protein (IL-22BP). IL-22BP is a soluble IL-22 receptor that lacks an intracellular domain and thus sequesters IL-22 to thereby act as an antagonist solely to IL-22 signaling.

As described herein, Riok2 haploinsufficiency increases T cell-derived IL-22, the production of which is controlled by aryl hydrocarbon receptor (AHR) (Monteleone et al. (2011) *Gastroenterology* 141(1):237-248). Haploinsufficient deletion of Il22 in Riok2$^{+/-}$ mice (Riok2$^{+/-}$Il22$^{+/-}$) reversed the erythroid differentiation defect in Riok2$^{+/-}$ mice and antibody-mediated neutralization of IL-22 in wt mice increases peripheral blood RBCs. To further confirm whether IL-22 depletion in Riok2$^{+/-}$ mice normalizes the anemic/25 myelodysplastic phenotype: (a) IL-22 is neutralized using an IL-22 antibody; (b) an AHR antagonist, stemregenin 1 (SR1), is used to abrogate AHR signaling and thus IL-22 production; and (c) the increased IL-22 seen in Riok2$^{+/-}$ mice is compared with examined IL-22 levels for other ribosomal protein haploinsufficiencies (e.g. Rps14, Rpl11, and the like).

Anti-IL-22 antibody (Clone IL22JOP, Thermo Fisher Scientific) has been shown to effectively neutralize IL-22 (Chan et al. (2017) Infect Immun. 85(2); Mielke et al. (2013) *J Exp Med.* 210(6):1117-1124). Riok2$^{+/-}$ mice (20-24 wk old) are treated intraperitoneally with anti-IL-22 antibody or isotype control (Rat IgG2aκ) at 100 μg/day/mouse twice every week for 8 weeks. After the 8-week treatment period, peripheral blood is analyzed for RBC numbers and other hematological parameters at 8-week intervals to ascertain the prolonged effect of IL-22 neutralization on alleviating anemia. For endpoint analysis at 16 weeks after the cessation of antibody treatment, BM is assessed for frequency and number of hematopoietic and erythroid progenitor cells using flow cytometry.

SR1 is an AHR antagonist that has been shown to maintain pluripotency of human CD34$^{+}$ stem cells (Boitano et al. (2010) *Science* 329(5997):1345-1348). SR1-pretreated CD34$^{+}$ cells showed a 129-fold increase in erythroid colonies as compared to untreated cells. No study has yet tested the effect of SR1 in the treatment of myelodysplasia. To this end, six to eight 20-24 wk old Riok2$^{+/-}$ mice are treated intraperitoneally with 0.1 mg/mL SR1 once every week for 8 wks. At the end of 8 weeks, hematological parameters and BM architecture are studied as described above.

For analyzing IL-22 secretion from T cells of ribosomal protein haploinsufficient mouse models, splenic naïve T cells are isolated and cultured in the presence of anti-CD3, anti-CD28, IL-1β, IL-23, and IL-6 for 3 days. IL-22 production is analyzed using flow cytometry and ELISA.

Optionally, the dose of SR1 being used is lowered or other available AHR antagonists (e.g., CH223191, 2',4',6-Trimethoxyflavone, and the like) are tested. Alternatively, this regimen is potentiated with low dose lenalidomide or erythropoiesis stimulating agents, such as erythropoietin.

Example 7: Materials and Methods for Examples 8-16 a. Human Samples and Processing

MDS and CKD patient samples were collected under IRB-approved protocols at Dana-Farber Cancer Institute (DFCI) and Brigham and Women's Hospital (BWH), respectively. All samples were de-identified at the time of inclusion in the study. All patients provided informed consent and the data collection was performed in accordance with the Declaration of Helsinki.

Peripheral blood mononuclear cells (PBMCs) from EDTA-treated whole blood were isolated using density gradient centrifugation. PBMCs were then incubated in RPMI with 10% FBS and Cell Activation Cocktail (Tonbo Biosciences) for 4 h and then processed for flow cytometry as described below. Relevant clinical information of MDS samples is provided in Table 3. Adult CKD plasma samples were stored at −80° C. until further use. Relevant clinical information of CKD samples is provided in Table 4.

b. Generation of Riok2 Floxed Mice

Riok2$^{f/f}$ mice were generated using frozen sperm obtained from Mutant Mouse Resource and Research Centers (MMRRC) (Riok2$^{tm1a(KOMP)Wtsi}$) In brief, a floxed Riok2 allele was created by inserting an FRT-flanked IRES-LacZ-neon cassette into intron 4 of the Riok2 gene. LoxP sites were inserted to flank exons 5 and 6. After germline transmission, the FRT cassette was removed by crossing to FLPe deleter mice and resulting floxed mice were bred with individual cre driver strains to create conditional Riok2-deleted mice (FIG. 1A). Genotyping (FIG. 22B) was carried out using the following primers:

```
Forward primer:
                                        (SEQ ID NO: 2)
5' GCATCAGTGATTTACAGACTAAAATGCC 3'

Reverse primer 1:
                                        (SEQ ID NO: 3)
5' GCTCTTACCCACTGAGTCATCTCACC 3'

Reverse primer 2:
                                        (SEQ ID NO: 4)
5' CCCAGACTCCTTCTTGAAGTTCTGC 3'
```

c. Mice

Wild-type C57BL/6J mice (Stock no. 000664), Vav-icre mice (Stock no. 008610), R26-CreErt2 mice (Stock no. 008463), Il22ra1-floxed (Stock no. 031003), CD45.1 C57BL/6J mice (Stock no. 002014), Trp53−/− (Stock no. 002101), Cd4-cre (Stock no. 022071), and Ape' (Stock no. 002020) mice were purchased from The Jackson Laboratory. Il22$^{-/-}$ mice were provided by R. Caspi (National Institutes of Health, Bethesda, MD) with permission from Genentech (San Francisco, CA). Epor-cre mice were a gift from U. Klingmüller (Deutsches Krebsforschungszentrum (DFKZ), Germany). Il22-tdtomato (Catch-22) mice were a gift from R. Locksley (University of California at San Francisco, CA). Rps14-floxed mice were a gift from B. Ebert (Dana-Farber Cancer Institute, Boston, MA). Mice were housed in the Animal Research Facility (ARF) at DFCI under ambient temperature and humidity with 12 h light/12 h dark cycle. Animal procedures and treatments were in compliance with the guidelines set forth by the Institutional Animal Care and Use Committee (IACUC) at DFCI. Age- and gender-matched mice were used within experiments.

d. Competitive Bone Marrow (BM) Transplantation

2×10$^6$ freshly isolated BM cells from CD45.2$^+$ Riok2$^{f/+}$ Ert2$^{cre}$ or Riok$^{+/+}$Ert2$^{cre}$ mice were transplanted in competition with 2×10$^6$ freshly isolated CD45.1$^+$ wild-type (WT) BM cells via retro-orbital injection into lethally irradiated 8-10 week old CD45.1$^+$ WT recipient mice. The donor cell chimerism was determined in the peripheral blood four weeks after transplantation before the excision of Riok2 was induced by tamoxifen injection as well as every four to eight weeks as indicated. Tamoxifen (75 mg/kg) (Cayman Chemical, Cat #13258) was administered for five consecutive days.

e. Flow Cytometry and Cell Isolation

Whole bone marrow (BM) cells were isolated by crushing hind leg bones (femur and tibia) with mortar and pestle in staining buffer (PBS (Corning) supplemented with 2% heat-inactivated fetal bovine serum (FBS, Atlanta Biologicals) and EDTA (GIBCO). Whole BM was lysed with 1× Pharm-Lyse (BD Biosciences) for 90 s, and the reaction was terminated by adding an excess of staining buffer. Cells were labeled with fluorochrome-conjugated antibodies in staining buffer for 30 min at 4° C. For flow cytometric analysis, cells were incubated with combinations of fluorochrome-conjugated antibodies to the following cell surface markers: CD3 (17A2, 1:500), CD5 (53-7.3, 1:500), CD11b (M1/70, 1:500), Gr1 (RB6-8C5, 1:500), B220 (RA3-6B2, 1:500), Ter119 (TER119, 1:500), CD71 (C2, 1:500), c-kit (2B8, 1:500), Sca-1 (D7, 1:500), CD16/32 (93, 1:500), CD150 (TC15-12F12.2, 1:150), CD48 (HM48-1, 1:500). For sorting of lineage-negative cells, lineage markers included CD3, CD5, CD11b, Gr1 and Ter119. For sorting erythroid progenitor cells, the lineage cocktail did not include Ter119. All reagents were acquired from BD Biosciences, Thermo Fisher Scientific, Novus Biologicals, Tonbo Biosciences, or BioLegend. Identification of apoptotic cells was carried out using the Annexin V Apoptosis Detection Kit (BioLegend). Intracytoplasmic and intranuclear staining was performed using Foxp3/Transcription Factor Staining Kit (Thermo Fisher Scientific) or 0.1% saponin in PBS supplemented with 3% FBS. For staining performed with AF647 p53 antibody (Cell Signaling Technology, 1:50), cells were permeabilized with 90% ice-cold methanol. To increase the sorting efficiency, whole BM samples were lineage-depleted using magnetic microbeads (Miltenyi Biotec) and autoMACS Pro magnetic separator (Miltenyi Biotec). Cell sorting was performed on a FACS Aria flow cytometer (BD Biosciences), data acquisition was performed on a BD Fortessa X-20 instrument equipped with 5 lasers (BD Biosciences) employing FACSDiva software. Data were analyzed by FlowJo (Tree Star) version 9 software. Flow analyses were performed on viable cells by exclusion of dead cells using either DAPI or a fixable viability dye (Tonbo Biosciences). Gating for early and committed hematopoietic progenitors was performed as described elsewhere. ILCs and NKT cells were identified as Lin$^-$CD45$^+$CD90$^+$ CD12$^+$ and CD3ε$^+$ NK1.1$^+$, respectively.

f. Complete Blood Count

Mice were bled via the submandibular facial vein to collect blood in EDTA-coated tubes (BD MICROTAINER™ Capillary Blood Collector, BD 365974). Complete blood counts were obtained using the HemaVet CBC Analyzer (Drew Scientific) or Advia 120 (Siemens Inc.,) instruments.

g. In Vivo Measurement of Protein Synthesis

100 μL of a 20 mM solution of 0-Propargyl-Puromycin (OP-Puro; BioMol) was injected intraperitoneally in mice and mice were then rested for 1 h. Mice injected with PBS were used as controls. BM was harvested after 1 h and stained with antibodies against cell surface markers, washed to remove excess unbound antibodies, fixed in 1% paraformaldehyde, and permeabilized in PBS with 3% FBS and 0.1% saponin. The azide-alkyne cyclo-addition was performed using the Click-iT Cell Reaction Buffer Kit (Thermo Fisher Scientific) and azide conjugated to Alexa Fluor 647 (Thermo Fisher Scientific) at 5 μM final concentration for 30 min. Cells were washed twice and analyzed by flow cytometry. 'Relative rate of protein synthesis' was calculated by normalizing OP-Puro signals to whole bone marrow after subtracting autofluorescence.

h. Methylcellulose Assay 250-500 BM $Lin^-c\text{-}kit^+Sca\text{-}1^+$ cells were flow sorted and plated in semi-solid methylcellulose culture medium (M3534, StemCell Technologies) and incubated at 37° C. in a humidified atmosphere for 7-10 days. At the end of the incubation period, each well was triturated with staining buffer to collect cells and then processed for flow cytometry as described above. Enumeration of colonies in MethoCult media was performed with StemVision instrument StemCell Technologies).

i. Phenylhydrazine Treatment

Phenylhydrazine (PhZ) was purchased from Sigma and injected intraperitoneally on 2 consecutive days (days 0 and 1) at the dose of 25 mg/kg (sublethal model) or 35 mg/kg (lethal model). Peripheral blood was collected 3-4 days before the start of treatment and at day 4, 7, and 11. PhZ treatment experiments were carried out in 8-12 week old mice.

j. T Cell Polarization

Single-cell suspensions of mouse spleens were prepared by pressing tissue through a 70-μm cell strainer followed by red blood cell lysis using PharmLyse. Total splenic $CD4^+$ T cells were isolated using CD4 T cell isolation kit (Miltenyi Biotec). Enriched $CD4^+$ T cells were then incubated with fluorochrome-conjugated antibodies to CD4, CD8, CD25, CD62L, and CD44 to purify naïve $CD4^+$ T cells using fluorescence activated cell sorting (FACS). In the presence of 1 μg/mL plate-bound anti-CD3ε and soluble 1 μg/mL anti-CD28, T cell polarizations were carried out in IMDM supplemented with 10% FBS, 2 mM L-glutamine, 100 mg/mL penicillin-streptomycin, HEPES (pH 7.2-7.6), non-essential amino acids, 100 μM β-mercaptoethanol (BME), and sodium pyruvate as follows—$T_H1$ (20 ng/mL IL-12, 10 μg/mL anti-IL-4), $T_H2$ (20 ng/mL IL-4, 10 μg/mL anti-IFN-γ), $T_H17$ (30 ng/mL IL-6, 20 ng/mL IL-23, 20 ng/mL IL-1β, 10 μg/mL anti-IL-4, 10 μg/mL anti-IFN-γ), $T_{reg}$ cells (1 ng/mL TGF-β, 10 μg/mL anti-IL-4, 10 μg/mL anti-IFN-γ), and $T_H22$ (30 ng/mL IL-6, 20 ng/mL IL-23, 20 ng/mL IL-1β, 10 μg/mL anti-IL-4, 10 μg/mL anti-IFN-γ, 400 nM FICZ). Pifithrin-α, p-Nitro and Nutlin-3a were purchased from Santa Cruz Biotechnology and Tocris Biosciences, respectively.

k. IL-22 Neutralization and Reconstitution

Monoclonal anti-IL-22 (Clone IL22JOP) blocking antibody and isotype control IgG2aκ (Clone eBR2a) were purchased from Thermo Fisher Scientific. Mice were administered anti-IL-22 (50 μg/mouse) or isotype intraperitoneally every 48 h until the conclusion of the experiment. For recombinant IL-22 treatment, mice were injected with recombinant IL-22 (500 ng/mouse; PeproTech) intraperitoneally every 24 h until the conclusion of the experiment. Mice were administered these reagents at least five times before inducing PhZ-mediated anemia.

l. Cytokine Quantitation

IL-22 in human samples was quantified using either Human IL-22 Quantikine ELISA Kit (D2200, R&D Systems) or SMCTM Human IL-22 High Sensitivity Immunoassay Kit (EMD Millipore, 03-0162-00) according to manufacturers' instructions. The SMC assay was read on a SMC Pro (EMD Millipore) instrument. The lower limit of quantification (LLOQ) of this immunoassay is 0.1 pg/mL. IL-22 in mouse samples was quantified using ELISA MAX™ Deluxe Set Mouse IL-22 (BioLegend, 436304). The LLOQ of this immunoassay is 3.9 pg/mL. S100A8 in human samples was quantified using Human S100A8 DuoSet ELISA (DY4570, R&D Systems).

Concentration of lineage-associated cytokines in cell culture supernatants of polarized T cells were quantified using a custom-made ProCarta Plex assay (Thermo Fisher Scientific) acquired on a Luminex platform. Hepcidin in mouse serum was quantified using a colorimetric assay from Hepcidin MURINE-COMPETE™ ELISA Kit from Intrinsic LifeSciences (HMC-001).

m. mRNA Quantitation

Cells were flow sorted directly into the lysis buffer provided with the CELLS-TO-CT 1-Step TAQMAN™ Kit (A25605, Thermo Fisher Scientific) and processed according to the manufacturer's instructions. Pre-designed TaqMan gene expression assays were used to quantify mRNA expression by qPCR using QuantStudio 6 (Thermo Fisher Scientific). Hprt was used as housekeeping control. Relative expression was calculated using the ΔCt method. Details on primers are indicated in Table 5 for primers details.

n. Chromatin Immunoprecipitation (ChIP)

ChIP was performed using EZ-ChIP Kit (EMD Millipore) according to manufacturer's instructions. Briefly, cells were fixed and cross-linked with 1% formaldehyde at 25° C. for 10 min and quenched with 125 mM glycine for an additional 10 min. Cells pellet was resuspended in lysis buffer and shearing was carried out Diagenode Bioruptor sonication system for a total of 40 cycles beads. Pre-cleared lysates were incubated with control Mouse IgG or anti-p53 (Santa Cruz Biotechnology) antibodies. Il22 promoter-specific primer pair was designed using Primer 3.0 Input and were as follows:

```
Forward Primer:
                                    (SEQ ID NO: 5)
5' CCAAACTTAACTTGACCTTGGC 3'

Reverse Primer:
                                    (SEQ ID NO: 6)
5' TTCTTCACAGCTCCCA TTGC 3'
```

o. In Vitro Erythroid Differentiation

Whole BM cells were labeled with biotin-conjugated lineage antibodies (cocktail of anti-CD3ε, anti-CD11b, anti-CD45R/B220, anti-Gr1, anti-CD5, and anti-TER-119) (BD Pharmingen) and purified using anti-biotin beads and negative selection on the AutoMACS Pro (Miltenyi). Purified cells were then seeded in fibronectin-coated (2 μg/$cm^2$) tissue-culture treated polystyrene wells (CORNING® BIOCOAT™ Cellware) at a cell density of $10^5$/mL. Erythroid differentiation was carried out according to modified published protocols. The erythropoietic medium was IMDM supplemented with erythropoietin at 10 U/mL, 10 ng/mL stem cell factor SCF, PeproTech), 10 μM Dexamethasone (Sigma-Aldrich), 15% FBS, 1% detoxified BSA (StemCell Technologies), 200 μg/mL holotransferrin (Sigma-Aldrich), 10 mg/mL human insulin (Sigma-Aldrich), 2 mM L-glutamine, 0.1 mM β-mercaptoethanol, and penicillin-streptomycin. After 48 h, the medium was replaced by IMDM medium containing 20% FBS, 2 mM L-glutamine, 0.1 mM β-mercaptoethanol, and penicillin-streptomycin. 50% of the culture media was replaced after 48 h and cell density was maintained at $0.5\times10^6$/mL. Total culture period for the assay was 6 days. Recombinant mouse IL-22 (PeproTech/Cell Signaling) was used where indicated. RII-RIV populations were gated as shown in FIG. 23A.

p. Proteomic Profiling

Proteomic profiling of sort-purified erythroid progenitors was performed as described elsewhere. Briefly, cells were captured in collection microreactors and stored at −80° C. Cell lysis was performed by adding 10 μL of 8 M urea, 10 mM TCEP and 10 mM iodoacetamide in 50 mM ammonium bicarbonate (ABC) to the cell pellet of $1\times10^6$ erythroid progenitors and incubated at room temperature for 30 min, shaking in the dark. 50 mM ABC was used to dilute the urea to less than 2 M and the appropriate amount of trypsin for a 1:100 enzyme to substrate ratio was added and allowed to incubate at 37° C. overnight. Once digestion is completed, the lysate is spun through the glass mesh directly onto a C18 Stage tip (Empore) at 3500×g until the entire digest passes through the C18 resin. 75 μL 0.1% formic acid (FA) is then used to ensure transfer of peptides to the C18 resin from the mesh while washing away the lysis buffer components. C18-bound peptides were immediately subjected to on-column TMT labeling.

On-column TMT Labeling—Resin was conditioned with 50 μL methanol (MeOH), followed by 50 μL 50% acetonitrile (ACN)/0.1% FA, and equilibrated with 75 μL 0.1% FA twice. The digest was loaded by spinning at 3500×g until the entire digest passed through. One μL of TMT reagent in 100% ACN was added to 100 μL freshly made HEPES, pH 8, and passed over the C18 resin at 350×g until the entire solution passed through. The HEPES and residual TMT was washed away with two applications of 75 μL 0.1% FA and peptides were eluted with 50 μL 50% ACN/0.1% FA followed by a second elution with 50% ACN/20 mM ammonium formate ($NH_4HCO_2$), pH 10. Peptide concentrations were estimated using an absorbance reading at 280 nm and checking of label efficiency was performed on ½0th of the elution. After using ½0th of the elution to test for labeling efficiency, the samples are mixed before fractionation and analysis.

Stage tip bSDB Fractionation—200 μL pipette tips were packed with two punches of sulfonated divinylbenzene (SDB-RPS, Empore) with a 16-gauge needle. After loading ~20 μg peptides total, a pH switch was performed using 25 μL 20 mM $NH_4HCO_2$, pH 10, and was considered part of fraction one. Then, step fractionation was performed using ACN concentrations of 5, 7.5, 10, 12.5, 15, 17.5, 20, 25, 42, and 50%. Each fraction was transferred to autosampler vials and dried via vacuum centrifugation and stored at 80° C. until analysis. Data Acquisition—Chromatography was performed using a Proxeon UHPLC at a flow rate of 200 nl/min. Peptides were separated at 50° C. using a 75 μm i.d. PicoFrit (New Objective) column packed with 1.9 μm AQ-C18 material (Dr. Maisch, Germany) to 20 cm in length over a 110 min run. The on-ine LC gradient went from 6% B at 1 min to 30% B in 85 mins, followed by an increase to 60% B by minute 94, then to 90% by min 95, and finally to 50% B until the end of the run. Mass spectrometry was performed on a Thermo Scientific Lumos Tribrid mass spectrometer. After a precursor scan from 350 to 1800 m/z at 60,000 resolution, the topmost intense multiply charged precursors in a 2 second window were selected for higher energy collisional dissociation (HCD) at a resolution of 50,000. Precursor isolation width was set to 0.7 m/z and the maximum MS2 injection time was 110 msecs for an automatic gain control of 6e4. Dynamic exclusion was set to 45 s and only charge states two to six were selected for MS2. Half of each fraction was injected for each data acquisition run.

Data Processing—Data were searched all together with Spectrum Mill (Agilent) using the Uniprot Mouse database (28 Dec. 2017), containing common laboratory contaminants and 553 smORFs. A fixed modification of carbamidomethylation of cysteine and variable modifications of N-terminal protein acetylation, oxidation of methionine, and TMT-11plex labels were searched. The enzyme specificity was set to trypsin and a maximum of three missed cleavages was used for searching. The maximum precursor-ion charge state was set to six. The MS1 and MS2 mass tolerance were set to 20 ppm. Peptide and protein FDRs were calculated to be less than 1% using a reverse, decoy database. Proteins were only reported if they were identified with at least two distinct peptides and a Spectrum Mill score protein level score ~20. TMT11 reporter ion intensities in each MS/MS spectrum were corrected for isotopic impurities by the Spectrum Mill protein/peptide summary module using the afRICA correction method which implements determinant calculations according to Cramer's Rule and general correction factors obtained from the reagent manufacturer's certificate of analysis. Differential Protein Abundance Analysis—The median normalized, median absolute deviation-scale data set was subjected to a moderated F-test, followed by Benjamini-Hochberg Procedure correcting for multiple hypothesis testing. An arbitrary cutoff were drew at adj. p val <0.05.

q. RNA Sequencing (RNA-Seq)

5000 IL-22$^+$(CD4$^+$IL-22(tdtomato)$^+$) cells were FACS sorted directly into TLC Butter (Qiagen) with 1% β-mercaptoethanol. For the preparation of libraries, cell lysates were thawed and RNA was purified with 12×RNAClean SPRI beads (Beckman Coulter Genomics) without final elution. The RNA captured beads were air-dried. and processed immediately for RNA secondary structure denaturation (72° C. for 3 min) and cDNA synthesis. SMART-seq2 was performed on the resultant samples following the published protocol with minor modifications in the reverse transcription (RI) step. A 15 μL reaction mix was used for subsequent PCR and performed 10 cycles for cDNA amplification. The amplified cDNA. from this reaction was purified with 0.8× Ampure SPRI beads (Beckman Coulter Genomics) and eluted in 21 μL TIE buffer. 0.2 ng cDNA and one-eighth of the standard Illwnina NexteraXT (Illumina FC-131-1096) reaction volume were used to perform both the tagmentation and PCR indexing steps. Uniquely indexed libraries were pooled and sequenced with NextSeq 500 high output V2 7:5 cycle kits (Illutnina FC-404-2005) and 38×38 paired-end reads on the NextSeq 500 instrument. Reads were aligned to the mouse mm10 transcriptome using Bowtie[62], and expression abundance TPM estimates were obtained using RSEM.

r. Pathway Analysis

Gene set enrichment analysis (GSEA) was performed with Broad Institute's GSEA Software. The 'IL-22 Signature' and 'Rps14 Increased' gene sets were created from the literature (FIG. 15A, D). Full lists of genes in the individual gene sets can be found in Table 2. Other reference gene sets are available from MSigDB. For GSEA analyses, mouse UniProt IDs were converted to their orthologous human gene symbols using MSigDB 7.1 CHIP file mappings. Pathway enrichment (FIG. 15C) was performed using Clarivate Analytics' METACORE™ software.

s. Microarray Data Analysis

Microarray data of $CD34^+$ cells from healthy, del(5q), and non-del(5q) MDS subjects was obtained from a previously published study submitted in Gene Expression Omnibus accessible under GSE19429.

t. Statistical Tests

Data are presented as mean±s.e.m unless otherwise indicated. Comparison of two groups was performed using paired or unpaired two-tailed t-test. For multiple group comparisons, analysis of variance (ANOVA) with Tukey's correction or Kruskal-Wallis test with Dunn's correction was depending on data requirements. Statistical analyses were performed using GraphPad Prism v8.0 (GraphPad Software Inc.). A P-value of less than 0.05 was considered significant.

TABLE 2

Signatures used for GSEA analyses.

| IL-22 Signature | | Rps14 Signature |
|---|---|---|
| Bcl1 | Ccl20 | S100a8 |
| Cldn1 | Muc1 | Pglyrp1 |
| Lbp | Muc3 | Retnlg |
| Il1 | Muc10 | Mgp |
| Il6 | Muc13 | S100a9 |
| Il8 | Defb2 | Ltf |
| Il11 | Defb3 | Lcn2 |
| Gcsf | Lcn2 | Chi3l1 |
| Gmcsf | Mmp1 | Camp |
| Ccl2 | Mmp3 | Ngp |
| Rankl | Il20 | Apobr |
| Cxcl1 | Saal1 | Lrg1 |
| Cxcl2 | Hp | Padi4 |
| Cxcl5 | Hamp | Hp |
| Cxcl8 | Cdk4 | Lyz2 |
| Reg3g | Myc | Anxa1 |
| Reg3b | p21 | Gys1 |
| Bcl2 | Il10 | Gda |
| Bclxl | Serpina3 | Nfrkb |
| S100a7 | Cdkn1a | Aldh3b1 |
| | Defb | |
| S100a8 | Prdx5 | S100a11 |
| S100a9 | Saa | Itgam |
| S100a10 | Saa1 | Itgb2 |
| S100a11 | | Ncf2 |
| | | Pygl |
| | | Cnn2 |

TABLE 3

Karyotype of MDS patients. ISCN = International System for Human Cytogenetic Nomenclature

| Patient | Karyotype (ISCN nomenclature) |
|---|---|
| non-del(5q)-1 | 46, XY[15] |
| non-del(5q)-2 | 46, XX[20] |
| non-del(5q)-3 | 45, XX, del(1)(p22), der(2)del(2)(p12)t(1; 2)(p22; q31), add(11)(p15), −13, 21<br>pstk+, add(22)(q11.2)[cp3]/46, XX[6] |
| non-del(5q)-4 | 42, X, −Y, −4, add(5)(q3?1), add(7)(q3?1), −13,<br>add(15)(p11.2), −16, −18, −20, +2mar[17]/46, XY[3} |
| del(5q)-1 | 43, X, −Y[4], del(1)(q11)[2], add(4)(q24), del(5)(q1?5q33), −7, −9, −12, add(16)(p11.2),<br>der(19)t(12; 19)(q13; p13.1), −22, +1-2r, +1-2mar[cp6]/46, XY[2] |
| non-del(5q)-5 | 46, XY[20] |
| non-del(5q)-6 | 46, XY[20] |
| non-del(5q)-7 | 46, XY[20] |
| non-del(5q)-8 | 46, XY[20] |
| non-del(5q)-9 | 46, XY, del(20)(q11.2q13.3)[cp8]/46, XY, +1, der(1)t(1; 13)(p12; q11), −13,<br>del(20)[cp12].nuc ish(D7Z1, D7S486)x2[100] |
| non-del(5q)-10 | 46, XY[20] |
| non-del(5q)-11 | K1: 47, XY, +12[9]/47, idem, del(14)(q21q31)[4]/46, XY[cp7]<br>K2: 47, XY, +14[2]/46, XY[18].nuc ish(IGHx3)[14/100] |
| non-del(5q)-12 | 45, XX, −7[4]/46, XX[12].nuc ish(D7Z1, D7S486)x1[32/100] |
| non-del(5q)-13 | 46, XX[20] |
| non-del(5q)-14 | 46, XY, del(3)(q13q24)[7]/46, XY[13] |
| non-del(5q)-15 | 46, XY[20] |
| non-del(5q)-16 | 44, XY, add(3)(p21), add(5)(q11.2), der(6)t(3; 6)(p13; q13), −7,<br>del(12)(p11.2p13), −18, −20, add(20)(p12), +r[cp20] |
| del(5q)-2 | 41~45, Y, t(X; 2)(q?24; ? q31), add(2)(p13), −5, add(8)(p21), ?inv(9)(p22q12),<br>del(11)(p13), −12, −13, −15, −15, −16, add(17)(p11.2), del(18)(q12.2), del(18)(q21), −add(19)(p13.3), −21,<br>add(21)(q22), add(22)(q13), +4-6 mar[12]/32~35,idem, −3, −4, −7, −10,<br>add(17), −del(18)(q21), −20, −add(22), +2-4mar[5]/44, XY, add(2)(q31), −5, add(8),<br>adel(11), −13, add(15)(p11.2), add(17), add(19)(p13), add(20)(q13.3), +mar[3]/46, XY[1] |
| non-del(5q)-17 | 46, XX[20] |
| non-del(5q)-18 | 47, XY, +8[16]/46, XY[4] |
| non-del(5q)-19 | 46, XX[10] |
| non-del(5q)-20 | 45, X, −Y[6]/46, XY[14] |
| non-del(5q)-21 | 46, XX[20] |
| non-del(5q)-22 | 46, XY[20] |
| del(5q)-3 | de15q (full report not available) |
| non-del(5q)-23 | 46, XY, del(8)(q2?2q2?4), add(14)(q32)[1]/46, XY[cp19 |
| non-del(5q)-24 | 46, XY[20] |

TABLE 4

Clinical Information for CKD samples. eGFR = Estimated glomerular filtration rate, Hgb - Hemoglobin.

| eGFR | Hgb |
|---|---|
| 29 | 15.2 |
| 25 | 13.5 |
| 25 | 14.9 |
| 34 | 9.9 |
| 16 | 14.7 |
| 18 | 13.9 |
| 15 | 10.3 |
| 26 | 12.6 |
| 29 | 14.5 |
| 23 | 13.7 |
| 28 | 9.2 |
| 19 | 14.4 |
| 26 | 14 |
| 21 | 9.4 |
| 21 | 11.9 |
| 19 | 9.9 |
| 27 | 13.3 |
| 12 | 9.8 |
| 15 | 12.6 |
| 13 | 10.5 |
| 17 | 9.6 |
| 27 | 14.9 |
| 17 | 7.7 |
| 33 | 9.7 |
| 58 | 13.3 |
| 10 | 13.8 |

TABLE 5 qRT-PCR Taqman primers used in this study.

| Gene | Catalog # |
|---|---|
| Mouse Riok2 | Mm00482415_m1 |
| Human RIOK2 | Hs01084566_m1 |
| Mouse S100a8 | Mm00496696_g1 |
| Mouse S100a9 | Mm00656925_m1 |
| Mouse Hprt | Mm03024075_m1 |
| Human HPRT1 | Hs02800695_m1 |
| Mouse Cdkn1a | Mm00432448_m1 |
| Mouse Il22ral | Mm01192943_m1 |
| Mouse Trp53 | Mm01731290_g1 |
| Mouse Gadd45a | Mm00432802_m1 |
| Mouse Bbc3 | Mm00519268_m1 |

Example 8: Riok2 Haploinsufficiency Leads to Anemia

Myelodysplastic syndromes (MDS) are a group of cancers characterized by failure of blood cells in the bone marrow to mature. About 7 out of 100,000 people are affected and the typical survival time following diagnosis is less than three years. While a sizable percentage of MDS cases progress to acute myelogenous leukemia (AML), most of the morbidity and mortality associated with MDS results not from transformation to AML but rather from hematological cytopenias.

Anemia is the most common hematologic manifestation of MDS, particularly in the subset of patients with del(5q) MDS. Del(5q), either isolated or accompanied by additional cytogenetic abnormalities, is the most commonly detected chromosomal abnormality in MDS, reported in 10-15% of patients. The severe anemia in del(5q) MDS patients has been linked to haploinsufficiency of ribosomal proteins such as RPS14 and RPS19. Previous studies using mice with haploinsufficient 5q gene deletions revealed diminished erythroid progenitor frequency but the mechanisms underlying this phenotype are incompletely understood. Right open-reading-frame kinase 2 (RIOK2) encodes an atypical serine-threonine protein kinase with an indispensable function as a component of the pre-40S ribosome subunit.

There is growing evidence for the role of activated innate immunity and inflammation as well as immune dysregulation in the pathogenesis of MDS. Abnormal expression of numerous cytokines has been reported in MDS. Chronic immune stimulation in both hematopoietic stem and progenitor cells (HSPCs) and the bone marrow (BM) microenvironment was suggested to be central to the pathogenesis of MDS. In patients with chronic inflammation, cytokines in the BM have been associated with inhibition of erythropoiesis. Despite growing evidence for a link between the immune system and MDS pathogenesis, no study has identified the mechanism by which the immune microenvironment may initiate or contribute to the MDS phenotype. Further it remains unclear how ribosomal protein haploinsufficiency is connected with the immune system in MIDS.

As disclosed herein, Riok2 expression was reduced in T cells lacking the endoplasmic reticulum stress transcription factor Xbp1. RIOK2 is a little-studied atypical serine-threonine protein kinase encoded by RIOK2 at 5q15 in the human genome (FIG. 1A), adjacent to the 5q commonly deleted regions in MDS and frequently lost in MDS and acute myeloid leukemia. Gene expression commons (GEXC) analysis revealed that in mouse BM, Riok2 expression is highest in primitive colony-forming-unit erythroid (pCFU-E) cells, suggesting that RIOK2 may be involved in maintaining red blood cell (RBC) output (FIG. 1B). To further study the role of RIOK2 in hematopoiesis, Vav1-Cre transgenic foxed Riok2 ($Riok2^{f/+}Vav1^{cre}$) mice were generated in which the Cre recombinase is under the control of the hematopoietic cell—specific Vav1 promoter. Riok2 foxed mice were generated with exons 5 and 6 flanked by loxP sites (FIGS. 22A and 22B). Interestingly, no Vav1-Cre foxed Riok2 homozygous-deficient mice (Riok2 f $Vav1^{cre}$) were recovered (FIG. 22D), indicating embryonic lethality from complete hematopoietic deletion of Riok2. However, heterozygous $Riok2^{f/+}Vav1^{cre}$ mice were viable with approximately 50% Riok2 mRNA expression in hematopoietic cells compared to that of $Vav1^{cre}$ controls (FIG. 22C). As seen with other ribosomal protein haploinsufficiency mouse models, BM cells from $Riok2^{f/+}Vav1^{cre}$ mice showed reduced nascent protein synthesis in vivo compared to $Vav1^{cre}$ controls (FIG. 22E), consistent with a RIOK2 role in maturation of the pre-40S ribosome. A recent study showed that ribosomal protein deficiency-mediated reduced protein synthesis predominantly affects erythropoiesis over myelopoiesis.

Consistent with the high expression of Riok2 in pCFU-e cells in the BM, aged (>60 wks) mice with heterozygous deletion of Riok2 in hematopoietic cells ($Riok2^{f/+}Vav1^{cre}$) displayed anemia with reduced peripheral blood (PB) RBC numbers, hemoglobin (Hb), and hematocrit (HCT) (FIG. 14A). Next, it was determined whether Riok2 haploinsufficiency-mediated anemia was secondary to a defect in erythroid development in the BM, the major site of erythropoiesis. The stages (referred to here as RI, RII, RIII and MV) of erythropoiesis were characterized by flow cytometry using the expression of Ter119 and CD71 (FIG. 23A). $Riok2^{f/+}Vav1^{cre}$ mice had impaired erythropoiesis in the BM (FIG. 14B, FIG. 23B), Moreover, Riok2 haploinsufficiency led to increased apoptosis in erythroid precursors compared to controls (FIG. 14C). Additionally, $Riok2^{f/+}Vav1^{cre}$ erythroid precursors showed a decrease in cell quiescence with cell cycle block at the G1 phase (FIG. 23C). A block in cell cycle is driven by a group of proteins known as cyclin-dependent kinase inhibitors (CM). The expression of p21 (a CKI encoded by Cdkn1a) was increased in erythroid precursors from Riok2$^{fl/+}$Vav1$^{cre}$ mice compared to Riok2$^{+/+}$Vav1$^{cre}$ controls (FIG. 23D).

The effect of Riok2 haploinsufficiency on stress-induced erythropoiesis were examined using 8-12 wk old mice in which hemolysis was induced by non-lethal phenylhydrazine treatment (25 mg/kg on days 0 and 1). After acute hemolytic stress, Riok2$^{fl/+}$Vav1$^{cre}$ mice developed more severe anemia and had a delayed RBC recovery response, as compared to Riok2$^{+/+}$Vav1$^{cre}$ control mice (FIG. 14D) and succumbed faster to a lethal dose of phenylhydrazine (35 mg/kg on days 0 and 1) compared to Vav1$^{cre}$ controls (FIG. 23E). The anemia in young phenylhydrazine-administered Riok2$^{fl/+}$Vav1$^{cre}$ mice seen on day 7 was preceded by a reduction in BM RIII and RI erythroid precursor frequency on day 6, highlighting an erythroid differentiation defect in Riok2 haploinsufficient mice (FIG. 14E, FIG. 23F). In line with a role for RIOK2 in driving erythroid differentiation, fewer CFU-e colonies were observed in erythropoietin-containing MethoCult cultures from Riok2 haploinsufficient Lin$^{-}$c-kit$^{+}$CD71$^{+}$ cells compared to Riok2 sufficient cells (FIG. 14F). To determine whether Riok2 haploinsufficiency in BM cells drives anemia, BM chimeras were generated. Wild-type (WO mice transplanted with Riok2$^{fl/+}$Vav1$^{cre}$ whole BM developed anemia compared to Riok2$^{+/+}$Vav1$^{cre}$ BM transplanted wt mice (FIG. 23G). In addition, tamoxifen-inducible deletion of Riok2 in Riok2$^{fl/+}$Ert2$^{cre}$ mice led to reduction in PB RBCs, Hb, and HCT compared to Riok2$^{+/+}$Ert2$^{cre}$ controls (FIG. 23H). Taken together, these data show that Riok2 haploinsufficiency leads to anemia owing to defective bone marrow erythroid differentiation.

Example 9: Riok2 Haploinsufficiency Increases Myelopoiesis

In addition to the reduction in RBC numbers in PB from aged Riok2$^{fl/+}$Vav1$^{cre}$ mice, an increased percentage of monocytes (monocytosis) and decreased percentage of neutrophils (neutropenia) were also observed compared to controls (FIG. 14G, FIG. 23I). Granulocyte macrophage progenitors (GMPs) in the BM give rise to PB myeloid cells. The percentage of proliferating (Ki67$^{+}$) GMPs in the BM was increased in Riok2$^{fl/+}$Vav1$^{cre}$ mice compared to Riok2$^{+/+}$Vav1$^{cre}$ controls (FIG. 14H, FIG. 23J). To analyze the effect of Riok2 haploinsufficiency on myelopoiesis in the absence of in vivo compensatory mechanisms, LSK (lineage$^{-}$Sca-1$^{+}$Kit+) cells from the BM of Riok2$^{fl/+}$Vav and Riok2$^{+/+}$Vav1$^{cre}$ controls were cultured in a MethoCult assay supplemented with growth factors (interleukin 6 (IL-6), IL-3, stem cell factor (SCF) but devoid of erythropoietin). LSKs from Riok2$^{fl/+}$Vav1$^{cre}$ mice gave rise to an increased percentage of CD11b$^{+}$ myeloid cells (FIG. 14I, FIG. 23K), suggesting a cell-intrinsic myeloproliferative effect due to Riok2 haploinsufficiency consistent with a myelodysplasia phenotype.

It was also evaluated whether Riok2 haploinsufficiency affects early hematopoietic progenitors. Frequency and numbers of early hematopoietic progenitors were comparable between young Riok2$^{fl/+}$Vav1$^{cre}$ and Riok2$^{+/+}$Vav1$^{cre}$ mice (FIG. 24A), however, long-term hematopoietic stem cells (LT-HSCs) were increased in the BM of aged Riok2$^{fl/+}$Vav1$^{cre}$ mice (FIG. 24A). To further corroborate this data, the capacity of Riok2 haploinsufficient cells were analyzed in a competitive transplantation assay. Starting at 8 weeks after tamoxifen treatment to induce Riok2 deletion, Riok2 haploinsufficient cells out-competed CD45.1$^{+}$ competitor cells, while Ert2$^{cre}$ control cells had no competitive advantage (FIG. 24B). Similar to non-transplanted mice (FIG. 24A), in competitive transplant experiments the frequency of Riok2-haploinsufficient LT-HSCs was significantly higher than Riok2-sufficient LT-HSCs in relation to competitor CD45.1$^{+}$ cells (FIG. 24C). Thus, in addition to its effect on erythroid differentiation, Riok2 haploinsufficiency increases myelopoiesis and affects early hematopoietic progenitor differentiation.

Example 10: Reduced Riok2 Induces Alarmins in Erythroid Precursors

To elucidate a mechanism for the erythroid differentiation defect observed in Riok2$^{fl/+}$Vav1$^{cre}$ mice, quantitative proteomic analysis of purified erythroid precursors were performed using mass spectrometry. Riok2 haploinsufficiency led to upregulation of 564 distinct proteins (adjusted p-value <0.05) in erythroid precursors compared to those from Vav/cre controls (FIG. 4A). Interestingly, Riok2 haploinsufficiency resulted in down-regulation of other ribosomal proteins, loss of some of which (RPS5, PRL11) has been implicated in driving anemias (FIG. 25A). The alarmins including S100A8, S100A9, CAMP, NGP, and others were the most highly upregulated proteins in our dataset and interestingly, correlated significantly with those observed upon haploinsufficiency of Rps14, another component of the 40S ribosomal complex (FIG. 4B). Using the 26 upregulated proteins in the Rps14 haploinsufficient dataset as an 'Rps14 signature' (Table 4, gene set enrichment analysis (GSEA) revealed a marked enrichment for the Rps14 signature in the Riok2 haploinsufficient dataset, suggesting a shared proteomic signature upon deletion of distinct ribosomal proteins (FIG. 15A). The increased expression of S100A8 and S100.A9 in Riok2$^{fl/+}$Vav1$^{cre}$ mice was confirmed by flow cytometry and qRT-PCR (FIG. 25B-E).

In Riok2$^{fl/+}$Vav1$^{cre}$ erythroid precursors cells, the upregulated proteins with the highest fold-change (S100A8, S100A9, CAMP, NGP) are proteins with known immune functions such as antimicrobial defense. GSEA analysis of the proteomics data indicated a possible role for the immune system in driving the proteomic changes seen in Riok2 haploinsufficient erythroid precursors (FIG. 15B). An independent analysis of the Riok2 proteomics dataset using MetaCore pathway analysis software showed immune response as the top differentially regulated pathway in Riok2$^{fl/+}$Vav1$^{cre}$ mice (FIG. 15C). To assess if Riok2 haploinsufficiency leads to changes in immune cell function, naïve T cells from Riok2$^{fl/+}$Vav1$^{cre}$ mice and Riok2$^{+/+}$Vav1$^{cre}$ controls were subjected to in vitro polarization towards known CD4$^{+}$ T helper cell lineages ($T_H1$, $T_H2$, $T_H17$, $T_H22$) and regulatory T cells ($T_{reg}$). Secretion of interferon-γ (IFN-γ), IL-2, IL-4, IL-5, IL-13, IL-17A, and the frequency of Foxp3$^{+}$ $T_{reg}$ cells was similar between Riok2$^{fl/+}$Vav1$^{cre}$ and Riok2$^{+/+}$Vav1$^{cre}$ T cells (FIG. 26A-G). Strikingly, however, an exclusive increase in IL-22 secretion were observed from Riok2$^{fl/+}$Vav1$^{cre}$ naïve T cells polarized towards the $T_H22$ lineage (FIG. 16A). The frequency of IL-22$^{+}$CD4$^{+}$ T cells was higher in Riok2$^{fl/+}$Vav1$^{cre}$ $T_H^{22}$ cultures compared to Vav/cre control $T_H22$ cultures (FIG. 16B). The concentration of IL-22 in the serum and BM fluid (BMF) of aged Riok2$^{fl/+}$Vav1$^{cre}$ mice was also significantly higher as compared to age-matched Vav/cre controls (FIG. 16C). Using known IL-2.2 target genes from the literature, an 'IL-22 signature' (Table 2) gene set were curated, which showed a statistically significant enrichment in the Riok2-haploinsufficient proteomics dataset using GS. EA (FIG. 15D), further suggesting that IL-22-induced inflammation is a contributing factor for Riok2 haploinsufficiency-mediated ineffective erythropoiesis and anemia. Increased numbers of splenic IL-22$^{+}$CD4$^{+}$ T, natural killer T (INKT), and innate lymphoid cells (ILCs) were observed in aged Riok2$^{fl/+}$Vav1$^{cre}$ mice compared to Riok2$^{+/+}$Vav1$^{cre}$ mice (FIG. 16D, FIG. 26H, I). Interestingly, mild anemia was observed in mice lacking Riok2 only in T cells (FIG. 26K). Expression of IL-23, required for IL-22 production, was enhanced in Riok2-haploinsufficient dendritic cells (FIG. 26J). Rps14 haploinsufficient $T_H$22 cells also secreted elevated concentrations of IL-22 compared to Vav1$^{cre}$ control $T_H$22 cells (FIG. 26L). Mutation(s) in the gene adenomatosis polyposis coli (Ape), also found on human chromosome 5q, lead to anemia in addition to adenomas. in vitro generated $T_H$22 cells from Ape$^{Min}$ mice secreted elevated IL-22 compared to littermate controls (FIG. 26M). In total, our analysis of three distinct heterozygous deletions of genes found on human chromosome 5q suggests that increased IL-22 is a generalized phenomenon observed upon heterozygous loss of genes found on chromosome 5q leading to anemia.

Example 11: p53 Upregulation Drives Increased IL-22 Secretion Upon Riok2 Loss

To identify cell-intrinsic molecular mechanism(s) driving the increase in IL-22 secretion upon Riok2 haploinsufficiency, RNA-sequencing (RNA-Seq) were performed on in vitro polarized $T_H$22) cells purified by flow cytometry from Riok2$^{+/+}$Il22$^{tdtomato/+}$Vav1$^{cre}$ and Riok2$^{fl/+}$Il22$^{tdtomato/+}$Vav1$^{cre}$ mice (FIG. 16E). GSEA analysis of the RNA-Seg dataset identified activation of the p53 pathway in Riok2$^{fl/+}$Vav1$^{cre}$ mice (FIG. 16F, G). p53 increase in $T_H$22 cells from Riok2$^{fl/+}$Vav1$^{cre}$ mice was confirmed by flow cytometry (FIG. 16H, I). p53 upregulation was also observed in Riok2$^{fl/+}$Vav1$^{cre}$ erythroid precursors (FIG. 26F, G). The p53 pathway is activated by decreased expression of ribosomal protein genes, however, its involvement in IL-22 regulation has not been known.

p53 is a transcription factor with well-defined consensus binding sites. To assess whether p53 drives Il22 transcription, the Il22 promoter for potential p53 binding sites were analyzed using LASAGNA algorithm and found putative p53 consensus binding sequences in the Il22 promoter (FIG. 16J). Chromatin immunoprecipitation (ChIP) confirmed the presence of p53 on the Il22 promoter (FIG. 16K). In line with the ChIP data, p53 inhibition by pifithrin-α, p-nitro decreased IL-22 concentrations while p53 activation by nutlin-3 increased IL-22 from in vitro polarized wild-type $T_H$22 cells (FIG. 16L, M). Treatment with either pifithrin-α, p-nitro or nutlin-3 did not decrease cell viability (FIG. 26N). Accordingly, genetic deletion of Trp53 blunted the increase in IL-22 secretion observed upon Riok2 haploinsufficiency (FIG. 16N). A significant decrease in IL-22 secretion was also observed upon Trp53 deletion in Riok2-sufficient cells further suggesting a homeostatic role for p53 in controlling IL-22 production (FIG. 16N). Taken together, these data show that Riok2 haploinsufficiency-mediated p53 upregulation drives increased IL-22 secretion in Riok2$^{fl/+}$Vav1$^{cre}$ mice.

Example 12: IL-22 Neutralization Alleviates Stress-Induced Anemia

Figure 27A:
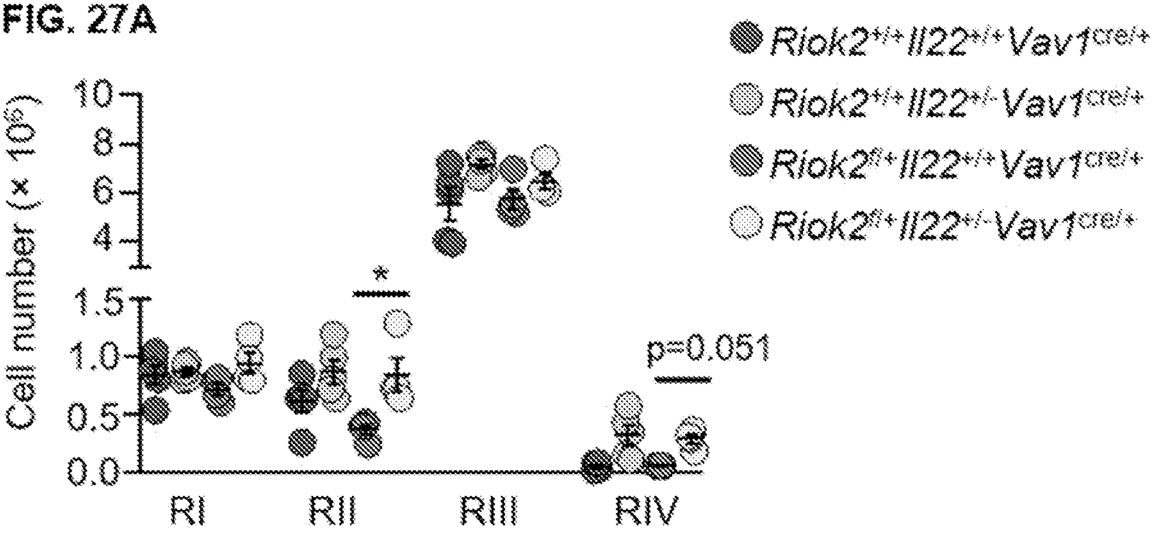
Figure 27B:
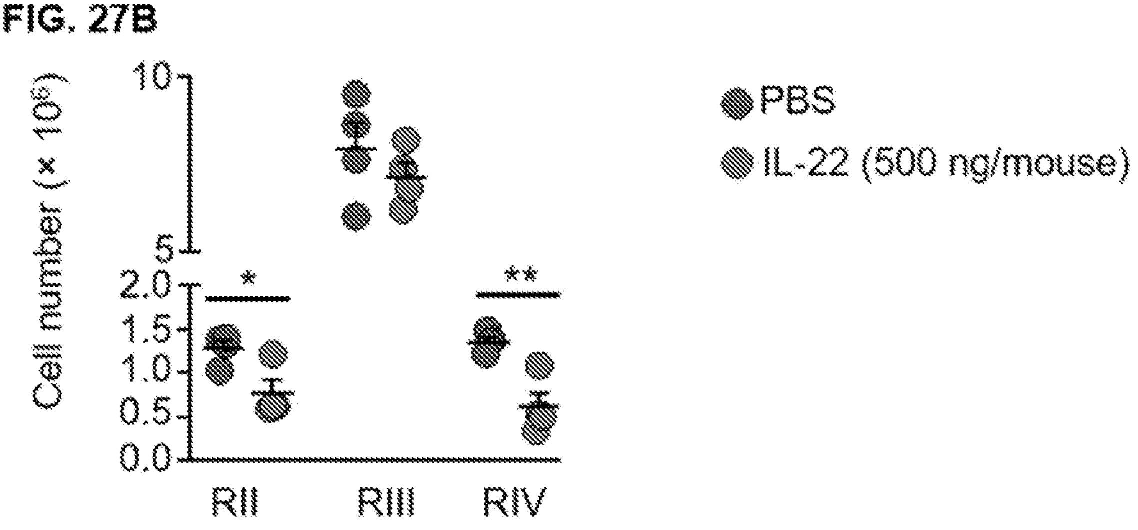

Mice with compound genetic deletion of Il22 on the Riok2 haploinsufficient background (Riok2$^{fl/+}$Il22$^{+/-}$ Vav1$^{cre}$) exhibited increased numbers of PB RBCs compared to IL-22 sufficient Riok2 haploinsufficient mice on day 7 after two treatments with 25 mg/kg phenylhydrazine treatment (FIG. 17A). Interestingly, an increase was also evidenced in PB RBCs in Riok2 sufficient mice heterozygous for Il22 deletion (Riok2$^{+/+}$Il22$^{+/+}$Vav1$^{cre}$) compared to Riok2 sufficient IL-22 sufficient mice (Riok2$^{+/+}$Il22$^{+/+}$ Vav1$^{cre}$). PB Hb and HCT also were increased in Il22 haploinsufficient mice, regardless of Riok2 background, however, this difference did not reach statistical significance (FIG. 17A). Next, it was assessed whether the increase in PB RBCs in Riok2$^{fl/+}$Il22$^{+/-}$ Vav1$^{cre}$ mice was due to increased erythropoiesis in the BM of these mice. An increase were observed in RII and RIV erythroid precursors in Riok2$^{fl/+}$ Il22$^{+/-}$Vav1$^{cre}$ compared to Riok2$^{fl/+}$Il22$^{+/+}$Vav1$^{cre}$ mice (FIG. 17B, FIG. 27A). Treatment of mice with a neutralizing IL-22 antibody in vivo, also reversed phenylhydrazine-induced anemia as evidenced by increase in PB RBCs and HCT in Riok2$^{fl/+}$Vav1$^{cre}$ mice as well as Riok2 sufficient (Riok2$^{+/+}$Vav1$^{cre}$) mice (FIG. 17C). Unexpectedly, IL-22 neutralization also reduced the frequency of apoptotic erythroid precursors in both Riok2 sufficient as well as Riok2$^{fl/+}$ Vav1$^{cre}$ mice (FIG. 17D). These data indicate that IL-22 neutralization reverses anemia, at least in part, by reducing apoptosis of erythroid precursors. Recently, dampening IL-22 signaling in intestinal epithelial stem cells was shown to reduce apoptosis. The effect of IL-22 deficiency (genetic as well as antibody-mediated) in alleviating anemia in genetically wild-type mice indicated a role for IL-22 in reversing anemia regardless of ribosomal haploinsufficiency. Accordingly, treatment of C57BL/6J mice undergoing phenylhydrazine-induced anemia with anti-IL-22 significantly increased PB RBCs, Hb, and HCT compared to isotype antibody-treated mice (FIG. 28B). This increase in PB RBCs could be attributed to the increased frequency of RIII and RIV erythroid precursors in the BM of mice treated with anti-IL-22 compared to isotype-administered controls (FIG. 28C). Of note, PB RBCs, Hb, and HCT did not differ in healthy, non-anemic wild-type mice injected with anti-IL-22 versus isotype-matched antibody (FIG. 28A). Thus, IL-22 neutralization, either by genetic deletion or antibody blockade, alleviates stress-induced anemia in Riok2$^{fl/+}$Vav1$^{cre}$ as well as wild-type mice.

Example 13: IL-22 Worsens Stress-Induced Anemia in Wild-Type Mice

Figures 5A, 5B, 5C, 5D, 5E, 5F, 5G:
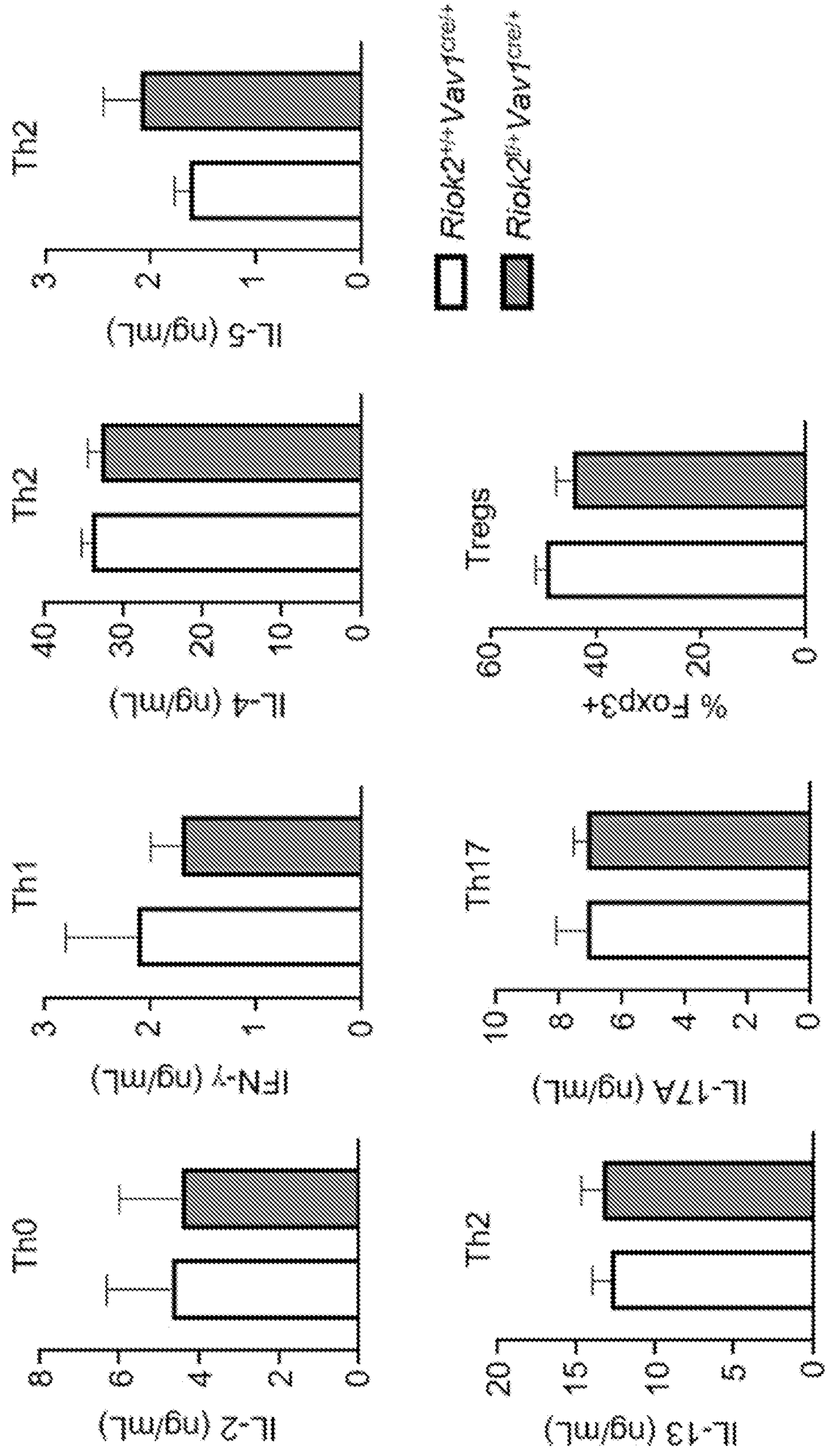
FIG. 5A-FIG. 5G show that expression of lineage-associated T cell factors is comparable between Riok2 haploinsufficient and sufficient cells. Concentration of IL-2 (FIG.

Phenylhydrazine administration to wild-type C57BL/6J mice treated intraperitoneally with recombinant IL-22 (rIL-22) led to decreased PB RBCs, Hb, and 1-ICT owing to decreased BM erythroid precursor cell frequency and number (FIG. 18A, C, FIG. 27B). rIL-22 treatment led to increased apoptosis of erythroid precursors (FIG. 5*d*). This treatment also led to an increase in PB reticulocytes, an indication of increased erythropoiesis under stress (FIG. 18B). Recombinant IL-22 also dose-dependently decreased terminal erythropoiesis in an in vitro erythropoiesis assay (FIG. 18E, F). Importantly, IL-22-mediated inhibition of in vitro erythropoiesis led to induction of p53 suggesting a feedback loop between IL-22 and p53 in driving dyserythropoiesis (FIG. 18G). Overall, these data show that exogenous recombinant IL-22 exacerbates stress-induced anemia in wild-type mice.

Example 14: Erythroid Precursors Express IL-22RA1 Receptors

IL-22 signals through a cell surface heterodimeric receptor composed of IL-10Rβ and IL-22RA1 (encoded by Il22ra1). IL-22RA1 expression has been reported to be restricted to cells of non-hematopoietic origin (e.g., epithelial cells and mesenchymal cells). It was discovered, however, that erythroid precursors in the BM also express IL-22RA1 (FIG. 19A, FIG. 29A). Moreover, among BM hematopoietic progenitors, IL-22RA1-expressing cells were exclusively of the erythroid lineage (FIG. 29B). Using a second IL-22RA1-specific antibody (targeting a different epitope than the antibody used in FIG. 4A), the presence of IL-22RA1 on erythroid precursors were confirmed (FIG. 29C), Il22ra1 mRNA expression was detected exclusively in erythroid precursors among all lineage-negative cells in the BM (FIG. 29D).

Figure 27C:
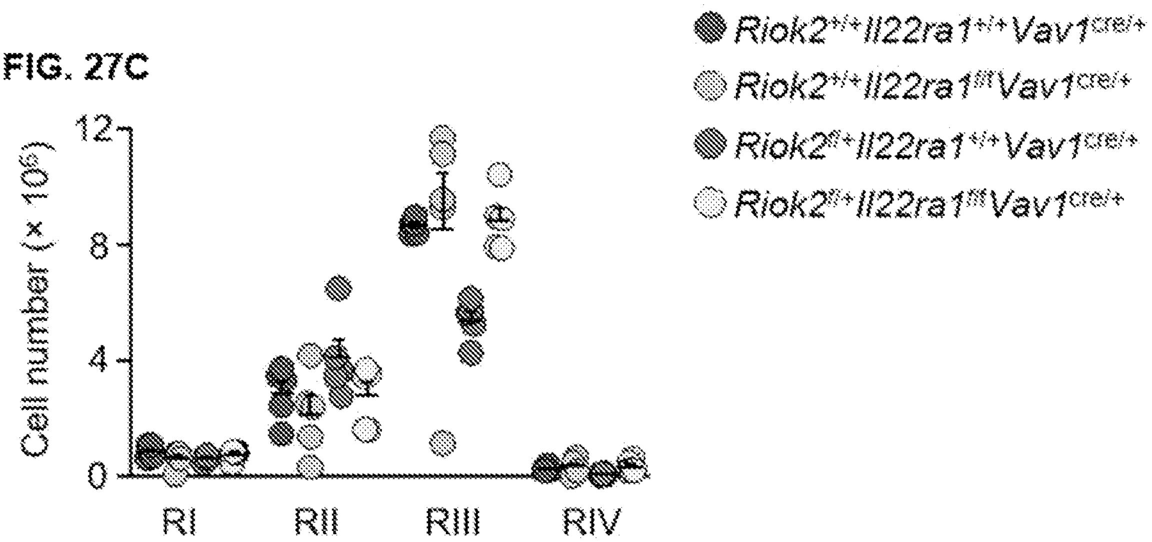

Deletion of Il22ra1 in Riok2 haploinsufficient mice (Riok2$^{f/+}$Il22ra1$^{f/f}$Vav1$^{cre}$) led to improvement in PB RBCs and HCT as compared to IL-22RA1 sufficient Riok2 haploinsufficient mice (Riok2$^{f/+}$Il22ra1$^{+/+}$Vav1$^{cre}$) (FIG. 1913). This improvement could be attributed to the increase in RIII and RIV erythroid precursors in the BM of Riok2$^{f/+}$Il22ra1$^{f/f}$Vav1$^{cre}$ mice (FIG. 19C, FIG. 27C).

In accordance with the upregulation of p53 upon in vitro IL-22 stimulation in an in vitro erythropoiesis assay (FIG. 18G) and p53 upregulation in erythroid precursors upon Riok2 haploinsufficiency (FIG. 25F, G), a synergistic effect of Riok2 haploinsufficiency was observed in IL-22-responsive (IL-22RA1$^+$) erythroid precursors in Riok2$^{f/+}$Vav1$^{cre}$ mice (FIG. 19D, E). p53 target genes such as Gadd45a and Cdkn1a1 were also increased in IL-22RA1$^+$ Riok2 haploinsufficient erythroid precursors compared to IL-22RA1$^+$ Riok2 sufficient erythroid precursors (FIG. 19F). Given that rIL-22 induced apoptosis in erythroid precursors in vivo (FIG. 18D), it was sought to determine if Riok2 haploinsufficiency-mediated p53 upregulation played an independent role in apoptosis induction. In an IL-22-free in vitro erythropoiesis assay, p53 inhibition by pifithrin-α, p-nitro inhibited the apoptosis induced by Riok2 haploinsufficiency (FIG. 19G).

Figure 27D:
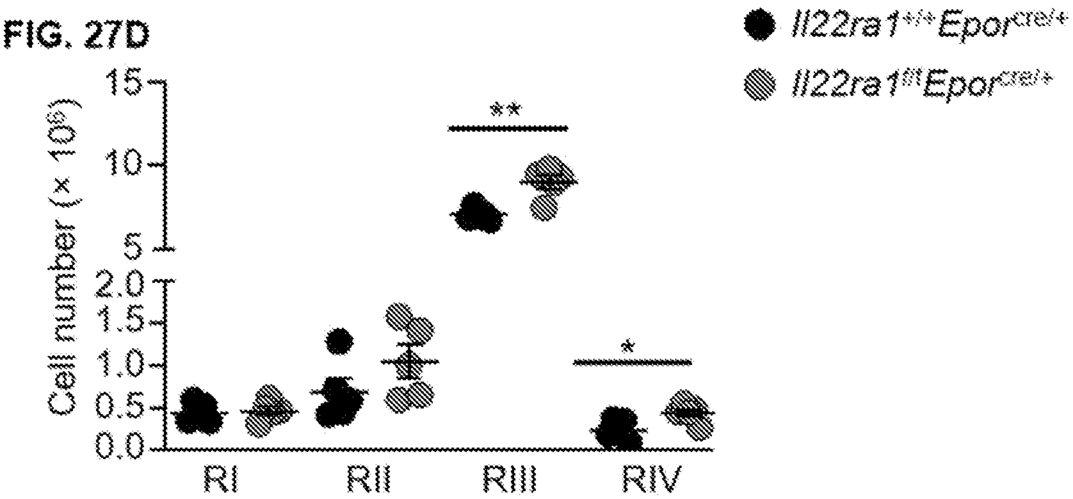

Erythroid cell-specific deletion of IL-22RA1 (using cre recombinase driven by the erythropoietin receptor (Epor) promoter) also increased numbers of PB RBCs and HCT (FIG. 7*a*) due to the increase in RIII and RIV erythroid precursors in the BM (FIG. 20B, FIG. 27D). Additionally, rIL-22 failed to exacerbate phenylhydrazine-induced anemia in Il22ra1$^{f/f}$Epor$^{cre}$ mice lacking the IL-22 receptor only on erythroid cells (FIG. 20C). These data reinforce our view that IL-22 signaling plays an important role in regulating erythroid development regardless of ribosomal haploinsufficiency. Thus, using three different approaches to neutralize IL-22 signaling, it is demonstrated herein that IL-22 plays a critical role in controlling RBC production by directly regulating early stages of erythropoiesis.

Example 15: IL-22 is Increased in del(5q) MDS Patients

Next, it was assessed whether IL-22. expression is increased in human disorders that display dyserythropoiesis due to ribosomal protein haploinsufficiencies. Given the localization of RIOK2 on human chromosome 5, it was focused on MDS with 5q deletion and compared it to MDS without 5q deletion and healthy controls. A significant increase was observed in IL-22 levels in the BM fluid (BMF) of del(5q) MDS patients compared to BMF from healthy controls and non-del(5q) MDS patients (FIG. 21A). Interestingly, a strong negative correlation between cellular RIOK2 mRNA expression and BMF IL-22 concentration was evident in the del(5q) MDS cohort (FIG. 21B) indicating that a decrease in RIOK2 expression is associated with increased IL-22 expression. In the MDS cohort, S100A8 concentrations were found to be higher than healthy controls regardless of del(5q) status (FIG. 21C). However, IL-22 positively correlated with S100A8 concentrations only in the del(5q) MDS group (FIG. 21D). Of note, S100A8 concentrations were higher in BMF from non-del(5q) MDS patients compared to MDS patients with del(5q) (FIG. 21C). These data suggest that the regulation of S100A8 expression may be IL-22-mediated in del(5q) MDS patients, but IL-22-independent in other subtypes of MDS. In a second cohort of MDS patients, the frequency of CD4$^+$ T cells producing IL-22 (T$_H$22 cells) among freshly isolated peripheral blood mononuclear cells (PBMCs) was significantly higher in MDS patients with 5q deletion compared to healthy controls (FIG. 21E—cumulative data of representative flow plots shown in FIG. 30A). As disclosed herein, the independent analysis of a large-scale microarray sequencing dataset of CD34$^+$ cells from normal, del(5q) MDS, and non-del(5q) MDS subjects showed that RIOK2 mRNA was significantly decreased in the del(5q) MDS cohort (78% (37/47)). Additionally, expression of known IL-22 target genes such as S100A10, 5100411, PTGS2, RAB7A, and LCN2 was specifically increased in the del(5q) MDS cohort compared to both the healthy control and non-del(5q) groups (FIG. 30B). Using differentially expressed proteins (adjusted p-value <0.01) from the Riok2 haploinsufficient proteomics dataset as a reference set, GSEA analyses of the CD34$^+$ microarray dataset revealed significant enrichment scores (FIG. 31A, B) further suggesting that the mouse model of Riok2 haploinsufficiency faithfully recapitulates the molecular changes seen in patients with del(5q) MDS.

Example 16: High IL-22 in Anemic Chronic Kidney Disease Patients

Anemia is frequently observed in CKD patients and is associated with poor outcomes. Anemia of CKD is resistant to erythropoiesis-stimulating agents (ESAs) in 10-20% of patients, suggesting that pathogenic mechanisms other than erythropoietin deficiency are at play. A significant increase was found in IL-22 concentration in the plasma of CKD patients with secondary anemia compared to healthy controls and to CKD patients without anemia (FIG. 21F). Plasma IL-22 concentration negatively correlated with hemoglobin in CKD patients (FIG. 21G), suggesting a function for IL-22 in driving anemia in some patients with CKD.

As described herein, IL-22 signaling directly controls bone marrow erythroid differentiation and that its neutralization is a potential therapeutic approach for anemias and MDS. By exploring the function of a little-studied atypical kinase Riok2 in mammalian biology, the erythroid precursors were identified as a novel target for IL-22 action via the IL-22RA1. IL-22 were further identified as a disease biomarker for the del(5q) subtype of MDS and lastly, identify IL-22 signaling blockade as a potential therapeutic for stress-induced anemias irrespective of the genetic background. Interestingly, elevated levels of IL-22 were also detected in patients with anemia secondary to chronic kidney disease (CKD) suggesting that IL-22 signaling blockade may be therapeutic in reversing anemia in a much wider patient population.

Del(5q), either isolated or accompanied by additional cytogenetic abnormalities, is the most commonly detected chromosomal abnormality in MDS, reported in 10-15% of patients and enriched in therapy-related MDS. The severe anemia in MDS patients with isolated del(5q) has been linked to haploinsufficiency of ribosomal proteins such as RPS14 and RPS19. While much research has focused on the effect of such gene deletions or mutations in hematopoietic stem cells and lineage-committed progenitors, the immunobiology underlying this MDS subtype has remained largely unexplored, thus impeding the development of immune-targeted therapies. With the exception of the TNF-α inhibitor etanercept which proved to be ineffective, the only other therapy against immune cell-derived cytokines, is luspatercept, a recombinant fusion protein derived from human activin receptor type IIb which has just been approved for use in anemia in lower risk MDS patients. Here, two critical and independent functions of an understudied atypical kinase, RIOK2, that synergize to induce dyserythropoiesis and anemia were identified. One effect of Riok2 loss in erythroid precursors is an intrinsic block in erythroid differentiation owing to its indispensable role in the maturation of the pre-40S ribosomal complex, leading to increased apoptosis and cell cycle arrest. The second effect of Riok2 loss is the induction of the erythropoiesis-suppressive cytokine IL-22 in T cells which then directly acts on the IL-22RA1 on erythroid precursors (FIG. 31C). While IL-22RA1 is known to be widely expressed on epithelial cells and hepatocytes, its expression has also been recently reported on specialized cells such as retinal Müller glial cells and now described here, on erythroid precursors. Data disclosed herein reveals a novel molecular link between haploinsufficiency of a ribosomal protein and induction of erythropoiesis-suppressive cytokine IL-22. While IL-22 has been shown to modulate RBC production by controlling the expression of iron-chelating proteins such as hepcidin and haptoglobin, a novel role for IL-22 were uncovered in directly binding to the previously unknown IL-22R on erythroid precursors leading to their apoptosis. Diminished expression of ribosomal proteins has been shown to increase p53 levels. Data disclosed herein shows that Riok2 haploinsufficiency leads to p53 upregulation in T cells which drives the increase in IL-22 secretion. Additionally, it also shows that IL-22-responsive erythroid precursors express elevated p53 further suggesting a role for p53 downstream of IL-22 signaling in driving dyserythropoiesis. Using banked and fresh del(5q) MDS and CKD patient samples, the data disclosed herein shows that IL-22 is elevated in these human diseases.

The role of inflammatory cytokines in directly regulating various aspects of BM hematopoiesis in steady-state and diseased conditions is increasingly being recognized. IL-22 is known to play a pathogenic role in some autoimmune diseases. Interestingly, autoimmune diseases such as colitis, Behçet's disease, and arthritis are common in MDS patients, with features of autoimmunity observed in up to 10% of patients. It is intriguing to hypothesize that IL-22 may account both for the onset of MDS and autoimmunity in this subset of patients. Studies have reported that in patients with co-existence of MDS and autoimmunity, treatment for one can alleviate the symptoms of the other. Low-level exposure to benzene, a hydrocarbon, has been associated with an increased risk of MDS. Hydrocarbons are known ligands for aryl hydrocarbon receptor (AHR), the transcription factor that controls IL-22 production in T cells. Stemregenin 1, an AHR antagonist, was shown to promote the ex vivo expansion of human HSCs, with the highest fold expansion seen in the erythroid lineage. Overall, data disclosed herein suggests that inhibition of the AHR-IL-22 axis may be an attractive approach for treating red blood cell disorders that arise from dyserythropoiesis.

Further, data disclosed herein provides that neutralization of IL-22 signaling may be effective not only in the treatment of MDS and other stress-induced anemias, but also in the anemia of chronic diseases such as CKD, which are very much in need of new therapeutic approaches. With currently approved MDS therapies (lenalidomide and other hypomethylating agents, erythropoiesis-stimulating agents), the survival time of MDS patients after diagnosis is only 2.5-3 yrs. Patients also develop resistance to these therapies thus intensifying the need for additional therapeutic modalities. IL-22-based therapies could be used in conjunction with already existing therapeutics or after first-line therapies have failed due to acquisition of resistance.

Example 17: Anti-IL-22 Inhibits Recombinant IL-22-Induced IL-10 Production

IL-22 has been shown to induce IL-10 production from COLO-205 cells. To measure the effectiveness of anti-IL-22 in neutralizing IL-22 biological activity, COLO-205 cells were treated with recombinant mouse IL-22 (FIG. 32A) or recombinant human IL-22 (FIG. 32B), each in the presence of either isotype control antibody or anti-IL-22 antibody (Clone F0025, which blocks the interaction between IL-22 and IL-22 receptor or a heterodimeric complex of IL-22 receptor and IL-10 receptor beta subunit).

Briefly, in vitro IL-22 neutralization assays using anti-IL-22 antibodies were performed as follows. COLO-205 cells were purchased from American Type Culture Collection (ATCC) and cultured in complete medium (RPMI supplemented with 10% Fetal Bovine Serum (FBS)). 30,000 COLO-205 cells were cultured per well of a 96-well plate overnight in 100 uL complete medium. On the next day, cells were stimulated with human or mouse recombinant IL-22 (Cell Signaling Technology, Inc.) in the presence of isotype or IL-22 antibody for 24 hrs. Cell-free supernatant was collected at the end of the 24 hr period and subjected to IL-10 measurement using Human IL-10 Quantikine ELISA Kit (R&D Systems, Inc.).

Anti-IL-22 effectively neutralized the biological activity of both mouse and human IL-22, as seen by the observed decrease in IL-10 secretion from COLO-205 cells (FIGS. 32A and 32B).

Similarly, in vivo IL-22 neutralization assays using anti-IL-22 antibodies were performed. Neutralizing anti-IL-22 (Clone F0025, which blocks the interaction between IL-22 and IL-22 receptor) and isotype control IgG1 (purchased from BioXCell). 8-10 week old C57BL/6 mice were administered anti-IL-22 (700 μg/mouse/dose) or isotype intraperitoneally every 48 hours until the conclusion of the experiment. For induction of stress-induced anemia, mice were administered 25 mg/kg phenylhydrazine on days 0 and 1. Blood was collected from mice via the submandibular vein on days 4 and 7 post-phenylhydrazine administration for quantifying RBC numbers, hemoglobin, and hematocrit.

Treatment of C57BL/6J mice undergoing PhZ-induced anemia with the anti-IL-22 antibody significantly increased PB RBCs, Hb, and HCT compared to isotype antibody-treated mice (FIG. 33).

TABLE 6

| Sequence of the anti-IL-22 antibody used in Example 17 | |
|---|---|
| Heavy chain | QVQLVQSGAE VKKPGASVKV SCKASGYTFT NYYMHWVRQA PGQGLEWVGW INPYTGSAFY<br>AQKFRGRVTM TRDTSISTAY MELSRLRSDD TAVYYCAREP EKFDSDDSDV WGRGTLVTVS<br>SASTKGPSVF PLAPSSKSTS GGTAALGCLV KDYFPEPVTV SWNSGALTSG VHTFPAVLQS<br>SGLYSLSSVV TVPSSSLGTQ TYICNVNHKP SNTKVDKKVE PKSCDKTHTC PPCPAPELLG<br>GPSVFLFPPK PKDTLMISRT PEVTCVVVDV SHEDPEVKFN WYVDGVEVHN AKTKPREEQY<br>NSTYRVVSVL TVLHQDWLNG KEYKCKVSNK ALPAPIEKTI SKAKGQPREP QVYTLPPSRE<br>EMTKNQVSLT CLVKGFYPSD IAVEWESNGQ PENNYKTTPP VLDSDGSFFL YSKLTVDKSR<br>WQQGNVFSCS VMHEALHNHY TQKSLSLSPG |
| Light chain | QAVLTQPPSV SGAPGQRVTI SCTGSSSNIG AGYGVHWYQQ LPGTAPKLLI YGDSNRPSGV<br>PDRFSGSKSG TSASLAITGL QAEDEADYYC QSYDNSLSGY VFGGGTQLTV LGQPKAAPSV<br>TLFPPSSEEL QANKATLVCL ISDFYPGAVT VAWKADSSPV KAGVETTTPS KQSNNKYAAS<br>SYLSLTPEQW KSHRSYSCQV THEGSTVEKT VAPTECS |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize or be able to ascertain using no more than routine experimentation, many equivalents to the specific embodiments of the invention described herein. Such equivalents are intended to be encompassed by the following claims.

The invention claimed is:

1. A method of treating anemia caused by a myelodysplastic syndrome in a human subject in need thereof, the method comprising administering to the human subject an effective amount of an anti-IL-22 antibody or an antigen binding fragment thereof or an anti-IL-22RA1 antibody or an antigen binding fragment thereof.

2. The method of claim 1, wherein the myelodysplastic syndrome is associated with a deletion in the long arm of human chromosome 5.

3. The method of claim 1, further comprising conjointly administering to the human subject an effective amount of erythropoietin, epoetin alfa, epoetin beta, epoetin omega, epoetin zeta, IL-9, or darbepoetin alfa.

4. A method of treating anemia caused by a myelodysplastic syndrome in a human subject in need thereof, the method comprising administering to the human subject an effective amount of fezakinumab.

5. The method of claim 4, wherein the myelodysplastic syndrome is associated with a deletion in the long arm of human chromosome 5.

6. The method of claim 4, further comprising conjointly administering to the human subject an effective amount of erythropoietin, epoetin alfa, epoetin beta, epoetin omega, epoetin zeta, IL-9, or darbepoetin alfa.

7. A method of promoting differentiation of an erythroid progenitor cell toward a mature red blood cell in a human subject in need thereof, the method comprising administering to the human subject an effective amount of an anti-IL-22 antibody or an antigen binding fragment thereof or an anti-IL-22RA1 antibody or an antigen binding fragment thereof, and wherein the subject is afflicted with anemia caused by myelodysplastic syndrome.

8. A method of promoting differentiation of an erythroid progenitor cell toward a mature red blood cell in a human subject afflicted with anemia caused by myelodysplastic syndrome, the method comprising administering to the human subject an effective amount of fezakinumab.

* * * * *